(12) United States Patent
Lopes et al.

(10) Patent No.: US 9,492,227 B2
(45) Date of Patent: Nov. 15, 2016

(54) ENHANCED MEDICAL DEVICE FOR USE IN BODILY CAVITIES, FOR EXAMPLE AN ATRIUM

(71) Applicant: Kardium Inc., Richmond (CA)

(72) Inventors: Fernando Lopes, Richmond (CA); Saar Moisa, Vancouver (CA); Jorge Jaramillo, Burnaby (CA); Douglas Goertzen, New Westminster (CA); Peter Hawes, Burnaby (CA); Ashkan Sardari, North Vancouver (CA); Aldo Antonio Salvestro, Burnaby (CA)

(73) Assignee: Kardium Inc., Richmond (CA)

( * ) Notice: Subject to any disclaimer, the term of this patent is extended or adjusted under 35 U.S.C. 154(b) by 343 days.

(21) Appl. No.: 13/782,867

(22) Filed: Mar. 1, 2013

(65) Prior Publication Data

US 2013/0172883 A1 Jul. 4, 2013

Related U.S. Application Data

(63) Continuation of application No. PCT/US2012/022061, filed on Jan. 20, 2012.

(60) Provisional application No. 61/435,213, filed on Jan. 21, 2011, provisional application No. 61/488,639, filed on May 20, 2011, provisional application No. 61/515,141, filed on Aug. 4, 2011, provisional application No. 61/485,987, filed on May 13, 2011.

(51) Int. Cl.
*A61B 5/0408* (2006.01)
*A61B 18/14* (2006.01)
(Continued)

(52) U.S. Cl.
CPC ......... *A61B 18/1492* (2013.01); *A61B 5/0422* (2013.01); *A61B 5/6858* (2013.01);
(Continued)

(58) Field of Classification Search
CPC ............ A61B 1/00085; A61B 5/0422; A61B 5/6846; A61B 5/6852; A61B 5/6858; A61B 5/6859; A61B 5/6869; A61B 18/1492; A61B 2017/00367–2017/00415; A61B 2018/00267; A61B 2018/00351–2018/00392; A61B 2018/0038; A61B 2018/00577; A61B 2018/1475
USPC ............ 600/372–357, 391, 393, 509; 606/41
See application file for complete search history.

(56) References Cited

U.S. PATENT DOCUMENTS

| 4,114,202 A | 9/1978 | Roy et al. |
| 4,164,046 A | 8/1979 | Cooley |

(Continued)

FOREIGN PATENT DOCUMENTS

| CN | 101797181 A | 8/2010 |
| EP | 0723467 B1 | 7/1996 |

(Continued)

OTHER PUBLICATIONS

Gelbart et al, "Apparatus and Method for Intra-Cardiac Mapping and Ablation", Amendment filed Apr. 10, 2014; Supplemental Amendment filed Feb. 12, 2013 for co-pending U.S. Appl. No. 11/475,950, 21 pgs.

(Continued)

*Primary Examiner* — Linda Dvorak
*Assistant Examiner* — Erin M Cardinal
(74) *Attorney, Agent, or Firm* — Rossi, Kimms & McDowell LLP

(57) ABSTRACT

Systems, methods, and devices allow intravascular or percutaneous mapping, orientation or ablation, or combinations thereof in bodily cavities or lumens. A device includes a plurality of elongate members which are moveable between an unexpanded configuration, a bent or coiled stack configuration and an expanded or fanned configuration. The elongate members form a stack arrangement in the unexpanded configuration to fit through a catheter sheath, The elongate members follow respective arcuate or curvilinear paths as advanced from the sheath into the bent or coiled stack configuration, adopting volute, scroll or rho shapes, and may be nested. The elongated members are fanned or radially spaced circumferentially with respect to one another into the expanded or fanned configuration. Transducers carried by elongate members may sense various physiological characteristics of or proximate tissue, for instance temperature, and/or may apply energy to or proximate tissue, for example to perform ablation. The device is retractable.

115 Claims, 53 Drawing Sheets

(51) Int. Cl.
*A61B 5/042* (2006.01)
*A61B 5/053* (2006.01)
*A61M 25/00* (2006.01)
*A61B 5/00* (2006.01)
*A61B 5/026* (2006.01)
*A61B 5/06* (2006.01)
*A61B 18/00* (2006.01)

(52) U.S. Cl.
CPC ............ *A61B 5/026* (2013.01); *A61B 5/0538* (2013.01); *A61B 5/06* (2013.01); *A61B 5/6843* (2013.01); *A61B 2018/0016* (2013.01); *A61B 2018/00267* (2013.01); *A61B 2018/00351* (2013.01); *A61B 2018/00357* (2013.01); *A61B 2018/00577* (2013.01); *A61B 2018/00791* (2013.01); *A61B 2018/00839* (2013.01); *A61B 2018/00863* (2013.01); *A61B 2018/00875* (2013.01); *A61B 2090/065* (2016.02); *A61M 25/0074* (2013.01); *A61M 25/0082* (2013.01)

(56) References Cited

U.S. PATENT DOCUMENTS

| | | | |
|---|---|---|---|
| 4,225,148 A | 9/1980 | Andersson | |
| 4,240,441 A | 12/1980 | Khalil | |
| 4,263,680 A | 4/1981 | Reul et al. | |
| 4,273,128 A | 6/1981 | Lary | |
| 4,411,266 A | 10/1983 | Cosman | |
| 4,490,859 A | 1/1985 | Black et al. | |
| 4,543,090 A | 9/1985 | McCoy | |
| 4,699,147 A | 10/1987 | Chilson et al. | |
| 4,770,187 A | 9/1988 | Lash et al. | |
| 4,787,369 A | 11/1988 | Allred, III et al. | |
| 4,794,912 A | 1/1989 | Lia | |
| 4,850,957 A | 7/1989 | Summers | |
| 4,887,613 A | 12/1989 | Farr et al. | |
| 4,890,602 A | 1/1990 | Hake | |
| 4,890,612 A | 1/1990 | Kensey | |
| 4,893,613 A | 1/1990 | Hake | |
| 4,895,166 A | 1/1990 | Farr et al. | |
| 4,905,667 A | 3/1990 | Foerster et al. | |
| 4,921,499 A | 5/1990 | Hoffman et al. | |
| 4,940,064 A | 7/1990 | Desai | |
| 4,942,788 A | 7/1990 | Farr et al. | |
| 4,979,514 A | 12/1990 | Sekii et al. | |
| 4,998,933 A | 3/1991 | Eggers et al. | |
| 5,026,384 A | 6/1991 | Farr et al. | |
| 5,047,047 A | 9/1991 | Yoon | |
| 5,122,137 A | 6/1992 | Lennox | |
| 5,127,902 A | 7/1992 | Fischell | |
| 5,156,151 A | 10/1992 | Imran | |
| 5,174,299 A | 12/1992 | Nelson | |
| 5,176,693 A | 1/1993 | Pannek, Jr. | |
| 5,178,620 A | 1/1993 | Eggers et al. | |
| 5,192,291 A | 3/1993 | Pannek, Jr. | |
| 5,195,505 A | 3/1993 | Josefsen | |
| 5,201,316 A | 4/1993 | Pomeranz et al. | |
| 5,228,442 A | 7/1993 | Imran | |
| 5,242,386 A | 9/1993 | Holzer | |
| 5,245,987 A | 9/1993 | Redmond et al. | |
| 5,255,679 A | 10/1993 | Imran | |
| 5,279,299 A | 1/1994 | Imran | |
| 5,293,869 A | 3/1994 | Edwards et al. | |
| 5,312,435 A | 5/1994 | Nash et al. | |
| 5,317,952 A | 6/1994 | Immega | |
| 5,324,284 A | 6/1994 | Imran | |
| 5,327,889 A | 7/1994 | Imran | |
| 5,341,807 A | 8/1994 | Nardella | |
| 5,345,936 A | 9/1994 | Pomeranz et al. | |
| 5,351,679 A | 10/1994 | Mayzels et al. | |
| 5,366,443 A | 11/1994 | Eggers et al. | |
| 5,370,679 A | 12/1994 | Atlee, III | |
| 5,379,773 A | 1/1995 | Hornsby | |
| 5,397,321 A | 3/1995 | Houser et al. | |
| 5,419,767 A | 5/1995 | Eggers et al. | |
| 5,450,860 A | 9/1995 | O'Connor | |
| 5,465,717 A | 11/1995 | Imran et al. | |
| 5,478,353 A | 12/1995 | Yoon | |
| 5,485,849 A | 1/1996 | Panescu et al. | |
| 5,496,267 A | 3/1996 | Drasler et al. | |
| 5,499,981 A | 3/1996 | Kordis | |
| 5,531,760 A | 7/1996 | Alwafaie | |
| 5,545,193 A | 8/1996 | Fleischman et al. | |
| 5,555,883 A | 9/1996 | Avitall | |
| 5,557,967 A | 9/1996 | Renger | |
| 5,575,810 A | 11/1996 | Swanson et al. | |
| 5,593,424 A | 1/1997 | Northrup, III | |
| 5,598,848 A | 2/1997 | Swanson et al. | |
| 5,599,345 A | 2/1997 | Edwards et al. | |
| 5,620,481 A | 4/1997 | Desai et al. | |
| 5,637,090 A | 6/1997 | McGee et al. | |
| 5,662,587 A | 9/1997 | Grundfest et al. | |
| 5,681,308 A | 10/1997 | Edwards et al. | |
| 5,681,336 A | 10/1997 | Clement et al. | |
| 5,687,723 A | 11/1997 | Avitall | |
| 5,687,737 A | 11/1997 | Branham et al. | |
| 5,697,285 A | 12/1997 | Nappi et al. | |
| 5,713,896 A | 2/1998 | Nardella | |
| 5,713,942 A | 2/1998 | Stern et al. | |
| 5,716,397 A | 2/1998 | Myers | |
| 5,720,726 A | 2/1998 | Marcadis et al. | |
| 5,728,114 A | 3/1998 | Evans et al. | |
| 5,730,127 A | 3/1998 | Avitall | |
| 5,762,066 A | 6/1998 | Law et al. | |
| 5,769,846 A | 6/1998 | Edwards et al. | |
| 5,782,239 A | 7/1998 | Webster, Jr. | |
| 5,782,879 A | 7/1998 | Rosborough et al. | |
| 5,800,495 A | 9/1998 | Machek et al. | |
| 5,823,189 A * | 10/1998 | Kordis | 600/373 |
| 5,824,066 A | 10/1998 | Gross | |
| 5,836,947 A | 11/1998 | Fleischman et al. | |
| 5,836,990 A | 11/1998 | Li | |
| 5,853,422 A | 12/1998 | Huebsch et al. | |
| 5,868,755 A | 2/1999 | Kanner et al. | |
| 5,876,343 A | 3/1999 | Teo | |
| 5,881,727 A | 3/1999 | Edwards | |
| 5,885,278 A | 3/1999 | Fleischman | |
| 5,891,136 A | 4/1999 | McGee et al. | |
| 5,904,711 A | 5/1999 | Flom et al. | |
| 5,916,163 A | 6/1999 | Panescu et al. | |
| 5,919,207 A | 7/1999 | Taheri | |
| 5,921,924 A | 7/1999 | Avitall | |
| 5,935,075 A | 8/1999 | Casscells et al. | |
| 5,935,079 A | 8/1999 | Swanson et al. | |
| 5,941,251 A | 8/1999 | Panescu et al. | |
| 5,944,715 A | 8/1999 | Goble et al. | |
| 5,961,440 A | 10/1999 | Schweich, Jr. et al. | |
| 5,968,040 A | 10/1999 | Swanson et al. | |
| 5,984,950 A | 11/1999 | Cragg et al. | |
| 6,001,069 A | 12/1999 | Tachibana et al. | |
| 6,001,093 A | 12/1999 | Swanson et al. | |
| 6,014,581 A | 1/2000 | Whayne et al. | |
| 6,023,638 A | 2/2000 | Swanson | |
| 6,030,382 A | 2/2000 | Fleischman et al. | |
| 6,036,689 A | 3/2000 | Tu et al. | |
| 6,063,082 A | 5/2000 | DeVore et al. | |
| 6,071,282 A | 6/2000 | Fleischman | |
| 6,104,944 A | 8/2000 | Martinelli | |
| 6,106,522 A | 8/2000 | Fleischman et al. | |
| 6,123,702 A | 9/2000 | Swanson et al. | |
| 6,138,043 A | 10/2000 | Avitall | |
| 6,142,993 A | 11/2000 | Whayne et al. | |
| 6,156,046 A | 12/2000 | Passafaro et al. | |
| 6,210,432 B1 | 4/2001 | Solem et al. | |
| 6,216,043 B1 | 4/2001 | Swanson et al. | |
| 6,217,573 B1 | 4/2001 | Webster | |
| 6,241,747 B1 | 6/2001 | Ruff | |
| 6,248,124 B1 | 6/2001 | Pedros et al. | |
| 6,258,258 B1 | 7/2001 | Sartori et al. | |
| 6,266,550 B1 | 7/2001 | Selmon et al. | |
| 6,304,769 B1 | 10/2001 | Arenson et al. | |
| 6,306,135 B1 | 10/2001 | Ellman et al. | |
| 6,308,091 B1 | 10/2001 | Avitall | |

(56) References Cited

U.S. PATENT DOCUMENTS

| | | |
|---|---|---|
| 6,319,249 B1 | 11/2001 | Tollner |
| 6,322,559 B1 | 11/2001 | Daulton et al. |
| 6,330,478 B1 | 12/2001 | Lee et al. |
| 6,346,105 B1 | 2/2002 | Tu et al. |
| 6,350,263 B1 | 2/2002 | Wetzig et al. |
| 6,358,258 B1 | 3/2002 | Arcia et al. |
| 6,383,151 B1 | 5/2002 | Diederich et al. |
| 6,389,311 B1 | 5/2002 | Whayne et al. |
| 6,391,024 B1 | 5/2002 | Sun et al. |
| 6,391,048 B1 | 5/2002 | Ginn et al. |
| 6,391,054 B2 | 5/2002 | Carpentier et al. |
| 6,402,781 B1 | 6/2002 | Langberg et al. |
| 6,436,052 B1 | 8/2002 | Nikolic et al. |
| 6,475,223 B1 | 11/2002 | Werp et al. |
| 6,485,409 B1 | 11/2002 | Voloshin et al. |
| 6,485,482 B1 | 11/2002 | Belef |
| 6,485,489 B2 | 11/2002 | Teirstein et al. |
| 6,506,210 B1 | 1/2003 | Kanner |
| 6,514,249 B1 | 2/2003 | Maguire et al. |
| 6,529,756 B1 | 3/2003 | Phan et al. |
| 6,537,198 B1 | 3/2003 | Vidlund et al. |
| 6,537,314 B2 | 3/2003 | Langberg et al. |
| 6,540,670 B1 | 4/2003 | Hirata et al. |
| 6,551,310 B1 | 4/2003 | Ganz et al. |
| 6,551,312 B2 | 4/2003 | Zhang et al. |
| 6,569,160 B1 | 5/2003 | Goldin et al. |
| 6,569,198 B1 | 5/2003 | Wilson et al. |
| 6,575,971 B2 | 6/2003 | Hauck et al. |
| 6,589,208 B2 | 7/2003 | Ewers et al. |
| 6,616,684 B1 | 9/2003 | Vidlund et al. |
| 6,626,930 B1 | 9/2003 | Allen et al. |
| 6,632,238 B2 | 10/2003 | Ginn et al. |
| 6,635,056 B2 | 10/2003 | Kadhiresan et al. |
| 6,640,119 B1 | 10/2003 | Budd et al. |
| 6,662,034 B2 | 12/2003 | Segner et al. |
| D484,979 S | 1/2004 | Fontaine |
| 6,704,590 B2 | 3/2004 | Haldeman |
| 6,723,038 B1 | 4/2004 | Schroeder et al. |
| 6,726,716 B2 | 4/2004 | Marquez |
| 6,760,616 B2 | 7/2004 | Hoey et al. |
| 6,780,197 B2 | 8/2004 | Roe et al. |
| 6,788,969 B2 | 9/2004 | Dupree et al. |
| 6,797,001 B2 | 9/2004 | Mathis et al. |
| 6,800,090 B2 | 10/2004 | Alferness et al. |
| 6,824,562 B2 | 11/2004 | Mathis et al. |
| 6,837,886 B2 | 1/2005 | Collins et al. |
| 6,852,076 B2 | 2/2005 | Nikolic et al. |
| 6,855,143 B2 | 2/2005 | Davison et al. |
| 6,890,353 B2 | 5/2005 | Cohn et al. |
| 6,892,091 B1 | 5/2005 | Ben-Haim et al. |
| 6,899,674 B2 | 5/2005 | Viebach et al. |
| 6,907,297 B2 | 6/2005 | Wellman et al. |
| 6,908,478 B2 | 6/2005 | Alferness et al. |
| 6,913,576 B2 | 7/2005 | Bowman |
| 6,918,903 B2 | 7/2005 | Bass |
| 6,926,669 B1 | 8/2005 | Stewart et al. |
| 6,942,657 B2 | 9/2005 | Sinofsky et al. |
| 6,949,122 B2 | 9/2005 | Adams et al. |
| 6,960,206 B2 | 11/2005 | Keane |
| 6,960,229 B2 | 11/2005 | Mathis et al. |
| 6,986,775 B2 | 1/2006 | Morales et al. |
| 6,989,010 B2 | 1/2006 | Francischelli et al. |
| 6,989,028 B2 | 1/2006 | Lashinski et al. |
| 6,994,093 B2 | 2/2006 | Murphy et al. |
| 6,997,951 B2 | 2/2006 | Solem et al. |
| 7,001,383 B2 | 2/2006 | Keidar |
| 7,025,776 B1 | 4/2006 | Houser et al. |
| 7,048,734 B1 | 5/2006 | Fleischman et al. |
| 7,050,848 B2 | 5/2006 | Hoey et al. |
| 7,052,487 B2 | 5/2006 | Cohn et al. |
| 7,068,867 B2 | 6/2006 | Adoram et al. |
| 7,141,019 B2 | 11/2006 | Pearlman |
| 7,144,363 B2 | 12/2006 | Pai et al. |
| 7,166,127 B2 | 1/2007 | Spence et al. |
| 7,174,201 B2 | 2/2007 | Govari et al. |
| 7,177,677 B2 | 2/2007 | Kaula et al. |
| 7,186,210 B2 | 3/2007 | Feld et al. |
| 7,187,964 B2 | 3/2007 | Khoury |
| 7,189,202 B2 | 3/2007 | Lau et al. |
| 7,255,695 B2 | 8/2007 | Falwell et al. |
| 7,276,044 B2 | 10/2007 | Ferry et al. |
| 7,279,007 B2 | 10/2007 | Nikolic et al. |
| 7,300,435 B2 | 11/2007 | Wham et al. |
| 7,303,526 B2 | 12/2007 | Sharkey et al. |
| 7,335,196 B2 | 2/2008 | Swanson et al. |
| 7,481,808 B2 | 1/2009 | Koyfman et al. |
| 7,507,252 B2 | 3/2009 | Lashinski et al. |
| 7,530,980 B2 | 5/2009 | Hooven |
| 7,736,388 B2 | 6/2010 | Goldfarb et al. |
| 7,738,967 B2 | 6/2010 | Salo |
| 8,103,338 B2 | 1/2012 | Harlev et al. |
| D654,588 S | 2/2012 | Taube et al. |
| 8,118,853 B2 | 2/2012 | Grewe |
| 8,150,499 B2 | 4/2012 | Gelbart et al. |
| D660,967 S | 5/2012 | Braido et al. |
| 8,224,432 B2 | 7/2012 | MacAdam et al. |
| D717,954 S | 11/2014 | Hjelle et al. |
| 9,198,713 B2 | 12/2015 | Wallace et al. |
| 2001/0003158 A1 | 6/2001 | Kensey et al. |
| 2001/0005787 A1 | 6/2001 | Oz et al. |
| 2001/0018611 A1 | 8/2001 | Solem et al. |
| 2001/0020126 A1 | 9/2001 | Swanson et al. |
| 2001/0021867 A1 | 9/2001 | Kordis et al. |
| 2002/0002329 A1 | 1/2002 | Avitall |
| 2002/0016628 A1 | 2/2002 | Langberg et al. |
| 2002/0087156 A1 | 7/2002 | Maguire et al. |
| 2002/0087173 A1 | 7/2002 | Alferness et al. |
| 2002/0099415 A1 | 7/2002 | Panescu et al. |
| 2002/0107478 A1 | 8/2002 | Wendlandt |
| 2002/0107511 A1 | 8/2002 | Collins et al. |
| 2002/0107530 A1 | 8/2002 | Saucer et al. |
| 2002/0115941 A1 | 8/2002 | Whayne et al. |
| 2002/0115944 A1 | 8/2002 | Mendes et al. |
| 2002/0169504 A1 | 11/2002 | Alferness et al. |
| 2002/0177782 A1 | 11/2002 | Penner |
| 2002/0183836 A1 | 12/2002 | Liddicoat et al. |
| 2002/0183841 A1 | 12/2002 | Cohn et al. |
| 2002/0188170 A1 | 12/2002 | Santamore et al. |
| 2003/0028118 A1 | 2/2003 | Dupree et al. |
| 2003/0028183 A1 | 2/2003 | Sanchez et al. |
| 2003/0050685 A1 | 3/2003 | Nikolic et al. |
| 2003/0055420 A1 | 3/2003 | Kadhiresan et al. |
| 2003/0069570 A1 | 4/2003 | Witzel et al. |
| 2003/0069636 A1 | 4/2003 | Solem et al. |
| 2003/0078465 A1 | 4/2003 | Pai et al. |
| 2003/0078671 A1 | 4/2003 | Lesniak et al. |
| 2003/0105384 A1 | 6/2003 | Sharkey et al. |
| 2003/0105520 A1 | 6/2003 | Alferness et al. |
| 2003/0109770 A1 | 6/2003 | Sharkey et al. |
| 2003/0176810 A1 | 9/2003 | Maahs et al. |
| 2003/0181819 A1 | 9/2003 | Desai |
| 2003/0229395 A1 | 12/2003 | Cox |
| 2004/0002626 A1 | 1/2004 | Feld et al. |
| 2004/0054279 A1 | 3/2004 | Hanley |
| 2004/0133220 A1 | 7/2004 | Lashinski et al. |
| 2004/0133273 A1 | 7/2004 | Cox |
| 2004/0138744 A1 | 7/2004 | Lashinski et al. |
| 2004/0153146 A1 | 8/2004 | Lashinski et al. |
| 2004/0158321 A1 | 8/2004 | Reuter et al. |
| 2004/0176797 A1 | 9/2004 | Opolski |
| 2004/0181139 A1* | 9/2004 | Falwell et al. ............... 600/374 |
| 2004/0186566 A1 | 9/2004 | Hindrichs et al. |
| 2004/0215232 A1 | 10/2004 | Belhe et al. |
| 2004/0243170 A1 | 12/2004 | Suresh et al. |
| 2004/0249408 A1 | 12/2004 | Murphy et al. |
| 2004/0249453 A1 | 12/2004 | Cartledge et al. |
| 2004/0267358 A1 | 12/2004 | Reitan |
| 2005/0004668 A1 | 1/2005 | Aklog et al. |
| 2005/0015109 A1 | 1/2005 | Lichtenstein |
| 2005/0054938 A1 | 3/2005 | Wehman et al. |
| 2005/0055089 A1 | 3/2005 | Macoviak et al. |
| 2005/0060030 A1 | 3/2005 | Lashinski et al. |
| 2005/0064665 A1 | 3/2005 | Han |
| 2005/0065420 A1 | 3/2005 | Collins et al. |

(56) References Cited

U.S. PATENT DOCUMENTS

| | | |
|---|---|---|
| 2005/0065504 A1 | 3/2005 | Melsky et al. |
| 2005/0080402 A1 | 4/2005 | Santamore et al. |
| 2005/0096047 A1 | 5/2005 | Haberman et al. |
| 2005/0096647 A1 | 5/2005 | Steinke et al. |
| 2005/0107723 A1 | 5/2005 | Wehman et al. |
| 2005/0107871 A1 | 5/2005 | Realyvasquez et al. |
| 2005/0125030 A1 | 6/2005 | Forsberg et al. |
| 2005/0148892 A1 | 7/2005 | Desai |
| 2005/0149014 A1 | 7/2005 | Hauck et al. |
| 2005/0149159 A1 | 7/2005 | Andreas et al. |
| 2005/0154252 A1 | 7/2005 | Sharkey et al. |
| 2005/0182365 A1 | 8/2005 | Hennemann et al. |
| 2005/0187620 A1 | 8/2005 | Pai et al. |
| 2005/0197593 A1 | 9/2005 | Burbank et al. |
| 2005/0197692 A1 | 9/2005 | Pai et al. |
| 2005/0197693 A1 | 9/2005 | Pai et al. |
| 2005/0197694 A1 | 9/2005 | Pai et al. |
| 2005/0203558 A1 | 9/2005 | Maschke |
| 2005/0209636 A1 | 9/2005 | Widomski et al. |
| 2005/0216054 A1 | 9/2005 | Widomski et al. |
| 2005/0240249 A1 | 10/2005 | Tu et al. |
| 2005/0251116 A1 | 11/2005 | Steinke et al. |
| 2005/0251132 A1 | 11/2005 | Oral et al. |
| 2005/0256521 A1 | 11/2005 | Kozel |
| 2005/0261580 A1 | 11/2005 | Willis et al. |
| 2005/0267458 A1 | 12/2005 | Paul et al. |
| 2005/0267574 A1 | 12/2005 | Cohn et al. |
| 2006/0009755 A1 | 1/2006 | Sra |
| 2006/0009756 A1 | 1/2006 | Francischelli et al. |
| 2006/0014998 A1 | 1/2006 | Sharkey et al. |
| 2006/0015002 A1 | 1/2006 | Moaddeb et al. |
| 2006/0015003 A1 | 1/2006 | Moaddes et al. |
| 2006/0015038 A1 | 1/2006 | Weymarn-Scharli |
| 2006/0015096 A1 | 1/2006 | Hauck et al. |
| 2006/0025800 A1 | 2/2006 | Suresh |
| 2006/0030881 A1 | 2/2006 | Sharkey et al. |
| 2006/0085049 A1 | 4/2006 | Cory et al. |
| 2006/0089637 A1 | 4/2006 | Werneth et al. |
| 2006/0100618 A1 | 5/2006 | Chan et al. |
| 2006/0106298 A1* | 5/2006 | Ahmed et al. .......... 600/381 |
| 2006/0135968 A1 | 6/2006 | Schaller |
| 2006/0135970 A1 | 6/2006 | Schaller |
| 2006/0184242 A1 | 8/2006 | Lichtenstein |
| 2006/0199995 A1 | 9/2006 | Vijay |
| 2006/0229491 A1 | 10/2006 | Sharkey et al. |
| 2006/0235286 A1 | 10/2006 | Stone et al. |
| 2006/0235314 A1 | 10/2006 | Migliuolo et al. |
| 2006/0264980 A1 | 11/2006 | Khairkhahan et al. |
| 2006/0281965 A1 | 12/2006 | Khairkhahan et al. |
| 2006/0293698 A1 | 12/2006 | Douk |
| 2006/0293725 A1 | 12/2006 | Rubinsky et al. |
| 2007/0016068 A1 | 1/2007 | Grunwald et al. |
| 2007/0027533 A1 | 2/2007 | Douk |
| 2007/0038208 A1 | 2/2007 | Kefer |
| 2007/0083193 A1 | 4/2007 | Werneth et al. |
| 2007/0083195 A1 | 4/2007 | Werneth et al. |
| 2007/0088362 A1 | 4/2007 | Bonutti et al. |
| 2007/0115390 A1 | 5/2007 | Makara et al. |
| 2007/0118215 A1 | 5/2007 | Moaddeb |
| 2007/0129717 A1 | 6/2007 | Brown, III et al. |
| 2007/0161846 A1 | 7/2007 | Nikolic et al. |
| 2007/0198058 A1 | 8/2007 | Gelbart et al. |
| 2007/0213578 A1 | 9/2007 | Khairkhahan et al. |
| 2007/0213815 A1 | 9/2007 | Khairkhahan et al. |
| 2007/0232858 A1 | 10/2007 | MacNamara et al. |
| 2007/0249999 A1 | 10/2007 | Sklar et al. |
| 2007/0270688 A1 | 11/2007 | Gelbart et al. |
| 2007/0299343 A1 | 12/2007 | Waters |
| 2008/0004534 A1 | 1/2008 | Gelbart et al. |
| 2008/0004643 A1 | 1/2008 | To et al. |
| 2008/0004697 A1 | 1/2008 | Lichtenstein et al. |
| 2008/0045778 A1 | 2/2008 | Lichtenstein et al. |
| 2008/0071298 A1 | 3/2008 | Khairkhahan et al. |
| 2008/0262337 A1 | 10/2008 | Falwell et al. |
| 2008/0281322 A1 | 11/2008 | Sherman et al. |
| 2008/0312713 A1 | 12/2008 | Wilfley et al. |
| 2009/0018617 A1 | 1/2009 | Skelton et al. |
| 2009/0024138 A1 | 1/2009 | Saleh |
| 2009/0069704 A1 | 3/2009 | MacAdam et al. |
| 2009/0131930 A1 | 5/2009 | Gelbart et al. |
| 2009/0157058 A1 | 6/2009 | Ferren et al. |
| 2009/0171274 A1 | 7/2009 | Harlev et al. |
| 2009/0192441 A1 | 7/2009 | Gelbart et al. |
| 2009/0270737 A1 | 10/2009 | Thornton |
| 2009/0287271 A1 | 11/2009 | Blum et al. |
| 2009/0287304 A1 | 11/2009 | Dahlgren et al. |
| 2010/0121147 A1 | 5/2010 | Oskin et al. |
| 2010/0211052 A1 | 8/2010 | Brown et al. |
| 2010/0249771 A1 | 9/2010 | Pearson et al. |
| 2010/0268059 A1 | 10/2010 | Ryu et al. |
| 2011/0125172 A1 | 5/2011 | Gelbart et al. |
| 2011/0172658 A1 | 7/2011 | Gelbart et al. |
| 2011/0282491 A1 | 11/2011 | Prisco et al. |
| 2012/0158016 A1 | 6/2012 | Gelbart et al. |
| 2012/0165829 A1 | 6/2012 | Chen et al. |
| 2012/0271135 A1* | 10/2012 | Burke et al. .......... 600/373 |
| 2013/0165916 A1 | 6/2013 | Mathur et al. |
| 2013/0178850 A1 | 7/2013 | Lopes et al. |
| 2013/0178851 A1 | 7/2013 | Lopes et al. |
| 2013/0184705 A1 | 7/2013 | Gelbart et al. |
| 2013/0184706 A1 | 7/2013 | Gelbart et al. |
| 2013/0190587 A1 | 7/2013 | Lopes et al. |
| 2013/0197513 A1 | 8/2013 | Lopes et al. |
| 2013/0241929 A1 | 9/2013 | Massarwa et al. |
| 2013/0304065 A1 | 11/2013 | Lopes et al. |
| 2013/0310828 A1 | 11/2013 | Reinders et al. |
| 2014/0114307 A1 | 4/2014 | Moisa et al. |
| 2014/0350552 A1 | 11/2014 | Highsmith |
| 2015/0126993 A1 | 5/2015 | Gelbart et al. |

FOREIGN PATENT DOCUMENTS

| | | |
|---|---|---|
| WO | 9510320 A1 | 4/1995 |
| WO | 95/20349 A1 | 8/1995 |
| WO | 97/17892 A1 | 5/1997 |
| WO | 0108575 A2 | 2/2001 |
| WO | 02087437 A1 | 11/2002 |
| WO | 03015611 A2 | 2/2003 |
| WO | 03077800 A1 | 9/2003 |
| WO | 2004012629 A1 | 2/2004 |
| WO | 2004047679 A1 | 6/2004 |
| WO | 2004084746 A2 | 10/2004 |
| WO | 2004100803 A1 | 11/2004 |
| WO | 2005070330 A1 | 8/2005 |
| WO | 2005102181 A1 | 11/2005 |
| WO | 2006017809 A2 | 2/2006 |
| WO | 2006105121 A2 | 10/2006 |
| WO | 2006135747 A2 | 12/2006 |
| WO | 2006135749 A2 | 12/2006 |
| WO | 2007021647 A2 | 2/2007 |
| WO | 2007115390 A1 | 10/2007 |
| WO | 2008002606 A2 | 1/2008 |
| WO | 2009011721 A1 | 1/2009 |
| WO | 2009065042 A2 | 5/2009 |
| WO | 2012/100184 A2 | 7/2012 |
| WO | 2012/100185 A2 | 7/2012 |
| WO | 2013/173917 A1 | 11/2013 |

OTHER PUBLICATIONS

Gelbart et al, "Amendment and Method for Intra-Cardiac Mapping and Ablation", Preliminary Amendment filed Aug. 22, 2014; Preliminary Amendment filed Mar. 5, 2013 for co-pending U.S. Appl. No. 13/785,910, 10 pgs.

Gelbart et al, "Apparatus and Method for Intra-Cardiac Mapping and Ablation", Preliminary Amendment filed Aug. 22, 2014; Preliminary Amendment filed Mar. 5, 2013 for co-pending U.S. Appl. No. 13/785,931, 10 pgs.

Lopes et al, "Enhanced Medical Device for Use in Bodily Cavities, for Example an Atrium", Preliminary Amendment filed Oct. 22, 2013 for co-pending U.S. Appl. No. 13/942,354, 13 pgs.

(56) References Cited

OTHER PUBLICATIONS

Lopes et al, "Enhanced Medical Device for Use in Bodily Cavities, for Example an Atrium", Preliminary Amendment filed Aug. 20, 2014 for co-pending U.S. Appl. No. 13/782,889, 11 pgs.
Gelbart et al., "Medical Device for Use in Bodily Lumens, for Example an Atrium", Preliminary Amendment filed May 12, 2014; Preliminary Amendment filed May 2, 2014 for U.S. Appl. No. 14/229,250, 10 pgs.
Gelbart et al., "Medical Device for Use in Bodily Lumens, for Example an Atrium", Amendment filed Jul. 3, 2014; Amendment filed Apr. 2, 2012; Amendment filed Mar. 1, 2012; Amendment filed Nov. 23, 2011; Replacement drawings filed Feb. 13, 2008 for U.S. Appl. No. 11/941,819, 155 pgs.
Gelbart et al., "Medical Device for Use in Bodily Lumens, for Example an Atrium", Preliminary Amendment filed May 12, 2014; Preliminary Amendment filed May 2, 2014 for U.S. Appl. No. 14/229,305, 12 pgs.
Bard, "Mesh Ablator Catheter", Brochure, 2008, 4 pgs, Bard Electrophysiology Division, C.R. Bard Inc., 55 Technology Drive Lowell, MA 07851 USA.
Biotronik's "AlCath Flutter Gold Cath for Atrial Flutter Available in EU", medGadget, 3 pgs, http://www.medgadget.com/2013/09/biotroniks-alcath-flutter-gold-cath-for-atrial-flutter-unveiled-in-europe.html[Jun. 24, 2014 2:37:09 PM].
"Constellation Mapping Catheters", Brochure, Boston Scientific Corp., 2 pgs © 2007 Boston Scientific Corporation.
"Waveforms and Segments", Ensite System Instructions for use, 54-06154-001 Rev02, Chapter 7 pp. 85-90 © 2007 St. Jude Medical.
"ThermoCool® Irrigated Tip Catheter", Brochure, Biosense Webster, 4 pgs , Biosense Webster, Inc. 3333 Diamond Canyon Road Diamond Bar, CA 91765, USA, © Biosense Webster, Inc. 2009 All rights reserved. 1109003.0.
Gelbart "Medical Device for Use in Bodily Lumens, for Example an Atrium", OA mailed Jul. 25, 2011 for U.S. Appl. No. 11/941,819, now published as US 2009-0131930 A1.
Extended European Search Report mailed Aug. 20, 2013 issued in EP Patent Application No. 13172848.7.
Written Opinion dated Aug. 22, 2012 for PCT/US2012/022061, 6 pgs.
International Search Report and Written Opinion mailed Aug. 2, 2013 issued in PCT/CA2013/050350.
International Search Report and Written Opinion mailed Sep. 17, 2013 issued in PCT/US2013/039982.
International Search Report and Written Opinion mailed Sep. 27, 2013 issued in PCT/US2013/039977.
International Search Report dated Jul. 30, 2012 for PCT/US2012/022062, 5 pgs.
Written Opinion dated Jul. 30, 2012 for PCT/US2012/022062, 5 pgs.
International Search Report dated Aug. 22, 2012 for PCT/US2012/022061, 5 pgs.
"Phased RF Catheter Ablation System", 2014 Medtronic Inc., 2 pgs, http://www.medtronic.eu/your-health/atrial-fibrillation/about-the-therapy/our-phased-rf-ablation-system/[Jun. 24, 2014 2:38:05 PM].
Gelbart et al, "Apparatus and Method for Intra-Cardiac Mapping and Ablation", Notice of Allowance dated Oct. 23, 2014 for U.S. Appl. No. 11/475,950, 10 pgs.
Gelbart et al., "Medical Device for Use in Bodily Lumens, for Example an Atrium", Supplemental Notice of Allowance dated Oct. 6, 2014 for U.S. Appl. No. 11/941,819, 4 pgs.
Gelbart et al., Medical Device for Use in Bodily Lumens, for Example an Atrium, Amendment filed Sep. 22, 2014, for co-pending U.S. Appl. No. 13/070,215, 18 pgs.
Gelbart et al., "Medical Device for Use in Bodily Lumens, for Example an Atrium", Notice of Allowance mailed Nov. 13, 2014 for U.S. Appl. No. 13/070,215, 54 pages.
Official Action issued in CN201280004400.9, mailed Dec. 3, 2014.

Gelbart et al, "Apparatus and Method for Intra-Cardiac Mapping and Ablation", Office Action dated Dec. 13, 2013; Notice of Allowance dated Jul. 25, 2014 for co-pending U.S. Appl. No. 11/475,950, 19 pgs.
Gelbart et al., "Medical Device for Use in Bodily Lumens, for Example an Atrium", Office Action dated Jan. 3, 2012; Office Action dated Apr. 3, 2014; Notice of Allowance dated Aug. 26, 2014 for co-pending U.S. Appl. No. 11/941,819, 35 pgs.
Gelbart et al., Medical Device for Use in Bodily Lumens, for Example an Atrium, Office Action dated Jun. 20, 2014, for co-pending U.S. Appl. No. 13/070,215, 8 pgs.
Buchbinder,Maurice MD, "Dynamic Mitral Valve Annuloplasty: A Reshapable Ring for Residual and Recurring MR," from the Foundation for Cardiovascular Medicine, La Jolla, CA. May 24, 2007.
Gabriel et al., "The Dielectric Properties of Biological Tissues: I. Literature Survey," Phys. Med. Biol. 41:2231-2249, 1996.
Konings et al., "Development of an Intravascular Impedance Catheter for Detection of Fatty Lesions in Arteries," IEEE Transactions on Medical Imaging, 16(4):439-446, 1997.
Mack, "New Techniques for Percutaneous Repair of the Mitral Valve," Heart Failure Review, 11:259-268, 2006.
Otasevic et al., "First-in-Man Implantation of Left Ventricular Partitioning Device in a Patient With Chronic Heart Failure: Twelve-Month Follow-up," Journal of Cardiac Failure 13(7):517-520, 2007.
Sharkey et al., "Left Ventricular Apex Occluder. Description of a Ventricular Partitioning Device," EuroIntervention 2:125-127, 2006.
Stiles, et al., "Simulated Characterization of Atherosclerotic Lesions in the Coronary Arteries by Measurement of Bioimpedance," IEE Transactions on Biomedical Engineering, 50(7):916-921,2003.
Tanaka et al., "Artificial SMA Valve for Treatment of Urinary Incontinence: Upgrading of Valve and Introduction of Transcutaneous Transformer," Bio-Medical Materials and Engineering 9:97-112, 1999.
Timek et al.., "Septal-Lateral Annular Cinching ('SLAC') Reduces Mitral Annular Size Without Perturbing Normal Annular Dynamics," Journal of Heart Valve Disease 11 (1):2-10, 2002.
Timek et al., "Septal-Lateral Annular Cinching Abolishes Acute Ischemic Mitral Regurgitation," Journal of Thoracic and Cardiovascular Surgery, 123(5):881-888, 2002.
Valvano et al., "Thermal Conductivity and Diffusivity of Biomaterials Measured with Self-Heated Thermistors," International Journal of Thermodynamics, 6(3):301-311, 1985.
Gelbart et al., "Automatic Atherectomy System," Office Action mailed Mar. 4, 2009 for U.S. Appl. No. 11/436,584, 6 pages.
Gelbart et al., "Automatic Atherectomy System," Amendment filed Aug. 4, 2009 for U.S. Appl. No. 11/436,584, 35 pages.
Gelbart et al., "Automatic Atherectomy System," Office Action mailed Dec. 1, 2009 for U.S. Appl. No. 11/436,584, 8 pages.
Gelbart et al., "Automatic Atherectomy System," Amendment filed Mar. 30, 2010 for U.S. Appl. No. 11/436,584, 20 pages.
Gelbart et al., "Automatic Atherectomy System," Amendment filed Oct. 25, 2010 for U.S. Appl. No. 11/436,584, 9 pages.
Gelbart et al., "Automatic Atherectomy System," Office Action mailed Dec. 14, 2010 for U.S. Appl. No. 11/436,584, 12 pages.
Gelbart et al., "Intra-Cardiac Mapping and Ablation Method," Preliminary Amendment filed Aug. 29, 2007 for U.S. Appl. No. 11/475,950,42 pages.
Gelbart et al., "Intra-Cardiac Mapping and Ablation Method," Amendment filed Mar. 5, 2008 for U.S. Appl. No. 11/475,950, 11 pages.
Gelbart et al., "Intra-Cardiac Mapping and Ablation Method," Office Action mailed Jun. 23, 2010 for U.S. Appl. No. 11/475,950, 18 pages.
Gelbart et al., "Intra-Cardiac Mapping and Ablation Method," Amendment filed Aug. 16, 2010 for U.S. Appl. No. 11/475,950,22 pages.
Gelbart et al., "Intra-Cardiac Mapping and Ablation Method," Office Action mailed Nov. 23, 2010 for U.S. Appl. No. 11/475,950,25 pages.

(56) References Cited

OTHER PUBLICATIONS

Gelbart et al., "Intra-Cardiac Mapping and Ablation Method," Amendment filed Feb. 23, 2011 for U.S. Appl. No. 11/475,950,28 pages.
Gelbart et al., "Automatic Atherectomy System," Office Action mailed Jun. 15, 2011, for U.S. Appl. No. 12/950,871, 16 pages.
Gelbart et al., "Liposuction System," Office Action mailed Mar. 16, 2011 for U.S. Appl. No. 12/010,458, 12 pages.
Gelbart et al., "Liposuction System," Amendment filed Jun. 10, 2011 for U.S. Appl. No. 12/010,458, 10 pages.
Lichtenstein "Method and Apparatus for Percutaneous Reduction of Anterior-Posterior Diameter of Mitral Valve," U.S. Appl. No. 10/690,131, filed Oct. 20, 2003, 31 pages.
International Search Report, mailed Dec. 5, 2007, for PCT/US2007/014902, 4 pages.
International Preliminary Report on Patentability, issued Jan. 6, 2009, for PCT /U52007/014902, 8 pages.
International Search Report, mailed Dec. 2, 2009, for PCT/US2008/083644, 4 pages.
Written Opinion, mailed Dec. 5, 2007, for PCT/US2007/014902, 7 pages.
Written Opinion, mailed Dec. 2, 2009, for PCT/US2008/083644, 9 pages.
Gelbart et al., "Automatic Atherectomy System," Amendment filed Sep. 15, 2011 for U.S. Appl. No. 12/950,871, 21 pages.
Gelbart et al., "Liposuction System," Amendment filed Dec. 7, 2011 for U.S. Appl. No. 12/010,458, 15 pages.
Gelbart et al., "Liposuction System," Office Action mailed Sep. 14, 2011 for U.S. Appl. No. 12/010,458, 9 pages.
Extended European Search Report for corresponding EP 12736677.1, mail date Mar. 28, 2014.
Extended European Search Report for corresponding EP 12736962.7, mail date Mar. 28, 2014.
Becker R. et al, "Ablation of Atrial Fibrillation: Energy Sources and Navigation Tools: A Review", Journal of Electrocardiology, 37 (Supplement 2004): 55-62, 2004.
Calkins, Hugh, "Electrophysiology: Radiofrequency Catheter Ablation of Supraventricular Arrhythmias", Heart, 85:594-600, 2001.
De Ponti et al., "Non-Fluoroscopic Mapping Systems for Electrophysiology: The 'Tool or Toy' Dilemma After 10 Years",European Heart Journal 27:1134-1136, 2006.
Gelbart et al., "Apparatus and Method for Intra-Cardiac Mapping and Ablation", Office Action mailed Aug. 5, 2015 for U.S. Appl. No. 13/785,910, 79 pages.
Lopes et al., "High-Density Electrode-Based Medical Device System", Office Action mailed Jul. 10, 2015 for U.S. Appl. No. 13/793,076, 98 pages.
Lopes et al., "High-Density Electrode-Based Medical Device System", Office Action mailed Jul. 9, 2015 for U.S. Appl. No. 13/793,213, 99 pages.
Lopes et al., "Enhanced Medical Device for Use in Bodily Cavities, for Example an Atrium", Amendment filed Aug. 24, 2015 for U.S. Appl. No. 13/782,889, 21 pages.
Lopes et al., "Enhanced Medical Device for Use in Bodily Cavities, for Example an Atrium", Amendment filed Aug. 28, 2015 for U.S. Appl. No. 13/782,903, 19 pages.
Examination Report issued in EP13172848.7, mailed Sep. 21, 2015.
Lopes et al., "High-Density Electrode-Based Medical Device System", Amendment filed Oct. 9, 2015 for U.S. Appl. No. 13/793,213, 26 pages.
Lopes et al., "High-Density Electrode-Based Medical Device System", Amendment filed Oct. 9, 2015 for U.S. Appl. No. 13/793,076, 14 pages.
Extended European Search Report issued in EP13793216.6, mailed Oct. 30, 2015.
Moisa et al., "Catheter System", Office Action mailed Nov. 16, 2015 for U.S. Appl. No. 14/136,946, 92 pages.
Office Action issued in U.S. Appl. No. 13/782,889, mailed Dec. 18, 2015.
Office Action issued in U.S. Appl. No. 13/782,903, mailed Dec. 18, 2015.
Non-final Office Action issued in co-pending U.S. Appl. No. 13/782,903, dated Apr. 28, 2015.
International Search Report mailed Mar. 10, 2015, for International Application PCT/CA2014/051144; 10 pages.
Written Opinion mailed Mar. 10, 2015, for International Application PCT/CA2014/051144; 4 pages.
Biotronik's "AlCath Flutter Gold Cath for Atrial Flutter Available in EU", Sep. 19, 2013, medGadget, 3 pgs, http://www.medgadget.com/2013/09/biotroniks-alcath-flutter-gold-cath-for-atrial-flutter-unveiled-in-europe.html [Jun. 24, 2014 2:37:09 PM].
Lopes et al., "Enhanced Medical Device for Use in Bodily Cavities, for Example an Atrium", Office Action mailed May 22, 2015 for U.S. Appl. No. 13/782,889, 86 pages.
Notice of Allowance issued in U.S. Appl. No. 14/136,946, mailed May 12, 2016.
Non-Final Office Action issued in U.S. Appl. No. 14/229,305, mailed Apr. 29, 2016.
Notice of Allowance issued in U.S. Appl. No. 13/793,076, mailed Feb. 10, 2016.
Non-Final Office Action issued in U.S. Appl. No. 29/509,719, mailed Feb. 25, 2016.
Quayle issued in U.S. Appl. No. 29/509,621, mailed Feb. 26, 2016.
Final Office Action issued in U.S. Appl. No. 13/793,213, mailed Feb. 26, 2016.
Quayle issued in U.S. Appl. No. 29/509,636, mailed Feb. 26, 2016.
Non-Final Office Action issued in U.S. Appl. No. 13/785,910, mailed Apr. 8, 2016.
Non-Final Office Action issued in U.S. Appl. No. 14/229,250, mailed Apr. 28, 2016.
Extended European Search Report issued in EP15188407.9, mailed Jan. 21, 2016.

* cited by examiner

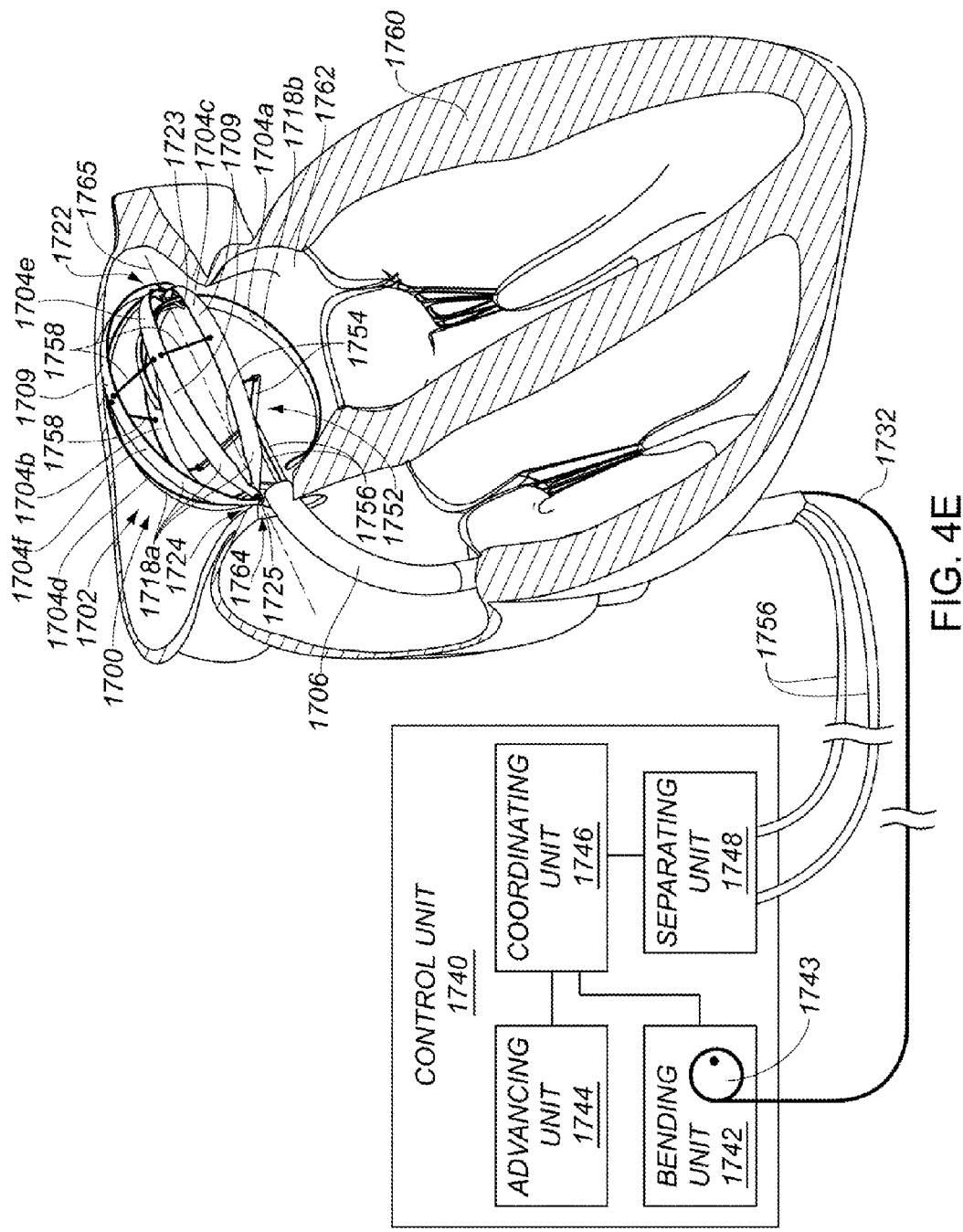

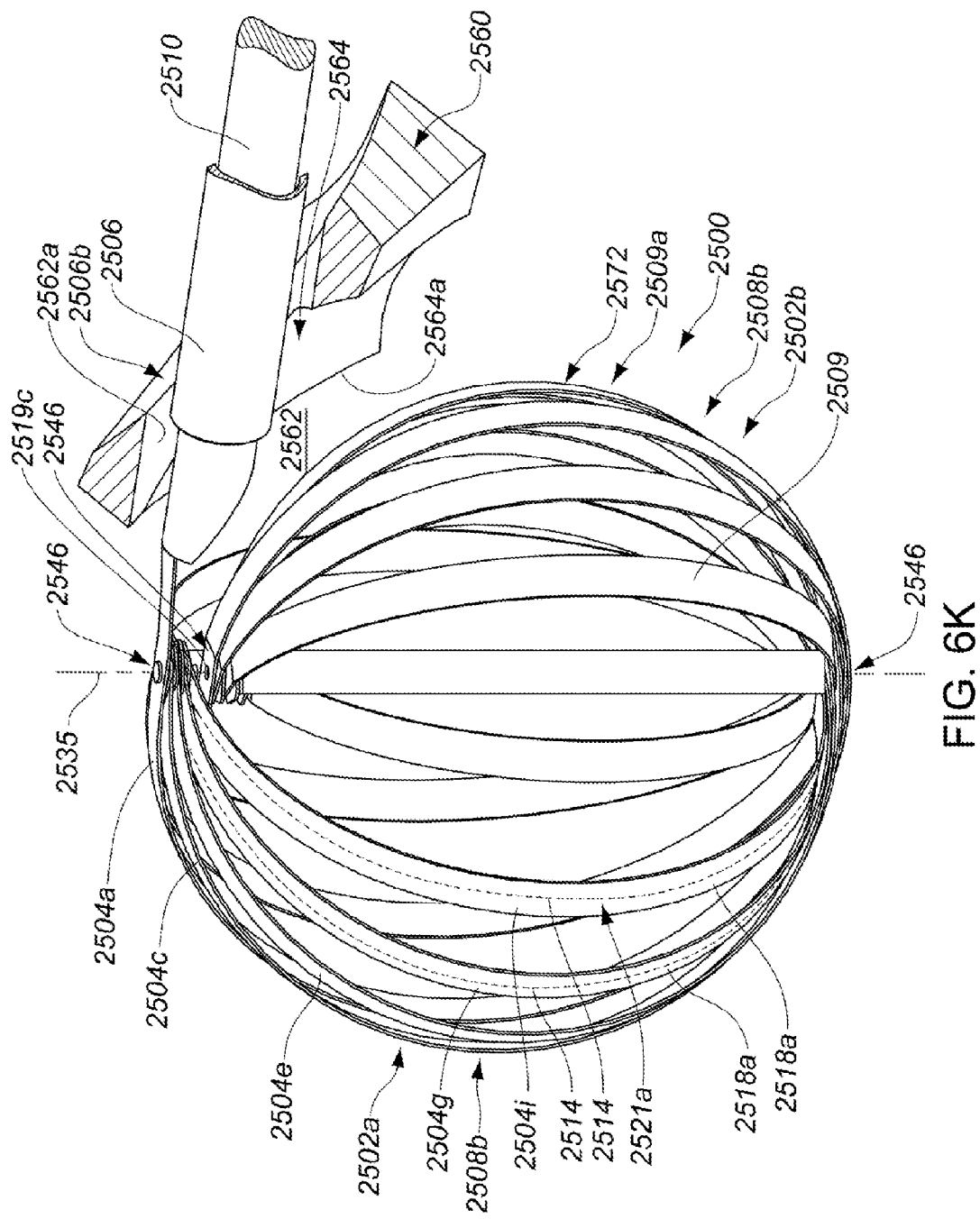

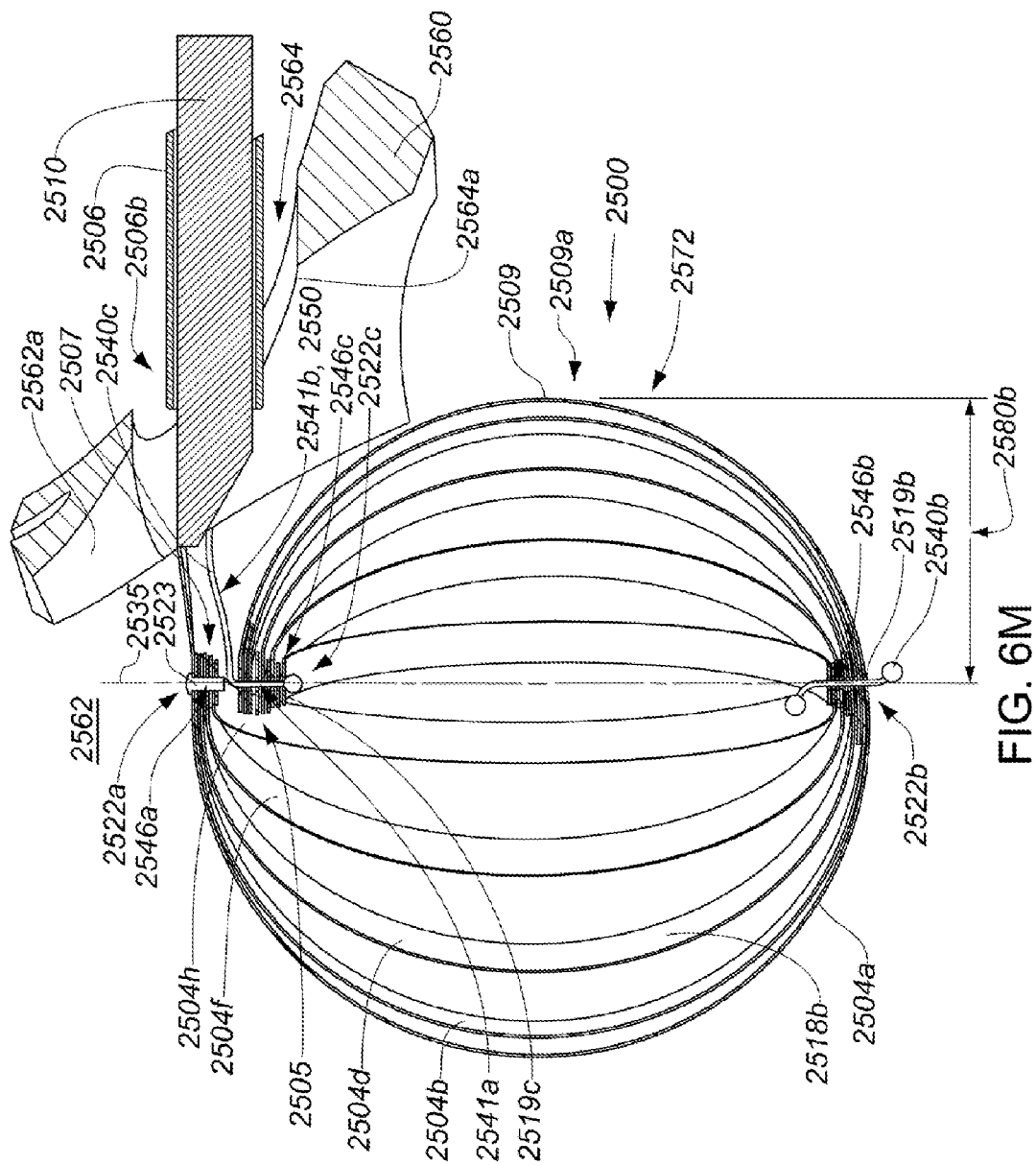

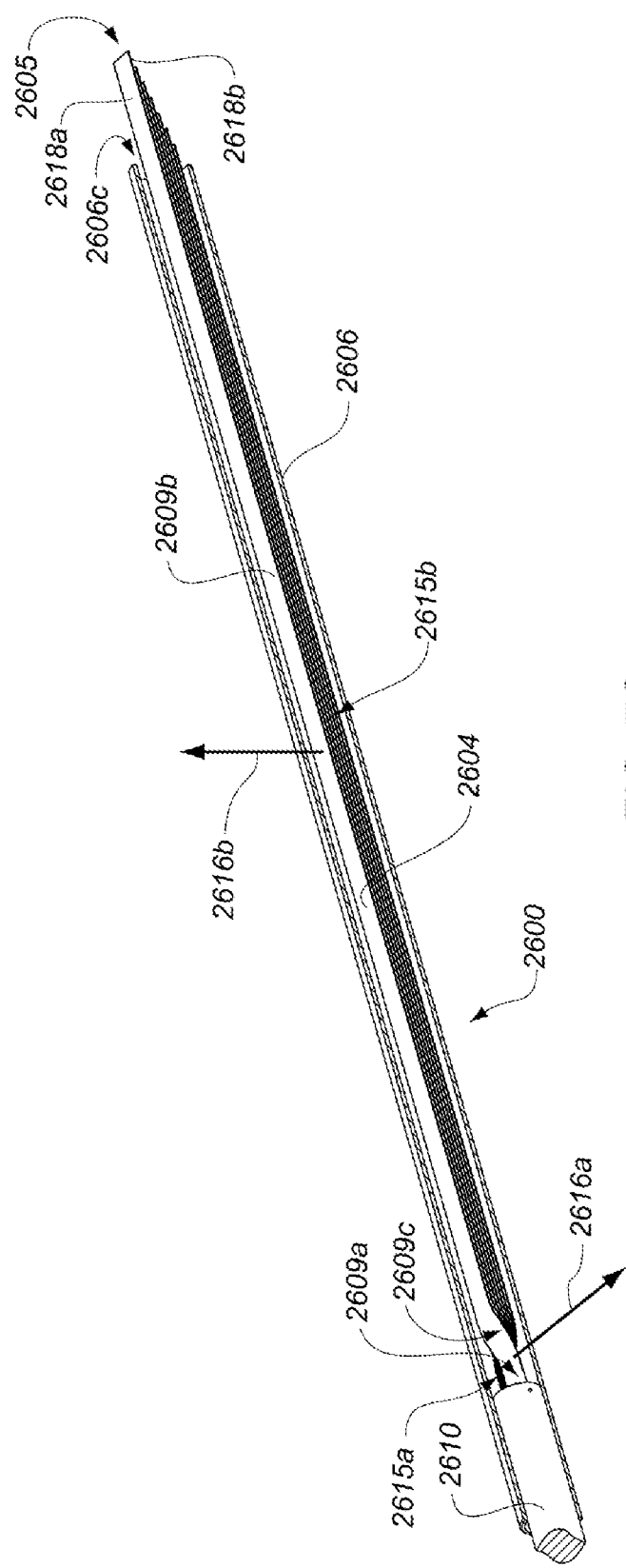

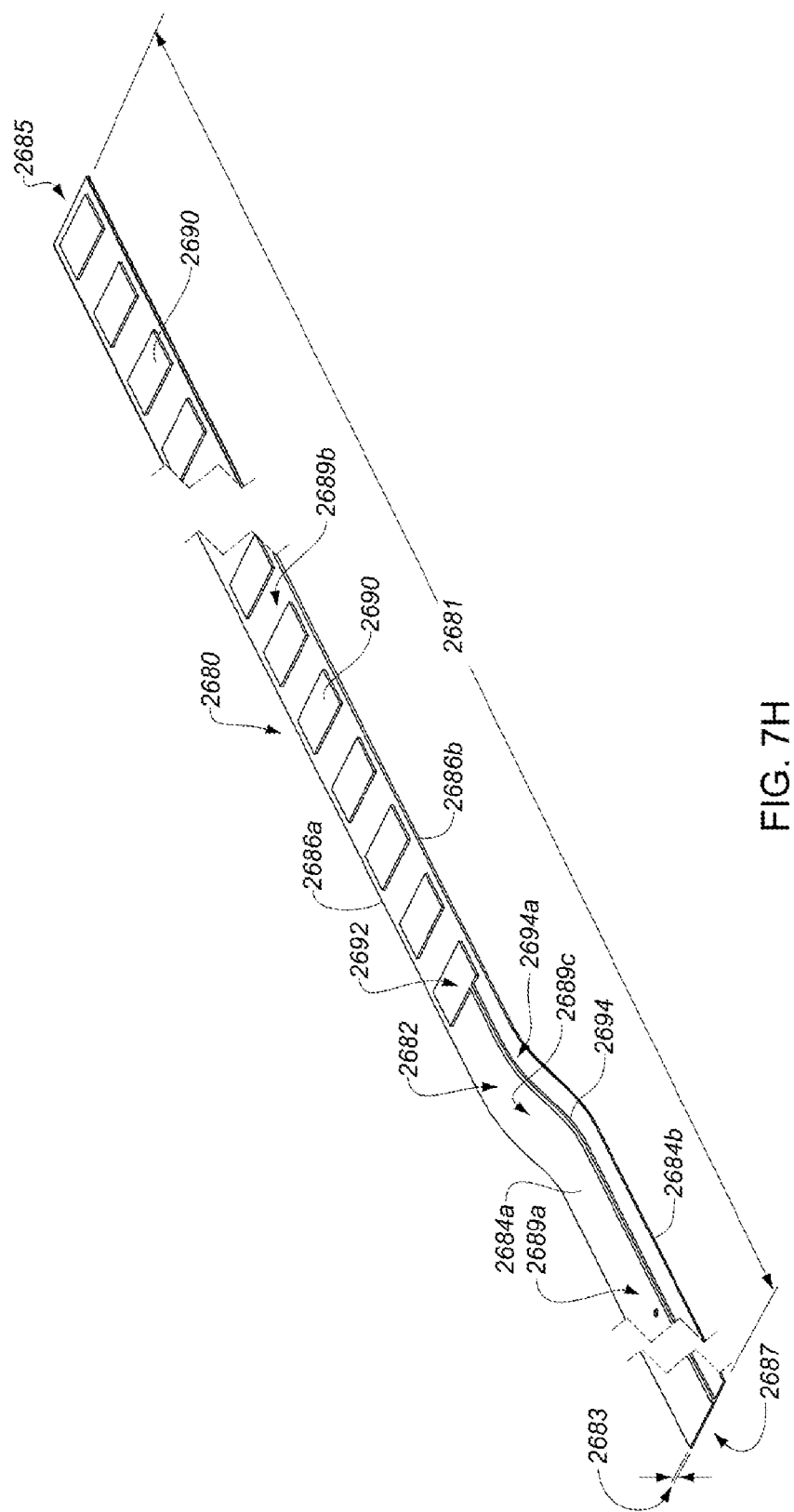

ENHANCED MEDICAL DEVICE FOR USE IN BODILY CAVITIES, FOR EXAMPLE AN ATRIUM

BACKGROUND

Technical Field

This disclosure is generally related to surgery, and more particularly to intravascularly or percutaneously deployed medical devices suitable for determining locations of cardiac features or ablating regions of cardiac tissue, or both.

Description of the Related Art

Cardiac surgery was initially undertaken using highly invasive open procedures. A sternotomy, which is a type of incision in the center of the chest that separates the sternum (chest bone) was typically employed to allow access to the heart. In the past several decades, more and more cardiac operations are performed using intravascular or percutaneous techniques, where access to inner organs or other tissue is gained via a catheter.

Intravascular or percutaneous surgeries benefit patients by reducing surgery risk, complications and recovery time. However, the use of intravascular or percutaneous technologies also raises some particular challenges. Medical devices used in intravascular or percutaneous surgery need to be deployed via catheter systems which significantly increase the complexity of the device structure. As well, doctors do not have direct visual contact with the medical devices once the devices are positioned within the body. Positioning these devices correctly and operating the devices successfully can often be very challenging.

One example of where percutaneous medical techniques have been employed is in the treatment of a heart disorder called atrial fibrillation. Atrial fibrillation is a disorder in which spurious electrical signals cause an irregular heartbeat. Atrial fibrillation has been treated with open heart methods using a technique known as the "Cox-Maze procedure." During this procedure, physicians create lesions in a specific pattern in the left and right atria which block various paths taken by the spurious electrical signals. Such lesions were originally created using incisions, but are now typically created by ablating the tissue with various techniques including radio frequency (RF) energy, microwave energy, laser energy and cryogenic techniques. The procedure is performed with a high success rate under the direct vision that is provided in open procedures, but is relatively complex to perform intravascularly or percutaneously because of the difficulty in creating the lesions in the correct locations. Various problems, potentially leading to severe adverse results, may occur if the lesions are placed incorrectly.

Key factors which are needed to dramatically improve the intravascular or percutaneous treatment of atrial fibrillation are enhanced methods for deployment, positioning and operation of the treatment device. It is particularly important to know the position of the elements which will be creating the lesions relative to cardiac features such as the pulmonary veins and mitral valve. The continuity and transmurality characteristics of the lesion patterns that are formed can impact the ability to block paths taken within the heart by spurious electrical signals.

Several methods have been previously developed for positioning intravascularly or percutaneously deployed medical devices within the heart. For example, commonly assigned U.S. Patent Application Publication 2009/0131930 A1, which is herein incorporated by reference in its entirety, describes a device that is percutaneously guided to a cavity of bodily organ (e.g., a heart). The device can discriminate between fluid within the cavity (e.g., blood) and tissue that forms an inner or interior surface of the cavity (i.e., surface tissue) to provide information or mapping indicative of a position or orientation, or both of the device in the cavity. Discrimination may be based on flow or some other characteristic, for example electrical permittivity or force. The device can selectively ablate portions of the surface tissue based on the information or the mapping. In some cases, the device may detect characteristics (e.g., electrical potentials) indicative of whether ablation was successful. The device includes a plurality of transducer elements that are percutaneously guided in an unexpanded configuration and positioned at least proximate the surface tissue in an expanded configuration. Various expansion mechanisms that include a helical member or an inflatable member are described.

The desire to employ intravascular or percutaneous techniques that employ devices that can fit through catheter sheaths of ever smaller sizes (e.g., on the order of approximately 20-24 French in some cases, 18-20 French in other cases and 16-18 French or less in yet other cases) has increased. In some instances, devices deliverable via larger or smaller sized catheter sheets may be employed. Additional challenges therefore exist in creating a device that can assume an unexpanded configuration for passage through these smaller sheaths and yet, can also assume an expanded configuration suitable for positioning a portion of the device proximate to a tissue surface within the cavity.

The treatment of atrial fibrillation is but one example of a cardiac surgery that requires improved configurable devices. There are many others that require similar improved devices, such as mitral valve repair.

There is a need for enhanced methods and apparatus that allow a portion of a configurable device to assume a delivery or unexpanded configuration suitable for passage though a small bodily opening leading to a bodily cavity, and a deployed or expanded configuration suitable for positioning the portion of the device at least proximate to a tissue that forms an interior surface of the cavity.

There is a need for enhanced methods and apparatus that allow a portion of a configurable device to assume a delivery or unexpanded configuration suitable for passage though a small bodily opening leading to a bodily cavity, and a deployed or expanded configuration suitable for positioning the portion of the device at least proximate to a tissue that forms an interior surface of the cavity, the enhanced methods and apparatus being further suitable for the determination of the relative position of anatomical features within the cavity such as pulmonary veins and a mitral valve with respect to the configurable medical device.

There is a further need for enhanced methods and apparatus that allow a portion of a configurable device to assume a delivery or unexpanded configuration suitable for passage though a small bodily opening leading to a bodily cavity, and a deployed or expanded configuration suitable for positioning the portion of the device at least proximate to a tissue that forms an interior tissue surface of the cavity, the enhanced methods and apparatus being further suitable for treatment of the interior tissue surface. Treatment may include the formation of lesions in a specified position relative to anatomical features within the cavity such as pulmonary veins and a mitral valve.

There is a further need for enhanced methods and apparatus that allow a portion of a configurable device to assume a delivery or unexpanded configuration suitable for passage though a small bodily opening leading to a bodily cavity, and a deployed or expanded configuration suitable for positioning a plurality of transducer elements over a region extending across a majority of an interior tissue surface of the cavity. In particular, there is a need for enhanced methods and apparatus to arrange a plurality of transducer elements in a two- or three-dimensional grid or array capable of mapping, ablating, and or stimulating an inside surface of a bodily cavity or lumen without requiring mechanical scanning.

BRIEF SUMMARY

The present design of a medical device with enhanced capabilities for deployment, positioning and ablating within a bodily cavity such as an intra-cardiac cavity is disclosed. In particular, the device is configurable from a first or unexpanded configuration in which a portion of the device is sized for delivery to a bodily cavity via a catheter sheath to a second or expanded configuration in which the portion of the device is expanded to position various transducer elements at least proximate a tissue surface within the bodily cavity. The device may employ a method for distinguishing tissue from blood and may be used to deliver positional information of the device relative to ports in the atrium, such as the pulmonary veins and mitral valve. The device may employ characteristics such as blood flow detection, impedance change detection or deflection force detection to discriminate between blood and tissue. The device may also improve ablation positioning and performance by ablating using the same elements used for discriminating between blood and tissue. Other advantages will become apparent from the teaching herein to those of skill in the art.

A medical system may be summarized as including a device that includes a plurality of elongate members, each elongate member in the plurality of elongate members including a first end and a second end, an intermediate portion positioned between the first end and the second end, and a respective length between the first end and the second end. A portion of the device is selectively moveable between an unexpanded configuration in which at least the respective intermediate portions of the elongate members of the plurality of elongate members are arranged successively with respect to one another along a first direction in a stacked arrangement, the stacked arrangement sized to be delivered through a bodily opening leading to a bodily cavity, and an expanded configuration in which each of at least some of the plurality of elongate members are fanned about each of one or more axes. When the portion of the device is in the expanded configuration, at least one elongate member of the plurality of elongate members is arranged such that the one or more axes pass through the at least one elongate member of the plurality of elongate members at two or more locations, each location of the two or more locations spaced from another location of the two or more locations along the respective length of the at least one elongate member of the plurality of elongate members.

The one or more axes may include two or more axes, and the at least one elongate member of the plurality of elongate members may be arranged such that each axis of the two or more axes passes through a respective one of the two or more locations when the portion of the device is in the expanded configuration. At least a first axis of the two or more axes may be collinear with a second axis of the two or more axes when the portion of the device is in the expanded configuration. Each elongate member of the at least some of the plurality of elongate members may cross the at least one elongate member of the plurality of elongate members in an X configuration about at least one axis of the one or more axes when the portion of the device is in the expanded configuration.

The device may include at least one coupler arranged to physically couple each elongate member of the at least some of the plurality of elongate members together with the at least one elongate member of the plurality of elongate members. The at least one coupler may include a plurality of the couplers, each coupler of the plurality of the couplers spaced from at least one other one of the plurality of the couplers along the respective length of the at least one elongate member of the plurality of elongate members. The at least one coupler may include a flexible line arranged to be received in at least one opening provided in the at least one elongate member of the plurality of elongate members.

The at least one elongate member of the plurality of elongate members may be twisted about a twist axis extending along a portion of the respective length of the at least one elongate member of the plurality of elongate members. The two or more locations may include at least three locations.

Various systems may include combinations and subsets of those summarized above.

A medical system may be summarized as including a structure that includes a plurality of elongate members. Each elongate member of the plurality of elongate members includes a proximal end, a distal end, an intermediate portion positioned between the proximal end and the distal end, and a thickness. Each intermediate portion includes a front surface and a back surface opposite across the thickness of the elongate member from the front surface. The structure is selectively moveable between an unexpanded configuration in which at least the respective intermediate portions of the elongate members of the plurality of elongate members are arranged with respect to one another front surface-toward-back surface in a stacked array sized for delivery through a bodily opening leading to a bodily cavity, and an expanded configuration in which the respective intermediate portions of at least some of the plurality of elongate members are angularly spaced with respect to one another about a first axis. Each of the at least some of the plurality of elongate members further includes a curved portion arranged to extend along at least a portion of a respective curved path that intersects the first axis at each of a respective at least two spaced apart locations along the first axis when the structure is in the expanded configuration.

In some embodiments each elongate member of the plurality of elongate members includes a respective length between the proximal end and the distal end, and at least a first elongate member of the at least some of the plurality of elongate members crosses a second elongate member of the at least some of the plurality of elongate members at a location along the respective length of the second elongate member of the at least some of the plurality of elongate members when the structure is in the expanded configuration. At least a first elongate member of the at least some of the plurality of elongate members may cross a second elongate member of the at least some of the plurality of elongate members in an X configuration at each of at least one of the respective at least two spaced apart locations along the first axis intersected by the at least a portion of the respective curved path extended along by the curved portion of the second elongate member of the at least some of the plurality of elongate members when the structure is in the expanded configuration.

The device may include at least one coupler arranged to physically couple each elongate member of the at least some of the plurality of elongate members together with at least one other elongate member of the plurality of elongate members. In some embodiments each elongate member of the plurality of elongate members includes a respective length between the proximal end and the distal end, and the at least one coupler includes a plurality of couplers, each coupler of the plurality of couplers spaced from another coupler of the plurality of couplers along the respective length of the at least one other elongate member of the plurality of elongate members. At least one of the respective at least two spaced apart locations along the first axis intersected by at least the portion of the respective curved path extended along by the curved portion of at least a first elongate member of the at least some of the plurality of elongate members may be positioned between a first coupler of the plurality of couplers and at least a second coupler of the plurality of couplers when the structure is in the expanded configuration.

In some embodiments each elongate member of the plurality of elongate members includes a respective length between the proximal end and the distal end, and at least one elongate member of the plurality of elongate members is twisted about a twist axis extending along a portion of the respective length of the at least one elongate member of the plurality of elongate members. The respective at least two spaced apart locations along the first axis intersected by at least the portion of the respective curved path extended along by the curved portion of at least a first one of the at least some of the plurality of elongate members when the structure is in the expanded configuration may include at least three spaced apart locations along the first axis.

Various systems may include combinations and subsets of those summarized above.

A medical system may be summarized as including a device that includes a plurality of elongate members and at least a first coupler arranged to physically couple each elongate member of the plurality of elongate members together with each other of the elongate members of the plurality of elongate members. Each elongate member of the plurality of elongate members includes a proximal end, a distal end, an intermediate portion positioned between the proximal end and the distal end, a respective length between the proximal end and the distal end, and a thickness. Each intermediate portion includes a front surface and a back surface opposite across the thickness of the elongate member from the front surface. A portion of the device is selectively moveable between an unexpanded configuration in which at least the respective intermediate portions of the elongate members of the plurality of elongate members are arranged with respect to each other front surface-toward-back surface in a stacked array sized for delivery through a bodily opening leading to a bodily cavity, each elongate member of the plurality of elongate members arranged to be advanced distal end first into the bodily cavity, and an expanded configuration in which at least a first elongate member of the plurality of elongate members is positioned to cross a second elongate member of the plurality of elongate members in an X configuration at a first location spaced along the respective length of the second elongate member from a location of at least the first coupler. The first location may be positioned between at least the first coupler and the respective distal end of the second elongate member. The first location may be spaced from the respective distal end of the second elongate member.

At least the first elongate member of the plurality of elongate members may be positioned to cross the second elongate member of the plurality of elongate members in an X configuration at a second location spaced from the first location along the respective length of the second elongate member of the plurality of elongate members when the portion of the device is in the expanded configuration. The medical system may further include a second coupler arranged to physically couple each elongate member of the plurality of elongate members together with each other of the elongate members of the plurality of elongate members. The first location may be spaced along the respective length of the second elongate member from a location of the second coupler and the first location may be positioned between at least the first coupler and the second coupler when the portion of the device is in the expanded configuration.

The respective intermediate portions of each of at least some of the plurality of elongate members may be angularly spaced, like lines of longitude, with respect to one another about a first axis extending through the first location when the portion of the device is in the expanded configuration. At least one elongate member of the plurality of elongate members may be twisted about an axis extending along a portion of the respective length of the at least one elongate member of the plurality of elongate members.

Various systems may include combinations and subsets of those summarized above.

A medical system may be summarized as including a structure that includes a plurality of elongate members. Each elongate member of the plurality of elongate members includes a proximal end, a distal end, an intermediate portion positioned between the proximal end and the distal end, a respective length between the proximal end and the distal end, and a thickness. Each intermediate portion includes a front surface and a back surface opposite across the thickness of the elongate member from the front surface. Each intermediate portion further includes a respective pair of side edges that define a portion of a periphery of at least one of the front surface and the back surface, the side edges of each pair of side edges opposed to one another across at least a portion of the length of the respective elongate member. The structure is selectively moveable between an unexpanded configuration in which at least the respective intermediate portions of the elongate members of the plurality of elongate members are arranged with respect to one another front surface-toward-back surface in a stacked array sized for delivery through a bodily opening leading to a bodily cavity, and an expanded configuration in which the structure is sized too large for delivery through the bodily opening leading to the bodily cavity. At least a first elongate member of the plurality of elongate members is positioned such that one of the side edges of the pair of side edges of the first elongate member crosses one of the side edges of the pair of side edges of a second elongate member of the plurality of elongate members at each of a plurality of spaced apart locations along the respective length of the second elongate member as viewed normally to each of a respective one of a plurality of portions of the front surface of the respective intermediate portion of the second elongate member over which each of the plurality of spaced apart locations along the respective length of the second elongate member is positioned when the structure is in the expanded configuration.

The respective intermediate portions of at least some of the plurality of elongate members may be fanned with respect to one another about an axis when the structure is in the expanded configuration. At least some of the plurality of elongate members may be fanned with respect to the second elongate member about one or more axes when the structure is in the expanded configuration, the second elongate member arranged such that the one or more axes passes through the second elongate member at each of two or more locations, each location of the two or more locations spaced from another location of the two or more locations along the respective length of the second elongate member. The plurality of spaced apart locations along the respective length of the second elongate member may include at least three spaced apart locations along the respective length of the second elongate member.

The device may further include at least one coupler arranged to physically couple at least some of the plurality of elongate members together with the second elongate member, the at least one coupler spaced along the respective length of the second elongate member from at least one of the plurality of spaced apart locations along the respective length of the second elongate member when the structure is in the expanded configuration. The at least one coupler may be positioned along the respective length of the second elongate member relatively closer to one of the respective proximal end and the respective distal end of the second elongate member than each of at least two of the plurality of spaced apart locations along the respective length of the second elongate member when the structure is in the expanded configuration. Each elongate member of the plurality of elongate members may be arranged to be advanced distal end first into the bodily cavity when the structure is in the unexpanded configuration, and the at least one coupler may be positioned along the respective length of the second elongate member relatively closer to the respective distal end of the second elongate member than at least one of the plurality of spaced apart locations along the respective length of the second elongate member when the structure is in the expanded configuration.

At least one elongate member of the plurality of elongate members may be twisted about an axis extending along a portion of the respective length of the at least one elongate member of the plurality of elongate members. The back surface of the respective intermediate portion of at least the first elongate member may, or may not be separated from the front surface of the respective intermediate portion of the second elongate member at each of at least one of the plurality of spaced apart locations along the respective length of the second elongate member when the structure is in the expanded configuration.

The one of the side edges of the pair of side edges of the first elongate member may be opposed to the one of the side edges of the pair of side edges of the second elongate member in the stacked array when the structure is in the unexpanded configuration. The first elongate member of the plurality of elongate members may be positioned such that the other one of the side edges of the pair of side edges of the first elongate member crosses the other one of the side edges of the pair of side edges of the second elongate member at each of one or more locations along the respective length of the second elongate member as viewed normally to each of a respective one of one or more portions of the front surface of the respective intermediate portion of the second elongate member over which each of the one or more locations along the respective length of the second elongate member is positioned when the structure is in the expanded configuration.

Various systems may include combinations and subsets of those summarized above.

A medical system may be summarized as including a structure that includes a plurality of elongate members and at least one coupler arranged to physically couple at least a first elongate member of the plurality of elongate members together with a second elongate member of the plurality of elongate members. Each elongate member of the plurality of elongate members includes a proximal end, a distal end, an intermediate portion positioned between the proximal end and the distal end, and a thickness. Each intermediate portion includes a front surface and a back surface opposite across the thickness of the elongate member from the front surface, a respective geodesic extending along a portion of each of the elongate members between a location at least proximate the proximal end and another location at least proximate the distal end of the elongate member. Each geodesic is located at least on the front surface of the respective intermediate portion of the elongate member. The structure is selectively moveable between an unexpanded configuration in which at least the respective intermediate portions of the elongate members of the plurality of elongate members are arranged with respect to one another front surface-toward-back surface in a stacked array sized for delivery through a bodily opening leading to a bodily cavity, each elongate member of the plurality of elongate members arranged to be advanced distal end first into the bodily cavity, and an expanded configuration in which the structure is sized too large for delivery through the bodily opening to the bodily cavity. At least the first elongate member is positioned such that the respective geodesic of the first elongate member crosses the respective geodesic of the second elongate member at a first location along the geodesic of the second elongate member as viewed normally to a respective portion of the front surface of the intermediate portion of the second elongate member over which the first location along the respective geodesic of the second elongate member is positioned. The first location is spaced from a location of the at least one coupler along the second elongate member, and the first location may be positioned between the at least one coupler and the respective distal end of the second elongate member when the structure is in the expanded configuration.

The respective intermediate portions of at least some of the plurality of elongate members may be fanned with respect to one another about an axis when the structure is in the expanded configuration. At least some of the plurality of elongate members may be fanned with respect to the second elongate member about one or more axes when the structure is in the expanded configuration, the second elongate member curved such that the one or more axes pass through the second elongate member at each of two or more locations, each location of the two or more locations spaced from each other between the respective proximal and distal ends of the second elongate member. The respective intermediate portions of at least some of the plurality of elongate members may be angularly spaced with respect to one another about a first axis, like lines of longitude, when the structure is in the expanded configuration, each of the least some of the plurality of elongate members including a curved portion arranged to extend along at least a portion of a respective curved path that intersects the first axis at each of a respective at least two spaced apart locations along the first axis.

At least one elongate member of the plurality of elongate members may be twisted about an axis extending along a portion of the at least one elongate member of the plurality of elongate members located between the respective proximal and distal ends of the at least one elongate member of the plurality of elongate members.

The structure may include at least one other coupler arranged to physically couple at least the first elongate member together with the second elongate member, the at least one other coupler positioned relatively closer to the respective distal end of the second elongate member than the at least one coupler, and the first location may be positioned between the at least one coupler and the at least one other coupler along the second elongate member when the structure is in the expanded configuration.

The structure may include at least one other coupler arranged to physically couple at least the first elongate member together with the second elongate member, the at least one other coupler spaced from the at least one coupler along the second elongate member, and the first location may be positioned along the second elongate member relatively closer to the respective distal end of the second elongate member than each of the at least one coupler and the at least one other coupler when the structure is in the expanded configuration.

The at least one coupler may include a flexible line arranged to pass through an opening provided in each of at least one of the first elongate member and the second elongate member. The back surface of the respective intermediate portion of at least the first elongate member may contact the front surface of the respective intermediate portion of the second elongate member at the first location when the structure is in the expanded configuration. The back surface of the respective intermediate portion of at least the first elongate member may be separated from the front surface of the respective intermediate portion of the second elongate member at the first location when the structure is in the expanded configuration.

Various systems may include combinations and subsets of those summarized above.

A medical system may be summarized as including a structure that includes a plurality of elongate members, each elongate member of the plurality of elongate members including a proximal end, a distal end, and a respective intermediate portion positioned between the proximal end and the distal end. The structure is selectively moveable between a delivery configuration in which the structure is suitably sized to allow the structure to be intravascularly or percutaneously delivered to a bodily cavity, and a deployed configuration in which the structure is expanded to have a size too large to allow the structure to be intravascularly or percutaneously delivered to the bodily cavity. The plurality of elongate members include a first set of the elongate members and a second set of the elongate members, at least the respective intermediate portions of the elongate members in each of the first and the second sets of the elongate members pivoting about at least one axis when the structure is moved into the deployed configuration, each of the respective intermediate portions of the elongate members in the first set of the elongate members pivoting along a first angular direction and each of the respective intermediate portions of the elongate members in the second set of the elongate members pivoting along a second angular direction opposite to the first angular direction. At least the respective intermediate portion of at least one of the elongate members in the first set of the elongate members is positioned between the respective intermediate portions of at least two of the elongate members in the second set of the elongate members when the structure is in the delivery configuration.

In some embodiments each elongate member of the plurality of elongate members includes a thickness, and the respective intermediate portion of each elongate member of the plurality of elongate members includes a front surface and a back surface opposite across the thickness of the elongate member from the front surface. At least one portion of the respective front surface of each elongate member of the plurality of elongate members may be positioned to directly face an interior tissue surface of the bodily cavity when the structure is moved into the deployed configuration within the bodily cavity, and the respective front surface of the at least one of the elongate members in the first set of the elongate members may be positioned to directly face the respective back surface of one of the at least two of the elongate members in the second set of the elongate members when the structure is in the delivery configuration. The respective intermediate portions of the elongate members of the plurality of elongate members may be arranged with respect to one another front surface-toward-back surface in a stacked array when the structure is in the delivery configuration. At least the respective intermediate portions of the elongate members in the first set of the elongate members may be interleaved with at least the respective intermediate portions of the elongate members in the second set of the elongate members in a stacked array when the structure is in the delivery configuration.

In some embodiments each elongate member of the plurality of elongate members includes a respective length between the respective proximal and distal ends of the elongate member, and at least a first elongate member of the plurality of elongate members crosses a second elongate member of the plurality of elongate members in an X configuration at each of at least one location along the respective length of the second elongate member of the plurality of elongate members when the structure is in the deployed configuration.

In some embodiments each elongate member of the plurality of elongate members includes a respective length between the respective proximal and distal ends of the elongate member, and at least one elongate member of the plurality of elongate members is arranged such that the at least one axis passes through the at least one elongate member of the plurality of elongate members at each of two or more locations, each location of the two or more locations spaced from another location of the two or more locations along the respective length of the at least one elongate member of the plurality of elongate members when the structure is in the deployed configuration. The two or more locations may include at least three spaced apart locations along the respective length of the at least one elongate member of the plurality of elongate members.

Various systems may include combinations and subsets of those summarized above.

A medical system may be summarized as including at least one transducer controller; and a device that includes a plurality of transducer elements and a plurality of flexible circuit structures. Each of the flexible circuit structures includes at least one flexible substrate and a set of one or more electrical conductors carried by the at least one flexible substrate, at least some the electrical conductors in the set of one or more electrical conductors providing at least a portion of a signal path between the at least one transducer controller and at least some of the transducer elements. At least one portion of each of the plurality of flexible circuit structures is positionable within a bodily cavity. A portion of the device is selectively moveable between an unexpanded configuration in which at least the respective at least one portions of the plurality of flexible circuit structures are arranged successively along a first direction in a stacked arrangement, the stacked arrangement sized to be intravascularly or percutaneously delivered through a bodily opening leading to the bodily cavity, and an expanded configuration in which the respective at least one portions of the plurality of flexible circuit structures are angularly spaced with respect to one another about at least one axis. The respective at least one portion of each of at least some of the flexible circuit structures may pivot about the least one axis when the portion of the device is moved between the unexpanded configuration and the expanded configuration.

At least one of the plurality of flexible circuit structures may be arranged such that the at least one axis passes through the at least one of the plurality of flexible circuit structures at each of two or more spaced apart locations when the portion of the device is in the expanded configuration. The two or more spaced apart locations may include at least three spaced apart locations. At least a first one of the plurality of flexible circuit structures may cross a second one of the plurality of flexible circuit structures in an X configuration when the portion of the device is in the expanded configuration.

The respective at least one flexible substrate of each of at least some of the plurality of flexible circuit structures may include a plurality of material layers, at least one of the material layers bonded to at least one other of the material layers with an adhesive. The respective at least one portion of at least one of the plurality of flexible circuit structures may include a different number of material layers than at least another portion of the at least one of the plurality of flexible circuit structures. At least one of the plurality of transducer elements may be carried by the respective at least one portion of each of the at least some of the plurality of flexible circuit structures. Each of the plurality of flexible circuit structures may be a printed flexible circuit structure. At least one of the plurality of flexible circuit structures includes a twist about a twist axis.

Various systems may include combinations and subsets of those summarized above.

A medical system may be summarized as including a device that includes a plurality of elongate members. Each elongate member of the plurality of elongate members includes a first end, a second end, an intermediate portion positioned between the first end and the second end, and a thickness. Each intermediate portion includes a front surface and a back surface opposite across the thickness of the elongate member from the front surface. A portion of the device is selectively moveable between a delivery configuration in which at least the respective intermediate portions of the elongate members of the plurality of elongate members are arranged with respect to one another front surface-toward-back surface in a stacked array sized for delivery through a bodily opening leading to a bodily cavity, and a deployed configuration in which at least the respective intermediate portion of each elongate member of at least some of the plurality of elongate members is arranged within the bodily cavity to position a first portion of the front surface of the respective intermediate portion of the elongate member of the at least some of the plurality of elongate members to face a first portion of an interior tissue surface within the bodily cavity and to position a second portion of the front surface of the respective intermediate portion of the elongate member of the at least some of the plurality of elongate members to face a second portion of the interior tissue surface, where the second portion of the interior tissue surface is opposed across the bodily cavity from the first portion of the interior tissue surface.

The at least some of the plurality of elongate members may be bent about a bending axis into an arcuate stacked array when the portion of the device is in the deployed configuration.

At least the respective intermediate portions of the elongate members of the at least some of the plurality of elongate members may be fanned with respect to at least one elongate member of the plurality of elongate members about each of one or more axes when the portion of the device is in the deployed configuration. In some embodiments each elongate member of the plurality of elongate members includes a respective length between the respective first end and the respective second end of the elongate member, and the one or more axes pass through the at least one elongate member of the plurality of elongate members at two or more locations when the portion of the device is in the deployed configuration, each location of the two or more locations spaced from another location of the two or more locations along the respective length of the at least one elongate member of the plurality of elongate members. The two or more locations may include at least three spaced apart locations along the respective length of the at least one elongate member of the plurality of elongate members.

In some embodiments each elongate member of the plurality of elongate members includes a respective length between the respective first end and the respective second end of the elongate member, and at least a first elongate member of the at least some of the plurality of elongate members crosses a second elongate member of the at least some of the plurality of elongate members in an X configuration at each of one or more locations along the respective length of the second elongate member of the at least some of the plurality of elongate members when the portion of the device is in the deployed configuration. At least one location of the one or more locations may be spaced along the respective length of the second elongate member of the at least some of the plurality of elongate members from each of the respective first end and the respective second end of the second elongate member. The at least one location of the one or more locations may be located along the respective length of the second elongate member of the at least some of the plurality of elongate members between the respective first and second portions of the front surface of the respective intermediate portion of the second elongate member of the at least some of the plurality of elongate members. The one or more locations along the respective length of the second elongate member of the at least some of the plurality of elongate members may include at least two spaced apart locations along the respective length of the second elongate member of the at least some of the plurality of elongate members. The device may further include at least one coupler that physically couples at least the first and the second elongate members of the at least some of the plurality of elongate members together. The at least one location of the one or more locations may be spaced along the respective length of the second elongate member of the at least some of the plurality of elongate members from a location of the at least one coupler when the portion of the device is in the deployed configuration. The device may further include a plurality of couplers which each physically couples at least the second elongate member of the at least some of the plurality of elongate members together with at least one other elongate member of the plurality of elongate members, each coupler of the plurality of couplers spaced from another of the plurality of couplers along the respective length of the second elongate member of the at least some of the plurality of elongate members. The at least one location of the one or more locations may be located along the respective length of the second elongate member of the at least some of the plurality of elongate members between the respective locations of at least two of the plurality of couplers when the portion of the device is in the deployed configuration. The at least one location of the one or more locations may be located along the respective length of the second elongate member of the at least some of the plurality of elongate members relatively closer to the respective first end of the second elongate member than a respective location of each of at least two of the plurality of couplers when the portion of the device is in the deployed configuration, the respective first end of each elongate member of the plurality of elongate members arranged to be advanced into the bodily cavity before the respective second end of the elongate member of the plurality of elongate members when the portion of the device is in the delivery configuration.

Each elongate member of the at least some of the plurality of elongate members may have a volute shape profile when the portion of the device is in the deployed configuration.

Each of the first and the second portions of the front surface of the respective intermediate portion of the elongate member of the at least some of the plurality of elongate members may include respective ones of one or more transducers which face a respective one of a pair of diametrically opposed portions of the interior tissue surface within the bodily cavity when the portion of the device is in the deployed configuration in use.

Various systems may include combinations and subsets of those summarized above.

A medical system may be summarized as including a structure that includes a plurality of elongate members. Each elongate member of the plurality of elongate members includes a proximal end, a distal end, and a respective intermediate portion positioned between the proximal end and the distal end. The structure is selectively moveable between a delivery configuration in which the structure is suitably sized to be intravascularly or percutaneously delivered to a bodily cavity, and a deployed configuration in which the structure has a size too large to be intravascularly or percutaneously delivered to the bodily cavity. The respective intermediate portions of at least two of the plurality of elongate members are angularly spaced with respect to one another about a first axis, similar to lines of longitude, and each of the at least two of the plurality of elongate members includes a curved portion that extends along at least a portion of a respective curved path that intersects the first axis at each of a respective at least two spaced apart locations along the first axis when the structure is in the deployed configuration. The medical system further includes a handle portion, and a shaft member. A portion of the shaft member sized and arranged to deliver the structure intravascularly or percutaneously to the bodily cavity. The shaft member includes a first end positioned at least proximate to the handle portion and a second end physically coupled to the structure at one or more locations on the structure. Each of the one or more locations on the structure to which the second end is physically coupled is positioned to one side of at least one spatial plane coincident with the first axis when the structure is in the deployed configuration.

At least one of the one or more locations on the structure to which the second end is physically coupled may be at least proximate to the respective proximal ends of at least some of the plurality of elongate members. Each of the at least two of the plurality of elongate members may extend tangentially from the second end of the shaft member when the structure is in the deployed configuration. Each of the proximal ends of the elongate members of the plurality of elongate members may be positioned to one side of the at least one spatial plane coincident with the first axis when the structure is in the deployed configuration. Each of the distal ends of the elongate members of the plurality of elongate members may be positioned to one side of the at least one spatial plane coincident with the first axis when the structure is in the deployed configuration. The shaft member may be arranged to avoid intersection by the first axis when the structure is in the deployed configuration. The shaft member may be arranged to avoid intersection of the second end of the shaft member by the first axis when the structure is in the deployed configuration.

The respective intermediate portion of each elongate member of the plurality of elongate members may include a front surface and a back surface opposite across a thickness of the elongate member from the front surface, and at least the respective intermediate portions of the elongate members of the plurality of elongate members may be arranged with respect to one another front surface-toward-back surface in a stacked array when the structure is in the delivery configuration.

In some embodiments each elongate member of the plurality of elongate members includes a respective length between the respective proximal end and the respective distal end of the elongate member, and the first axis passes through each of at least one elongate member of the plurality of elongate members at two or more locations when the structure is in the deployed configuration, each location of the two or more locations spaced from another location of the two or more locations along the respective length of the at least one elongate member of the plurality of elongate members. The two or more locations may include at least three locations spaced along the respective length of the at least one elongate member of the plurality of elongate members.

In some embodiments each elongate member of the plurality of elongate members includes a respective length between the respective proximal end and the respective distal end of the elongate member, and at least a first elongate member of the plurality of elongate members crosses a second elongate member of the plurality of elongate member in an X configuration at a location along the respective length of the second elongate member spaced from each of the respective proximal end and the respective distal end of the second elongate member when the structure is in the deployed configuration. Each elongate member of at least some of the plurality of elongate members may have a volute shape profile when the structure is in the deployed configuration.

Various systems may include combinations and subsets of those summarized above.

A medical system may be summarized as including a device that includes a plurality of elongate members. Each elongate member of the plurality of elongate members includes a proximal end, a distal end, an intermediate portion positioned between the proximal end and the distal end, and a thickness. Each intermediate portion includes a front surface and a back surface opposite across the thickness of the elongate member from the front surface. A portion of the device is selectively moveable between a delivery configuration in which at least the respective intermediate portions of the elongate members of the plurality of elongate members are arranged with respect to one another front surface-toward-back surface in a stacked array sized for delivery through a bodily opening leading to a bodily cavity, and a deployed configuration in which the respective intermediate portion of each elongate member of at least some of the plurality of elongate members has a volute shape profile.

At least the respective intermediate portions of the elongate members of the at least some of the plurality of elongate members may be fanned with respect to at least one elongate member of the plurality of elongate members about at least one axis when the portion of the device is in the deployed configuration. In some embodiments each elongate member of the plurality of elongate members includes a respective length between the respective proximal end and the respective distal end of the elongate member, and the at least one axis passes through the at least one elongate member of the plurality of elongate members at two or more locations when the portion of the device is in the deployed configuration, each location of the two or more locations spaced from another location of the two or more locations along the respective length of the at least one elongate member of the plurality of elongate members. The two or more locations may include at least three spaced apart locations along the respective length of the at least one elongate member of the plurality of elongate members.

In some embodiments each elongate member of the plurality of elongate members includes a respective length between the respective proximal end and the respective distal end of the elongate member, and at least a first elongate member of the plurality of elongate members crosses a second elongate member of the plurality of elongate member in an X configuration at each of one or more locations along the respective length of the second elongate member spaced from each of the respective proximal end and the respective distal end of the second elongate member when the portion of the device is in the deployed configuration. The device may further include a plurality of couplers which each physically couples at least the second elongate member of the plurality of elongate members together with at least one other elongate member of the plurality of elongate members, each coupler of the plurality of couplers spaced from another of the plurality of couplers along the respective length of the second elongate member of the plurality of elongate members. At least one location of the one or more locations may be located along the respective length of the second elongate member of the plurality of elongate members between the respective locations of at least two of the plurality of couplers when the portion of the device is in the deployed configuration. Each elongate member of the plurality of elongate members in the stacked array may be arranged to be advanced distal end first into the bodily cavity when the portion of the device is in the delivery configuration, and at least one location of the one or more locations may be located along the respective length of the second elongate member of the plurality of elongate members relatively closer to the respective distal end of the second elongate member than a respective location of each of at least two of the plurality of couplers when the portion of the device is in the deployed configuration.

Various systems may include combinations and subsets of those summarized above.

A medical system may be summarized as including a catheter sheath that includes a first end, a second end and a lumen therebetween. The medical system further includes a device that includes a plurality of elongate members. Each elongate member of the plurality of elongate members includes a proximal end, a distal end, an intermediate portion positioned between the proximal end and the distal end, and a thickness. Each intermediate portion includes a front surface and a back surface opposite across the thickness of the elongate member from the front surface. A portion of the device is selectively moveable between a first configuration in which at least the respective intermediate portions of the elongate members of the plurality of elongate members are arranged with respect to one another front surface-toward-back surface in a stacked array sized for delivery through the lumen of the catheter sheath, each elongate member of the plurality of elongate members arranged to be advanced distal end first out from the lumen of the catheter sheath, and a second configuration in which the respective distal end of each of at least some of the plurality of elongate members moves along a respective coiled path as the elongate members advance out of the lumen of the catheter sheath, the respective intermediate portions of each elongate member of the at least some of the plurality of elongate members bent about a respective bending axis into an arcuate stacked array sized too large for delivery though the lumen of the catheter sheath.

At least part of the coiled path may extend along a volute path. At least the respective intermediate portion of each elongate member of the at least some of the plurality of elongate members may have a volute shape profile when the portion of the device is in the second configuration.

In some embodiments each elongate member of the plurality of elongate members includes a respective length between the respective proximal end and the respective distal end of the elongate member, and the portion of the device is further selectively moveable between at least the second configuration and a third configuration in which at least the respective intermediate portions of the elongate members of the at least some of the plurality of elongate members are fanned with respect to at least one elongate member of the plurality of elongate members about each of one or more axes. The one or more axes may pass through the at least one elongate member of the plurality of elongate members at two or more locations when the portion of the device is in the third configuration, each location of the two or more locations spaced from another location of the two or more locations along the respective length of the at least one elongate member of the plurality of elongate members. The two or more locations may include at least three spaced apart locations along the respective length of the at least one elongate member of the plurality of elongate members.

In some embodiments each elongate member of the plurality of elongate members includes a respective length between the respective proximal end and the respective distal end of the elongate member, and the portion of the device is further selectively moveable between at least the second configuration and a third configuration in which at least a first elongate member of the plurality of elongate members crosses a second elongate member of the plurality of elongate members in an X configuration at each of one or more locations along the respective length of the second elongate member spaced from each of the respective proximal end and the respective distal end of the second elongate member. The device may further include a plurality of couplers which each physically couples at least the second elongate member of the plurality of elongate members together with at least one other elongate member of the plurality of elongate members, each coupler of the plurality of couplers spaced from another of the plurality of couplers along the respective length of the second elongate member. At least one location of the one or more locations may be located along the respective length of the second elongate member between the respective locations of at least two of the plurality of couplers when the portion of the device is in the third configuration. At least one location of the one or more locations may be located along the respective length of the second elongate member relatively closer to the respective distal end of the second elongate member than a respective location of each of at least two of the plurality of couplers when the portion of the device is in the third configuration.

At least one elongate member of the at least some of the plurality of elongate members may have an annular shape profile in the second configuration, the annular profile interrupted by a separation. The respective intermediate portion of each elongate member of the at least some of the plurality of elongate members may be preformed to autonomously bend about the respective bending axis of the elongate member of the at least some of the plurality of elongate members as the respective intermediate portion is advanced out from the lumen of the catheter sheath. The medical system may further include a bending unit that acts on at least one of the plurality of elongate members to bend the respective intermediate portion of each elongate member of the at least some of the plurality of elongate members about the respective bending axis of the elongate member of the at least some of the plurality of elongate members when the portion of the device is moved between the first configuration and the second configuration.

Various systems may include combinations and subsets of those summarized above.

A medical system may be summarized as including a device that includes a plurality of elongate members. Each elongate member of the plurality of elongate members includes a first end and a second end, an intermediate portion between the first end and the second end, and a respective length between the first end and the second end. The device further includes a plurality of couplers that includes a proximal coupler, a distal coupler and at least one intermediate coupler. Each coupler of the plurality of couplers is spaced from another of the plurality of couplers along the respective length of at least a first elongate member of the plurality of elongate members with the at least one intermediate coupler positioned between the proximal coupler and the distal coupler. Each coupler of the plurality of couplers is arranged to couple at least the first elongate member together with least one other elongate member of the plurality of elongate members. A portion of the device is selectively moveable between an unexpanded configuration in which at least the respective intermediate portions of the elongate members of the plurality of elongate members are sized and arranged to be delivered through a bodily opening leading to a bodily cavity within a body, the bodily cavity having an interior tissue surface interrupted by a port of the bodily opening, and the plurality of couplers arranged to be advanced distal coupler first into the bodily cavity, and an expanded configuration in which at least the respective intermediate portions of at least some of the plurality of elongate members are arranged such that at least the distal coupler is located within the bodily cavity at a respective location positioned relatively closer to the port of the bodily opening than a respective location of the at least one intermediate coupler within the bodily cavity.

When the portion of the device is in the expanded configuration, the proximal coupler may be positioned relatively closer to the port of the bodily opening than the distal coupler within the bodily cavity. When the portion of the device is in the expanded configuration, the distal coupler may be positioned relatively closer to the port of the bodily opening than the proximal coupler. At least the respective intermediate portions of the at least some of the plurality of elongate members may be arranged such that the proximal coupler is located within the body at a location outside of the bodily cavity when the portion of the device is in the expanded configuration.

At least the respective intermediate portions of the elongate members of the plurality of elongate members may be arranged successively with respect to one another along a first direction in a stacked arrangement when the portion of the device is in the unexpanded configuration.

The respective intermediate portion of each elongate member of the plurality of elongate members may include a thickness, a front surface and a back surface opposite across the thickness from the front surface. At least the respective intermediate portions of the elongate members of the plurality of elongate members may be arranged with respect to one another front surface-toward-back surface in a stacked array sized for delivery through the bodily opening leading to the bodily cavity when the portion of the device is in the unexpanded configuration, and the respective intermediate portion of each elongate member of the at least some of the plurality of elongate members may be bent about a respective bending axis when the portion of the device is in the expanded configuration. The respective intermediate portion of each elongate member of the at least some of the plurality of elongate members may be preformed to autonomously bend about the respective bending axis of the elongate member of the at least some of the plurality of elongate members when the respective intermediate portion of the elongate member of the at least some of the plurality of elongate members is advanced into the bodily cavity.

At least the respective intermediate portions of the elongate members of the at least some of the plurality of elongate members may be fanned with respect to at least one elongate member of the plurality of elongate members about each of one or more axes, and the one or more axes may pass through the at least one elongate member of the plurality of elongate members at two or more locations when the portion of the device is in the expanded configuration. Each location of the two or more locations may be spaced from another location of the two or more locations along the respective length of the at least one elongate member of the plurality of elongate members. The two or more locations may include at least three spaced apart locations along the respective length of the at least one elongate member of the plurality of elongate members. At least a second elongate member of the plurality of elongate members may cross the first elongate member at a location along the respective length of the first elongate member spaced from each of the proximal coupler and the distal coupler when the portion of the device is in the expanded configuration.

Various systems may include combinations and subsets of those summarized above.

A medical system may be summarized as including a device that includes a plurality of elongate members. Each elongate member of the plurality of elongate members includes a proximal end, a distal end, an intermediate portion positioned between the proximal end and the distal end, and a thickness. Each intermediate portion includes a front surface and a back surface opposite across the thickness of the elongate member from the front surface. A respective geodesic defined for each elongate member extends along the respective elongate member between a first location at least proximate the proximal end and a second location at least proximate the distal end of the elongate member, each geodesic defined at least on the front surface of the respective intermediate portion of the elongate member. A portion of the device is selectively moveable between an unexpanded configuration in which at least the respective intermediate portions of the elongate members of the plurality of elongate members are arranged front surface-toward-back surface in a stacked array sized to be delivered through a bodily opening leading to a bodily cavity having an interior tissue surface interrupted by a port of the bodily opening, each elongate member of the plurality of elongate members arranged to be advanced distal end first into the bodily cavity, and an expanded configuration in which at least a first elongate member of the plurality of elongate members is positioned to cross a second elongate member of the plurality of elongate members at each of one or more crossing locations within the bodily cavity. Each of the one or more crossing locations is located on the front surface of the second elongate member at a respective one of one or more locations along the respective geodesic of the second elongate member that is crossed by the respective geodesic of the first elongate member as viewed normally to a respective one of one or more portions of the front surface of the second elongate member over which each respective one of the one or more locations along the respective geodesic of the second elongate member is located. The elongate members of the plurality of elongate members are arranged such that the respective distal end of each elongate member of at least some of the plurality of elongate members is positioned within the bodily cavity at a respective location located relatively closer to the port of the bodily opening than at least one crossing location of the one or more crossing locations within the bodily cavity when the portion of the device is in the expanded configuration.

The one or more crossing locations within the bodily cavity may include at least one other crossing location, the at least one other crossing location located within the bodily cavity relatively closer to the port of the bodily opening than the respective location within the bodily cavity of the respective distal end of each elongate member of the at least some of the plurality of elongate members when the portion of the device is moved between the unexpanded configuration and the expanded configuration.

The respective intermediate portion of each elongate member of the at least some of the plurality of elongate members may be arranged within the bodily cavity to position a first portion of the front surface of the respective intermediate portion of the elongate member of the at least some of the plurality of elongate members to face a first portion of an interior tissue surface within the bodily cavity and to position a second portion of the front surface of the respective intermediate portion of the elongate member of the at least some of the plurality of elongate members to face a second portion of the interior tissue surface when the portion of the device is in the expanded configuration, the second portion of the interior tissue surface positioned diametrically opposite to the first portion of the interior tissue surface.

The device may further include a plurality of couplers which each physically couples at least the second elongate member together with at least one other elongate member of the plurality of elongate members, each coupler of the plurality of couplers spaced from another coupler of the plurality of couplers along the second elongate member. The location of the at least one crossing location along the respective geodesic of the second elongate member may be positioned along the second elongate member between the respective locations of two of the plurality of couplers when the portion of the device is in the expanded configuration. The location of the at least one crossing location along the respective geodesic of the second elongate member may be located along the second elongate member relatively closer to the respective distal end of the second elongate member than a respective location of each of at least two of the plurality of couplers when the portion of the device is in the expanded configuration.

The respective intermediate portion of each elongate member of the at least some of the plurality of elongate members may be preformed to autonomously bend about a respective bending axis as the respective intermediate portion of the elongate member of the at least some of the plurality of elongate members is advanced into the bodily cavity. The medical system may further include a bending unit that acts on at least one of the plurality of elongate members to bend each elongate member of the at least some of the plurality of elongate members about a respective bending axis within the bodily cavity when the portion of the device is moved between the unexpanded configuration and the expanded configuration.

Various systems may include combinations and subsets of those summarized above.

A medical system may be summarized as including a catheter sheath that includes a first end, a second end and a lumen therebetween. The medical system further includes a structure that includes a plurality of elongate members, each elongate member of the plurality of elongate members including a proximal end, a distal end, and an intermediate portion positioned between the proximal and the distal ends. The structure is selectively moveable between an unexpanded configuration in which the elongate members of the plurality of elongate members are arranged successively with respect to one another along a first direction in a stacked arrangement, the stacked arrangement sized to be delivered through the lumen of the catheter sheath from the first end of the catheter sheath towards the second end of the catheter sheath, a portion of at least one elongate member of the plurality of elongate members in the stacked arrangement positioned to be advanced from the second end of the catheter sheath prior to each of the other elongate members of the plurality of elongate members in the stacked arrangement as the stacked arrangement is delivered through the lumen of the catheter sheath from the first end of the catheter sheath towards the second end of the catheter sheath, and an expanded configuration in which the structure is expanded to have a size too large to be delivered through the lumen of the catheter sheath.

In some embodiments each elongate member of the plurality of elongate members includes a respective length between the proximal and the distal ends of the elongate member, and the respective length of the at least one elongate member of the plurality of elongate members is longer than each of the respective lengths of the other elongate members of the plurality of elongate members. The portion of the at least one elongate member of the plurality of elongate members may be cantilevered from the stacked arrangement when the structure is in the unexpanded configuration. The at least one elongate member of the plurality of elongate members may include an outermost elongate member in the stacked arrangement when the structure is in the unexpanded configuration. The at least one elongate member of the plurality of elongate members may include an elongate member located between two outermost elongate members in the stacked arrangement when the structure is in the unexpanded configuration. The at least one elongate member of the plurality of elongate members may include at least two elongate members of the plurality of elongate members.

In some embodiments each elongate member of the plurality of elongate members includes a respective length between the proximal and the distal ends of the elongate member, and at least a first elongate member of the plurality of elongate members crosses a second elongate member of the plurality of elongate members in an X configuration at each of one or more locations along the respective length of the second elongate member when the structure is in the expanded configuration, each of the one or more locations spaced from each of the respective proximal end and the respective distal end of the second elongate member.

The respective intermediate portion of each elongate member of at least some of the plurality of elongate members may be preformed to autonomously bend about a respective bending axis as the respective intermediate portion of the elongate member of the at least some of the plurality of elongate members is advanced from the second end of the catheter sheath as the stacked arrangement is delivered through the lumen of the catheter sheath from the first end of the catheter sheath towards the second end of the catheter sheath. The medical system may further include a bending unit that acts on at least one of the plurality of elongate members to bend each elongate member of at least some of the plurality of elongate members about a respective bending axis when the respective intermediate portion of the elongate member of the at least some of the plurality of elongate members is advanced from the second end of the catheter sheath.

Each elongate member of the plurality of elongate members may be arranged to be advanced distal end first as the stacked arrangement is delivered through the lumen of the catheter sheath from the first end of the catheter sheath towards the second end of the catheter sheath.

Various systems may include combinations and subsets of those summarized above.

A medical system may be summarized as including a structure that includes a plurality of elongate members. Each elongate member of the plurality of elongate members includes a proximal end, a distal end, a respective intermediate portion positioned between the proximal end and the distal end, and a respective length between the proximal and the distal ends. A method employing the medical system may be summarized as including intravascularly or percutaneously delivering at least a portion of the structure to a location within an intra-cardiac cavity formed at least in part by a tissue wall having an interior tissue surface, each elongate member of the plurality of elongate members introduced distal end first into the intra-cardiac cavity and the distal end of each elongate member of the plurality of elongate members curling away from the interior tissue surface as the distal end of the elongate member of the plurality of elongate members is advanced along a respective path within the intra-cardiac cavity during the intravascular or percutaneous delivery. The method further includes fanning at least some of the plurality of elongate members with respect to at least one elongate member of the plurality of elongate members about each of one or more axes within the intra-cardiac cavity. The one or more axes pass through the at least one elongate member of the plurality of elongate members at two or more locations, each location of the two or more locations spaced from another location of the two or more locations along the respective length of the at least one elongate member of the plurality of elongate members.

In some embodiments the respective intermediate portion of each elongate member of the plurality of elongate members includes a front surface and a back surface opposite across a thickness of the elongate member from the front surface, and the method further includes positioning a first portion of the front surface of the respective intermediate portion of at least a first elongate member of the plurality of elongate members to face a first portion of the interior tissue surface and positioning a second portion of the front surface of the respective intermediate portion of at least the first elongate member of the plurality of elongate members to face a second portion of the interior tissue surface, the second portion of the interior tissue surface positioned diametrically opposite to the first portion of the interior tissue surface.

In some embodiments, the respective intermediate portion of each elongate member of the plurality of elongate members may include a front surface and a back surface opposite across a thickness of the elongate member from the front surface, and at least the respective intermediate portions of the elongate members of the plurality of elongate members may be arranged with respect to one another front surface-toward-back surface in a stacked array when intravascularly or percutaneously delivering at least the portion of the structure to the location within the intra-cardiac cavity.

The method may further include crossing a second elongate member of the plurality of elongate members with a first elongate member of the plurality of elongate members in an X configuration at each of one or more locations along the respective length of the second elongate member, each of the one or more locations spaced from each of the respective proximal end and the respective distal end of the second elongate member.

Various methods may include combinations and subsets of those summarized above.

A medical system may be summarized as including a structure that includes a plurality of elongate members. Each elongate member includes a first end, a second end, and an intermediate portion positioned between the first and the second ends. Each intermediate portion includes a thickness, a front surface and a back surface opposite across the thickness from the front surface. The structure further includes a proximal portion and a distal portion, each of the proximal and the distal portions of the structure including a respective part of each of at least some of the plurality of elongate members. The structure is selectively moveable between a delivery configuration in which the structure is sized for delivery through a bodily opening leading to a bodily cavity, at least the respective intermediate portions of the elongate members of the plurality of elongate members arranged front surface-toward-back surface in a stacked array when the structure is in the delivery configuration, and a deployed configuration in which the structure is sized too large for delivery through the bodily opening leading to the bodily cavity, the proximal portion of the structure forming a first domed shape and the distal portion of the structure forming a second domed shape when the structure is in the deployed configuration.

At least one of the first domed shape and the second domed shape may have a first radius of curvature in a first spatial plane and a second radius of curvature in a second spatial plane that intersects the first spatial plane, a magnitude of the second radius of curvature different than a magnitude of the first radius of curvature.

Each elongate member of the at least some of the plurality of elongate members may cross at least one other elongate member of the plurality of elongate members at least at one location between the proximal and the distal portions of the structure when the structure is in the deployed configuration.

In some embodiments each elongate member of the plurality of elongate members includes a respective length between the first end and the second end of the elongate member, and each elongate member of the at least some of the plurality of elongate members crosses at least one other elongate member of the plurality of elongate members at each of a plurality of spaced apart locations along the respective length of at least the one other elongate member of the plurality of elongate members when the structure is in the deployed configuration. At least some of the plurality of elongate members may be fanned with respect to at least one of the plurality of elongate members about an axis passing through a location between the proximal and the distal portions of the structure when the structure is in the deployed configuration.

In some embodiments, the medical system further includes at least one flexible line arranged to physically couple the proximal and the distal portions of the structure together, the at least one flexible line manipulable to vary a distance between the proximal and the distal portions of the structure when the structure is in the deployed configuration.

Various systems may include combinations and subsets of those summarized above.

A medical system may be summarized as including a structure that includes a plurality of elongate members. Each elongate member of the plurality of elongate members includes a proximal end, a distal end, and a respective intermediate portion positioned between the proximal end and the distal end. The structure is selectively moveable between a delivery configuration in which the structure is suitably sized to be intravascularly or percutaneously delivered to a bodily cavity, and a deployed configuration in which the structure is expanded to have a size too large to be intravascularly or percutaneously delivered to the bodily cavity. The respective intermediate portions of at least some of the plurality of elongate members are angularly spaced with respect to one another about a first axis, similar to lines of longitude, when the structure is in the deployed configuration. The medical system further includes a handle portion and a shaft member, a portion of the shaft member sized and arranged to deliver the structure intravascularly or percutaneously to the bodily cavity. The shaft member includes a first end positioned at least proximate to the handle portion and a second end physically coupled to the structure. In the deployed configuration the structure and the shaft member have a projected outline in the shape of the Greek letter rho, where a point where a loop of the letter would intersect a tail of the letter may be open or not closed. Such outline may be either without, or with, an opening defined by a loop portion of the letter represented.

Each of the at least some of the plurality of elongate members may include a curved portion that extends along at least a portion of a respective curved path that intersects the first axis at each of a respective at least two spaced apart locations along the first axis when the structure is in the deployed configuration.

In some embodiments the respective intermediate portion of each elongate member of the plurality of elongate members includes a front surface and a back surface opposite across a thickness of the elongate member, and at least the respective intermediate portions of the elongate members of the plurality of elongate members are arranged with respect to one another front surface-toward-back surface in a stacked array when the structure is in the delivery configuration.

In some embodiments each elongate member of the plurality of elongate members includes a respective length between the respective proximal end and the respective distal end of the elongate member, and the first axis passes through each of at least one elongate member of the plurality of elongate members at two or more locations when the structure is in the deployed configuration, each location of the two or more locations spaced from another location of the two or more locations along the respective length of the at least one elongate member of the plurality of elongate members. The two or more locations may include at least three locations spaced along the respective length of the at least one elongate member of the plurality of elongate members.

In some embodiments each elongate member of the plurality of elongate members includes a respective length between the respective proximal end and the respective distal end of the elongate member, and at least a first elongate member of the plurality of elongate members crosses a second elongate member of the plurality of elongate member in an X configuration at each of one or more locations along the respective length of the second elongate member spaced from each of the respective proximal end and the respective distal end of the second elongate member when the structure is in the deployed configuration. The medical system may further include a plurality of couplers which each physically couples at least the second elongate member of the plurality of elongate members together with at least one other elongate member of the plurality of elongate members, each coupler of the plurality of couplers spaced from another of the plurality of couplers along the respective length of the second elongate member of the plurality of elongate members. At least one location of the one or more locations may be located along the respective length of the second elongate member of the plurality of elongate members between the respective locations of at least two of the plurality of couplers when the structure is in the deployed configuration. Each elongate member of the plurality of elongate members may be arranged to be advanced distal end first into the bodily cavity when the structure is in the delivery configuration, and at least one location of the one or more locations may be located along the respective length of the second elongate member of the plurality of elongate members relatively closer to the respective distal end of the second elongate member than a respective location of each of at least two of the plurality of couplers when the structure is in the deployed configuration.

Various systems may include combinations and subsets of those summarized above.

A medical system may be summarized as including a structure that includes a proximal portion and a distal portion. The structure is selectively movable between a delivery configuration in which the structure is sized for delivery through a bodily opening leading to a bodily cavity, the structure arranged to be advanced distal portion first into the bodily cavity, and a deployed configuration in which the structure is sized too large for delivery through the bodily opening leading to the bodily cavity. The proximal portion of the structure forms a first domed shape and the distal portion of the structure forms a second domed shape when the structure is in the deployed configuration. The proximal and the distal portions of the structure are arranged in a clam shell configuration when the structure is in the deployed configuration.

At least one of the first domed shape and the second domed shape may have a first radius of curvature in a first spatial plane and a second radius of curvature in a second spatial plane that intersects the first spatial plane. A magnitude of the second radius of curvature may be different than a magnitude of the first radius of curvature. The proximal and the distal portions of the structure may be physically coupled together to pivot with respect to one another when the structure is in the deployed configuration. The proximal and the distal portions of the structure may be pivotably coupled together by a flexure portion of the structure when the structure is in the deployed configuration.

The medical system may further include at least one actuator operably coupled to the structure to selectively pivot the proximal and the distal portions of the structure with respect to one another when the structure is in the deployed configuration. In some embodiments, the medical system further includes at least one flexible line arranged to physically couple the proximal and the distal portions of the structure together, the at least one flexible line manipulable to vary a distance between the proximal and the distal portions of the structure when the structure is in the deployed configuration.

The medical system may further include at least one actuator selectively operable to act on at least one of the proximal and the distal portions of the structure to distort a respective one of the first domed shape and the second domed shape when the structure is in the deployed configuration. Each of the first domed shape and the second domed shape may have a respective volume therein, and the medical system may further include at least one actuator selectively operable to act on the structure to vary the respective volume of at least one of the first domed shape and the second domed shape when the structure is in the deployed configuration. The medical system may further include at least one actuator selectively operable to act on at least one of the proximal and the distal portions of the structure to vary a difference between the respective volumes of the first and the second domed shapes when the structure is in the deployed configuration.

Each of the proximal and the distal portions of the structure may be arranged to pivot with respect to one another about a pivot location when the structure is in the deployed configuration. Each of the first domed shape and the second domed shape may include a respective apex and a respective height extending normally from a respective spatial plane to the respective apex, each respective spatial plane positioned to intersect the pivot location. The medical system may further include at least one actuator selectively operable to act on at least one of the proximal and the distal portions of the structure to vary at least one of a magnitude of the respective height of the first domed shape and a magnitude of the respective height of the second domed shape when the structure is in the deployed configuration.

The structure may further include a plurality of elongate members, each of the proximal and the distal portions of the structure comprising a respective portion of each elongate member of the plurality of elongate members. Each elongate member of at least some of the plurality of elongate members may cross at least one other elongate member of the plurality of elongate members at least at one location between the proximal and the distal portions of the structure when the structure is in the deployed configuration. Each elongate member of the plurality of elongate members may include a first end, a second end, and a respective length between the first end and the second end. Each elongate member of at least some of the plurality of elongate members may cross at least one other elongate member of the plurality of elongate members at each of a plurality of spaced apart locations along the respective length of at least the one other elongate member of the plurality of elongate members when the structure is in the deployed configuration. The plurality of spaced apart locations along the respective length of at least the one other elongate member of the plurality of elongate members may include at least one location between the respective portion of the one other elongate member of the plurality of elongate members comprised by the proximal portion of the structure and the respective portion of the one other elongate member of the plurality of elongate members comprised by the distal portion of the structure. At least some of the plurality of elongate members may be fanned with respect to one another about an axis that passes through a location between the proximal and the distal portions of the structure when the structure is in the deployed configuration.

Each elongate member of the plurality of elongate members may include a first end, a second end, an intermediate portion positioned between the first end and the second end, and a thickness, the respective intermediate portion of each elongate member including a front surface and a back surface opposite across the thickness from the front surface. The respective intermediate portions of the plurality of elongate members may be arranged front surface-toward-back surface in a stacked array when the structure is in the delivery configuration. The respective intermediate portion of each elongate member of at least some of the plurality of elongate members may include a slotted opening between the respective first and the second ends of the elongate member, at least two of the slotted openings arranged to cross one another when the structure is in the deployed configuration. The medical system may further include at least one actuator selectively operable to act on the structure to change a location where the at least two slotted openings cross one another when the structure is in the deployed configuration.

Various systems may include combinations and subsets of those summarized above.

A medical system may be summarized as including a structure that includes a plurality of elongate members. Each elongate member of the plurality of elongate members includes a plurality of ends including a proximal end and a distal end. Each elongate member of the plurality of elongate members further includes a respective intermediate portion positioned between the proximal and the distal ends of the elongate member, and a respective length between the proximal and the distal ends of the elongate member. The structure further includes a plurality of couplers arranged to physically couple each elongate member of the plurality of elongate members together with at least one other elongate member of the plurality of elongate members at each of at least two spaced apart locations along the respective length of the elongate member of the plurality of elongate members. A method employing the medical system may be summarized as including providing a catheter sheath that includes a first end, a second end and a lumen extending therebetween, and arranging the structure to have a size suitable for delivery though the lumen of the catheter sheath, each of the elongate members in the structure arranged to be advanced distal end first out from the lumen of the catheter sheath. The method includes expanding the structure to have a size too large for delivery through the lumen of the catheter sheath. The method includes providing at least one of a) relative movement between at least some of the ends in a first set of the proximal ends of the elongate members of the plurality of elongate members to reduce an end-to-end distance between the at least some of the ends in the first set during the expanding or b) relative movement between at least some of the ends in a second set of the distal ends of the elongate members of the plurality of elongate members to reduce an end-to-end distance between the at least some of the ends in the second set during the expanding.

The method may further include providing the relative movement between the at least some of the ends in the first set or between the at least some of the ends in the second set while restraining relative movement between at least some of the ends in the other of the first set and the second set along at least one direction during the expanding. The method may further include providing the relative movement between the at least some of the ends in the first set or between the at least some of the ends in the second set while restraining relative movement between the respective intermediate portions of at least some of the plurality of elongate members along at least one direction during the expanding.

The method may further include providing the relative movement between the at least some of the ends in the first set or between the at least some of the ends in the second set while decreasing a distance between the respective distal end and the respective proximal end of each of at least some of the plurality of elongate members during the expanding.

The method may further include arranging the respective intermediate portions of at least some of the plurality of elongate members to cross one another at a crossing location, and varying a respective distance between the crossing location and each of the at least some of the ends in the first set or each of the at least some of the ends in the second set. The method may further include arranging the respective intermediate portions of at least some of the plurality of elongate members to cross one another at a crossing location, and providing the relative movement between the at least some of the ends in the first set while varying a respective distance between the crossing location and each of the at least some of the ends in the first set or providing the relative movement between the at least some of the ends in the second set while varying a respective distance between the crossing location and each of the at least some of the ends in the second set. The method may further include arranging the respective intermediate portions of at least some of the plurality of elongate members to cross one another at a crossing location; varying a respective distance between the crossing location and at least a first one of the ends of the respective at least some of the ends in one of the first set and the second set by a first amount; and varying a respective distance between the crossing location and at least a second one of the ends of the respective at least some of the ends in the one of the first set and the second set by a second amount different from the first amount.

The method may further include arranging at least the respective intermediate portions of at least some of the plurality of elongate members to be angularly spaced with respect to one another about a first axis. The respective intermediate portion of each elongate member of the plurality of elongate members may include a thickness, a front surface and a back surface opposite across the thickness from the front surface, and arranging the structure to have the size suitable for delivery through the lumen of the catheter sheath may include arranging the respective intermediate portions of the elongate members with respect to one another front surface-toward-back surface in a stacked array.

Various methods may include combinations and subsets of those summarized above.

A medical system may be summarized as including a structure that includes a plurality of elongate members. Each elongate member of the plurality of elongate members includes a proximal end, a distal end, a respective intermediate portion positioned between the proximal and the distal ends, and a respective length between the proximal and the distal ends. The structure is selectively moveable between a delivery configuration in which the structure is sized to be delivered through a bodily opening leading to a bodily cavity, and a deployed configuration in which the structure is expanded to have a size too large to be delivered through the bodily opening leading to the bodily cavity. The respective intermediate portions of at least some of the plurality of elongate members are angularly spaced with respect to one another about a first axis and each of the at least some of the plurality of elongate members further includes a curved portion arranged to extend along at least a portion of a respective curved path that intersects the first axis at each of a respective at least two spaced apart locations along the first axis when the structure is in the deployed configuration. A portion of the structure is radially spaced from the first axis by a first dimension when the structure is in the deployed configuration. The medical system further includes at least one actuator operably coupled to the structure to selectively reduce a curvature of the respective curved portion of at least one of the at least some of the plurality of elongate members to increase the first dimension when the structure is in the deployed configuration.

The structure may include a second dimension along the first axis when the structure is in the deployed configuration, and the at least one actuator may be operably coupled to the structure to selectively reduce the curvature of the respective curved portion of the at least one of the at least some of the plurality of elongate members to increase the second dimension when the structure is in the deployed configuration. The at least one actuator may be operably coupled to the structure to selectively reduce the curvature of the respective curved portion of the at least one of the at least some of the plurality of elongate members to concurrently increase each of the first and the second dimensions. The second dimension may be an overall dimension of the structure along the first axis when the structure is in the deployed configuration. The first axis may pass through the at least one of the at least some of the plurality of elongate members at each of a first location and a second location spaced along the respective length of the at least one of the at least some of the plurality of elongate members from the first location when the structure is in the deployed configuration. The second dimension may be a dimension between the first location and the second location along the first axis.

The portion of the structure may include the respective curved portion of the at least one of the at least some of the plurality of elongate members when the structure is in the deployed configuration. The first axis may pass through the at least one of the at least some of the plurality of elongate members at a first location spaced along the respective length of the at least one of the at least some of the plurality of elongate members from one of the respective proximal end and the respective distal end of the at least one of the at least some of the plurality of elongate members, and the at least one actuator may be operably coupled to the structure to selectively reduce the curvature of the respective curved portion of the at least one of the at least some of the plurality of elongate members to reduce a distance between the first location and the one of the respective proximal end and the respective distal end of the at least one of the at least some of the plurality of elongate members when the structure is in the deployed configuration.

The respective intermediate portion of each elongate member of the plurality of elongate members may include a front surface and a back surface opposite across a thickness of the elongate member. At least the respective intermediate portions of the elongate members of the plurality of elongate members may be arranged with respect to one another front surface-toward-back surface in a stacked array when the structure is in the delivery configuration.

The first axis may pass through at least a first elongate member of the plurality of elongate members at two or more locations when the structure is in the deployed configuration. Each location of the two or more locations may be spaced from another location of the two or more locations along the respective length of at least the first elongate member of the plurality of elongate members. The two or more locations may include at least three locations spaced with respect to one another along the respective length of the first elongate member of the plurality of elongate members.

At least a first elongate member of the plurality of elongate members may cross a second elongate member of the plurality of elongate members in an X configuration at one or more locations along the respective length of the second elongate member spaced from each of the respective proximal end and the respective distal end of the second elongate member when the structure is in the deployed configuration. The structure may further include a plurality of couplers, each coupler of the plurality of couplers arranged to physically couple at least the second elongate member of the plurality of elongate members together with at least one other elongate member of the plurality of elongate members, each coupler of the plurality of couplers spaced from another of the plurality of couplers along the respective length of the second elongate member of the plurality of elongate members. At least one location of the one or more locations may be located along the respective length of the second elongate member of the plurality of elongate members between the respective locations of at least two of the plurality of couplers when the structure is in the deployed configuration. Each elongate member of the plurality of elongate members may be arranged to be advanced distal end first into the bodily cavity when the structure is in the delivery configuration, and at least one location of the one or more locations may be located along the respective length of the second elongate member of the plurality of elongate members relatively closer to the respective distal end of the second elongate member than a respective location of each of at least two of the plurality of couplers when the structure is in the deployed configuration.

Various systems may include combinations and subsets of those summarized above.

A medical system may be summarized as including a device that includes a plurality of elongate members. Each elongate member of the plurality of elongate members includes a first end, a second end, a respective length between the first end and the second end, a thickness, a respective front surface and a respective back surface opposite across the thickness. The plurality of elongate members include at least one elongate member that has a unitary or single piece structure having a plurality of portions arranged between the respective first end and the respective second end of the at least one elongate member. The plurality of portions include at least a first portion, a second portion and a third portion positioned between the first portion and the second portion. Each of the plurality of portions further includes a respective pair of side edges that form a portion of a periphery of at least one of the respective front surface and the respective back surface of the at least one elongate member. The third portion of the at least one elongate member includes a twist about a twist axis extending across at least part of the third portion of the at least one elongate member. The twist in the third portion of the at least one elongate member angularly offsets the second portion of the at least one elongate member from the first portion of the at least one elongate member about the twist axis. In the absence of the twist in the third portion of the at least one elongate member, the plurality of portions of the at least one elongate member are arranged such that the second portion of the at least one elongate member is laterally offset from the first portion of the at least one elongate member across at least a portion of the respective length of the at least one elongate member. At least part of the device is selectively moveable between a delivery configuration in which the elongate members of the plurality of elongate members are arranged in a first arrangement sized for intravascular or percutaneous delivery to a bodily cavity, and a deployed configuration in which the elongate members of the plurality of elongate members are arranged in a second arrangement sized too large for intravascular or percutaneous delivery to the bodily cavity.

The first portion of the at least one elongate member may be bent about a first axis having a directional component extending transversely across at least one of the respective pair of side edges of the first portion of the at least one elongate member when the at least part of the device is in the deployed configuration. The second portion of the at least one elongate member may be bent about a second axis having a directional component extending transversely across at least one of the respective pair of side edges of the second portion of the at least one elongate member when the at least part of the device is in the deployed configuration.

The twist in the third portion of the at least one elongate member may bias the at least one elongate member to autonomously fan with respect to at least one other elongate member of the plurality of elongate members when the plurality of elongate members are advanced into the bodily cavity. The first portion of the at least one elongate member may be preformed to autonomously bend about a first axis to urge the at least one elongate member to fan with respect to at least one other elongate member of the plurality of elongate members when the plurality of elongate members are advanced into the bodily cavity. The second portion of the at least one elongate member may be preformed to autonomously bend about a second axis when the plurality of elongate members are advanced into the bodily cavity. The first axis and the second axis may be non-parallel axes.

In use a first portion of the respective front surface of the at least one elongate member may face towards a first portion of an interior tissue surface within the bodily cavity and a second portion of the respective front surface of the at least one elongate member may face towards a second portion of the interior tissue surface within the bodily cavity when the at least part of the device is moved into the deployed configuration within the bodily cavity, the second portion of the interior tissue surface positioned diametrically opposite to the first portion of the interior tissue surface within the bodily cavity.

At least the second portion of the at least one elongate member may include a volute shape profile when the at least part of the device is in the deployed configuration. The at least one elongate member may include at least a first elongate member and a second elongate member. The respective second portion of the first elongate member may be laterally offset from the respective first portion of the first elongate member by a first distance across at least the portion of the respective length of the first elongate member in the absence of the twist in the respective third portion of the first elongate member, and the respective second portion of the second elongate member may be laterally offset from the respective first portion of the second elongate member by a second distance across at least the portion of the respective length of the second elongate member in the absence of the twist in the respective third portion of the second elongate member. The second distance may be different from the first distance.

The at least one elongate member may include multiple elongate members of the plurality of elongate members. The respective first portions of the elongate members of the multiple elongate members may be arranged front surface-toward-back surface along a first direction in a first stacked array when the at least part of the device is in the delivery configuration. The respective second portions of the elongate members of the multiple elongate members may be arranged front surface-toward-back surface along a second direction in a second stacked array when the at least part of the device is in the delivery configuration. The first direction and the second direction may be non-parallel directions.

The respective pair of side edges of each portion of the plurality of portions of the at least one elongate member may include a respective first side edge portion arranged on a first side of the at least one elongate member and a respective second side edge portion arranged on a second side of the at least one elongate member, the second side opposite to the first side. At least one of the first side edge portion and the second side edge portion of the second portion of the at least one elongate member may be laterally offset from the corresponding one of the first side edge portion and the second side edge portion of the first portion of the at least one elongate member across at least the portion of the respective length of the at least one elongate member in the absence of the twist in the third portion of the at least one elongate member. The respective first side edge of one of the first portion and the second portion of the at least one elongate member may converge with the respective first side edge of the third portion of the at least one elongate member to enclose an obtuse angle therebetween in the absence of the twist in the third portion of the at least one elongate member. The obtuse angle may extend across the at least one of the respective front surface and the respective back surface of the at least one elongate member towards the respective second side edge of at least one portion of the plurality of portions of the at least one elongate member.

The at least one elongate member may include a flexible circuit structure that includes at least one base layer and at least one electrically conductive layer patterned to provide at least one electrically conductive trace supported directly or indirectly by the at least one base layer, the at least one electrically conductive trace extending along a path across each of at least the first, the third and the second portions of the at least one elongate member. The at least one electrically conductive trace may include at least one jogged portion as viewed perpendicularly to a portion of the surface of the at least one base layer located at least proximate to a location on the surface of the at least one base layer where the path extends across the third portion of the at least one elongate member.

Various systems may include combinations and subsets of those summarized above.

A method for forming a portion of a medical system may be summarized as including providing a plurality of elongate members, each elongate member of the plurality of elongate members including a first end, a second end, a respective length between the first end and the second end, a thickness, a respective front surface and a respective back surface opposite across the thickness. Each elongate member of the plurality of elongate members further includes a plurality of portions arranged between the respective first end and the respective second end of the elongate member. The plurality of portions includes at least a first portion, a second portion and a third portion positioned between the first portion and the second portion. Each of the plurality of portions further includes a respective pair of side edges that form a portion of a periphery of at least one of the respective front surface and the respective back surface of the elongate member. The respective second portion of each elongate member of at least some of the plurality of elongate members is laterally offset from the respective first portion of the elongate member of the at least some of the plurality of elongate members across at least a portion of the respective length of the elongate member of the at least some of the plurality of elongate members. The method includes for each elongate member in the provided plurality of elongate members, distorting the respective third portion of the elongate member to rotationally offset the respective second portion of the elongate member from the respective first portion of the elongate member along the respective length of the elongate member. The method includes arranging each elongate member in the provided plurality of elongate members into an arrangement, the arrangement configurable to a size suitable for intravascular or percutaneous delivery through an opening in a tissue wall leading to a bodily cavity.

Distorting the respective third portion of the elongate member to rotationally offset the respective second portion of the elongate member from the respective first portion of the elongate member along the respective length of the elongate member may cause the respective third portion of the elongate member to have a twisted shape. Distorting the respective third portion of the elongate member to rotationally offset the respective second portion of the elongate member from the respective first portion of the elongate member along the respective length of the elongate member may include forming at least one twist in the respective third portion of the elongate member about a respective twist axis extending across at least part of the respective third portion of the elongate member.

The at least some of the plurality of elongate members that are provided may include at least a first elongate member and a second elongate member, and the method may further include forming at least one twist in the respective third portion of each of the provided first elongate member and the provided second elongate member about the respective twist axis of each of the provided first elongate member and the provided second elongate member to rotationally offset the respective second portion of the provided first elongate member from the respective first portion of the provided first elongate member along the respective length of the provided first elongate member by a first angular amount and to rotationally offset the respective second portion of the provided second elongate member from the respective first portion of the provided second elongate member along the respective length of the provided second elongate member by a second angular amount. The second angular amount may be different from the first angular amount.

The at least some of the plurality of elongate members that are provided may include at least a first elongate member and a second elongate member, the respective second portion of the provided first elongate member laterally offset from the respective first portion of the provided first elongate member by a first distance across at least the portion of the respective length of the provided first elongate member, and the respective second portion of the provided second elongate member laterally offset from the respective first portion of the provided second elongate member by a second distance across at least the portion of the respective length of the provided second elongate member. The second distance may be different from the first distance.

The method may further include selecting a set of the elongate members from the provided plurality of elongate members and forming at least one twist in the respective third portion of each elongate member in the set of the elongate members to at least in part cause at least the respective second portions of the elongate members in the set of the elongate members to be fanned with respect to one another when at least the respective first portions of each elongate member in the provided plurality of elongate members are arranged into the arrangement. The method may further include selecting a set of the elongate members from the provided plurality of elongate members and bending the respective first portion of each elongate member in the set of the elongate members about a respective bending axis to at least in part cause at least the respective second portions of the elongate members in the set of the elongate members to be fanned with respect to one another when at least the respective first portions of each elongate member in the provided plurality of elongate members are arranged into the arrangement. Each respective bending axis may be skewed with respect to at least one of the pair of side edges of the respective first portion of the associated elongate member in the set of the elongate members.

The method may further include selecting a set of the elongate members from the provided plurality of elongate members and bending the respective second portion of each elongate member in the set of the elongate members about a respective bending axis such that a first portion of the respective back surface of each elongate member of the set of the elongate members is positioned diametrically opposite to a second portion of the respective back surface of the elongate member in the set of the elongate members.

Arranging each elongate member in the provided plurality of elongate members in the arrangement may include arranging the respective first portions of each elongate member in the provided plurality of elongate members front surface-toward-back surface in a stacked array. The method may further include physically coupling the respective first portions of at least two of the elongate members in the provided plurality of elongate members together and physically coupling the respective second portions of the at least two of the elongate members in the provided plurality of elongate members together. The method may include providing a plurality of flexible circuit structures, each flexible circuit structure of the plurality of flexible circuit structures including at least one base layer and at least one patterned electrically conductive layer. The method may further include interleaving a portion of each flexible circuit structure of the provided plurality of flexible circuit structures with the respective first portions of each elongate member in the provided plurality of elongate members in the array. The respective at least one patterned electrically conductive layer of at least one of the provided plurality of flexible circuits may include at least one electrically conductive trace having at least one jogged portion formed by a patterning process. The method may further include securing each of the at least one of the provided plurality of flexible circuits to a respective one of the provided plurality of elongate members such that the at least one electrically conductive trace extends along a path across each of the first, the third and the second portions of the respective one of the provided plurality of elongate members with the at least one jogged portion of the at least one electrically conductive trace positioned at least proximate to the third portion of the respective one of the provided plurality of elongate members.

The respective pair of side edges of each portion of the plurality of portions of at least one elongate member of the plurality of elongate members may include a respective first side edge arranged on a first side of the at least one elongate member of the plurality of elongate members and a respective second side edge arranged on a second side of the at least one elongate member of the plurality of elongate members, the second side opposite to the first side. Providing the plurality of elongate members may include providing the plurality of elongate members such that at least one of the first side edge and the second side edge of the second portion of the at least one elongate member of the plurality of elongate members is laterally offset from the corresponding one of the first side edge and the second side edge of the first portion of the at least one elongate member of the plurality of elongate members. Providing the plurality of elongate members may include providing the plurality of elongate members such that the at least one elongate member of the plurality of elongate members includes at least one corner formed by a convergence of the respective first side edge of one of the first portion and the second portion of the at least one elongate member of the plurality of elongate members with the respective first side edge of the third portion of the at least one elongate member of the plurality of elongate members. The at least one corner may enclose an angle extending across the at least one of the respective front surface and the respective back surface of the at least one elongate member of the plurality of elongate members towards the respective second edge of at least one portion of the plurality of portions of the at least one elongate member of the plurality of elongate members.

Various methods may include combinations and subsets of those summarized above.

A medical system may be summarized as including a device that includes a plurality of transducer element sets and a plurality of flexible circuit structures. Each transducer element set includes one or more transducer elements. Each flexible circuit structure includes a respective at least one base layer, each at least one base layer including a first end, a second end, a respective length between the first end and the second end, a thickness, a respective front surface and a respective back surface opposite across the thickness, and a respective plurality of portions arranged between the first end and the second end. Each portion of the plurality of portions further includes a respective pair of side edges that form a portion of a periphery of at least one of the respective front surface and the respective back surface of the at least one base layer. Each respective plurality of portions further includes at least a first portion, a second portion and a third portion positioned between the first portion and the second portion. The respective third portion of each at least one base layer further includes a twist arranged to rotationally offset the second portion of the at least one base layer from the first portion of the at least one base layer along the respective length of the at least one base layer. Each flexible circuit structure further includes a respective at least one patterned electrically conductive layer. Each at least one patterned electrically conductive layer is arranged to provide at least one electrically conductive trace supported at least indirectly by the respective at least one base layer of the flexible circuit structure. Each at least one electrically conductive trace is electrically connected to a respective one of the plurality of transducer element sets, and each at least one electrically conductive trace extends along a path across each of the first, the third and the second portions of the respective at least one base layer of the flexible circuit structure. For each of at least some of the plurality of flexible circuit structures, the respective at least one electrically conductive trace includes at least one jogged portion as viewed normally to a portion of the front surface of the respective at least one base layer located at least proximate to a location on the front surface of the respective at least one base layer where the path extends across the respective third portion of the respective at least one base layer. At least part of the device is selectively moveable between an unexpanded configuration in which the flexible circuit structures of the plurality of flexible circuit structures are arranged in a first arrangement sized for delivery through a bodily opening leading to a bodily cavity, and an expanded configuration in which the flexible circuit structures of the plurality of flexible circuit structures are arranged in a second arrangement sized too large for delivery through the bodily opening leading to the bodily cavity.

The flexible circuit structures in the plurality of flexible circuit structures may be arranged such that the respective first portions of each at least one base layer are arranged front surface-toward-back surface in a first stacked array and the respective second portions of each at least one base layer are arranged front surface-toward-back surface in a second stacked array when the at least part of the device is in the unexpanded configuration. The flexible circuit structures in the plurality of flexible circuit structures may be arranged such that at least the respective second portions of each at least one base layer are arranged in a fanned array when the at least part of the device is in the expanded configuration. The twist in the respective third portion of the at least one base layer of each flexible circuit structure of the at least some of the plurality of flexible circuits may bias the respective second portion of the at least one base layer of the flexible circuit structure of the at least some of the plurality of flexible circuit structures into the fanned array as the plurality of flexible circuit structures are advanced into the bodily cavity.

The respective first portion of the at least one base layer of each flexible circuit structure of the at least some of the plurality of flexible circuit structures may be preformed to bend about a respective bending axis to bias the respective second portion of the at least one base layer of the flexible circuit structure of the at least some of the plurality of flexible circuit structures into the fanned array as the plurality of flexible circuit structures are advanced into the bodily cavity.

The respective second end of the at least one base layer of each of the at least some of the plurality of flexible circuit structures may move along a curved path that bends back on itself when the at least part of the device is selectively moved from the unexpanded configuration to the expanded configuration. At least part of the curved path may be a volute path. The respective second portion of the at least one base layer of each flexible circuit structure of the at least some of the plurality of flexible circuit structures may include a volute shape profile when the at least part of the device is in the expanded configuration. A first portion of the respective front surface of the at least one base layer of at least one of the plurality of flexible circuit structures may face towards a first portion of an interior tissue surface within the bodily cavity and a second portion of the respective front surface of the at least one base layer of the at least one of the plurality of flexible circuit structures may face towards a second portion of the interior tissue surface within the bodily cavity when the at least part of the device is moved into the expanded configuration within the bodily cavity, the second portion of the interior tissue surface positioned diametrically opposite to the first portion of the interior tissue surface within the bodily cavity.

Various systems may include combinations and subsets of those summarized above.

Various systems and methods may include combinations and subsets of all those summarized above.

In any of the above systems, at least some of the elongate members may each comprise respective ones of one or more transducers.

BRIEF DESCRIPTION OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn are not intended to convey any information regarding the actual shape of the particular elements, and have been solely selected for ease of recognition in the drawings.

FIGS. 4A, 4B, 4C, 4D and 4E are sequential elevation views of a portion of a device positioned within a bodily cavity at five successive intervals of time according to an illustrated embodiment, including a control unit illustrated in FIGS. 4B-4E.

FIGS. 6K and 6L are various isometric views of the elongate members of the device of FIG. 6A extending from the catheter sheath, the elongate members arranged in a second expanded or fanned array.

FIG. 6M is a sectioned side elevation view of the elongate members of the device of FIG. 6A extending from the catheter sheath, the elongate members arranged in a second expanded or fanned array.

FIGS. 7C, 7D, 7E, and 7F are various isometric views of the portion of the device of FIG. 7A extending at least partially from the catheter sheath and positioned at four successive intervals of time according to an example embodiment.

FIG. 7H is an isometric view of a representative flexible circuit structure provided to form at least a portion of a respective one of the elongate members employed by the device of FIG. 7A.

FIGS. 7L (A-A), 7L (B-B) and 7L (C-C) are various cross-sectional views of the arrangement of elongate members of FIG. 7L taken along section lines A-A, B-B and C-C, respectively.

DETAILED DESCRIPTION

Figure 1:
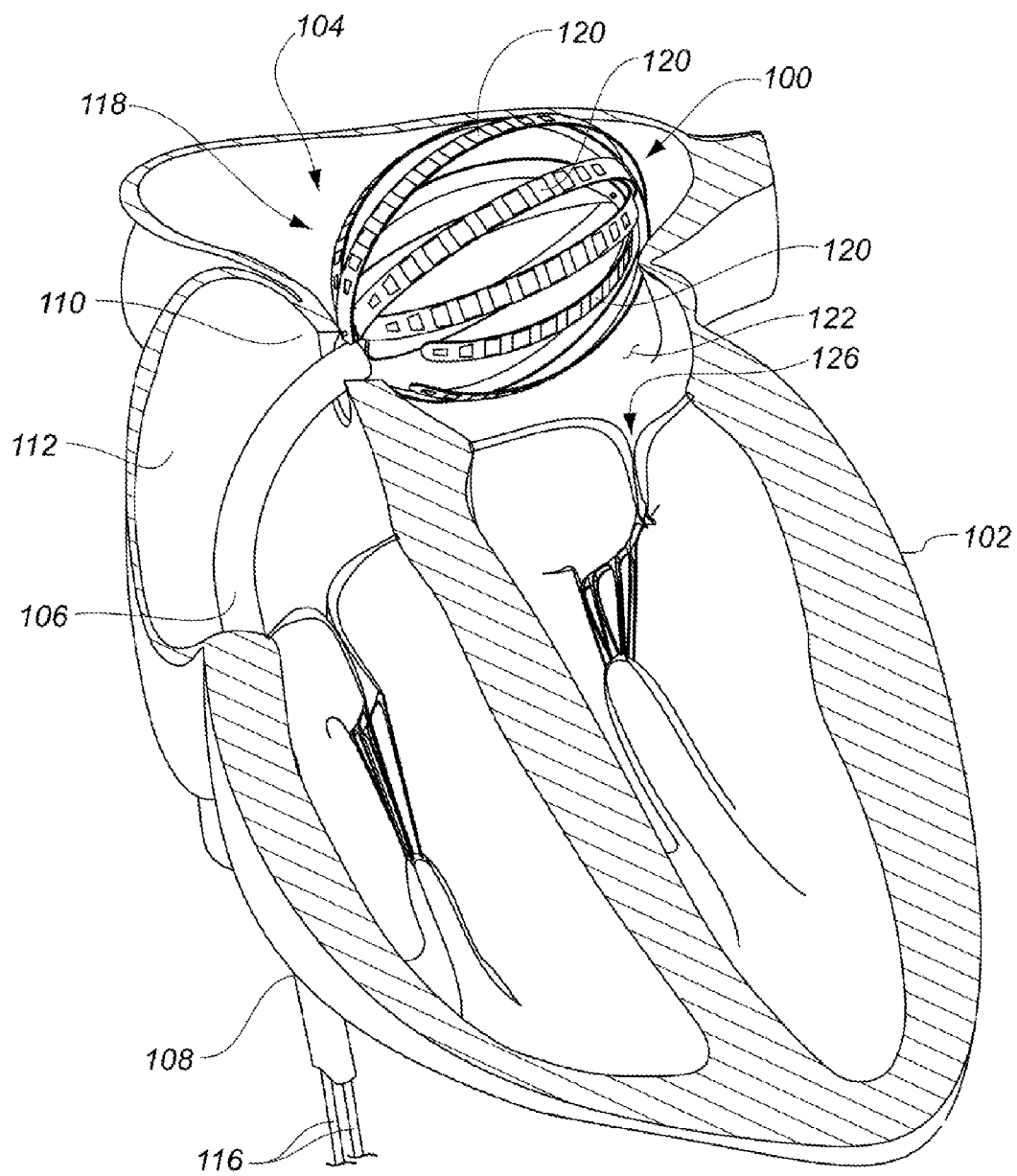
FIG. 1 is a cutaway diagram of a heart showing a medical device according to one illustrated embodiment percutaneously placed in a left atrium of the heart.

In the following description, certain specific details are set forth in order to provide a thorough understanding of various embodiments of the invention. However, one skilled in the art will understand that the invention may be practiced without these details. In other instances, well-known structures associated with Radio Frequency (RF) ablation and electronic controls such as multiplexers have not been shown or described in detail to avoid unnecessarily obscuring descriptions of the embodiments of the invention.

The word "ablation" should be understood to mean any disruption to certain properties of the tissue. Most commonly, the disruption is to the electrical conductivity and is achieved by heating, which can be generated with resistive or of Radio Frequencies (RF) techniques for example. Other properties, such as mechanical or chemical, and other means of disruption, such as optical, are included when the term "ablation" is used.

The word "fluid" should be understood to mean any fluid that can be contained within a bodily cavity or can flow into or out, or both into and out of a bodily cavity via one or more bodily openings positioned in fluid communication with the bodily cavity. In the case of cardiac applications, fluid such as blood will flow into and out of various intra-cardiac cavities (e.g., the left atrium and the right atrium).

The words "bodily opening" should be understood to be a naturally occurring bodily opening or channel or lumen; a bodily opening or channel or lumen formed by an instrument or tool using techniques that can include, but are not limited to, mechanical, thermal, electrical, chemical, and exposure or illumination techniques; a bodily opening or channel or lumen formed by trauma to a body; or various combinations of one or more of the above. Various elements having respective openings, lumens or channels and positioned within the bodily opening (e.g., a catheter sheath) may be present in various embodiments. These elements may provide a passageway through a bodily opening for various devices employed in various embodiments.

The word "tissue" should be understood to mean any tissue that is used to form a surface within a bodily cavity, a surface of a feature within a bodily cavity or a surface of a feature associated with a bodily opening positioned in fluid communication with the bodily cavity. The tissue can include part or all of a tissue wall or membrane that includes a surface that defines a surface of the bodily cavity. In this regard, the tissue can form an interior surface of the cavity that surrounds a fluid within the cavity. In the case of cardiac applications, tissue can include tissue used to form an interior surface of an intra-cardiac cavity such as a left atrium or right atrium.

The term "transducer element" in this disclosure should be interpreted broadly as any device capable of distinguishing between fluid and tissue, sensing temperature, creating heat, ablating tissue and measuring electrical activity of a tissue surface, or any combination thereof. A transducer element can convert input energy of one form into output energy of another form. Without limitation, a transducer element can include an electrode or a sensing device. A transducer element may be constructed from several parts, which may be discrete components or may be integrally formed.

Reference throughout this specification to "one embodiment" or "an embodiment" or "an example embodiment" or "an illustrated embodiment" means that a particular feature, structure or characteristic described in connection with the embodiment is included in at least one embodiment of the present invention. Thus, the appearances of the phrases "in one embodiment" or "in an embodiment" or "in an example embodiment" or "in this illustrated embodiment" in various places throughout this specification are not necessarily all referring to the same embodiment. Furthermore, the particular features, structures or characteristics may be combined in any suitable manner in one or more embodiments.

Various embodiments of percutaneously or intravascularly deployed medical devices are described herein. Many of the described devices are moveable between a delivery or unexpanded configuration in which a portion of the device is sized for passage though a bodily opening leading to cavity within a body, and a deployed or expanded configuration in which the portion of the device has a size too large for passage through the bodily opening leading to the cavity. In some example embodiments, the device senses characteristics (e.g., convective cooling, permittivity, force) that distinguish between fluid (e.g., blood) and tissue forming an interior surface of the bodily cavity. Such sensed characteristics allow a medical system to map the cavity, for example using positions of openings or ports into and out of the cavity to determine a position or orientation (i.e., pose), or both a position and orientation of the portion of the device in the bodily cavity. In some example embodiments, the devices are capable of ablating tissue in a desired pattern within the bodily cavity. In some example embodiments, the devices are capable of sensing characteristics (e.g., electrical activity) indicative of whether an ablation has been successful. In some example embodiments, the devices are capable of providing stimulation (e.g., electrical stimulation) to tissue within the bodily cavity. Electrical stimulation may include pacing.

An example of the mapping performed by devices according to various embodiments would be to locate the position of various bodily openings leading to the pulmonary veins as well as the mitral valve on the interior surface of the left atrium. In some example embodiments, the mapping is based at least on locating such bodily openings by differentiating between fluid and tissue. There are many ways to differentiate tissue from a fluid such as blood or to differentiate tissue from a bodily opening in case a fluid is not present. By the way of example, three approaches may include:

1. The use of convective cooling of heated transducer elements by the blood. A slightly heated arrangement of transducer elements that is positioned adjacent to the tissue that forms the interior surface(s) of the atrium and across the ports of the atrium will be cooler at the areas which are spanning the ports carrying blood flow. For example, commonly assigned U.S. Patent Application Publication 2008/0004534 A1, which is herein incorporated by reference in its entirety, describes a heart chamber mapping system based on the convective cooling effect of blood flow.

2. The use of the differing change in dielectric constant as a function of frequency between blood and tissue. An arrangement of transducer elements positioned around the tissue that forms the interior surface(s) of the atrium and across the ports of the atrium monitors the ratio of the dielectric constant from 1 KHz to 100 KHz. Such can be used to determine which of those transducer elements are not proximate to tissue, which is indicative of the locations of the ports.

3. The use of transducer elements that sense force (i.e., force sensors). A set of force detection transducer elements positioned around the tissue that forms the interior surface of the atrium and across the ports of the atrium can be used to determine which of the transducer elements are not in contact with the tissue, which is indicative of the locations of the ports.

FIG. 1 shows a device 100 useful in investigating or treating, or both investigating and treating a bodily organ, for example a heart 102, according to one illustrated embodiment.

Device 100 can be percutaneously or intravascularly inserted into a portion of the heart 102, such as an intra-cardiac cavity like left atrium 104. In this example, the device 100 is part of a catheter 106 inserted via the inferior vena cava 108 and penetrating through a bodily opening in transatrial septum 110 from right atrium 112. In other embodiments, other paths may be taken.

Catheter 106 includes an elongated flexible rod or shaft member appropriately sized to be delivered percutaneously or intravascularly. Catheter 106 may include one or more lumens (not shown). The lumen(s) may carry one or more communications or power paths, or both communications and power paths, for example one or more electrical conductors 116. Electrical conductors 116 provide electrical connections to device 100 that are accessible externally from a patient in which device 100 is inserted.

As discussed in more detail herein, device 100 includes a structure or frame 118 which assumes an unexpanded configuration for delivery to left atrium 104. Frame 118 is expanded (i.e., shown in an expanded configuration in FIG. 1) upon delivery to left atrium 104 to position a plurality of transducer elements 120 (only three called out in FIG. 1) proximate the interior surface formed by tissue 122 of left atrium 104. In this example embodiment, at least some of the transducer elements 120 are used to sense a physical characteristic of a fluid (i.e., blood) or tissue 122, or both, that may be used to determine a position or orientation (i.e., pose), or both of a portion of a device 100 within, or within respect to left atrium 104. For example, transducer elements 120 may be used to determine a location of pulmonary vein ostia (not shown) and/or a mitral valve 126. In this example embodiment, at least some of the transducer elements 120 may be used to selectively ablate portions of the tissue 122.

For example, some of the elements may be used to ablate a pattern around the bodily openings, ports or pulmonary vein ostia, for instance to reduce or eliminate the occurrence of atrial fibrillation.

Figure 2:
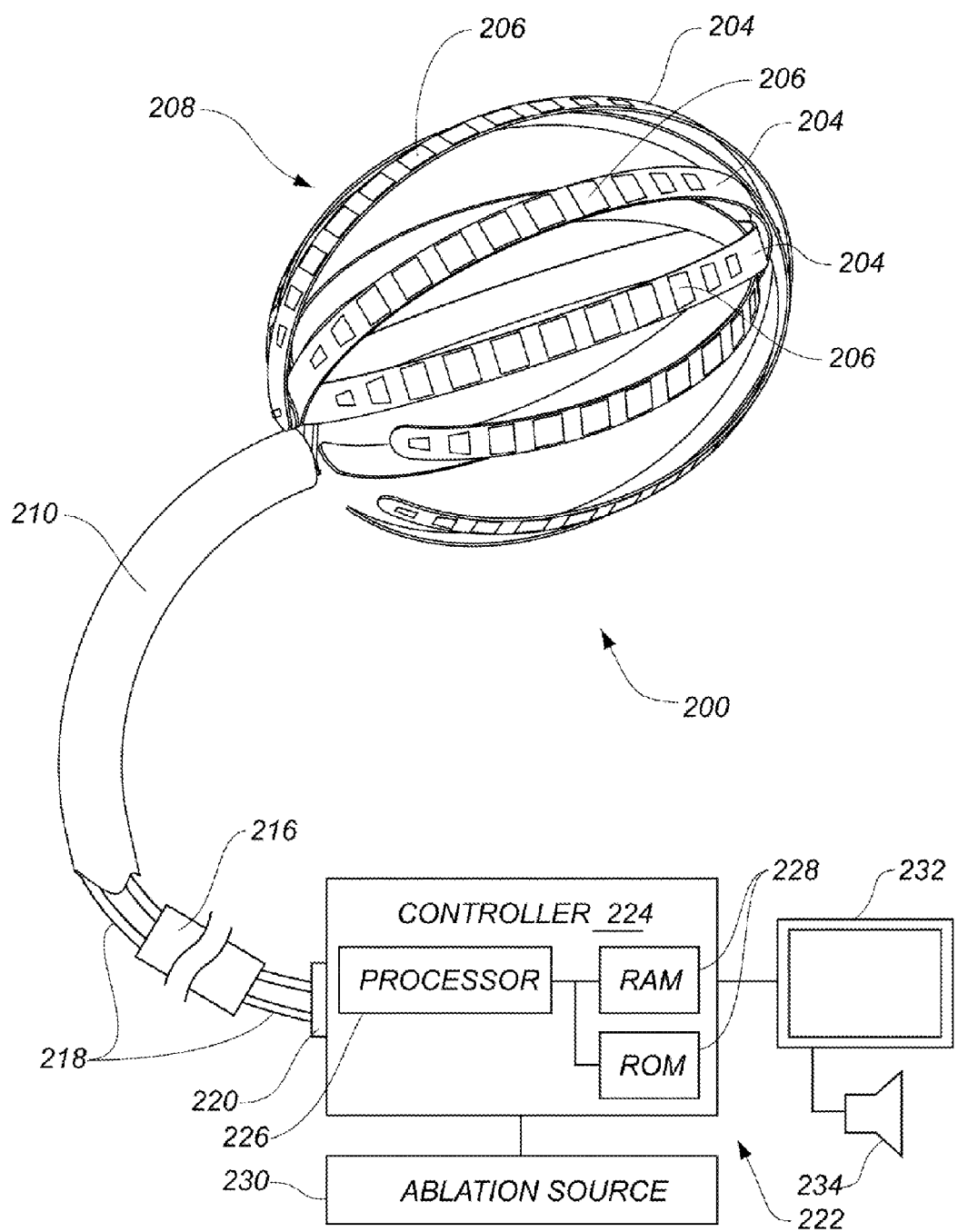
FIG. 2 is a partially schematic diagram of a medical system according to one illustrated embodiment, including a control unit, a display and a medical device having an expandable frame and an assembly of elements.

FIG. 2 schematically shows a system that includes a device 200 according to one illustrated embodiment. Device 200 includes a plurality of flexible strips 204 (three called out in FIG. 2) and a plurality of transducer elements 206 (three called out in FIG. 2) arranged to form a two- or three-dimensional grid or array capable of mapping, ablating, stimulating, or combinations thereof, an inside surface of a bodily cavity or lumen without requiring mechanical scanning. The flexible strips 204 are arranged in a framed structure 208 that is selectively movable between an unexpanded configuration and an expanded configuration that may be used to force flexible strips 204 against a tissue surface within the bodily cavity or position the flexible strips in the vicinity of the tissue surface. The flexible strips 204 can form part of a flexible circuit structure (i.e., also known as a flexible printed circuit board (PCB) circuit). The flexible strips 204 can include a plurality of different material layers. The expandable frame 208 can include one or more resilient members. The expandable frame 208 can include one or more elongate members. Each of the one or more elongate members can include a plurality of different material layers. Expandable frame 208 can include a shape memory material, for instance Nitinol. Expandable frame 208 can include a metallic material, for instance stainless steel, or non-metallic material, for instance polyimide, or both a metallic and non metallic material by way of non-limiting example. The incorporation of a specific material into expandable frame 208 may be motivated by various factors including the specific requirements of each of the unexpanded configuration and expanded configuration, the required position or orientation (i.e., pose), or both of expandable frame 208 in the bodily cavity or the requirements for successful ablation of a desired pattern.

Expandable frame 208, as well as flexible strips 204 can be delivered and retrieved via a catheter member, for example a catheter sheath introducer 210, which in some embodiments may have a diameter of about 24 French or smaller while in other embodiments may have a diameter of 16 French or smaller. In some instances, devices deliverable via larger or smaller sized catheter sheets may be employed. Flexible strips 204 may include one or more material layers. Flexible strips 204 may include one or more thin layers of Kapton® (polyimide), for instance 0.1 mm thick. Transducer elements (e.g., electrodes or sensors, or both) 206 may be built on the flexible strips 204 using conventional printed circuit board processes. An overlay of a thin electrical insulation layer (e.g., polyimide about 10-20 microns thick) may be used to provide electrical insulation, except in areas needing electrical contact to blood and tissue. In some embodiments, flexible strips 204 can form a portion of an elongated cable 216 of control leads 218, for example by stacking multiple layers, and terminating at a connector 220. In some example embodiments, flexible strips 204 are formed from flexible substrates onto which electrically conductive elements (e.g., conductive lines or traces) are provided. In some example embodiments flexible strips 204 form flexible circuit structures. In some example embodiments, a portion of device 200 is typically disposable.

Device 200 can communicate with, receive power from or be controlled by a control system 222, or combinations thereof. The control system 222 may include a controller 224 having one or more processors 226 and one or more non-transitory storage mediums 228 that store instructions that are executable by the processors 226 to process information received from device 200 or to control operation of device 200, or both. For example, controller 224 can control activating selected transducer elements 206 to ablate tissue. Controller 224 may include one or more controllers. Control system 222 may include an ablation source 230. The ablation source 230 may, for example, provide electrical current or power, light or low temperature fluid to the selected transducer elements 206 to cause ablation. The ablation source may include an electrical current source or an electrical power source. Control system 222 may also include one or more user interface or input/output (I/O) devices, for example one or more displays 232, speakers 234, keyboards, mice, joysticks, track pads, touch screens or other transducers to transfer information to and from a user, for example a care provider such as a physician or technician. For example, output from the mapping process may be displayed on a display 232.

In some embodiments, a frame provides expansion and contraction capabilities for a portion of the medical device (e.g., arrangement or array of transducer elements) used to distinguish between blood and tissue. The transducer elements used to sense a parameter or characteristic to distinguish between a fluid such as blood and tissue may be mounted or otherwise carried on a frame, or may form an integral component of the frame itself. The frame may be flexible enough to slide within a catheter sheath in order to be deployed percutaneously or intravascularly. FIG. 2, discussed previously, showed one embodiment of such a frame.

Figure 3A:
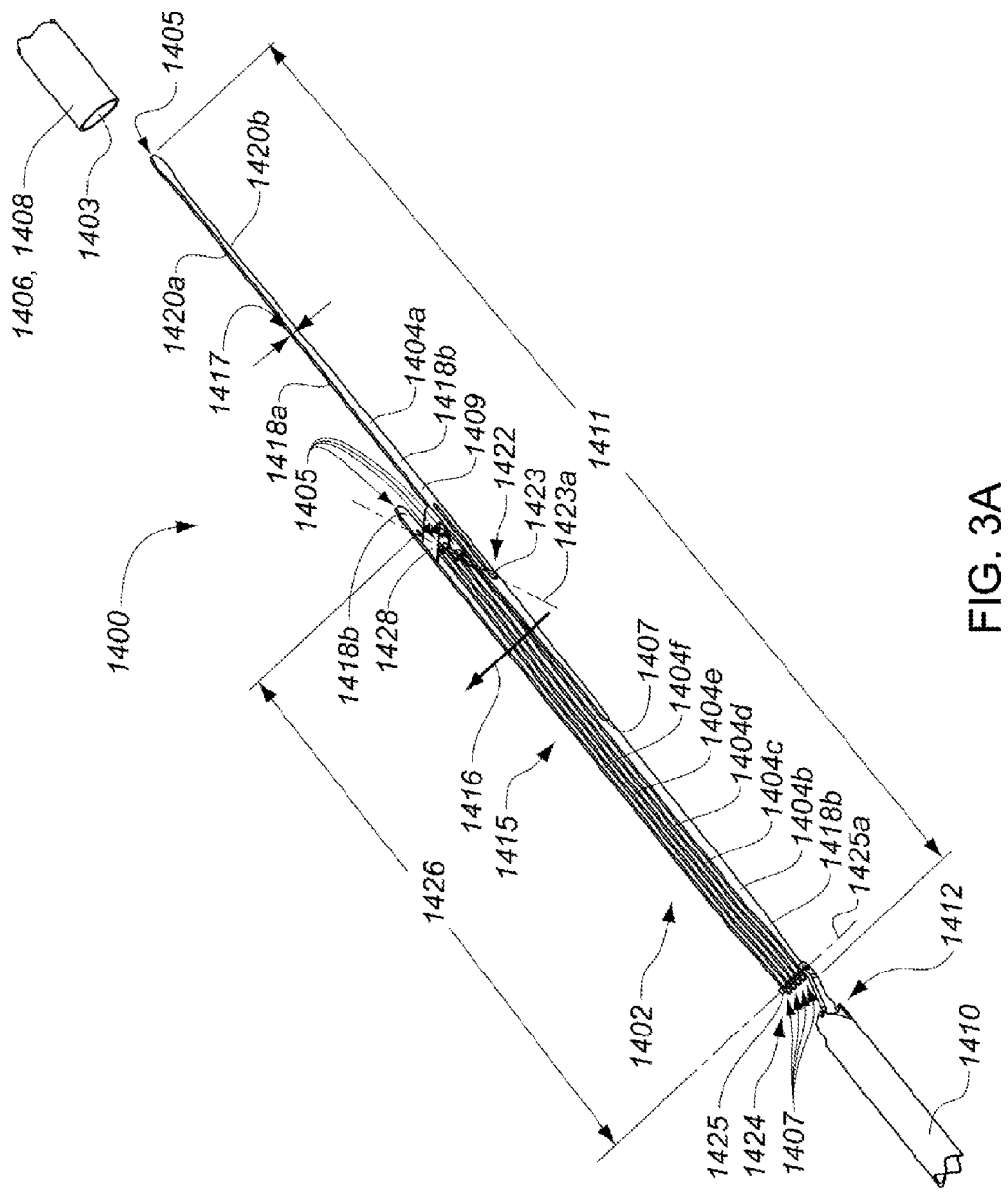
FIG. 3A is an isometric view of a frame in a first or unexpanded configuration according to one illustrated embodiment.
Figure 3B:
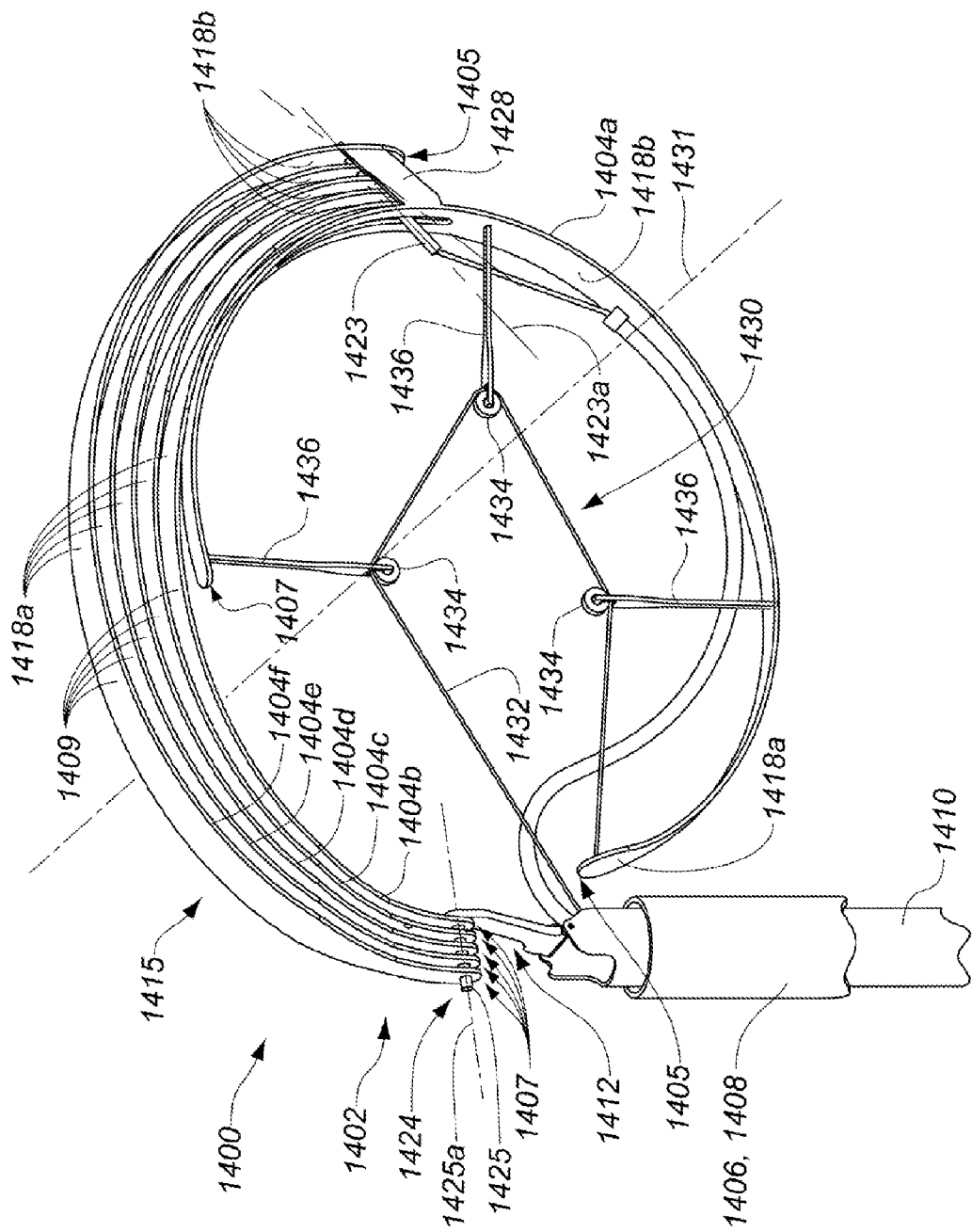
FIG. 3B is an isometric view of an example of the frame of FIG. 3A in a second or bent configuration.
Figure 3C:
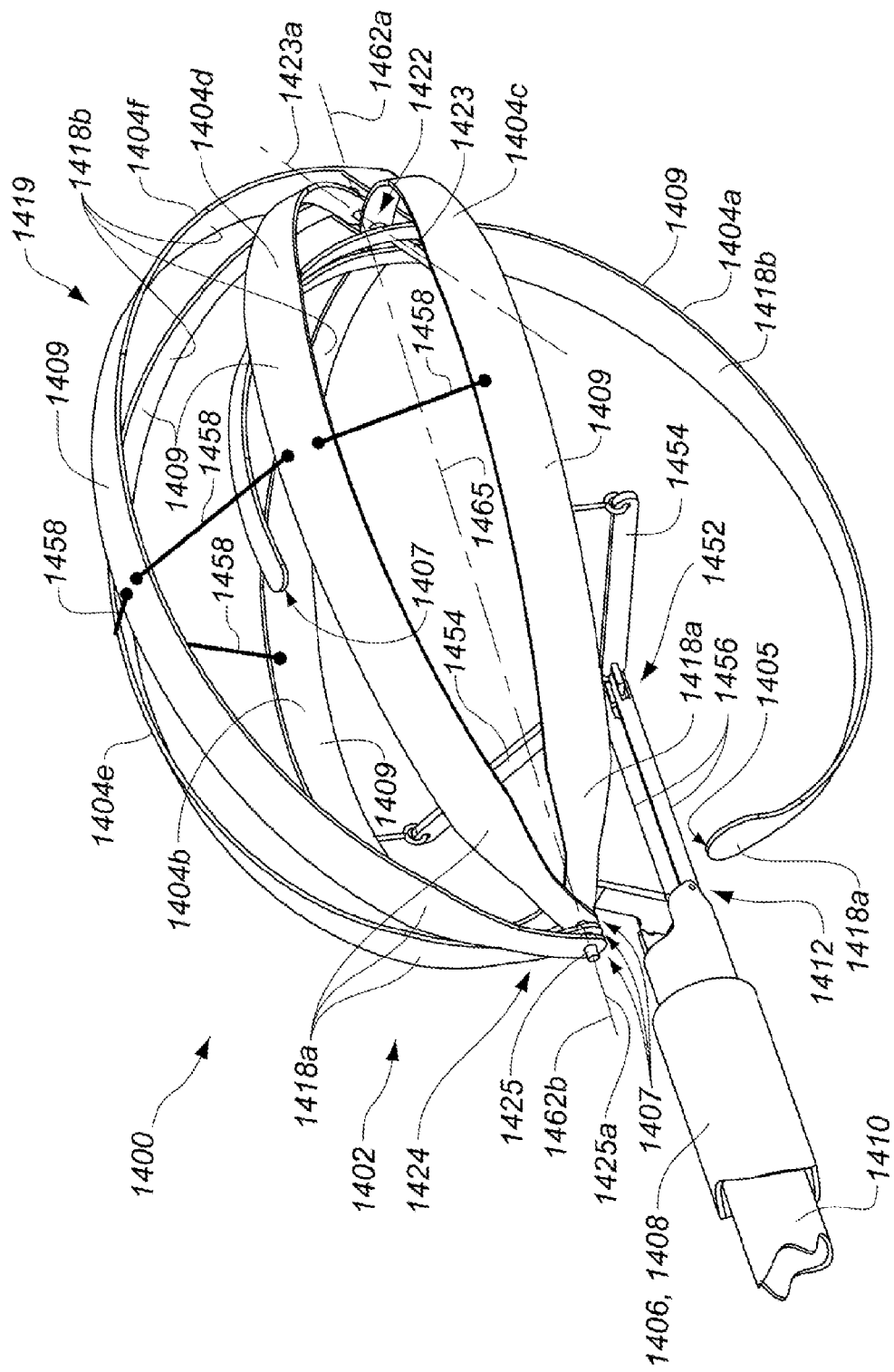
FIG. 3C is an isometric view of an example of the frame of FIG. 3A in a third or expanded configuration.

FIGS. 3A, 3B and 3C show a portion of the medical device 1400 in various configurations. Specifically, FIG. 3A shows that the portion of the device 1400 includes a structure or frame 1402 made from a plurality of elongate members 1404a, 1404b, 1404c, 1404d, 1404e and 1404f (collectively 1404). The elongate members 1404 can be selectively arranged in one of a plurality of different arrangements. The elongate members 1404 can be selectively moved between various different configurations. The portion of the device 1400 (i.e., including frame 1402) is shown in a first, or an unexpanded configuration suitably sized for delivery within a catheter sheath 1406 of a catheter system 1408 in FIG. 3A. In some embodiments, employed catheter sheaths may be steerable devices with a portion thereof deflected by an actuator contained in a control portion (e.g., a handle portion). Various levers, knobs, wheels, pulleys, sheathes, etcetera may be employed to steer a deflectable portion of a catheter sheath. Catheter system 1408 is employed to percutaneously or intravascularly deliver a portion of device 1400 through a bodily opening leading to a bodily cavity such as an intra-cardiac cavity (not shown) by way of non-limiting example. FIG. 3B shows the portion of device 1400 including frame 1402 in a second or bent or expanded and unfanned configuration. In this embodiment, the second/bent configuration is assumed as various portions of frame 1402 are advanced from catheter sheath 1406. FIG. 3C shows the portion of device 1400 including frame 1402 in a third, or expanded configuration. In this illustrated embodiment, the third or expanded or fanned configuration is also alternatively referred to in this application as a fanned configuration, expanded configuration or expanded fanned configuration. The portion of device 1400 including frame 1402 can assume either of the second/bent or the third/expanded or fanned configuration when positioned within the bodily cavity (not shown) by way of example. In this illustrated embodiment, the first configuration is an example of a delivery configuration in which a portion of frame 1402 is suitably sized for delivery through a bodily opening leading to a bodily cavity. In this illustrated embodiment, each of the second and the third configurations is an example of a deployed configuration in which various portions of frame 1402 are manipulated to have a size too large for delivery through the opening leading to the bodily cavity. The portion of device 1400 including frame 1402 is moved into the third/expanded or fanned configuration from the second/bent configuration in this embodiment. In this illustrated embodiment, frame 1402 is sized too large for delivery through catheter sheath 1406 when frame 1402 is in either of the second/bent configuration or the third/expanded or fanned configuration.

Figure 3D:
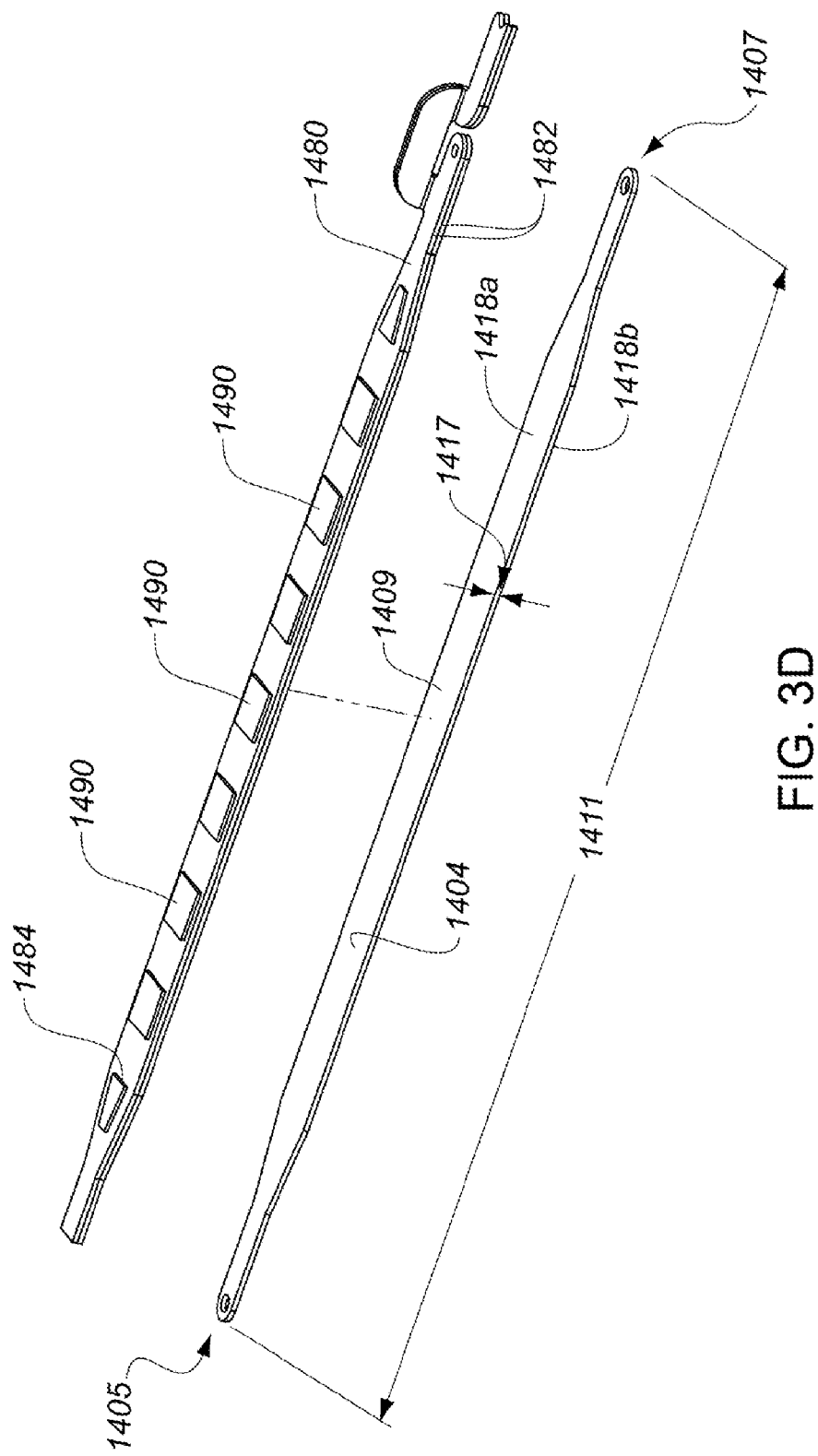
FIG. 3D is an exploded isometric view of an elongate member including a flexible circuit structure employed in the frame of FIG. 3A.

In a manner similar to that described in some previous embodiments, various transducer elements may be carried into a bodily cavity by various ones of elongate members 1404. In some embodiments, various transducer elements can be provided on, or by, various flexible circuit structures made up of various flexible substrates which can include by way of non-limiting example, elongate member 1404 itself. FIG. 3D shows an exploded view of an elongate member 1404 and a flexible circuit structure 1480. Flexible circuit structure 1480 can include one or more flexible substrates 1482 (i.e., two in this illustrated embodiment) and at least one electrically conductive layer 1484. In this example embodiment, the at least one conductive layer 1484 has been patterned to form a plurality of transducer elements 1490 (three called out). In this embodiment, the at least one conductive layer 1484 has been patterned to form a plurality of electrodes. Various ones of the at least one conductive layers can be patterned to form other features and elements including conductive traces or lines by way of non-limiting example. For clarity, various transducer elements 1490 associated with device 1400 are not shown in FIGS. 3A, 3B and 3C. For clarity, various flexible circuit structures 1480 associated with device 1400 are not shown in FIGS. 3A, 3B and 3C.

The elongate members 1404 may be transported by a transporter through catheter sheath 1406. In this embodiment, the elongate members 1404 are transported by shaft member 1410 through catheter sheath 1406. Shaft member 1410 is typically sized to extend along a path that leads from a location outside the body to a destination at least proximate to the cavity within the body. Shaft member 1410 is typically a flexible member. Shaft member 1410 can include various lumens and passageways (not shown) some of which can be employed as conduits for various control lines, actuators, force transmitters, irrigation channels, suction channels, etcetera. In this embodiment, wrist coupler 1412 articulably couples the frame 1402 to shaft member 1410. In other example embodiments, other articulated or non-articulated couplers can be employed to couple the frame 1402 to shaft member 1410. In some example embodiments, a handle (not shown) can be provided at an end of shaft member 1410 opposite to wrist coupler 1412. The handle may be employed by a care provider to help manipulate the shaft member 1410 through catheter sheath 1406 in some embodiments. The handle may include various controls or actuators, or both, employed for manipulation of various portions of device 1400. In some embodiments, shaft member 1410 may be a steerable device with a portion thereof deflected by an actuator contained in a control portion (e.g., a handle portion). Various levers, wheels, pulleys, sheathes may be employed to steer a deflectable portion of shaft member 1410.

While six (6) elongate members 1404 are shown in this illustrated embodiment, some embodiments may employ a greater or a fewer number of elongate members 1404. The present inventors have built devices having fewer than six (6) elongate members (e.g., three (3) elongate members) in some embodiments and more than six (6) elongate members (e.g., eleven (11) elongate members) in other embodiments by way of non-limiting example.

As best shown in FIG. 3D, each of the elongate members 1404 includes a respective distal or first end 1405, a respective proximal or second end 1407, a respective intermediate portion 1409 positioned between the first end 1405 and the second end 1407, and respective length 1411 between the first end 1405 and the second end 1407. In this embodiment, various ones of the elongate members 1404 has a different respective length 1411 than the respective length 1411 of another of the elongate members 1404. In other embodiments, two or more of the elongate members 1404 may have substantially equal lengths 1411. In this embodiment, each of the elongate members 1404 is compliant about at least one axis. Various embodiments can include elongate members 1404 that are pliable, flexible or resilient elongate members. Various embodiments can include elongate members 1404 that have a different bending stiffness when bent about each of a plurality of differently oriented axes.

As shown in FIG. 3A, the elongate members 1404 are arranged successively with respect to one another in a stacked arrangement 1415 when the portion of device 1400 is in the first/unexpanded configuration. In this embodiment, the arrangement of the elongate members 1404 in the stacked arrangement 1415 is an orderly one with each of the elongate members arranged successively with respect to one another along a first direction (i.e., a stacking direction) represented by arrow 1416. It is understood that the first direction need not be a vertical or "up-down" direction but can also include other orientations. For instance in some embodiments, elongate members 1404 which are successively adjacent one another along the first direction 1416 may be stepped with respect to one another in one or more other directions. Thus, the set of elongate members 1404 may be arranged in a non-stepped stacked arrangement fitting in a rectangular parallelepiped or may be arranged in a stepped stacked arrangement for instance fitting in a non-rectangular parallelepiped.

In the illustrated example embodiment, each of the elongate members 1404 is a strip-like member. In this example embodiment, the intermediate portion 1409 of each of the elongate members 1404 includes a set of two opposing surfaces or major faces 1418 made up of a first surface 1418*a* (i.e., also referred to as front surface 1418*a*) (one called out in FIG. 3A) and a second surface 1418*b* (i.e., also referred to as back surface 1418*b*) (three called out in FIG. 3A). In this example embodiment, the two opposing surfaces 1418 are separated from one another across a thickness 1417 (only one called out in FIG. 3A) of the elongate member 1404. In this illustrated example, the two opposing surfaces 1418 are joined by a set of two opposing edge surfaces 1420*a* and 1420*b* (collectively 1420) (only one set called out in FIG. 3A) and hence spaced from each other by the thickness of the edge surfaces 1420*a*, 1420*b*. In this illustrated embodiment, the surfaces 1418 are arranged successively with respect to one another in the stacked arrangement 1415. In this embodiment, the elongate members 1404 are successively arranged in an arrayed arrangement sized to be delivered through a lumen of catheter sheath 1406, with each elongate member 1404 positioned in the arrayed arrangement such that the first surface 1418*a* of the elongate member 1404 is towards the second surface 1418*b* of an additional elongate member 1404 in the arrayed arrangement, or the second surface 1418*b* of the elongate member 1404 is towards the first surface 1418*a* of the additional elongate member 1404 in the arrayed arrangement, or both. For example, one of the outermost elongate members in the arrayed arrangement (i.e., elongate member 1404*a*) is positioned in the arrayed arrangement such that its first surface 1418*a* is towards the second surface 1418*b* of elongate member 1404*b*. Outermost elongate member 1404*f* is positioned in the arrayed arrangement such that its second surface 1418*b* is towards the first surface 1418*a* (not called out) of elongate member 1404*e*. An inboard elongate member in the arrayed arrangement such as elongate member 1404*d* is positioned such that its first surface 1418*a* (not called out) is positioned towards the second surface 1418*b* (not called out) of elongate member 1404*e* and the second surface 1418*b* (not called out) of elongate member 1404*d* is towards the first surface 1418*a* (not called out) of elongate member 1404*c*. In this example embodiment, the first and the second surfaces 1418*a*, 1418*b* of the elongate members 1404 are interleaved in the stacked arrangement 1415.

In various embodiments, each of the elongate members 1404 has at least one surface that has a common characteristic with, or corresponds to, at least one surface of each of the other elongate members 1404, and the elongate members 1404 are arranged in an arrayed arrangement or stacked arrangement such that the at least one surfaces of the elongate members 1404 are successively arranged along the first direction of stacked arrangement 1415. In this respect, it is noted that the stacked arrangement does not require that the individual elongated members 1404 actually rest on one another. In many instances of the stacked arrangement, the elongated members or portions thereof may be separated from successively adjacent elongate members, for instance by space, such as in an embodiment of an interleaved arrangement. In some of these various embodiments, each at least one surface is a first surface that is positionable adjacent to a tissue surface in the bodily cavity when the portion of device 1400 is in the third/expanded configuration within the bodily cavity. In some of these various embodiments, each at least one surface is a first surface that is positionable to face or contact a tissue surface in the bodily cavity when the portion of device 1400 is moved into the third/expanded configuration within the bodily cavity. In some of these various embodiments, each at least one surface is a first surface that includes, or supports (i.e., directly or indirectly) one or more transducer elements. In some of these various embodiments, each at least one surface is a first surface that includes, or supports (i.e., directly or indirectly) one or more transducer elements (e.g., an electrode) that are positionable adjacent to a tissue surface in the bodily cavity when the portion of device 1400 is in the third/expanded configuration within the bodily cavity. In some of these various embodiments, each at least one surface is a first surface that includes, or supports (i.e., directly or indirectly) a flexible circuit structure. In some of these various embodiments, each at least one surface is a second surface that is positionable to face away from a tissue surface in the bodily cavity when the portion of device 1400 is in the third/expanded configuration within the bodily cavity. In some of these various embodiments, each at least one surface is arranged to face away from an axis about which the elongate members 1404 are angularly spaced when the portion of device 1400 is in the third/expanded configuration.

In some embodiments, the elongate members 1404 are arranged successively adjacent to one another. In some embodiments, partial or full separations or gaps can be present between two elongate members 1404 of various ones of the successive pairs of elongate members 1404 in stacked arrangement 1415. Substantially uniform separations or varying sized separations between the two elongate members 1404 of each successive pair of the elongate members 1404 in the stacked arrangement 1415 can be present. In some example embodiments, various other elements may be disposed between two elongate members 1404 of various ones of the successive pairs of the elongate members 1404 in the stacked arrangement 1415. For example, various transducer elements may be positioned between two elongate members 1404 of various ones of the successive pairs of the elongate members 1404 in the stacked arrangement 1415. The elongate members 1404 can be linearly arrayed along the first direction (i.e., as represented by arrow 1416) in the stacked arrangement 1415. In some embodiments, at least three elongate members 1404 are linearly arrayed along a first direction (i.e., as represented by arrow 1416) in an arrayed arrangement. In some embodiments, at least three elongate members 1404 are successively arranged with respect to one another along a first direction (i.e., as represented by arrow 1416) in the stacked arrangement 1415.

Figure 3E:
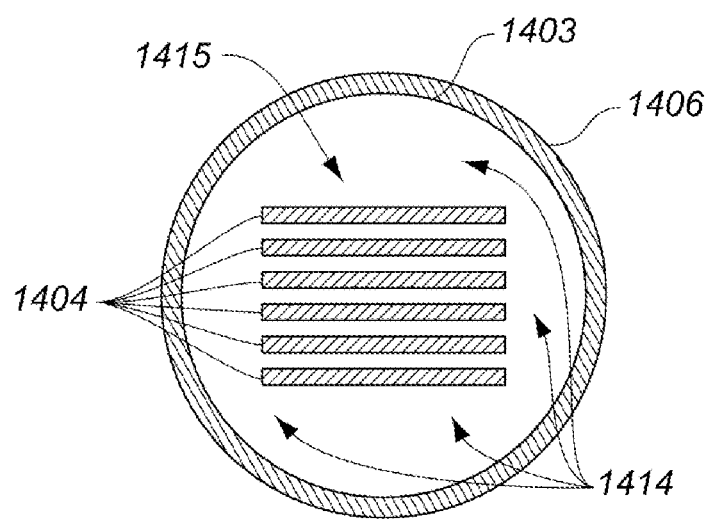
FIG. 3E is a cross-sectional view of the frame of FIG. 3A in a catheter sheath.

Elongate members 1404 may be substantially planar members or may have some initial curvature when the portion of device 1400 is in the first/unexpanded configuration. At least one of surfaces 1418*a* and 1418*b* need not be a flat surface. In this example embodiment, elongate members 1404 have a shape that allows them to be successively stacked in stacked arrangement 1415. FIG. 3E shows a cross-section view of stacked arrangement 1415 in a lumen 1403 of catheter sheath 1406 as viewed through lumen 1403. Stacked arrangement 1415 advantageously allows elongate members 1404 to be arranged in a substantially spatially efficient manner to allow for delivery through catheter sheaths 1406, enabling a reduced dimension (e.g., a diameter dimension) of catheter sheath 1406. FIG. 3E shows that additional space 1414 within lumen 1403 is also advantageously provided for control lines, actuators and force transmission members (all not shown). Various conventional "basket-type" catheter systems that include resilient members that "spring" outwardly when they are advanced from a catheter sheath into a bodily typically are arranged in a relatively bulky and random or quasi-random arrangement when they are delivered within a catheter sheath which can disadvantageously require the use of larger catheter sheaths. Larger catheter sheaths can also be required for conventional "basket-type" catheter systems that employ buckling mechanisms that outwardly buckle an arrangement of members. Larger catheter sheaths can also be required for conventional ablator systems that employ a substrate that is required to fold upon itself for delivery though the catheter sheath as is the case with various conventional inflatable balloon or bladder based catheter systems.

Advantageously, the strip-like elongate members 1404 in this embodiment additionally allows for a reduced bending stiffness about a bending axis arranged perpendicularly to the first or stacking direction of the elongate members 1404 in stacked arrangement 1415, especially when the elongate members are allowed to slide relatively with respect to one another during the bending. A reduced bending stiffness can facilitate the delivery of the stacked arrangement 1415 through catheter sheath 1406 especially when catheter sheath 1406 extends along a tortuous path to a bodily cavity. The members in many conventional basket-type catheter systems are coupled together in a manner that typically disadvantageously limits sliding movement between the members in a manner that can adversely impact delivery through a catheter sheath. As shown in FIG. 3A, a portion of elongate member 1404a is cantilevered from stacked arrangement 1415 in this embodiment. In this illustrated embodiment, the second end 1407 of elongate member 1404a is positioned between the respective first and the second ends 1405, 1407 of each of the other elongate members 1404 in stacked arrangement 1415. In this illustrated embodiment, the length 1411 of elongate member 1404a is greater than each of the respective lengths 1411 of the other elongate members 1404 in stacked arrangement 1415.

The elongate members 1404 may be constructed from various materials including, but not limited to, various metal and non-metal compositions, composite materials such as carbon fiber, or flexible PCB substrates with a fiberglass or Nitinol backing. The elongate members 1404 can include one or more material layers. The elongate members 1404 may form an integral component of the transducer elements 1490. When the transducer elements (e.g., transducer elements 1490) form an integral component of the frame 1402, various material components used in the frame may require various mechanical and electrical properties. If the device 1400 is distinguishing between blood and tissue by sensing convective cooling associated with a moving fluid (i.e., the blood), the material used for at least part of each of various ones of the elongate members 1404 preferably has a measurable change in resistance with temperature that is independent of elongate member 1404 deformation. In some embodiments, a resistance of several ohms per centimeter or higher is preferable as it will reduce the amount of current needed to heat the transducer element. The elongate members 1404 may also act as a support for a secondary assembly that carries the sensing and ablation transducer elements. An example of this is a stainless steel or Nitinol structure used to support transducer elements made with a flexible PCB circuit structure. In this embodiment, elongate members 1404 are resilient metallic elongate members. In this example embodiment, each of elongate members 1404b, 1404c, 1404d, 1404e and 1404f and are made from 17-7 stainless steel while elongate member 1404a is made from Nitinol. The use of Nitinol may be advantageous when a portion of an elongate member 1404 is to be subjected to relative tighter bending conditions or greater angular deflections.

In various embodiments, one or more couplers or joints are employed to physically couple some or all of the elongate members 1404 together in stacked arrangement 1415. In various embodiments, two or more couplers or joints are employed to physically couple some or all of the elongate members 1404 in stacked arrangement 1415. In some example embodiments, at least one of the couplers or joints is employed to pivotally or articulably or articulatably (used interchangeably herein) couple at least some of the elongate members 1404 together in stacked arrangement 1415. In this illustrated embodiment, a first coupler 1422 and a second coupler 1424 couple various ones of the elongate members 1404 together. In this example embodiment, second coupler 1424 pivotally couples some of the elongate members 1404 (i.e., 1404b, 1404c, 1404d, 1404e and 14040 together at a location proximate the respective second ends 1407 of these elongate members 1404. In this embodiment, first coupler 1422 pivotally couples each of the elongate members 1404 (i.e., 1404a, 1404b, 1404c, 1404d, 1404e and 14040 together at a location spaced from second coupler 1424 along the respective lengths 1411 of each of the elongate members 1404. In this embodiment, all of the elongate members 1404 are pivotally coupled together directly by first coupler 1422 while only some, but not all of the elongate members 1404 are directly pivotally coupled together by second coupler 1424. It is noted however, that in this illustrated embodiment, elongate member 1404a is fixedly coupled to elongate member 1404f by offset member 1428 and is thereby indirectly pivotally coupled to another of the elongate members 1404 by second coupler 1424. In some example embodiments, each of the elongate members in a stacked arrangement is directly pivotally or articulably coupled to another of the elongate members in the stacked arrangement by each of at least two couplers or joints.

In this illustrated embodiment, each of the first and the second couplers 1422, 1424 respectively include first pivot member 1423 and second pivot member 1425 arranged to pivotally couple various ones of the elongate members 1404 together in stacked arrangement 1415. Second pivot member 1425 is spaced apart from first pivot member 1423 along a respectively coupled one of the elongate members 1404 by a respective length 1426 (only one called out in FIG. 3A) along the elongate member 1404. Each length 1426 can vary as the stacked arrangement 1415 is moved between the first/unexpanded configuration and the second/bent configuration or between the second/bent configuration and the third/expanded or fanned configuration. In this example embodiment, each of the first pivot member 1423 and the second pivot member 1425 takes the form of a pin about which various ones of the elongate members 1402 is configured to turn, revolve or rotate about when the stacked arrangement 1415 is moved to or from the third/expanded or fanned configuration shown in FIG. 3C. In this embodiment, each of the pivot members 1423, 1425 includes two opposing ends and a longitudinal axis extending between the opposing ends. Specifically, first longitudinal axis 1423a is associated with first pivot member 1423 and second longitudinal axis 1425a is associated with second pivot member 1425. In this embodiment, each of the first and the second pivot members 1423, 1425 is sized to be received in a respective opening provided in various ones of the elongate members 1404. Each of the first and the second pivot members 1423, 1425 can include restraining features (not shown) that additionally restrain the elongate members 1404 from axially escaping from the pivot members. Suitable restraining features can be formed by welding operations, heading operations, machining operations or assembly operations in which additional components are physically coupled to the pivot members 1423, 1425.

In other embodiments, other forms of couplings can be employed to physically couple two or more of the elongate members 1404 together. For example, various articulated joints including flexure-type joints can be employed. In some example embodiments, one or more flexible lines are employed to physically couple at least two of the elongate members 1404 together. In some embodiments, each elongate member 1404 has a portion that is positioned between a set of at least two spaced apart articulated joints, the portion being articulable about each of the at least two articulated, articulable or articulation (used interchangeably herein) joints when the stacked arrangement 1415 is in the third/expanded configuration. In this example embodiment, if the elongate members 1404 are arranged successively with respect to one another to form a planar or flat stacked arrangement of the elongate members 1404, each elongate member 1404 is restrained from turning about each of the first pivot member 1423 and the second pivot member 1425. In this example embodiment, the orientation of the first and second pivot members 1423 and 1425 and the inherent continuous structure of the elongate members 1404 restrain the elongate members 1404 from turning about each of the first and second pivot members 1423 and 1425 if the elongate members 1404 were to be arranged in a planar or flat stacked arrangement.

FIG. 3B shows the portion of the device 1400 including the plurality of elongate members 1404 positioned in the second/bent configuration. This configuration may be established within a bodily cavity in accordance with various embodiments. In this illustrated embodiment, various ones of the elongate members 1404 have been bent by a bending action created by bender 1430. In this embodiment, each elongate member 1404 in the stacked arrangement 1415 is bent about a respective bending axis 1431 (only one shown), each bending axis 1431 extending along a direction having a directional component transversely oriented to the respective length 1411 (not called out in FIG. 3B) of the elongate member 1404. In this embodiment, bender 1430 includes at least one control element 1432 configured to alter a curvature or shape of one or more of the elongate members 1404. In this illustrated embodiment, control element 1432 includes a control line sized to be received by a number of pulleys 1434 (i.e., three called out) that are physically coupled to stacked arrangement 1415. In this embodiment, each of the pulleys 1434 is physically coupled to elongate member 1404*a*, while in other embodiments, one or more of the pulleys can be physically coupled to other ones of the elongate members 1404. Pulleys 1434 can be employed to reduce the frictional effects and facilitate the bending of various ones of the elongate members 1404 when a tensile force is applied to control element 1432. In some embodiments, one or more control elements 1432 are directly coupled to various ones of the elongate members 1404. In this embodiment, each of the pulleys 1434 is coupled to an elongate member 1404 by a respective control line 1436 (i.e., three called out). The control lines 1436 are, in turn, coupled together by control element 1432. Various arrangements of control elements 1432 and control lines 1436 can be employed to impart a desired curvature or shape change to various portions of selective ones of the elongate members 1404. Different shape changes can be achieved by changing a location on an elongate member 1404 to which a shape-changing force is applied to by a given one of the control lines 1436. A relative movement between various ones of the control elements 1432 or an activation timing of various ones of the control elements 1432, or both can be controlled to impart a desired shape change to a given one of the elongate members 1404 in stacked arrangement 1415. Control elements 1432 other than control lines can be employed in other example embodiments. For example, a control element 1432 can include a push member configured to apply a compressive force. In this example embodiment, bender 1430 has altered a curvature of each of the elongate members 1404 in stacked arrangement 1415. In this example embodiment, bender 1430 has coiled elongate member 1404*a*.

In this embodiment, each of the bent elongate members 1404 assumes a respective arcuate shape between the respective first and second ends 1405, 1407 of the elongate member. The arcuate shape can include circular, elliptical arcuate or parabolic forms by way of non-limiting example. In various embodiments, the coupling locations of various control elements 1432 to stacked arrangement 1415 can be selectively chosen to impart a particular curvature or shape to various ones of the elongate members 1404 when the stacked arrangement is moved into the second/bent configuration.

FIG. 3C shows a portion of device 1400 in a third expanded configuration. In this illustrated embodiment, the portion of the device 1400 is moved from the second/bent configuration shown in FIG. 3B to the third/expanded configuration shown in FIG. 3C. In this illustrated embodiment, at least some of the elongate members 1404 are repositioned. In this example embodiment, various ones of the elongate members 1404 are moved to space the intermediate portions 1409 of at least some of the elongate members 1404 apart from one another. In this example embodiment, the respective intermediate portions 1409 of elongate members 1404*b*, 1404*c*, 1404*d*, 1404*e* and 1404*f* are angularly spaced with respect to one another about a first axis 1465. In this example embodiment, the respective intermediate portions 1409 of elongate members 1404*b*, 1404*c*, 1404*d*, 1404*e* and 1404*f* are radially oriented about first axis 1465. In this embodiment, the respective intermediate portions 1409 of elongate members 1404*b*, 1404*c*, 1404*d*, 1404*e* and 1404*f* spread out in a ray-like manner from first axis 1465. In this illustrated embodiment, each of the respective intermediate portions 1409 of elongate members 1404*b*, 1404*c*, 1404*d*, 1404*e* and 1404*f* is at a different radial distance from first axis 1465. In this embodiment, the radial distance from first axis 1465 that each of the respective intermediate portions 1409 of elongate members 1404*b*, 1404*c*, 1404*d*, 1404*e* and 1404*f* is positioned at, varies at least in part, based on a positioning of the elongate member 1404 in the bent stacked arrangement shown in FIG. 3B. In this illustrated embodiment, each of the respective intermediate portions 1409 of elongate members 1404*b*, 1404*c*, 1404*d*, 1404*e* and 1404*f* has a different curvature. In this example embodiment, various portions of each of the elongate members 1404*b*, 1404*c*, 1404*d*, 1404*e* and 1404*f* are arranged to form a structure having a domed shape 1419 when the portion of device 1400 is in the third/expanded or fanned configuration. In this example embodiment, the dome-shaped structure is positioned opposite from a portion of at least one of the elongate members 1404 (i.e., elongate member 1404*a*). In some example embodiments the domed-shaped structure may have a generally hemi-spherical shape. In other example embodiments, the domed shape structure may have a different shape. For example, the structure's domed shape may have a first radius of curvature in a first spatial plane and a second radius of curvature in a second spatial plane that intersects the first spatial plane, a magnitude of the second radius of curvature different than a magnitude of the first radius of curvature.

In this illustrated embodiment, various ones of the elongate members 1404 are fanned with respect to one another about a fanning axis in a fanned array when the portion of the device 1400 is in the third/expanded configuration. The fanning axis extends along a direction that has a directional component that is transversely oriented to the bending axis 1431 shown in FIG. 3B. In this illustrated embodiment, various ones of the elongate members 1404 turn, revolve, or rotate (used interchangeably herein) about each of a respective pivot axis associated with each of first coupler 1422 and second coupler 1424 when the portion of the device 1400 is moved into the third/expanded configuration. In this illustrated embodiment, various ones of elongate members 1404 turn about pivot axis 1462*a* and pivot axis 1462*b*. In this illustrated embodiment, various ones of elongate members 1404 turn about each of first pivot member 1423 and second pivot member 1425 as the elongate members 1404 are fanned. The respective openings in various ones of the elongate members 1404 in which each of the first and the second pivot members 1423, 1425 is located can be appropriately sized to accommodate misalignment between the pivot members 1423, 1425 and respective ones of the pivot axes 1462a, 1462b. In this illustrated embodiment, the respective intermediate portions 1409 of various ones of the elongate members 1404 are angularly spaced about first axis 1465 when the portion of the device 1400 is moved into third/expanded configuration. In this example embodiment, the front surface 1418a of each of the elongate members 1404 is positioned to face away from the first axis 1465 when the portion of the device 1400 is in the third/expanded or fanned configuration.

In this example embodiment, separator 1452 moves various ones of the elongate members 1404 to move the portion of device 1400 into the third/expanded or fanned configuration. In this example embodiment, separator 1452 includes two crank members 1454, each crank member 1454 physically coupled to one of two flexible rotary shafts 1456. Various articulated joints pivotally couple each of crank members 1454 to a respective one of flexible rotary shafts 1456 to allow the crank members 1454 to assume one configuration suitable for delivery through catheter sheath 1406 and another configuration suitable for applying sufficient force to move various ones of elongate members 1404. Selectively applied torque to each of the crank members 1454 via a respective one of flexible rotary shafts 1456 can be applied by various actuators (not shown). In this embodiment, oppositely oriented torques are applied to crank members 1454 to fan different ones of the elongate members 1404 in different directions. In this illustrated embodiment, one of the crank members 1454 is physically coupled to elongate member 1404b while the other crank member 1454 is physically coupled to elongate member 1404c. In this example embodiment, each of the crank members 1454 is physically coupled to a respective one of the elongate members 1404 by a flexible line. The application of sufficient torque to each of the crank members 1454 causes respective ones of the elongate members 1404b and 1404c to move. Other separators may be employed additionally or alternatively in other example embodiments. For example, various elements (e.g., flexible lines) may be physically coupled to at least some of the elongate members 1404 to apply a force suitable for fanning various ones of the elongate members 1404 with respect to one another.

Various coupling members 1458 (four called out) physically couple various ones of the elongate members 1404 together. In this example embodiment, each coupling member 1458 allows movement of one of the elongate members 1404 coupled by the coupling member 1458 to also cause movement of another of the elongate members 1404 coupled by the coupling member 1458. In this example embodiment, the coupling members 1458 are arranged to restrict or limit an amount of movement that an elongate member 1404 undergoes as the portion of the device is moved into the third/expanded configuration. In this embodiment, each coupling member 1458 is a flexible line. For clarity, bender 1430 is not shown in FIG. 3C. For clarity, separator 1452 is not shown in FIG. 3B. For clarity, bender 1430 and separator 1452 are not shown in FIG. 3A.

Figure 4A:
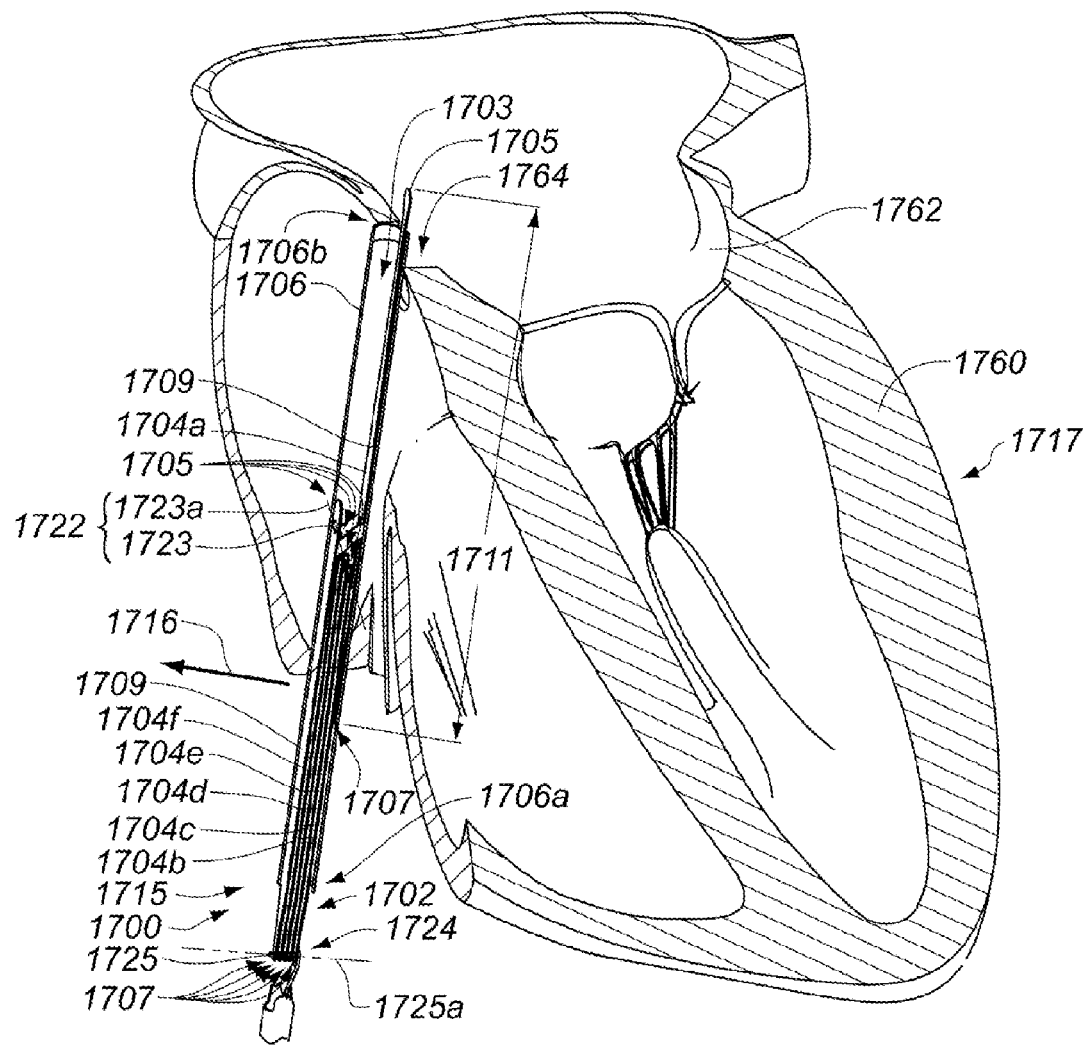
Figure 4B:
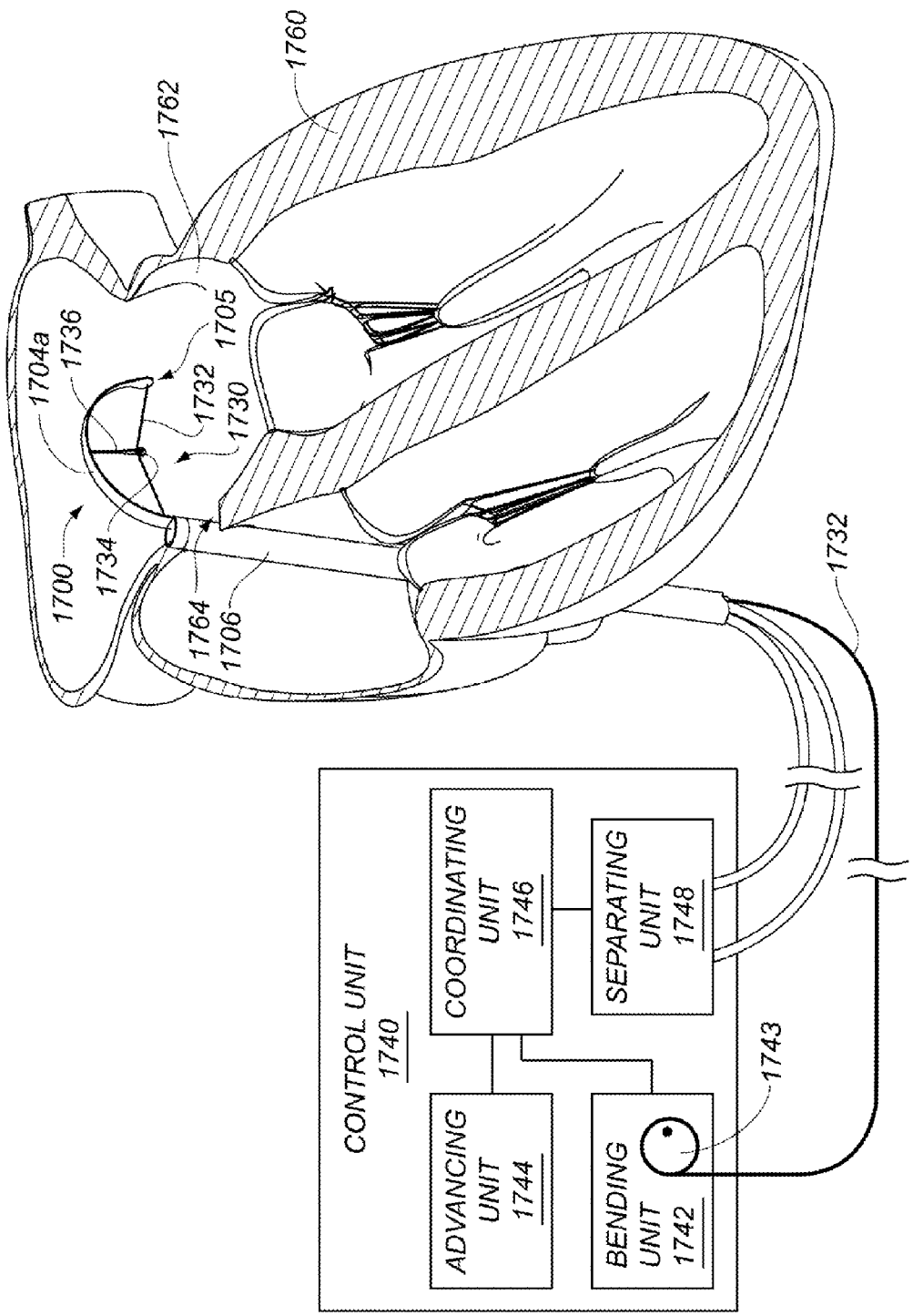
Figure 4C:
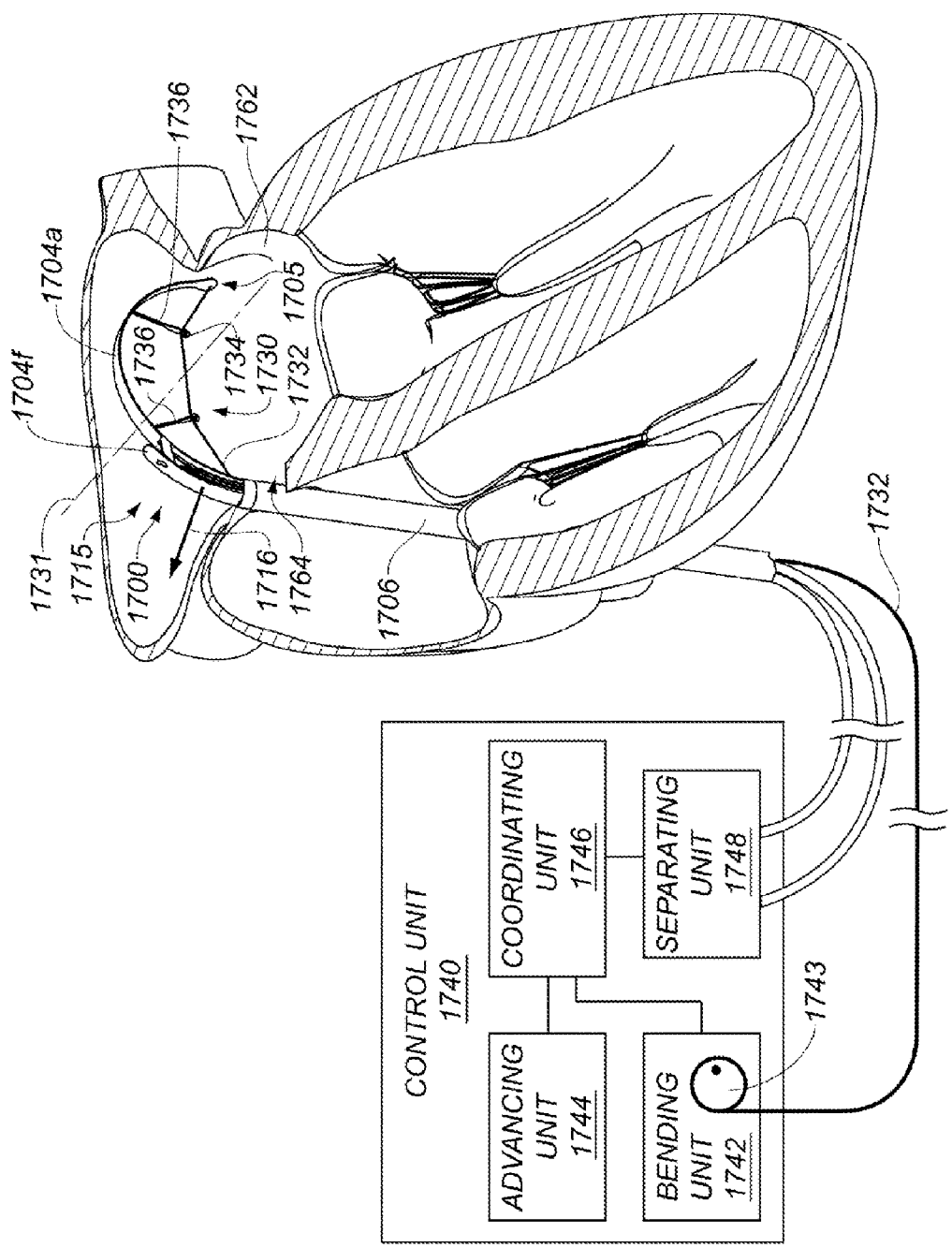
Figure 4D:
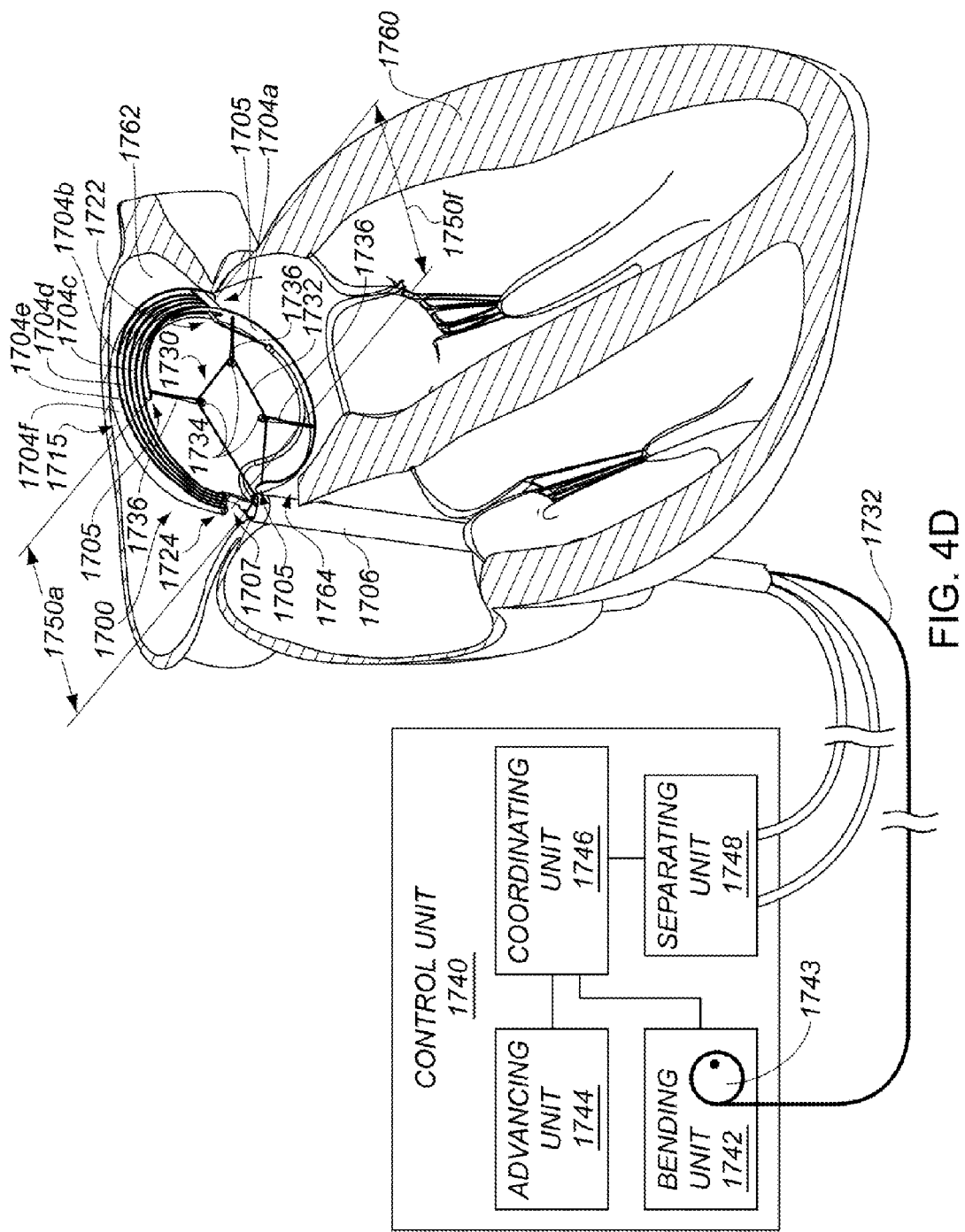
Figure 4F:
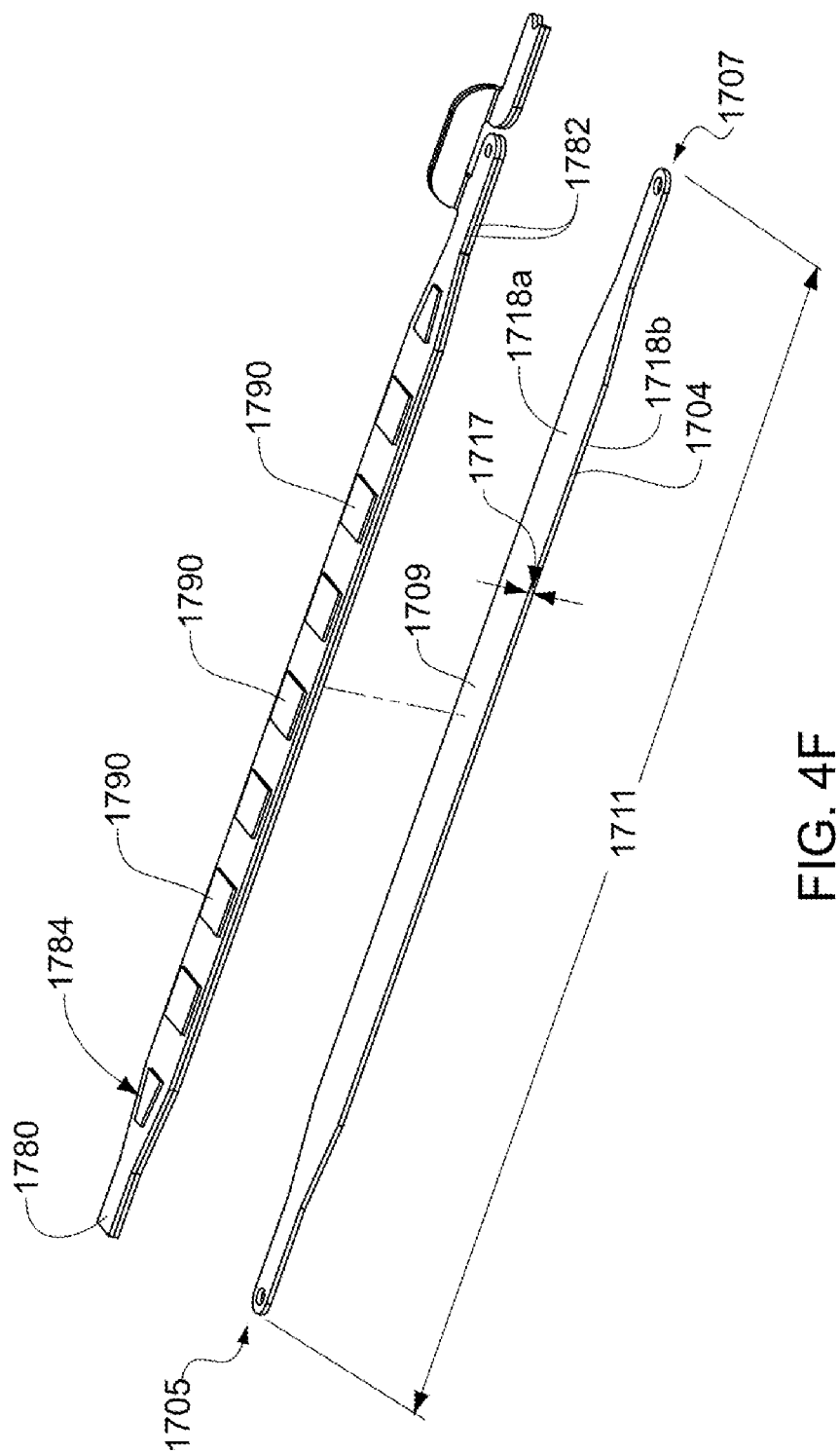
FIG. 4F is a partially exploded isometric view of an elongate member of FIGS. 4A, 4B, 4C, 4D and 4E including a flexible circuit structure.

FIGS. 4A, 4B, 4C, 4D and 4E show various elevation views of a portion of a device 1700 positioned within a bodily cavity at five successive intervals of time according to an example embodiment. In this illustrated embodiment, the bodily cavity is a left atrium 1762 of a heart 1760 which is showed sectioned for clarity. Device 1700 includes a structure or frame 1702 that includes a plurality of elongate members 1704a, 1704b, 1704c, 1704d, 1704e and 1704f (collectively 1704) as best shown in FIGS. 4D, 4E. In a manner similar to the embodiment illustrated in FIGS. 3A, 3B, and 3C, and as best exemplified in FIG. 4F, each of the elongate members 1704 includes a respective distal or first end 1705, a respective proximal or second end 1707, a respective intermediate portion 1709 positioned between the first end 1705 and the second end 1707, and a respective length 1711 between the first end 1705 and the second end 1707. FIG. 4F shows an exploded view of an elongate member 1704 and a flexible circuit structure 1780.

As best shown in FIG. 4A, each of the elongate members 1704 has a different respective length 1711 in this example embodiment. In some embodiments, two or more of the elongate members 1704 may have substantially equal lengths 1711. As shown in FIG. 4F, each elongate member 1704 includes a front surface 1718a and a back surface 1718b positioned opposite to the first surface 1718a across a thickness 1717 of the elongate member 1704. In a manner similar to that described in some previous embodiments, various transducer elements can be carried into a bodily cavity by various ones of elongate members 1704. In some embodiments, various transducer elements can be provided on, or by various flexible circuit structures made up of various flexible substrates which can include by way of non-limiting example, elongate member 1704 itself. Flexible circuit structure 1780 shown in FIG. 4F can include one or more flexible substrates 1782 (i.e., two in this illustrated embodiment) and at least one electrically conductive layer 1784. In this example embodiment, the at least one conductive layer 1784 has been patterned to form a plurality of transducer elements 1790 (three called out). In this embodiment, the at least one conductive layer has been patterned to form a plurality of electrodes. Various ones of the at least one conductive layers can be patterned to form other features and elements including conductive traces or lines by way of non-limiting example. For clarity, various transducer elements 1790 associated with device 1700 are not shown in FIGS. 4A, 4B, 4C, 4D, 4E, 4G and 4H. For clarity, various flexible circuit structures 1780 associated with device 1700 are not shown in FIGS. 4A, 4B, 4C, 4D, 4G and 4H.

In this embodiment, the elongate members 1704 are arranged successively with respect to one another in stacked arrangement 1715 when the portion of device 1700 is in the first or unexpanded configuration shown in FIG. 4A. In this embodiment, the arrangement of the elongate members 1704 in the stacked arrangement 1715 is an orderly one with each of the elongate members 1704 arranged successively with respect to one another along a first direction (i.e., a stacking direction) represented by arrow 1716. In this example embodiment, the elongate members 1704 are arranged with one another front surface 1718a-toward-back surface 1718b in an array. In some example embodiments, the elongate members 1704 can be interleaved with one another front surface 1718a-toward-back surface 1718b in an array. In this illustrated embodiment, the elongate members 1704 are arranged in a stacked array (i.e., stacked arrangement 1715) when delivered through catheter sheath 1706 (shown sectioned in FIG. 4A for clarity) which gains access to left atrium 1762 via bodily opening 1764. Catheter sheath 1706 includes a first end 1706a, a second end 1706b and a lumen 1703 extending between the first and the second ends 1706a, 1706b. In this example embodiment, catheter sheath 1706 is typically positioned such that the second end 1706b of the catheter sheath 1706 is positioned at least proximate to a bodily cavity such as left atrium 1762 when catheter sheath 1706 is employed to provide at least part of a percutaneous or intravascular delivery channel. In this example embodiment, each of the elongate members 1704 is arranged to be delivered through the lumen 1703 of catheter sheath 1706 from the first end 1706a of catheter sheath 1706 to the second end 1706b of catheter sheath 1706. In this embodiment, each of the elongate members 1704 is arranged in stacked arrangement 1715 such that its respective first end 1705 (i.e., also referred to as the distal end) is advanced out from lumen 1703 from the second end 1706b of catheter sheath 1706 before the respective second end 1707 (i.e., also referred to as the proximal end) is advanced out from lumen 1703. In this example embodiment, the elongate members are arranged to be advanced out from lumen 1703 into left atrium 1762. In this illustrated embodiment, elongate member 1704a is an outermost elongate member in stacked arrangement 1715. In some embodiments, elongate member 1704a is positioned between two of the outermost elongate members 1704 in stacked arrangement 1715. In this illustrated embodiment, the elongate members 1704 are sized and positioned in stacked arrangement 1715 so that a portion of elongate member 1704a is advanced into left atrium 1762 prior to a portion of each of the other ones of the elongate members 1704 in stacked arrangement 1715. In this illustrated embodiment, the elongate members 1704 are sized and positioned in stacked arrangement 1715 so that a portion of elongate member 1704a is advanced from the second end 1706b of catheter sheath 1706 prior to a portion of each of the other ones of the elongate members 1704 in stacked arrangement 1715. In some example embodiments, a respective portion of each of at least two of the elongate members is advanced from the second end 1706b of catheter sheath 1706 prior to a portion of each of the other ones of the elongate members 1704 in stacked arrangement 1715. In this example embodiment, a portion of elongate member 1704a is cantilevered from stacked arrangement 1715. In this illustrated embodiment, the elongate members 1704 are sized and positioned in stacked arrangement 1715 so that the first end 1705 of elongate member 1704a is advanced into left atrium 1762 prior to each respective first end 1705 of each of the other ones of the elongate members 1704 in stacked arrangement 1715. In this example embodiment, the length 1711 of elongate member 1704a is greater than each of the respective lengths of each of the other elongate members 1704 in stacked arrangement 1715. In some example embodiments, a portion of each of at least two elongate members 1704 of a plurality of elongate members 1704 can be advanced into a bodily cavity prior to a portion of any other elongate member 1704 in the plurality of elongate members 1704.

In this illustrated embodiment, a first coupler 1722 and a second coupler 1724 physically couple various ones of the elongate members 1704 together. In this example embodiment, second coupler 1724 pivotally couples at least some of the elongate members 1704 (i.e., 1704b, 1704c, 1704d, 1704e and 1704f) together at location proximate the respective second ends 1707 of these elongate members 1704. First coupler 1722 pivotally couples various ones of the elongate members 1704 (i.e., 1704a, 1704b, 1704c, 1704d, 1704e and 1704f) together at a location spaced apart from second coupler 1724 along the respective lengths 1711 of each of these elongate members 1704. As shown in FIG. 4A each of the first coupler 1722 and the second coupler 1724 respectively include first pivot member 1723 and second pivot member 1725 arranged to pivotally couple various ones of the elongate members 1704 together in stacked arrangement 1715 in this embodiment. In this example embodiment, each of the first pivot member 1723 and the second pivot member 1725 takes the form of a pin about which various ones of the elongate members 1704 is configured to turn, revolve or rotate about when the stacked arrangement 1715 is moved to, or from, the third/expanded configuration shown in FIG. 4E. In this embodiment, each of the pivot members 1723, 1725 includes two opposing ends and a longitudinal axis extending between the opposing ends. Specifically, first longitudinal axis 1723a is associated with first pivot member 1723 and second longitudinal axis 1725a is associated with second pivot member 1725. In this embodiment, each of the first and the second pivot members 1723, 1725 is sized to be received in a respective opening provided in various ones of the elongate members 1704. Other embodiments may employ other forms of couplers or joints.

As shown in FIGS. 4B to 4D, various portions of stacked arrangement 1715 are bent within the left atrium 1762 by bender 1730. Bender 1730 includes a control element 1732, which in this illustrated embodiment includes a control line that is coupled to various control lines 1736 that are each coupled to an elongate member 1704. In this example embodiment, each control line 1736 is coupled to control element 1732 via a pulley 1734. Control element 1732 is coupled to a control unit 1740 (i.e., schematically shown) that is typically positioned outside of the body. In some embodiments, control unit 1740 is included as part of a catheter system, for example a handle portion of the catheter system that is directly controlled or manipulated by a care provider. In this embodiment, control element 1732 is provided to bending unit 1742. In this embodiment, control element 1732 is controlled by tensioner 1743 that selectively applies and controls tension provided to control element 1732. Tensioner 1743 can include various tensioning devices such as cams by way of non limiting example.

In this illustrated embodiment, a portion of the stacked arrangement 1715 is bent within left atrium 1762 by bender 1730 as the portion of the stacked arrangement 1715 is advanced into left atrium 1762. In this embodiment, each of the elongate members 1704 in each portion of the stacked arrangement 1715 bent by bender 1730 is bent about at least one bending axis 1731 (shown in FIG. 4C) within left atrium 1762. In this embodiment, the direction that at least one bending axis 1731 extends along has a directional component transversely oriented to the first or stacking arrangement represented by arrow 1716. In this embodiment, each of the elongate members 1704 in each portion of the stacked arrangement 1715 bent by bender 1730 is bent in a same direction. FIGS. 4B, 4C and 4D show successive portions of stacked arrangement 1715 bending as each portion is advanced into left atrium 1762. In some embodiments, various portions of stacked arrangement 1715 are each bent by a substantially same angular amount as the portions are advanced into left atrium 1762. In some embodiments, various portions of the stacked arrangement 1715 are bent by different angular amounts as the portions are advanced into left atrium 1762. Each angular amount can be predetermined based at least on various factors including, but not limited to, a measured or estimated dimension of left atrium 1762. As shown in FIG. 4D, the various elongate members 1704 have been bent into an arcuate stacked array. In this illustrated embodiment, the elongate members 1704 are still arranged front surface 1718a-toward-back surface 1718b in the arcuate stacked array.

In this example embodiment, advancing unit 1744 is employed to advance a portion of device 1700 including stacked arrangement 1715 into left atrium 1762. Advancing unit 1744 can include various manual or powered actuators suitable for delivering a portion of device 1700 through catheters sheath 1706 into left atrium 1762. In this embodiment, coordinating unit 1746 coordinates the bending of various portions of stacked arrangement 1715 under the influence of bending unit 1742 with the advancement of the portions of stacked arrangement 1715 into left atrium 1762 under the influence of advancing unit 1744. Coordinating unit 1746 can include various drive components including gears, pulleys, sprockets and timing belts, etcetera suitably arranged to provide the desired coordinated movement. In various embodiments, coordinating unit 1746 may control bending unit 1742 based on various information (e.g., positional information) associated with, or provided by an operation of advancing unit 1744.

As shown in FIGS. 4B, 4C and 4D, bender 1730 directly bends various portions of elongate member 1704*a* as these portions are advanced into left atrium 1762 in this illustrated embodiment. Elongate member 1704*a* is suitably arranged and coupled with the other elongate members 1704 in stacked arrangement 1715 to cause the other elongate members 1704 to also bend in a desired manner. In this embodiment, the respective first end 1705 of each of the elongate members 1704 moves from bodily opening 1764 into left atrium 1762 along a respective path in left atrium 1762 during the bending and advancement of various portions of stacked arrangement 1715. In various embodiments, a portion of each of the respective paths extends along an arcuate trajectory. In this example embodiment, the respective path of the first end 1705 of elongate member 1704*a* is longer than each of the respective paths within the left atrium 1762 of the first ends 1705 of the other ones of the elongate members 1704. In this embodiment, the second end 1707 of elongate member 1704*a* is advanced into left atrium 1762 prior to the respective second ends 1707 of the other elongate members 1704 in stacked arrangement 1715. In this embodiment, elongate member 1704*a* is coiled in left atrium 1762.

The advancement and bending of various portions of stacked arrangement 1715 into left atrium 1762 moves stacked arrangement 1715 into a second or bent configuration shown in FIG. 4D. Each of the elongate members 1704 has a generally compact form (e.g., a curled form) when the stacked arrangement 1715 is positioned in the second/bent configuration shown in FIG. 4D. In this embodiment, the respective first ends 1705 and the respective second ends 1707 of each elongate member 1704 is positioned within left atrium 1762 when stacked arrangement 1715 is in the second/bent configuration. Each of the elongate members 1704 has a respective end-to-end dimension between the respective first end 1705 and the respective second end 1707 of the elongate member 1704. In this embodiment, elongate member 1704*a* has a smaller end-to-end dimension 1750*a* than the end-to-end dimension of the other elongate members 1704 (e.g., the end-to-end dimension 1750*f* of elongate member 17040 in the second/bent configuration. In this embodiment, each of the elongate members 1704 has a smaller end-to-end dimension when the portion of the device 1700 is in the second/bent configuration than when the portion of the device is in the first/unexpanded configuration. In some embodiments, the end-to-end dimension of each elongate member 1704 may be approximately equal to the respective length 1711 of the elongate member when the portion of the device 1700 is in the first/unexpanded configuration. In various embodiments, the bent stacked arrangement 1715 assumes a shape in the second/bent configuration having dimensions suitably sized to allow the bent stacked arrangement 1715 to be positioned at one or more locations within left atrium 1762 with reduced or no contact between the elongate members 1704 and a tissue surface within left atrium 1762.

Advantageously, in this embodiment, stacked arrangement 1715 is bent as it is advanced from bodily opening 1764 into left atrium 1762 to reduce physical interactions between stacked arrangement 1715 and a tissue surface within left atrium 1762. A reduction of contact and other physical interaction with the tissue surface within left atrium 1762 during this positioning can reduce occurrences of, or the severity of, damage inflicted to various tissue structures within left atrium 1762 during this positioning. Some conventional "basket-type" catheter systems include resilient members that "spring" outwardly or employ buckling mechanisms that outwardly buckle an arrangement of members, typically have longitudinal lengths (i.e., lengths generally oriented along a direction of advancement from a bodily opening into a left atrium) that are too large to be directly accommodated within the atrium (i.e., the lengths must be sufficiently sized to allow the members to spring outwardly or buckle laterally within the atrium). Typically, these systems require that the arrangement of members be guided within the atrium to position part of the arrangement into another bodily opening leading to the left atrium (e.g., a pulmonary vein opening) to accommodate their excess length prior to expansion of the portion of device 1700 within the left atrium. This can potentially inflict damage to the pulmonary vein and other structures within the atrium. In various embodiments, catheter sheath 1706 is preferably oriented to allow stacked arrangement 1715 to be introduced generally tangentially to an interior tissue surface of left atrium 1762. As various portions of stacked arrangement 1715 are subsequently advanced and bent within the left atrium 1762, the generally tangential orientation with the interior tissue surface of left atrium 1762 is substantially maintained to accommodate the overall length of stacked arrangement 1715 while advantageously reducing occurrences of contact with the tissue surface and allowing the stacked arrangement 1715 to be subsequently positioned in a desired expanded or third configuration as shown in FIG. 4E. In this example embodiment, elongate member 1704*a* moves along a coiled path within left atrium 1762 to advantageously reduce occurrences of contact with the tissue surface. In this example embodiment, elongate member 1704*a* curls away from an interior tissue surface with left atrium 1762 as the elongate member 1704*a* is advanced into left atrium 1762.

FIG. 4E shows the portion of the device 1700 in a third or expanded configuration in left atrium 1762. In this illustrated embodiment, the elongate members 1704 were moved from the second/bent configuration shown in FIG. 4D to the third/expanded or fanned configuration shown in FIG. 4E. In this illustrated embodiment, at least some of the elongate members 1704 are repositioned in left atrium 1762. In this example embodiment, various ones of the elongate members 1704 are moved to space the intermediate portions 1709 of at least some of the elongate members 1704 apart from one another within left atrium 1762. In this example embodiment, the respective intermediate portions 1709 of elongate members 1704*b*, 1704*c*, 1704*d*, 1704*e* and 1704*f* are angularly spaced with respect to one another about a first axis 1765 within left atrium 1762. In this example embodiment, the respective intermediate portions 1709 of elongate members 1704*b*, 1704*c*, 1704*d*, 1704*e* and 1704*f* are radially oriented about first axis 1765 within left atrium 1762. In this illustrated embodiment, various ones of the elongate members 1704 are fanned with respect to one another about at least one fanning axis into a fanned array. Each fanning axis extends along a direction that has a directional component that is transversely oriented to the bending axis 1731 shown in FIG. 4C. In this embodiment, elongate member 1704*a* is positioned inboard within the fanned array. In this illustrated embodiment, various ones of the elongate members 1704 are fanned about each a respective pivot axis associated with each of first coupler 1722 and second coupler 1724. In this illustrated embodiment, various ones of elongate members 1704 turn about each of first pivot member 1723 and second pivot member 1725 as the elongate members 1704 are moved into the fanned arrangement. Spacings between various ones of the elongate members can be adjusted in various manners to facilitate the fanning of the elongate members 1704. In this example embodiment, the front surfaces 1718*a* of each of the elongate members is positioned to face a tissue surface within left atrium 1762 when the portion of the device 1700 is in the third/expanded or fanned configuration.

Various ones of the elongate members 1704 can be moved in various ways as the portion of device 1700 is moved into the third/expanded configuration. As shown in the cross-section views shown in FIGS. 4G and 4H, a first set of elongate members 1704 made up of elongate members 1704*b* and 1704*d* is moved, pivoted, rotated, turned or revolved (used interchangeably herein) along an angular direction represented by arrow 1768 while a second set of the elongate members 1704 made up of elongate members 1704*c* and 1704*e* is moved along an angular direction represented by arrow 1766 when the portion of device 1700 is moved, pivoted, rotated, turned or revolved (used interchangeably herein) from the second/bent configuration shown in FIG. 4G to the third/expanded configuration shown in FIG. 4H. In this illustrated embodiment, the first set of elongate members 1704 is moved along an angular direction that is opposite to the angular direction that the second set of elongate members 1704 is moved along.

Figure 4G:
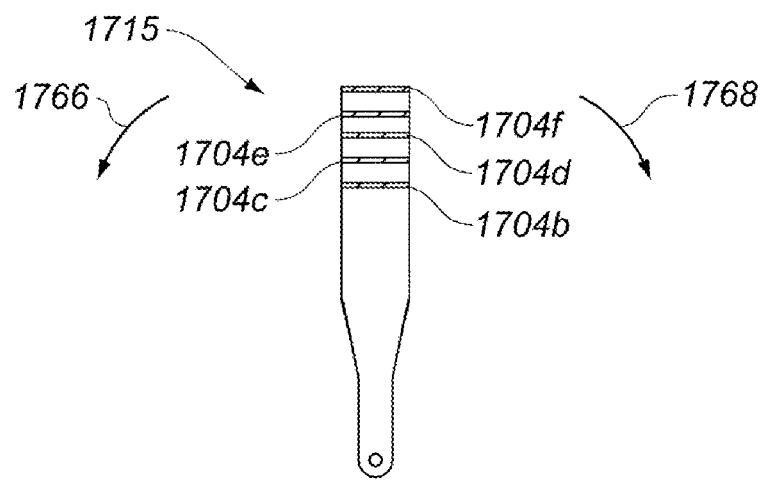
FIG. 4G is a cross-section view of a first set and a second set of various ones of the elongate members of FIGS. 4A, 4B, 4C, 4D and 4E arranged in a second or bent configuration.
Figure 4H:
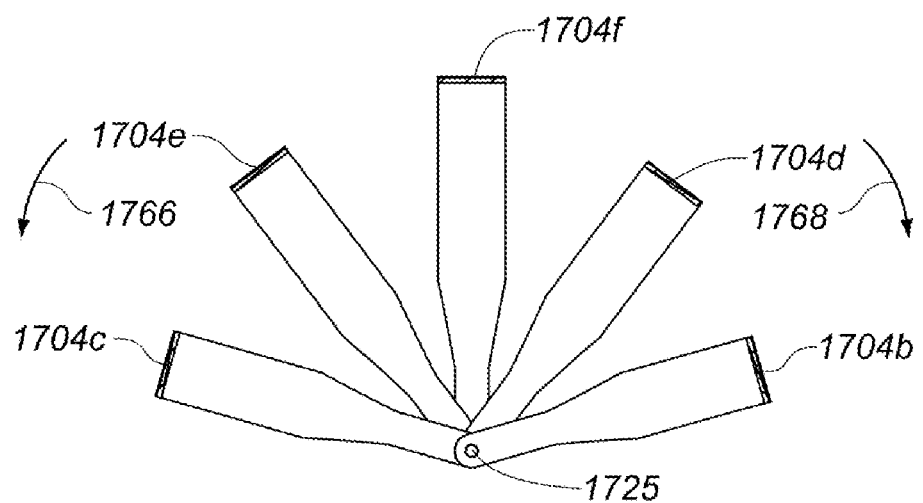
FIG. 4H is a cross-section view of the first set and the second set of the elongate members of FIG. 4G arranged in a third or expanded configuration.

In this example embodiment, a portion of at least a one of the elongate members 1704 in the first set of the elongate members 1704 (e.g., elongate member 1704*d*) is positioned between respective portions of at least two of the elongate members 1704 in the second set of elongate members 1704 (i.e., elongate members 1704*c* and 1704*e*) when the portion of the device 1700 is at least in the first/unexpanded configuration. In this example embodiment, the elongate members 1704*b* and 1704*d* in the first set of elongate members 1704 are interleaved in the bent stacked arrangement 1715 with the elongate members 1704*c* and 1704*e* when the portion of device 1700 is in the second/bent configuration as shown in FIG. 4G and when the portion of the device 1700 is in the first/unexpanded configuration (not shown). It is understood that the elongate members 1704 can be arranged differently in other embodiments. For example, the elongate members 1704*b* and 1704*d* in the first set of elongate members 1704 can be arranged successively adjacent to one another in the stacked arrangement 1715 and the elongate members 1704*c* and 1704*e* in the second set of elongate members 1704 can be arranged successively adjacent to one another in the stacked arrangement 1715 when the portion of the device 1700 is in the first/unexpanded configuration or the second/bent configuration. In other embodiments, each of the first and the second sets of elongate members 1704 can have different numbers of elongate members than shown in FIGS. 4G and 4H. For clarity, elongate member 1704*a* is not shown in FIGS. 4G and 4H. In some embodiments, an elongate member 1704 that is introduced first in left atrium 1762 (e.g., elongate member 1704*a*) can be positioned between at least two of the elongate members 1704 in the fanned arrangement of the elongate members 1704. In some embodiments, an elongate member 1704 that is introduced first in left atrium 1762 (e.g., elongate member 1704*a*) can be positioned as an outboard elongate member 1704 in the fanned arrangement of the elongate members 1704.

As shown in FIG. 4E, separator 1752 moves various ones of the elongate members 1704 to move the portion of device 1700 including stacked arrangement 1715 into the third/expanded configuration. In this example embodiment, separator 1752 includes two crank members 1754, each crank member 1754 physically coupled to one of two flexible rotary shafts 1756. Various articulated joints (not shown) pivotally couple each of crank members 1754 to a respective one of flexible rotary shafts 1756 to allow the crank members 1754 to assume a first configuration suitable for delivery through catheter sheath 1706 and a second configuration within left atrium 1762 suitable for applying sufficient force to move various ones of elongate members 1704. Flexible rotary shafts 1756 are coupled to separating unit 1748 provided by control unit 1740. Separating unit 1748 is selectively controllable to selectively apply torque to each of the crank members 1754 via a respective one of flexible rotary shafts 1756. In this embodiment, oppositely oriented torques are applied to crank members 1754 to fan different ones of the elongate members 1704 in different directions. In this illustrated embodiment, one of the crank members 1754 is physically coupled to elongate member 1704*b* while the other crank member 1754 is physically coupled to elongate member 1704*c*. The application of sufficient torque to each of the crank members 1754 causes respective ones of the elongate members 1704*b* and 1704*c* to move. Various coupling members 1758 (three called out) physically couple various ones of the elongate members 1704 together. In this example embodiment, each coupling member 1758 allows movement of one of the elongate members 1704 coupled by the coupling member 1758 to also cause movement of another of the elongate members 1704 coupled by the coupling member 1758. In this example embodiment, the coupling members 1758 are arranged to restrict or limit an amount of movement that an elongate member 1704 undergoes as the portion of the device is moved into the third/expanded configuration. In this embodiment, each coupling member 1758 is a flexible line. In this example embodiment, coordinating unit 1746 restricts separator 1752 from being operated to cause movement of various ones of elongate members 1704 until the portion of the device 1700 is in the second/bent configuration. For clarity, various ones of bender 1730 and separator 1752 are not shown in FIGS. 4A, 4D and 4E.

In this example embodiment, once the portion of device 1700 has been appropriately positioned at a given location within left atrium 1762, determination of the locations of various components of device 1700 (e.g., transducer elements 1790 including sensors or electrodes or related support structures such as elongate members 1704) or the locations of various anatomical features within left atrium 1762 can be determined. In this example embodiment, after the portion of device 1700 has been appropriately positioned at a given location within left atrium 1762, ablation of various regions of a tissue surface within left atrium 1762 can commence.

Typically, when the elongate members 1704 arranged in an arcuate stacked array (i.e., as shown in FIG. 4D) are repositioned into a fanned array (i.e., as shown in FIG. 4E), the elongate members 1704 are preferably arranged away from various tissue surfaces within the left atrium 1762 to avoid obstructions that could hinder repositioning or to reduce occurrences in which damage may be inflicted on the tissue surfaces, or both. In some example embodiments, portions of each of some of the elongate members 1704 can be positioned away from a tissue surface within a bodily cavity such as left atrium 1762 when the portion of the device 1700 is in the third/expanded or fanned configuration. In some example embodiments, additional manipulation of a portion of device 1700 including elongate members 1704 within a bodily cavity such as left atrium 1762 is initiated when the portion of the device 1700 is moved into the third/expanded or fanned configuration. In some example embodiments, some of the elongate members 1704 are further manipulated to conform to a shape of a tissue surface with a bodily cavity such as left atrium 1762 when the portion of the device 1700 is moved into the third/expanded or fanned configuration. In some example embodiments, a tissue surface within a bodily cavity such as left atrium 1762 is further manipulated to conform to a shape of a number of the elongate members 1704 when the portion of the device 1700 is moved into the third/expanded or fanned configuration. In some example embodiments, a portion of the elongate members 1704 and a tissue surface within a bodily cavity such as left atrium 1762 are each further manipulated to create conformance between a number of the elongate members 1704 and a portion of the tissue surface when the portion of the device 1700 is moved into the third/expanded configuration. In some example embodiments, bending unit 1742 is operated to further manipulate various ones of the elongate members 1704 when the portion of the device 1700 is moved into the third/expanded or fanned configuration. For example, bending unit 1742 can be operated to adjust tension on control element 1732 to release stored potential energy from various ones of the elongate members 1704. In some example embodiments, an adjustment in tension will cause a resilient elongate member 1704 to uncoil or unbend and bear against a proximate tissue surface within left atrium 1762 by an amount sufficient to bias the remaining elongate members 1704*b*, 1704*c*, 1704*d*, 1704*e* and 1704*f* towards portions of the tissue surface proximate these elongate members. A location of various transducer elements (e.g., sensors or electrodes, or both) carried by various ones of the elongate members 1704 relative to a tissue surface within left atrium 1762 can also be adjusted by this or other manipulations of the elongate members 1704.

Figure 5A:
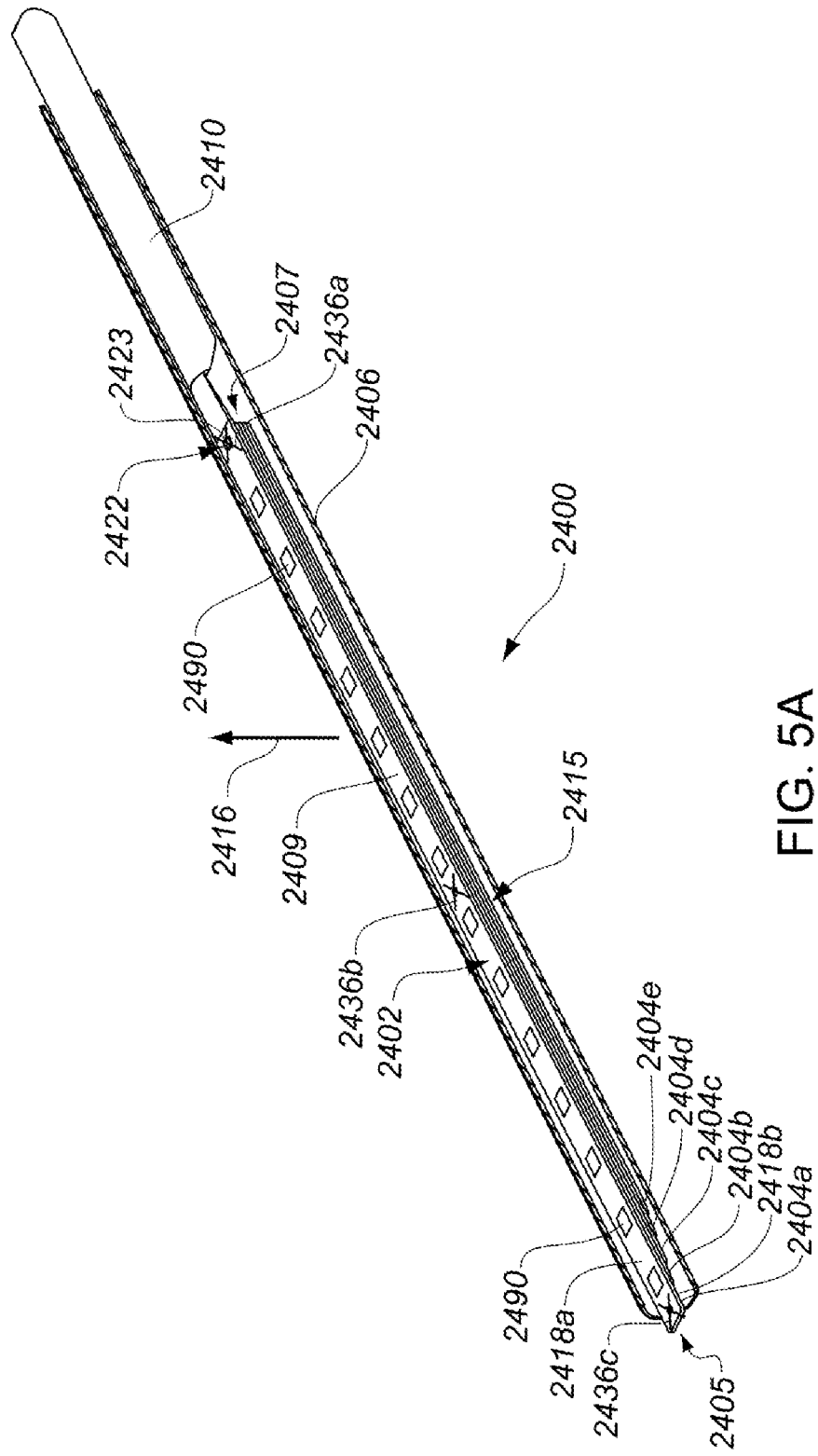
FIG. 5A is an isometric view of a portion of a device that includes an arrangement of elongate members in a first/unexpanded configuration received via a catheter sheath, according to one example embodiment.

FIG. 5A is an isometric view of a portion of a device 2400 according to one example embodiment. Device 2400 includes a structure or frame 2402 that includes an arrangement of elongate members 2404*a*, 2404*b*, 2404*c*, 2404*d*, and 2404*e* (collectively 2404) illustrated in FIG. 5A in a first/unexpanded configuration suitably sized for delivery through catheter sheath 2406 (i.e., showed sectioned). The elongate members 2404 are physically coupled to shaft member 2410 which is employed to convey the elongate members 2404 through catheter sheath 2406. Each of the elongate members 2404 includes a respective distal end 2405 (only one called out), a respective proximal end 2407 (only one called out), a respective intermediate portion 2409 (only one called out) positioned between the distal end 2405 and the proximal end 2407. In this example embodiment, each elongate member 2404 is arranged in frame 2402 to be advanced distal end 2405 first into a bodily cavity (not shown).

Figure 5B:
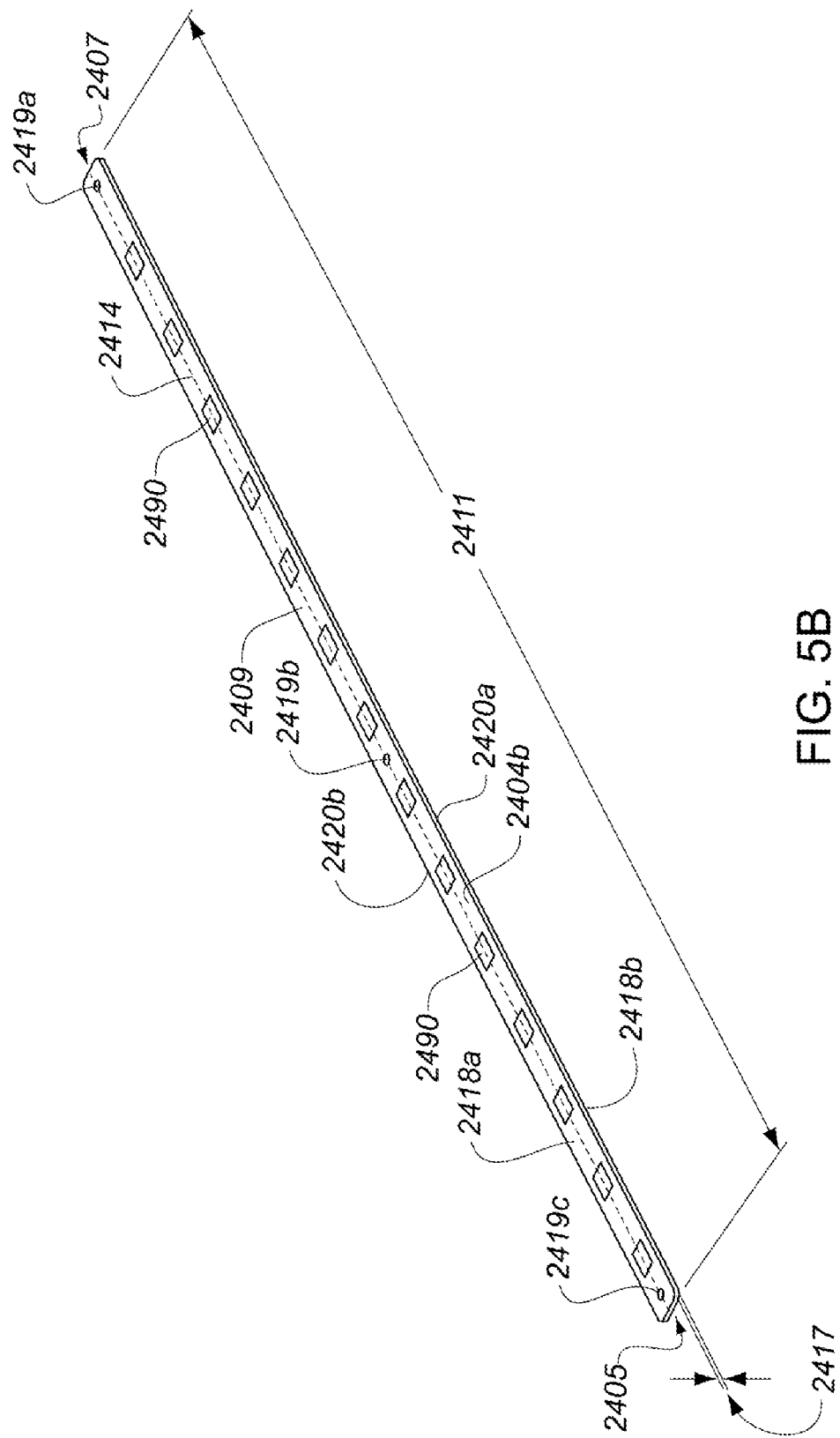
FIG. 5B is an isometric view of an elongate member of the device of FIG. 5A.

FIG. 5B is an isometric view of one of the elongate members 2404 (i.e., elongate member 2404*b*). Each of the elongate members 2404 includes a respective length 2411 between the distal end 2405 and the proximal end 2407. As shown in FIG. 5A, each of various ones of the elongate members 2404 has a different respective length 2411 (not called out) than the respective length 2411 (not called out) of another of the elongate members 2404. In a manner similar to that described in some previous embodiments, various transducer elements can be carried into a bodily cavity by various ones of elongate members 2404. In some embodiments, various transducer elements can be provided on, or by various flexible circuit structures made up of various flexible substrates which can include by way of non-limiting example, elongate member 2404 itself. As exemplified in FIG. 5B, each of the elongate members 2404 includes a plurality of transducer elements 2490 (two called out in each of FIGS. 5A and 5B) distributed along the respective length 2411 of the elongate member in this example embodiment. For clarity, various transducer elements 2490 associated with device 2400 are not shown in FIGS. 5C, 5D, 5E, 5F, 5G, and 5H.

In some previously described embodiments, various elongate members had respective lengths that were sized to be substantially less than a circumference of a portion of an interior surface of a bodily cavity to which the elongate member was to be positioned at least proximate to when in a deployed configuration. The circumference of the portion of the interior tissue surface may have a measured or anticipated value. For example, in the deployed configuration of device 1700 of the embodiment shown in FIG. 4E, various ones of the elongate members 1704 have a respective length 1711 that is sized to be equal to approximately half an internal circumference of left atrium 1762. In the embodiment shown in FIG. 4E, elongate members 1704*b*, 1704*c*, 1704*d*, 1704*e* and 1704*f* in the deployed configuration are arranged in a generally domed-shaped structure. In the deployed configuration of device 1700 of the embodiment shown in FIG. 4E, the domed shape structure enclosing a volume sized to be on the order of a volume of a hemispherical half of left atrium 1762. Various transducer elements (e.g., sensors or electrodes, or both) (not shown) carried by various ones of the elongate members 1704*b*, 1704*c*, 1704*d*, 1704*e* and 1704*f* are essentially distributed across a first region of the interior tissue surface of left atrium 1762 and not across a second region separate from the first region like a region diametrically opposed to the first region. If investigation, sensing or treatment of the second region of the interior tissue surface of left atrium 1762 is additionally required, further operations or manipulations to redeploy device 1700 such that at least a portion of elongate members 1704*b*, 1704*c*, 1704*d*, 1704*e* and 1704*f* are essentially distributed across the second region of the interior tissue surface of left atrium 1762 may be required. This can impose additional requirements when the investigation, sensing or treatment of one region of the interior tissue surface of left atrium 1762 is dependent on a previous investigation, sensing or treatment of another region of the interior tissue surface of left atrium 1762. For example, in mapping applications, the mapping of features on one region of the interior tissue surface of left atrium 1762 may need to be registered with the mapping of features on another region of the interior tissue surface of left atrium 1762 to provide a global map of the interior surface. In ablation treatment applications, the formation of an ablation lesion extending continuously across both these interior tissue regions may need to employ various stitching techniques to ensure continuity of the ablation lesion.

Unlike some previously described embodiments, each of the elongate members 2404 has a respective length 2411 (not called out in FIGS. 5A, 5C, 5D, 5E, 5F and 5G) that is at least approximately equal to, or greater than a circumference of a portion of a interior tissue surface of a bodily cavity (again not shown) to which the elongate member 2404 is to be positioned at least proximate to when the portion of the device 2400 is in a deployed configuration. The circumference of the portion of the interior tissue surface may have a measured or anticipated value. In this example embodiment, transducer elements 2490 carried by a given one of elongate members 2404 can be distributed across approximately the entirety of the circumference of a region of an interior tissue surface of a bodily cavity (again, not shown) over which the given one of the elongate members 2404 is positioned at least proximate to in a deployed configuration. In some embodiments, two or more of the elongate members 2404 may have substantially equal lengths 2411.

As shown in FIG. 5A, at least the respective intermediate portions 2409 of each of the elongate members 2404 are arranged successively with respect to one another in a stacked arrangement 2415 when the portion of device 2400 is in the first/unexpanded configuration. In this embodiment, the arrangement of the respective intermediate portions 2409 in the stacked arrangement 2415 is an orderly one with each of respective intermediate portions 2409 arranged successively with respect to one another along a first direction (i.e., a stacking direction) represented by arrow 2416. In the illustrated example embodiment, each of the elongate members 2404 is a strip-like member. As shown in FIG. 5B, the intermediate portion 2409 of each of the elongate members 2404 includes a set of two opposing major faces or surfaces or 2418 made up of a front surface 2418a and a back surface 2418b. In this example embodiment, the two opposing surfaces 2418 are separated from one another by a thickness 2417 of the elongate member 2404. In this illustrated example, the intermediate portion 2409 of each of the elongate members 2404 further includes a pair of side edges 2420a, 2420b (collectively 2420) of at least one of the front surface 2418a and the back surface 2418b, the side edges of each pair of side edges 2420 opposed to one another across at least a portion of the length 2411 of the respective elongate member 2404. As used herein and in the claims, the term stacked and variations thereof (e.g., stack) refers to an orientation and does not necessarily require that any one member be carried directly on or supported directly by a next successively adjacent elongate member 2404 in the stack.

As best shown in FIG. 5B, each elongate member includes a geodesic 2414 (i.e., represented by a broken line) extending along a portion of the respective length 2411 between a first location at least proximate the respective proximal end 2407 and a second location at least proximate the distal end 2405 of the elongate member 2404. As used herein and in the claims the term "geodesic" should be understood to mean the shortest line extending between two points on a given surface (e.g., planar surface, curved surface) of an elongate member employed in various embodiments. In some example embodiments, a geodesic may extend over or bridge a localized opening or other local disruption in the surface of the elongate member as that shortest line extends along the surface between the two points. In this example embodiment, each geodesic 2414 is located at least on the front surface 2418a of the intermediate portion 2409 of a respective elongate member 2404. Each geodesic 2414 is the shortest line on the front surface 2418a of the intermediate portion 2409 of a respective elongate member 2404 extending between a first location on the front surface 2418a at least proximate the respective proximal end 2407 and a second location on the front surface 2418a at least proximate the respective distal end 2405 of the elongate member 2404. In various embodiments, the distal end 2405 is the portion of the elongate member 2404 is advanced first into a bodily cavity. In some example embodiments, each geodesic 2414 is parallel to a midline, center line, longitudinal axis, etcetera, of a respective major surface 2418 of the elongate members 2404. In some example embodiments, each geodesic 2414 is a midline, center line, longitudinal axis, etcetera of a respective major surface 2418 of the elongate members 2404. In some example embodiments, various ones of the elongate members 2404 may be shaped to have a plurality of geodesics 2414 (i.e., each equally sized) extending between locations at least proximate the respective proximal end 2407 and the respective distal end 2405 of the elongate member 2404. For example, in this illustrated embodiment, the relatively "blunt" or "square" proximal and distal ends 2407, 2405 of various ones of the elongate members 2404 allow for a plurality of equally sized geodesics 2414 to be defined across the front surface 2418a of each respective elongate member 2404, each geodesic 2414 spaced from each of the opposing side edges 2420 of the respective elongate member 2404 and each geodesic extending between respective locations at least proximate the proximal and the distal ends 2407, 2405 of the respective elongate member 2404. In this illustrated embodiment, a single geodesic 2414 is shown on a respective front surface 2418a at a location spaced from the side edges 2420a-2420b of the front surface 2418a for clarity. Some of the other geodesics 2414 that are not shown but having the same length as the illustrated geodesic 2414 may extend over a continuous portion of the front surface 2418a between locations at least proximate the respective proximal end 2407 and the respective distal end 2405 of a given elongate member 2404.

As shown in FIG. 5A, the elongate members 2404 are arranged in a delivery configuration in this example embodiment. The elongate members 2404 are arranged with respect to one another front surface 2418a-toward-back surface 2418b in a stacked array sized to be delivered through a bodily opening (i.e., via a lumen of catheter sheath 2406) leading to a bodily cavity. In various embodiments, the front surface 2418a is positionable adjacent to an interior tissue surface in the bodily cavity (not shown) when the portion of device 2400 is in a deployed configuration within the bodily cavity. In some embodiments, each front surface 2418a is positionable to face an interior tissue surface in the bodily cavity when the portion of device 2400 is in a deployed configuration within the bodily cavity. In this embodiment, each front surface 2418a includes, or supports a transducer element 2490 that is positionable adjacent to an interior tissue surface in the bodily cavity when the portion of device 2400 is in a deployed configuration within the bodily cavity.

As shown in FIG. 5B, various ones of elongate members 2404 each includes a plurality of openings 2419 including first opening 2419a, second opening 2419b and third opening 2419c in this example embodiment. Each of first opening 2419a, second opening 2419b and third opening 2419c provides a passageway through a respective elongate member 2404. Each of first opening 2419a, second opening 2419b and third opening 2419c are spaced from one another along the length 2411 of a respective elongate member 2404.

In various example embodiments, various ones of the elongate members 2404 are physically coupled together by at least one coupler. In this example embodiment, the at least one coupler includes coupler 2422 (i.e., not shown in FIG. 5B) which forms part of an articulable joint and includes a pivot member 2423 in the form of a pin sized to be received in the first opening 2419a. In this embodiment, each of various ones of the elongate members 2404 is configured to turn, revolve, pivot or rotate about pivot member 2423. The at least one coupler can include other articulated or non-articulated joints in various embodiments.

Figure 5C:
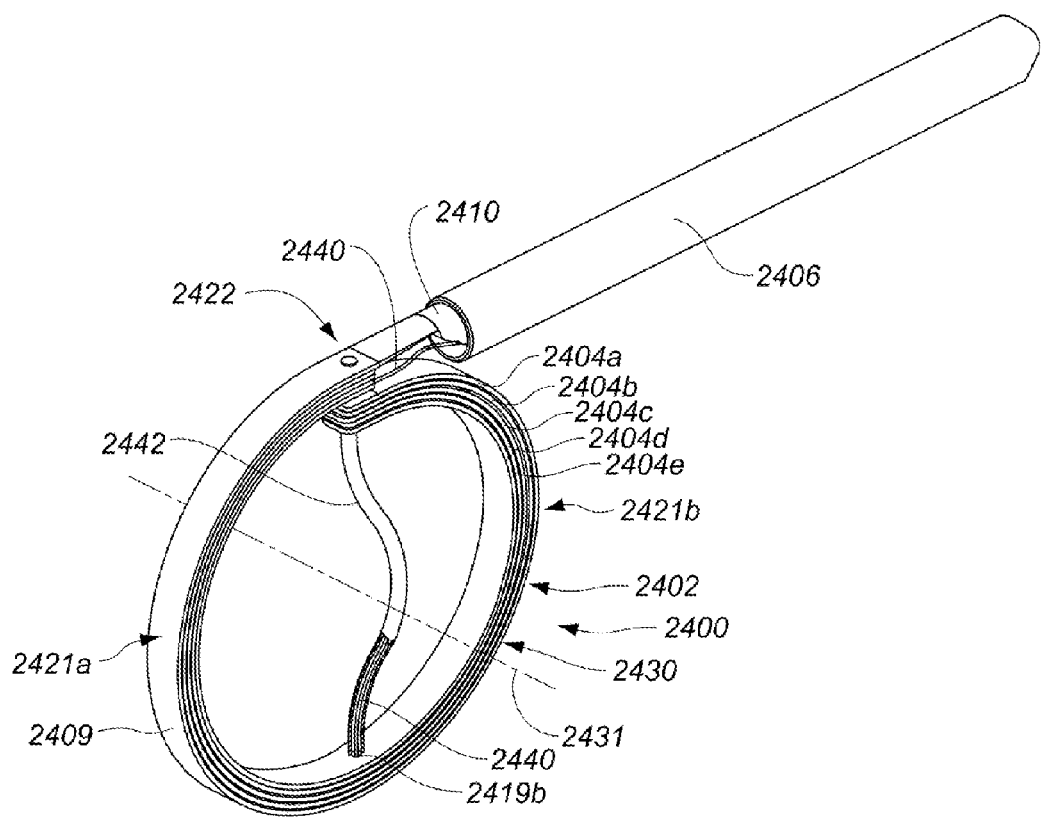
FIG. 5C is an isometric view of the portion of the device of FIG. 5A extending from the catheter sheath positioned in a second/bent configuration.

FIG. 5C is an isometric view of the portion of the device 2400 including the plurality of elongate members 2404 illustrated as positioned in a second/bent configuration (i.e., an example of one deployed configuration). This configuration can be established within a bodily cavity in accordance with various embodiments. In this example embodiment, each elongate member 2404 in the stacked array shown in FIG. 5A is bent about a respective bending axis 2431 (only one shown) into an arcuate stacked array as shown in FIG. 5C. Each bending axis 2431 extends along a direction having a directional component transversely oriented to the respective length 2411 (not called out in FIG. 5C) of the elongate member 2404. In this example embodiment, each elongate member 2404 in the stacked array/stacked arrangement 2415 shown in FIG. 5A is coiled or curved back on itself about a respective bending axis 2431 into a coiled stacked array 2430 as shown in FIG. 5C.

In this example embodiment, each elongate member 2404 in frame 2402 is bent to have a generally annular or ring-like profile, with each annular or ring-like profile interrupted by a separation. When positioned in the second/bent configuration, a first portion 2421a of the front surface 2418a of the respective intermediate portion 2409 of each elongate member 2404 is positioned diametrically opposite to a second portion 2421b of the front surface 2418a in the annular shaped frame 2402. When positioned in the second/bent configuration, the coiled arrangement of elongate members 2404 is sized too large for delivery through a lumen of catheter sheath 2406. In some example embodiments, various ones of the elongate members 2404 are bent by a bending action or force created by a bender (i.e., not shown but similar in function to that of benders 1430 and 1730) that may include at least one control element configured to alter a curvature or shape of one or more of the elongate members 2404.

Figure 5D:
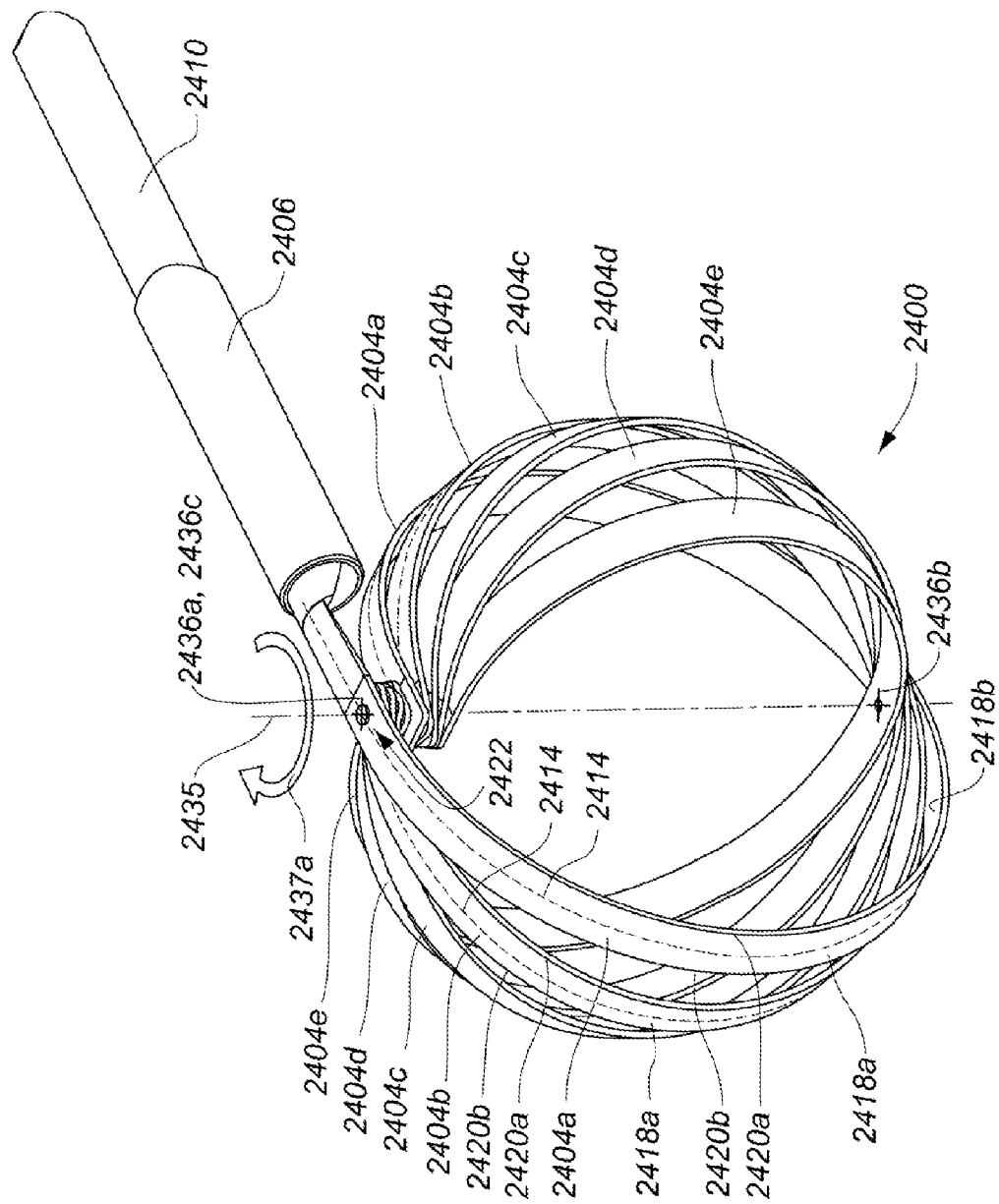
FIGS. 5D and 5E are isometric views of the portion of the device of FIG. 5A extending from the catheter sheath in a third/expanded or fanned configuration.
Figure 5E:
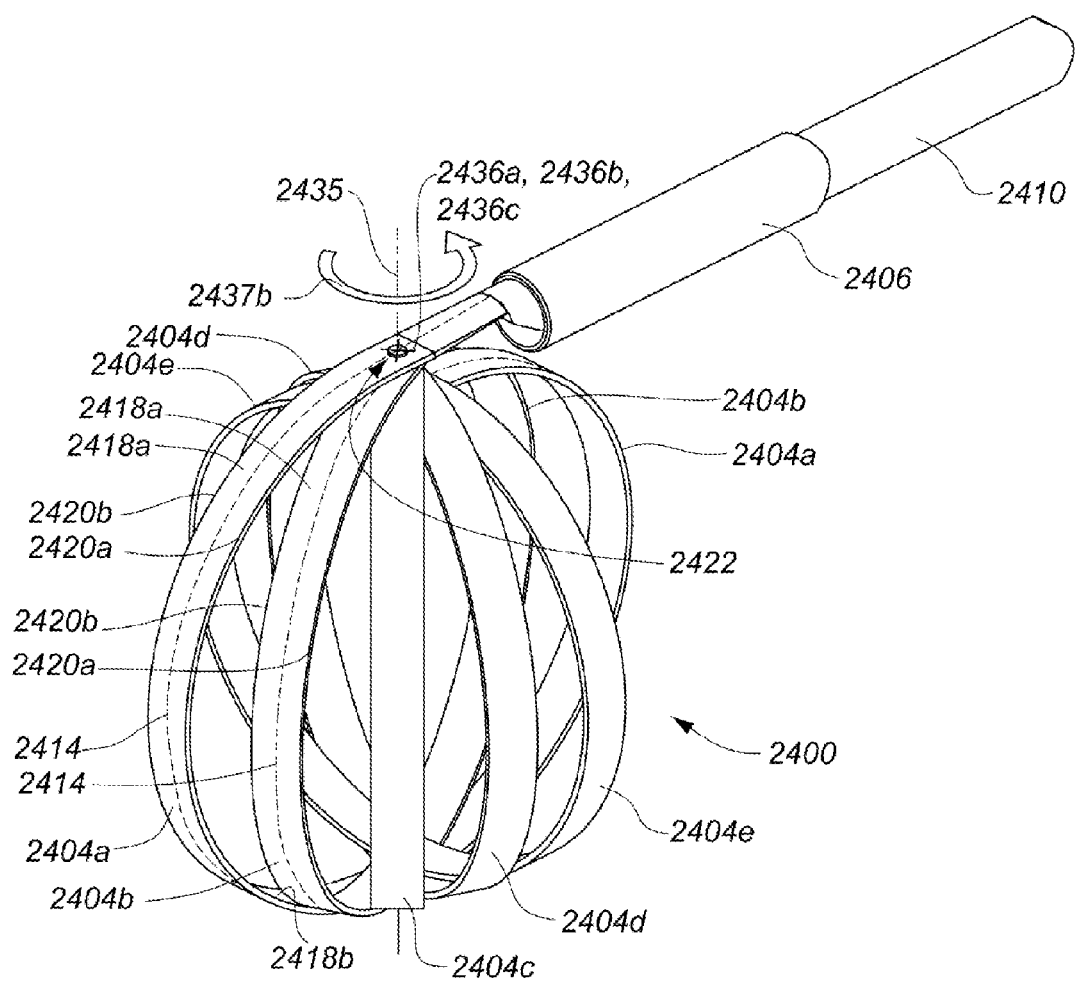
Figure 5F:
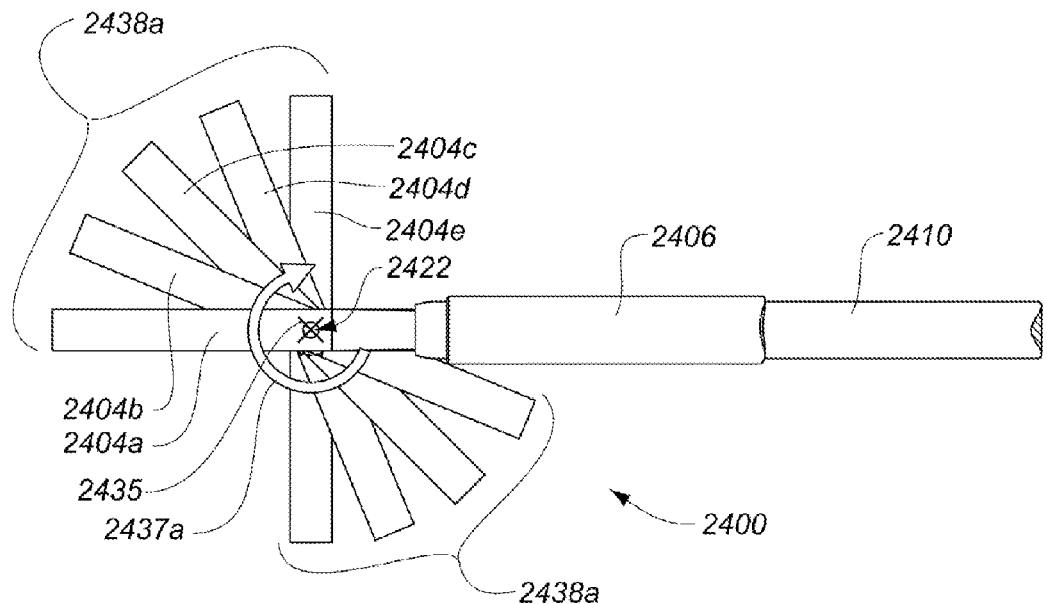
FIGS. 5F and 5G are respective top plan views of the isometric views of a portion of the device extending from the catheter sheath shown in the configurations of FIGS. 5D and 5E, respectively.
Figure 5G:
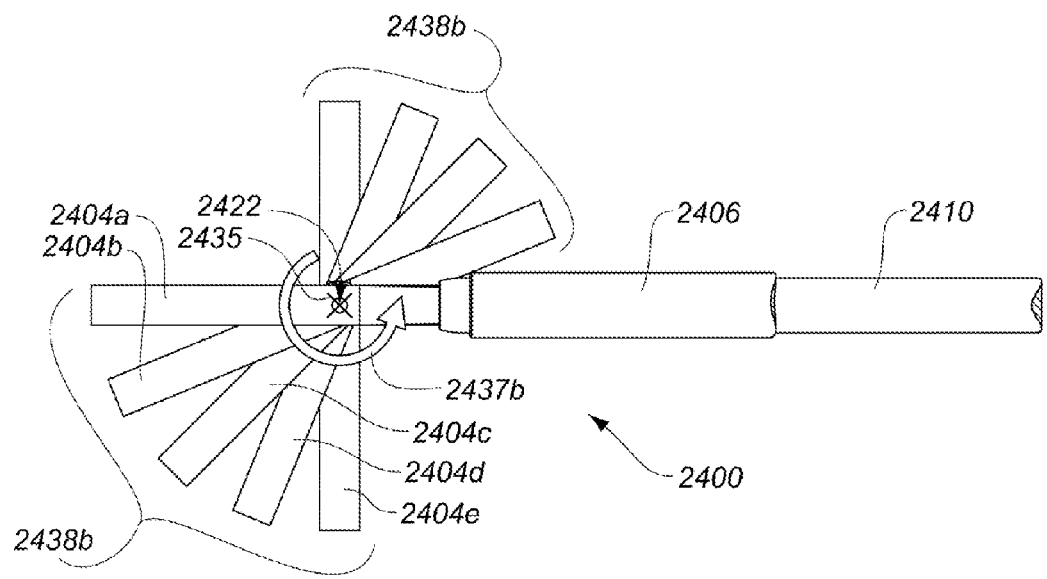

FIGS. 5D and 5F show a portion of device 2400 in a third/expanded or fanned configuration (i.e., an example of a deployed configuration), according to one embodiment. FIGS. 5E and 5G show a portion of device 2400 in a third/expanded or fanned configuration, (i.e., an example of a deployed configuration) according to another embodiment. The third/expanded or fanned configuration can be established within a bodily cavity (not shown) in accordance with various embodiments. In one embodiment, the portion of the device 2400 is moved from the second/bent configuration shown in FIG. 5B to the third/expanded or fanned configuration shown as exemplified by either FIGS. 5D and 5F or by FIGS. 5E and 5G.

In this illustrated embodiment, at least some of the elongate members 2404 are repositioned with respect to at least one other elongate member 2404 in the coiled stacked array 2430. In some embodiments, various ones of the elongate members 2404 are fanned, pivoted or turned with respect to at least one other elongate member 2404 about each of one or more axes, the one or more axes positioned to pass through the at least one other elongate member 2404 at two or more locations, each of the two or more locations spaced from another of the two or more locations along the respective length 2411 (not called out in FIGS. 5D, 5E, 5F and 5G) of the at least one other elongate member 2404. For example, as shown in FIGS. 5D and 5E, various ones of elongate members 2404b, 2404c, 2404d and 2404e are rotated about the one or more axes 2435 which is or are arranged to pass through elongate member 2404a at each of three spaced apart locations 2436a, 2436b and 2436c along the respective length 2411 of elongate member 2404a. Various ones of locations 2436b and 2436c are not easily seen in each of FIGS. 5D and 5E because of the overlapping elongate members 2404 and are called out along with location 2436a. It is understood that locations 2436a, 2436b and 2436c are each respectively spaced apart from one another along the one or more axes 2435. For clarity, the locations 2436a, 2436b and 2436c are represented by a respective "x" in FIG. 5A which shows elongate member 2404a in the first/unexpanded configuration.

In this example embodiment, various ones of elongate members 2404b, 2404c, 2404d and 2404e can be fanned with respect to elongate member 2404a along a first rotational direction (i.e., represented by first arrow 2437a) as shown in FIG. 5D, and along a second rotational direction (i.e., represented by second arrow 2437b) as shown in FIG. 5E that is opposite to the first rotational direction. When the portion of device 2400 is positioned in the second/bent configuration, location 2436b would be located along the respective length 2411 of elongate member 2404a between the respective first portion 2421a (i.e., called out in FIG. 5C) and the respective second portion 2421b (i.e., called out in FIG. 5C) of the front surface 2418a of elongate member 2404a. For clarity, various ones of elongate members 2404a, 2404b, 2404c, 2404d and 2404e have been called out twice in each of FIGS. 5D and 5E to illustrate their annular or quasi-annular or ring-like profile in the third/expanded configuration.

As best illustrated in FIG. 5F, various elongate members 2404 sweep out two opposing fanned sectors 2438a about the one or more axes 2435 (i.e., shown by an "x") when rotated in the first rotational direction (i.e., represented by first arrow 2437a). As best illustrated in FIG. 5G, the various elongate members 2404 sweep out two opposing fanned sectors 2438b about one or more axes 2435 (i.e., shown by an "x") when rotated in the second rotational direction (i.e., represented by second arrow 2437b). In this example embodiment, each fanned sector 2438a and 2438b forms a quadrant of an approximately spherical fanned envelope created by a combination of the two oppositely fanned rotations. A separator (i.e., not shown, but similar in function to that of separators 1452 and 1752) may be employed to fan the various elongate members 2404.

In one example embodiment, elongate member 2404a is manipulated separately from the other elongate members 2404 to unbend and bear against a proximate interior tissue surface within the bodily cavity by an amount sufficient to hold elongate member 2404a relatively fast to the interior tissue surface of the bodily cavity. This can be accomplished, for example, by the use of a bending unit (i.e., not shown but similar in function to that of benders 1430 and 1730) which increases or releases stored potential energy in elongate member 2404a independently from the other elongate members 2404. With elongate member 2404a substantially fixed with respect to the interior surface of the bodily cavity, various ones of elongate members 2404b, 2404c, 2404d and 2404e can be fanned with respect to elongate member 2404a along the first rotational direction (i.e., represented by first arrow 2437a) to distribute transducer elements 2490 (not shown in FIGS. 5D, 5E, 5F, and 5G) across a first set of two opposing regional quadrants of an interior tissue surface within the bodily cavity.

With elongate member 2404a substantially fixed with respect to the interior surface of the bodily cavity, various ones of elongate members 2404b, 2404c, 2404d and 2404e can be fanned with respect to elongate member 2404a along the second rotational direction (i.e., represented by second arrow 2437*b*) to distribute the transducer elements 2490 (again not shown in FIGS. 5D, 5E, 5F, and 5G) across another set of two opposing regional quadrants of interior tissue surface within the bodily cavity. After each of the first and the second rotational movements, an investigational, sensing or treatment action may be undertaken on the respective two opposing quadrants of interior surface region of the bodily cavity associated with each of the first and the second rotational movements. Preferably, elongate members 2404*b*, 2404*c*, 2404*d* and 2404*e* are positioned to reduce contact between the elongate members and an interior tissue surface of the bodily cavity during each of the first and the second rotational movements to reduce occurrences of damage to the interior tissue surface during these movements. After each of the first and the second rotational movements, various ones of elongate members 2404*b*, 2404*c*, 2404*d* and 2404*e* may be additionally manipulated to engage with, or be positioned at least proximate to, the interior tissue surface within the bodily cavity using a same or different mechanism employed to cause the engagement of elongate member 2404*a* with the interior tissue surface.

Advantageously, the substantial fixing of elongate member 2404*a* to the tissue surface can reduce the burden of a registration requirement associated with the investigation, sensing or treatment of each of the two sets of two opposing quadrants of the interior tissue surface region within the bodily cavity. Specifically, in mapping applications, the mapping of features on one set of opposing regional quadrants of the interior surface the bodily cavity can be readily registered with mapping of features on the other set of opposing regional quadrants of the interior surface of the bodily cavity to provide a greater contiguous area map or even a global map of the interior tissue surface. In ablation treatment applications, the formation of an ablation lesion extending continuously across both adjacent regional quadrants of the interior surface of the bodily cavity can reduce stitching burdens to better ensure continuity of the ablation lesion.

Advantageously, the number of elongate members 2404 employed in this embodiment allows for the investigating, sensing or treatment of a larger region of the interior tissue surface of a bodily cavity while reducing a need to add additional elongate members 2404 that would increase the stacked size of stacked arrangement 2415 and possibly necessitate a use of a larger diameter catheter sheath 2406. This is possible since each elongate member 2404 has a respective length 2411 approximately equal or greater than a circumference of a portion of an interior tissue surface of a bodily cavity to which the elongate member 2404 is positioned at least proximate to when the portion of the device 2400 is in a deployed configuration. This allows for a greater region of the tissue surface to be investigated, sensed or treated while providing a stacked arrangement 2415 having a relatively small stacked size along the first direction (i.e., as represented by arrow 2416). It is additionally noted that the greater respective lengths 2411 of the elongate members 2404 can increase their flexibility to further facilitate their delivery through catheter 2406 when the portion of the device is in the first/unexpanded configuration. The respective length 2411 of each elongate member 2404 may be preselected to be greater than a circumference of a portion of an interior tissue surface of a bodily cavity to which the elongate member 2404 is positioned to account for variances in the actual circumference of the portion of the interior tissue surface. The circumference of the portion of the interior tissue surface may have a measured or anticipated value.

Referring back to FIGS. 5D and 5E, the one or more axes 2435 is or are represented as a single axis arranged to pass through at least elongate member 2404*a* at each of three spaced apart locations 2436*a*, 2436*b* and 2436*c* along the respective length 2411 of elongate member 2404*a* in this embodiment. Again, the three spaced apart locations 2436*a*, 2436*b* and 2436*c* are best seen in FIG. 5A. In some embodiments, the one or more axes 2435 may include two or more axes, each of the two or more axes passing though a respective one of at least one of the locations 2436*a*, 2436*b* and 2436*c* that are spaced along the respective length 2411 of at least elongate member 2404*a*. In some embodiments, at least a first axis of the two or more axes is collinear with a second axis of the two or more axes. In some embodiments, at least a first axis of the two or more axes is not collinear with a second axis of the two or more axes. Minor distortions in the elongate members 2404 or various pivot clearances may allow for some degree of non-collinearity between the axes during the fanning.

In this illustrated embodiment, each of the elongate members 2404*b*, 2404*c*, 2404*d* and 2404*e* cross elongate member 2404*a* in an "X" configuration at location 2436*b* in the third/expanded configuration. In various example embodiments, a first elongate member 2404 may cross a second elongate member 2404 in an "X" configuration at two or more locations spaced apart from one another along the respective length 2411 of the second elongate member 2404 in the third/expanded configuration. In some example embodiments, a first elongate member 2404 may cross a second elongate member 2404 in an "X" configuration at least at three locations spaced apart from one another along the respective length 2411 of the second elongate member 2404 in the third/expanded configuration. As used herein and in the claims, when a first elongate member crosses a second elongate member in an X configuration at each of one or more locations, a respective portion of the first elongate member crosses a respective portion of the second elongate member at each location of the one or more locations in a crossed configuration similar in form to the letter "X" as viewed or projected perpendicularly from one of the elongate members at the portion, location or point of the crossing. It is understood that a crossing angle between respective pairs of crossed first and second elongate members may vary within a given embodiment or between different embodiments.

In this example embodiment, one of the respective side edges 2420 of at least a first elongate member 2404 crosses one of the respective side edges 2420 of a second elongate member 2404 at each of a plurality of spaced apart locations along the respective length 2411 of the second elongate member 2404 as viewed normally to each of a respective one of a plurality of portions of the front surface 2418*a* of the second elongate member 2404 over which each of the plurality of spaced apart locations along the respective length 2411 of the second elongate member 2404 is positioned in the third/expanded configuration. In this example embodiment, one of the respective side edges 2420*a* and 2420*b* of at least a first elongate member 2404 crosses an opposite or opposed one of the respective side edges 2420*a* and 2420*b* of a second elongate member 2404 at each of a plurality of spaced apart locations along the respective length 2411 of the second elongate member 2404 as viewed normally to each of a respective one of a plurality of portions of the front surface 2418*a* of the second elongate member 2404 over which each of the plurality of spaced apart locations along the respective length 2411 of the second elongate member 2404 is positioned in the third/expanded configuration. That is, the one of the respective side edges 2420*a* and 2420*b* of the first elongate member 2404 and the crossed one of side edges 2420*a* and 2420*b* of the second elongate member 2404 are on opposing sides of the stacked arrangement 2415 during the first/unexpanded configuration. For example, as shown in FIG. 5D, the side edge 2420*b* of elongate member 2404*a* crosses the side edge 2420*a* of elongate member 2404*b* at each of a plurality of spaced apart locations along the respective length 2411 of elongate member 2404*b* as viewed normally to each of a respective one of a plurality of portions of the front surface 2418*a* of elongate member 2404*b* over which each of the spaced apart locations along the respective length 2411 of elongate member 2404*b* is positioned when the various elongate members 2404 are fanned along the first rotational direction (i.e., as represented by first arrow 2437*a*). Conversely, the side edge 2420*a* of elongate member 2404*a* crosses the side edge 2420*b* of elongate member 2404*b* at each of a plurality of spaced apart locations along the respective length 2411 of elongate member 2404*b* as viewed normally to each of a respective one of a plurality of portions of the front surface 2418*a* of elongate member 2404*b* over which each of the spaced apart locations along the respective length 2411 of elongate member 2404*b* is positioned when the various elongate members 2404 are fanned along the second rotational direction (i.e., as represented by second arrow 2437*b*) as shown in FIG. 5E. The various side edges 2420 of elongate member 2404*a* cross the side edges 2420 of the other elongate members 2404*c*, 2404*d* and 2404*e* in a similar manner in this illustrated embodiment. It is additionally noted in this illustrated embodiment that each of the respective side edges 2420*a* and 2420*b* of at least a first elongate member 2404 crosses a same one (i.e., edges on a same side of stacked arrangement 2415) of the respective side edges 2420*a* and 2420*b* of a second elongate member 2404 at each of a respective plurality of spaced apart locations along the respective length 2411 of the second elongate member 2404 as viewed normally to each of a respective one of a plurality of portions of the front surface 2418*a* of the second elongate member 2404 over which each of the respective plurality of spaced apart locations along the respective length 2411 of the second elongate member 2404 is positioned when the portion of device 2400 is in the third/expanded configuration.

In this example embodiment, the back surface 2418*b* of elongate member 2404*a* contacts the front surface 2418*a* of elongate member 2404*b* at each of at least one of the spaced apart locations along the respective length 2411 of elongate member 2404*b* where a side edge 2420 of elongate member 2404*a* crosses a side edge 2420 of elongate member 2404*b*. In this example embodiment, the back surface 2418*b* of elongate member 2404*a* is separated or spaced from the front surface 2418*a* of each of elongate members 2404*c*, 2404*d* and 2404*e* at each of at least one of the spaced apart locations along the respective length 2411 of each of elongate members 2404*c*, 2404*d* and 2404*e* where a side edge 2420 of elongate member 2404*a* crosses a side edge 2420 of each of elongate members 2404*c*, 2404*d* and 2404*e*.

In this example embodiment, each of locations 2436*b* and 2436*c* passed through by one or more axes 2435 is spaced along the respective length 2411 of elongate member 2404*a* from a location of coupler 2422. In this example embodiment, coupler 2422 forms part of an articulable joint comprising a pivot axis that is generally coincident with the one or more axes 2435 at location 2436*a* in the third/expanded or fanned configuration. In this example embodiment, coupler 2422 is located relatively closer to the proximal end 2407 of elongate member 2404*a* than each of locations 2436*b* and 2436*c* as best exemplified in FIG. 5A. Additional couplers may be employed in other example embodiments. For example, an additional coupler may be employed to couple various ones of the elongate members 2404 together to cause the elongate members 2404 to cross or fan with respect to each other at location 2436*c* in the third/expanded or fanned configuration or maintain a crossed or fanned state at location 2436*c* in the third/expanded or fanned configuration. Additionally, a coupler may be employed to couple the elongate members 2404 at a location at least proximate to location 2436*b*. It is noted that various shearing translational movements typically are present between adjacent ones of the elongate members 2404 in stacked arrangement 2415 when the stacked arrangement 2415 is moved from the first/unexpanded configuration to the third/expanded or fanned configuration especially when the stacked arrangement 2415 is coiled within a bodily cavity. In some example embodiments, couplers employing obliquely oriented pivot members may be employed to allow for the shearing movement. In various embodiments, an employed pivot member may be a relatively rigid member or a relatively flexible member. In this example embodiment, each opening 2419*b* and 2419*c* is sized to receive at least one flexible line 2440 (called out twice) arranged to pass through each of the opening 2419*b* (i.e., shown in broken lines) and 2419*c* (not called out) provided in each of the elongate members 2404 as shown in FIG. 5C. A tubular member 2442 having a lumen sized to receive the at least one flexible line 2440 is additionally provided. Tubular member 2442 is partially sectioned to show flexible line 2440. Upon the application of tension to flexible line 2440 after the stacked arrangement 2415 has been coiled within a bodily cavity, the various elongate members 2404 can be drawn together to align respective ones of the openings 2419*b* together and respective ones of the openings 2419*c* together. Tubular member 2442 is provided to control or impede undesired movement of various portions of the elongate members 2404 towards one another along the at least one axis 2435 (not shown in FIG. 5C) under the influence of the tension in flexible line 2440 when the portion of the device 2400 is in the third/expanded or fanned configuration. In the first/unexpanded configuration, little tension is typically provided in flexible line 2440 and tubular member 2442 is conveyed along with the stacked arrangement 2415 through catheter sheath 2406. For clarity, flexible line 2440 and tubular member 2442 are not shown in FIGS. 5A, 5B, 5D, 5E, 5F, 5G and 5H.

The respective geodesics 2414 of the elongate members 2404 may also cross themselves in the third/expanded or fanned configuration. As best shown in FIGS. 5D and 5E, the respective geodesic 2414 of elongate member 2404*a* crosses the respective geodesic 2414 of at least one other elongate member 2404 (i.e., elongate member 2404*b* in this exemplary case) at various locations along the respective length 2411 of the at least one other elongate member 2404 as viewed normally to a respective portion of the front surface 2418*a* of the at least one other elongate member 2404 over which each respective location is positioned in the third/expanded or fanned configuration. For clarity of illustration, the respective geodesics 2414 of other ones of the elongate members 2404 are not shown in FIGS. 5D and 5E.

Figure 5H:
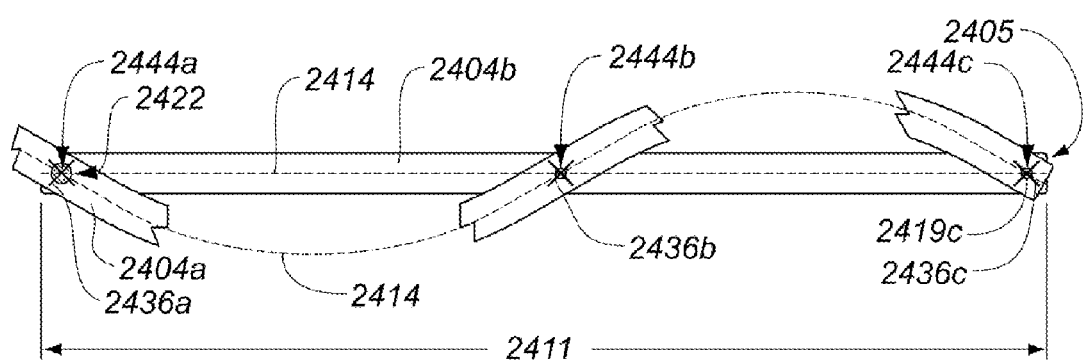
FIG. 5H is a schematic representation of an elongate member of the device of FIG. 5A crossed by various portions of another elongate member in the third/expanded or fanned configuration.

FIG. 5H is a schematic representation of elongate member 2404*b* crossed by various portions of elongate member 2404*a* in the third/expanded or fanned configuration. For clarity, each of elongate members 2404*b* and 2404*a* are shown in a "flattened" state and it is understood that these elongate members comprise respective arcuate profiles as exemplified in FIGS. 5D and 5E. In this example embodiment, elongate member 2404b is crossed by various portions of elongate member 2404a in an X configuration. In this example embodiment, the respective geodesic 2414 of elongate member 2404a advantageously crosses the respective geodesic 2414 of elongate member 2404b at three spaced apart locations including a first location 2444b positioned between two other locations 2444a and 2444c along the respective geodesic 2414 of elongate member 2404b in the third/expanded or fanned configuration. In this illustrated embodiment, each of the three spaced apart locations 2444a, 2444b and 2444c is positioned at least proximate to one of locations 2436a, 2436b and 2436c (i.e., marked by an "X" in FIG. 5H) on elongate member passed though by the one or more axes 2435 (not shown in FIG. 5H). It is noted that other geodesics 2414 defined on each of elongate members 2404a and 2404b may also cross each other in a similar manner. Other embodiments may employ other spatial relationships between the geodesic crossing locations and the locations 2436a, 2436b and 2436c passed through by the one or more axes 2435. In some embodiments, various ones of the geodesic crossing locations or various ones of the locations 2436a, 2436b and 2436c passed through by the one or more axes 2435 may not coincide with a location of a coupler (e.g., coupler 2422) employed to couple an elongate member 2404 with at least one other elongate member 2404.

In this example embodiment, various ones of the three spaced geodesic crossing locations including geodesic crossing location 2444b are located along the respective length 2411 of elongate member 2404b between a location of the coupler 2422 and the respective distal end 2405 of elongate member 2404b. In this example embodiment, geodesic crossing location 2444b is also located along the respective length 2411 of elongate member 2404b between coupler 2422 and a second coupler comprising flexible line 2440 (not shown in FIG. 5H) passing through opening 2419c in elongate member 2404b.

Figure 6A:
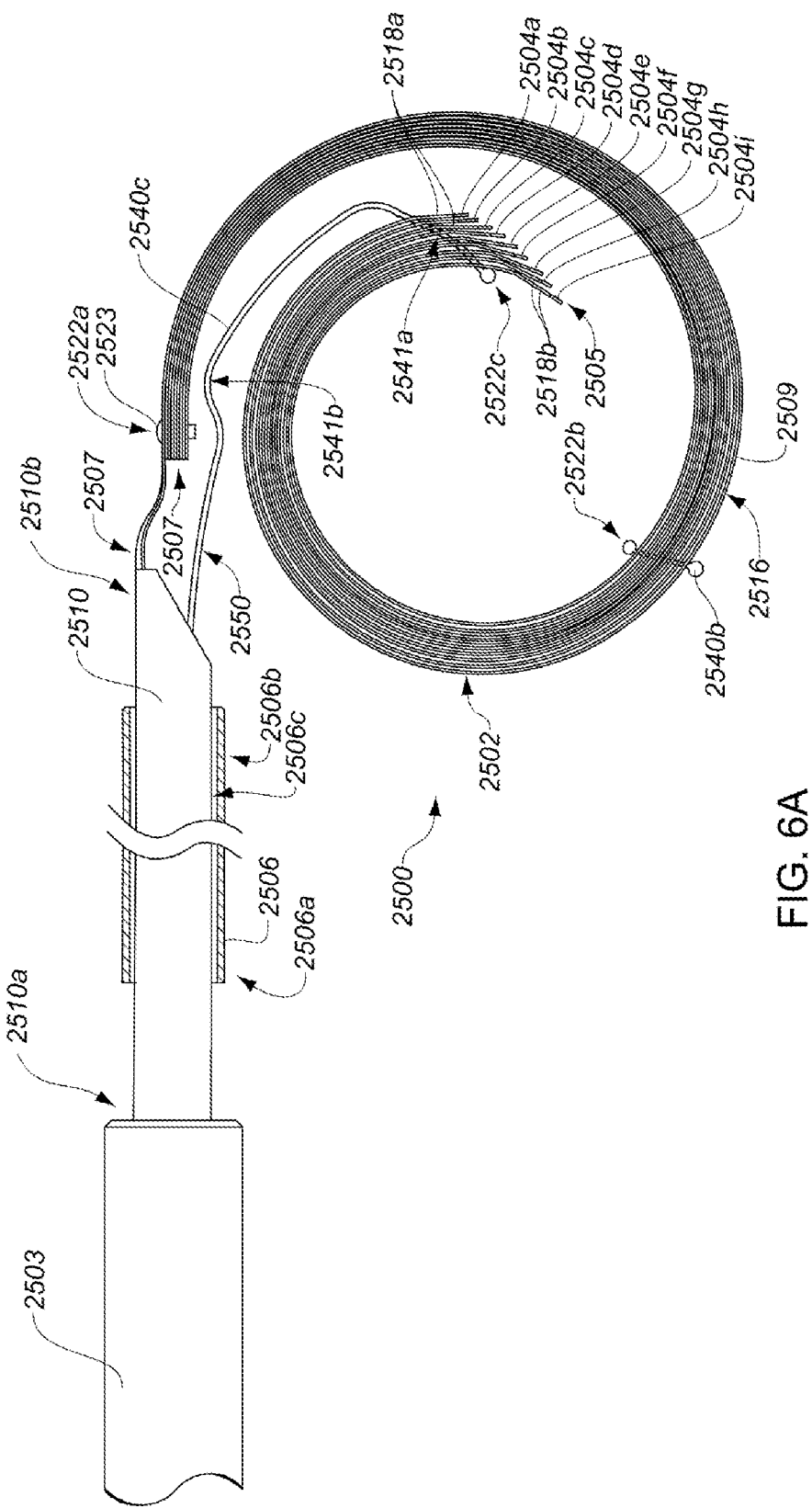
FIG. 6A is a side elevation view a portion of a device that includes a number of elongate members extending from a catheter sheath and in an initial configuration according to another example embodiment.

FIG. 6A is a side elevation view of a portion of a device 2500 according to one example embodiment. Device 2500 includes a structure or frame 2502 that includes an arrangement of elongate members 2504a, 2504b, 2504c, 2504d, 2504e, 2504f, 2504g, 2504h, and 2504i (collectively 2504). Various ones of the elongate members 2504 are physically coupled to shaft member 2510 which is sized to convey the elongate members 2504 through catheter sheath 2506. Shaft member 2510 includes a first end portion 2510a physically coupled to a handle portion 2503 and a second end portion 2510b physically coupled to frame 2502. In this example embodiment, the second end portion 2510b of shaft member 2510 is coupled to frame 2502 at one or more locations proximate to the respective proximal ends 2507 (only one called out) of various ones of the elongate members 2504. In this example embodiment, the second end portion 2510b of shaft member 2510 is physically coupled to frame 2502 at a location proximate the respective proximal end 2507 of elongate member 2504a.

Figure 6B:
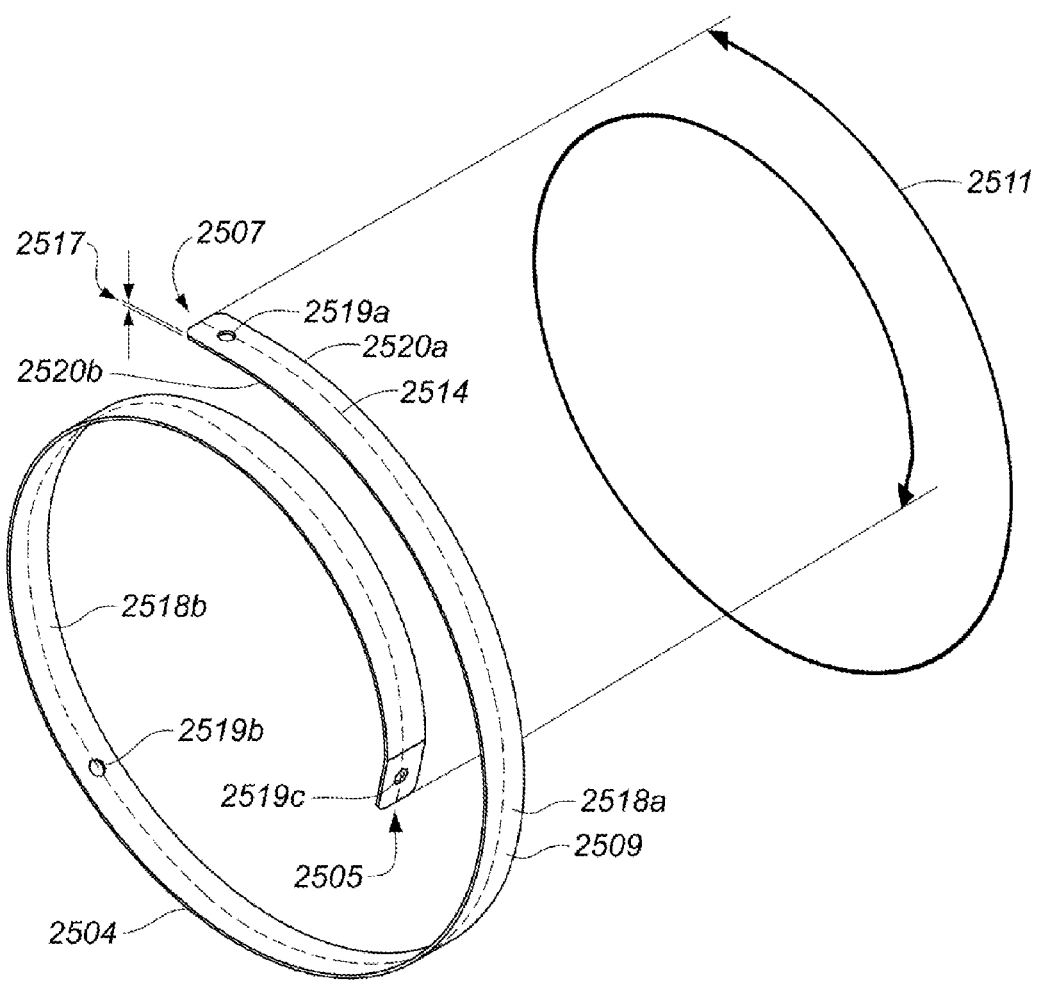
FIG. 6B is an isometric view of a representative one of the elongate members of the device of FIG. 6A, and a projection of that elongate member.

FIG. 6B is an isometric view of a representative one of the elongate members 2504. Each of the elongate members 2504 includes a respective distal end 2505, a respective proximal end 2507 and an intermediate portion 2509 positioned between the proximal end 2507 and the distal end 2505. Each elongate member 2504 includes a respective length 2511 between the respective proximal and distal ends 2507, 2505 of the elongate member. In this example embodiment, each of various ones of the elongate members 2504 has a different respective length 2511 than the respective length 2511 of another of the elongate members 2504. In some embodiments, two or more of the elongate members 2504 may have substantially equal lengths 2511. In a manner similar to the respective length of various previously described elongate members, each of the elongate members 2504 has a respective length 2511 (not called out in FIGS. 6A, 6C, 6D, 6E, 6F, 6G, 6H, 6I, 6J, 6K, 6L, and 6M) that is at least approximately equal or greater than a circumference of a portion of an interior tissue surface of a bodily cavity (not shown) to which the elongate member 2504 is positioned at least proximate to when the portion of the device 2500 is in a deployed configuration. In a manner similar to other described embodiments, transducer elements (not shown) may be distributed along the respective length 2511 of various ones of the elongate members 2504. Transducer elements carried by a given one of elongate members 2504 can be distributed around a circumferential region of the interior tissue surface of a bodily cavity (again not shown) over which the given one of the elongate members 2504 is positioned at least proximate to in a deployed configuration.

Referring back to FIG. 6B, the intermediate portion 2509 of each of the elongate members 2504 includes a set of two opposing major faces or surfaces 2518 made up of a front surface 2518a and a back surface 2518b. In this example embodiment, the two opposing surfaces 2518 are separated from one another by a thickness 2517 of the elongate member 2504. In this illustrated example, the intermediate portion 2509 of each elongate member 2504 further includes a pair of side edges 2520a, 2520b (collectively 2520) of at least one of the front surface 2518a and the back surface 2518b (i.e., front surface 2518a in this embodiment), the side edges of each pair of side edges 2520 opposed to one another across at least a portion of the length 2511 of the respective elongate member 2504. In this example embodiment, the pair of side edges 2520 defines a portion of a periphery of the front surface 2518a of the elongate member 2504. A geodesic 2514 (i.e., shown as a broken line) is definable for each elongate member 2504. Each geodesic 2514 extends along a portion of the elongate member 2504 between a first location at least proximate the proximal end 2507 and a second location at least proximate the distal end 2505 of the elongate member 2504. In this embodiment, each geodesic 2514 extends across the respective front surface 2518a of the elongate member 2504. A portion of geodesic 2514 is shown on the back surface 2518b of elongate member 2504b in FIG. 6B for clarity only. It is understood that the geodesic 2514 in FIG. 6B extends across the front surface 2518a of elongate member 2504. Each elongate member 2504 includes a plurality of openings including first opening 2519a, second opening 2519b and third opening 2519c. In this embodiment, each of first opening 2519a, second opening 2519b and third opening 2519c provides a passageway through the intermediate portion 2509 of a respective elongate member 2504. Each of first opening 2519a, second opening 2519b and third opening 2519c is spaced from one another along the length 2511 of a respective elongate member 2504.

In this example embodiment, at least the respective intermediate portions 2509 (one called out in FIG. 6A) of various ones of the elongate members 2504 are preformed to have a substantially bent, arcuate or curved profile in an initial state (i.e., a low energy state). As best shown in FIG. 6A, each of various ones of the elongate members 2504 has a coiled profile (e.g., a profile that curves back on itself) in the initial or low energy state. In some example embodiments, various ones of the elongate members 2504 are coiled in the initial or low energy state. In this particular embodiment, each of the elongate members 2504 includes a scrolled or volute shape profile in the initial configuration. As shown in FIG. 6A, each of the respective intermediate portions 2509 of the elongate members 2504 are arranged with respect to one another front surface 2518a-toward-back surface 2518b in an initial stacked array 2516 in the initial configuration. In this illustrated embodiment, the initial stacked array 2516 is an arcuate stacked array. In this illustrated embodiment, the initial stacked array 2516 is a coiled stacked array. In this illustrated embodiment, each of the elongate members 2504 has a different curvature along its respective length 2511 in the initial stacked array 2516. In this example embodiment, each of the elongate members 2504 makes at least one full turn within the initial stacked array 2516.

In various example embodiments, each of various ones of the elongate members 2504 is physically coupled together with at least one other elongate member 2504 by at least one coupler. In this illustrated embodiment, device 2500 includes a plurality of couplers 2522 including a proximal coupler 2522a, a distal coupler 2522c and at least one intermediate coupler 2522b. In various example embodiments, each of proximal coupler 2522a, distal coupler 2522c and at least one intermediate coupler 2522b is arranged to couple at least a first one of the elongate members 2504 with at least one other of the elongate members 2504. In this illustrated embodiment, proximal coupler 2522a forms part of a pivotable joint and includes a pivot member 2523. In this embodiment pivot member 2523 is in the form of a pin sized to be received in the respective first opening 2519a (i.e., first opening 2519a shown in FIG. 6B) provided in each of the elongate members 2504. Each of various ones of the elongate members 2504 is configured to turn, revolve, pivot or rotate (i.e., used interchangeably herein) about a pivot axis associated with pivot member 2523.

In this example embodiment, distal coupler 2522c includes a first portion 2541a of a flexible line 2540c sized and arranged to be received in the respective third opening 2519c (i.e., best seen in FIG. 6B) of each of the elongate members 2504 thereby physically coupling each of the elongate members 2504 together. In this example embodiment, at least a second portion 2541b of flexible line 2540c forms part of a control member of an elongate member manipulator 2550, a portion of which may extend along a path through catheter sheath 2506. Elongate member manipulator 2550 may include various actuators (not shown) operably coupled to various control members to transmit force via the various control members. Suitable actuators may include powered or passive actuators. Suitable actuators may include a handle, knob, lever, etcetera (not shown) manipulated by a care provider to cause force to be transmitted via a control member. In some embodiments, a separate control member is coupled to the first portion 2541a of flexible line 2540c. In this example embodiment, intermediate coupler 2522b includes a flexible line 2540b sized and arranged to be received in the respective second opening 2519b (i.e., best seen in FIG. 6B) of each of the elongate members 2504 thereby physically coupling each of the elongate members together. Various knots, ferrules, bushings, etcetera may be employed to restrain a flexible line positioned in at least one of second and third openings 2519b, 2519c from escaping from the openings. It is noted that alternative or additional couplers 2522 can be employed in some embodiments. For example, couplers such as coupling members 1458, 1758 may be employed to couple various ones of the elongate members 2504 together. It is noted that the number of couplers 2522 is not limited to three and may include a number less than or greater than three. In some example embodiments only proximal coupler 2522a and distal coupler 2522c are employed. Various ones of the proximal coupler 2522a, distal coupler 2522c and at least one intermediate coupler 2522b may each couple some or all of the elongate members 2504 in various example embodiments.

Figure 6C:
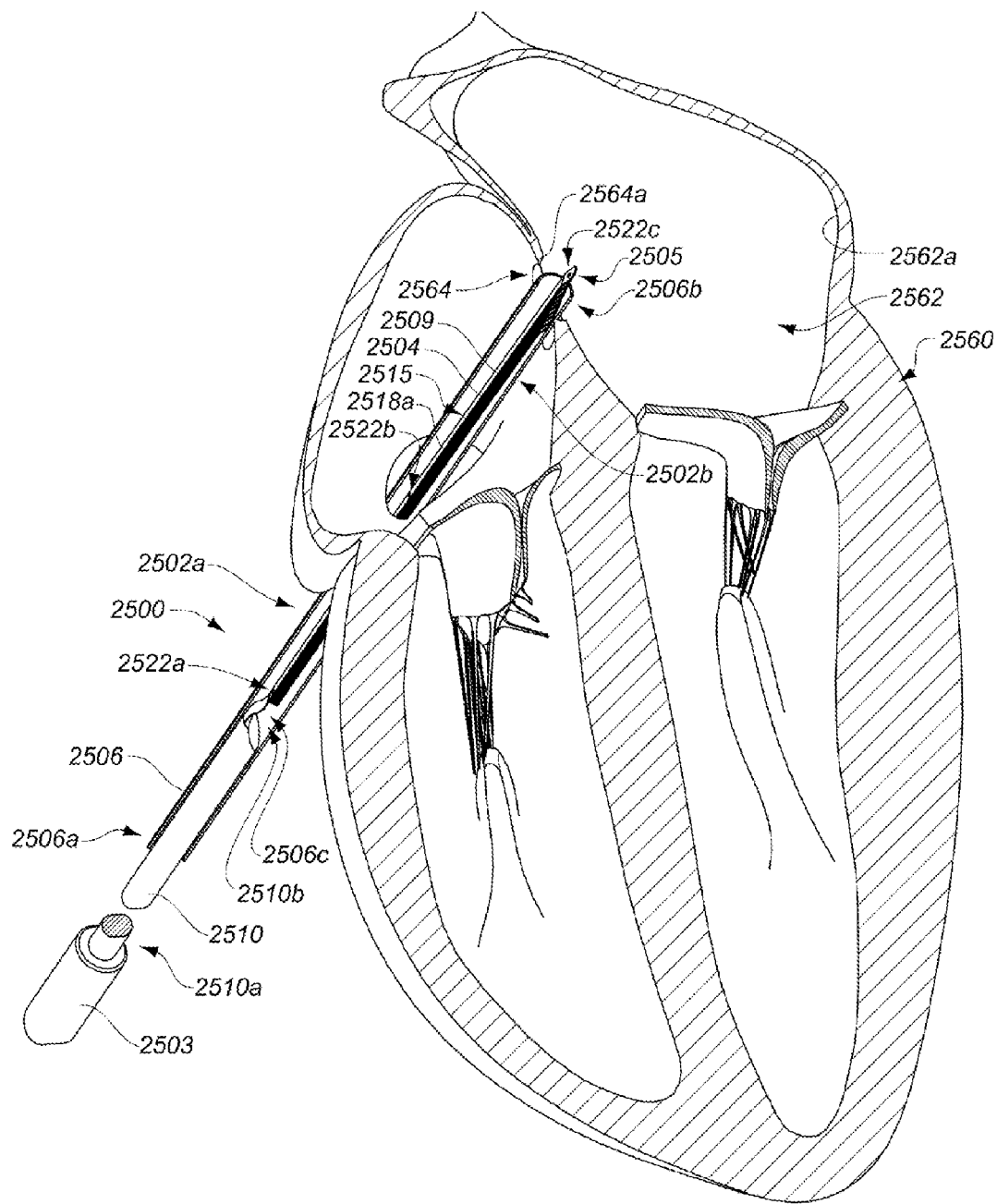
FIGS. 6C, 6D, 6E, and 6F are various side elevation views of a portion of the device in FIG. 6A positioned within a bodily cavity at four successive intervals of time according to an example embodiment.

In this example embodiment, FIGS. 6C, 6D, 6E, and 6F are various side elevation views of a portion of device 2500 positioned within a bodily cavity at four successive intervals of time according to an example embodiment. In this illustrated embodiment, the bodily cavity is a left atrium 2562 of a heart 2560 which is shown sectioned for clarity. As shown in FIG. 6C, the elongate members 2504 (only one called out) are interleaved with one front surface 2518a toward another's back surface 2518b (not called out in FIG. 6C) in a stacked array 2515 sized to be delivered through a bodily opening 2564 (i.e., via a lumen 2506c of catheter sheath 2506 shown sectioned in FIG. 6C) when a portion of device 2500 is in a delivery configuration also known as a first or unexpanded configuration. In this example embodiment, the bodily opening 2564 leads to left atrium 2562 which includes an interior tissue surface 2562a that is interrupted by a port 2564a of opening 2564. In this example embodiment, the respective intermediate portions 2509 (only one called out) of the elongate members 2504 are arranged in stacked array 2515 such that each elongate member 2504 is advanced distal end 2505 first into left atrium 2562 in the first/unexpanded configuration. In this example embodiment, the plurality of couplers 2522 are arranged to be advanced distal coupler 2522c first into left atrium 2562 in the delivery configuration. For clarity, flexible lines 2540b and 2540c associated with respective ones of intermediate coupler 2522b and distal coupler 2522c are not shown in FIGS. 6C, 6D, 6E, 6F, 6G, 6H, 6I, 6K, 6L, 6N and 6O.

In this example embodiment, the respective intermediate portions 2509 of various ones of the elongate members 2504 in the initial stacked array 2516 have been stressed into a higher energy state from their initial or low energy state shown in FIG. 6A. In this example embodiment, the elongate members 2504 in the initial stacked array 2516 have been stressed into a higher energy state suitable for unbending them sufficiently enough for delivery through catheter sheath 2506 during the delivery configuration as shown in FIG. 6C. In this example embodiment, the initial stacked array 2516 is stressed into a higher energy state by retracting the initial stacked array 2516 into catheter sheath 2506 prior to inserting catheter sheath 2506 into a body. In some example embodiments, the initial stacked array 2516 is stressed into a higher energy state by uncoiling the initial stacked array 2516 and inserting the initial stacked array into catheter sheath 2506. In some example embodiments, the arrangement of elongate members 2504 is reconfigured from the initial configuration shown in FIG. 6A to the delivery configuration shown in FIG. 6C at a point-of-use. In some example embodiments, the arrangement of elongate members 2504 is reconfigured from the initial configuration shown in FIG. 6A to the delivery configuration shown in FIG. 6C at a place of manufacture, assembly or distribution. In various embodiments, various devices including various guides or manipulators may be employed to reconfigure the arrangement of elongate members 2504 from the initial configuration shown in FIG. 6A to the delivery configuration shown in FIG. 6C. In some of these various embodiments, the devices form part of device 2500. In some of these various embodiments, the devices are extraneous to device 2500. Preferably, the higher energy states are controlled to not cause damage to device 2500 or catheter sheath 2506 during delivery therethrough.

In this example embodiment, potential energy is imparted into the various elongate members 2504 in the stacked array 2515 by the higher energy state, the potential energy sufficient to return the arrangement of elongate members 2504 generally back to their initial energy state when released from the confines of catheter sheath 2506. In this example embodiment, the lumen 2506c is positioned between a first end 2506a of catheter sheath 2506 and a second end 2506b of catheter sheath 2506. In some embodiments, catheter sheath 2506 may include a plurality of lumens. In this embodiment, each of the elongate members 2504 is arranged to be delivered through the lumen 2506c of the catheter sheath from the first end 2506a toward the second end 2506b in the delivery configuration. In this example embodiment, each of the elongate members 2504 is arranged to be advanced distal end 2505 first out from the lumen 2506c of the catheter sheath 2506 in the delivery configuration.

Figure 6D:
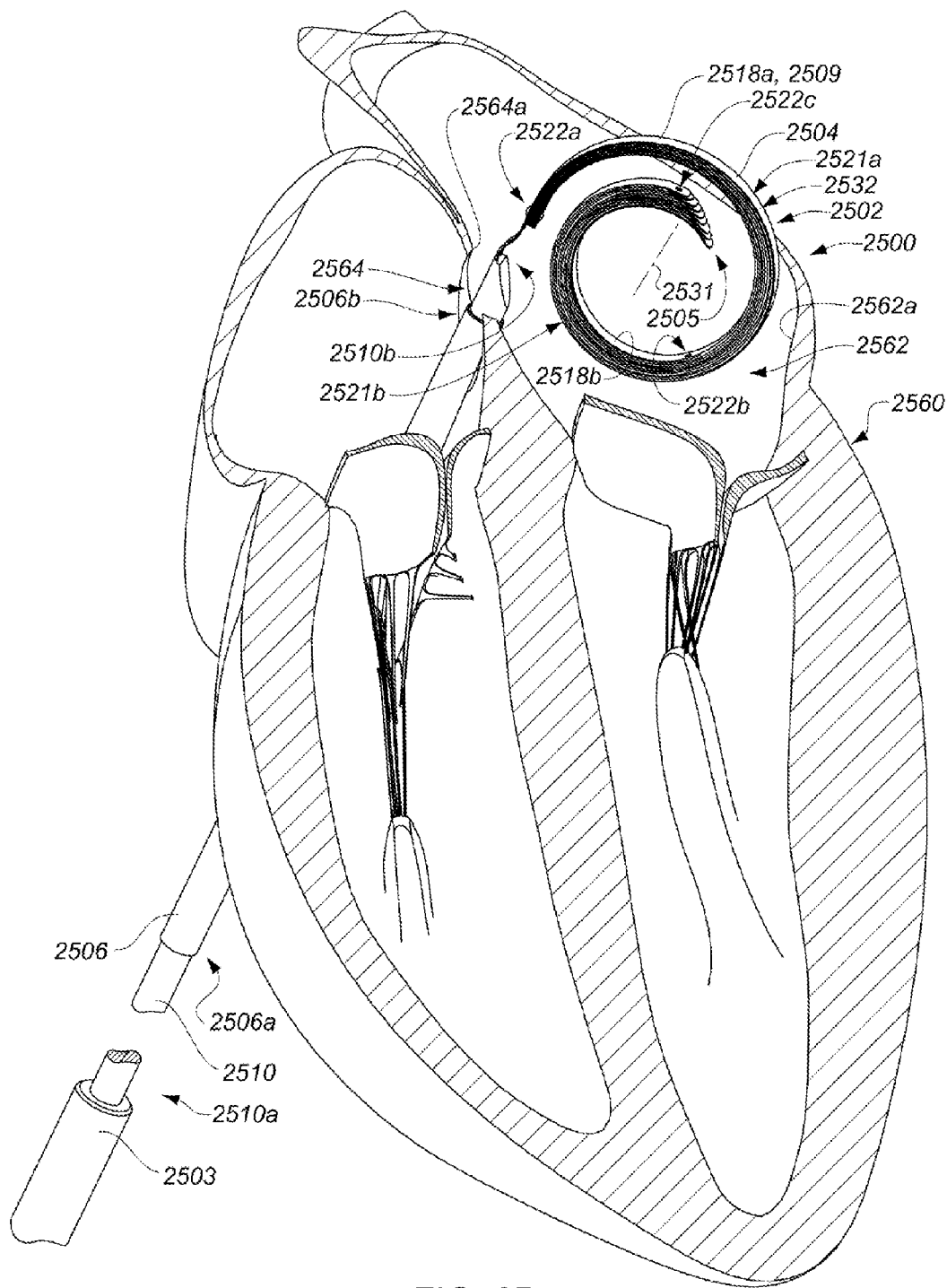

FIG. 6D shows the portion of the device 2500 including the plurality of elongate members 2504 positioned in a deployed configuration also known as a second or bent configuration within left atrium 2562. In this example embodiment, each elongate member 2504 (only one called out) is bent about a respective bending axis 2531 (only one shown) into an arcuate stacked array 2532. In some embodiments, a portion of each of various ones of the elongate members 2504 is bent with a substantially constant curvature about a respective bending axis 2531. In some embodiments, a portion of each various ones of the elongate members 2504 is bent with a varying curvature about a respective bending axis 2531. Each bending axis 2531 extends along a direction having a directional component transversely oriented to the respective length 2511 (not called out in FIG. 6D) of the elongate member 2504. In this example embodiment, each elongate member 2504 in the arcuate stacked array 2532 is coiled about a respective bending axis 2531 into a coiled stacked array. In this example embodiment, each elongate member 2504 is bent to have a volute shape profile within the left atrium 2562. In this example embodiment, each elongate member is bent to have a curvature within the left atrium that varies at least once along the respective length 2511 of the elongate member 2504. When positioned in the second/bent configuration, a first portion 2521a of the front surface 2518a of the respective intermediate portion 2509 (only one called out) of each elongate member 2504 is positioned diametrically opposite to a second portion 2521b of the front surface 2518a in the volute shaped frame 2502. When positioned in the second/bent configuration, the coiled arrangement of elongate members 2504 is sized too large for delivery through the lumen 2506c of catheter sheath 2506.

In this illustrated embodiment, the respective intermediate portions 2509 of various ones of the elongate members 2504 have been preformed to autonomously bend when the intermediate portions 2509 are advanced into a bodily cavity such as left atrium 2562. As the respective intermediate portions 2509 are advanced into left atrium 2562, they are freed of the confines of catheter sheath 2506 and return to their low energy state (i.e., their initial coiled configuration). In this example embodiment, the respective distal end 2505 of various ones of the elongate members 2504 moves along a coiled path (e.g., a path that curves back on itself) within the left atrium 2562 when the portion of the device 2500 is moved between the first/unexpanded configuration and the second/bent configuration. In this example embodiment, the coiled path makes at least one full turn within left atrium 2562. In some embodiments, at least part of the coiled path may extend along a volute path. In this example embodiment, the elongate members 2504 in the second/bent configuration are arranged in an arcuate stacked array 2532 that is similar to the initial stacked array 2516 that elongate members 2504 are arranged in their initial state (i.e., as shown in FIG. 6A). In this example embodiment, shaft member 2510 and frame 2502 have a projected outline generally in the shape of the Greek letter rho (ρ) in the second/bent configuration, which letter may be open at point where a loop of the letter would intersect a tail of the letter, and either without, or with, an opening defined by the loop portion of the letter represented in the projected outline.

In this embodiment, various elongate members 2504 are preformed to cause stacked array 2515 to autonomously coil as it is advanced into left atrium 2562 in a manner that may advantageously reduce physical interactions between stacked arrangement 2515 and interior tissue surface 2562a within left atrium 2562 since the respective distal ends 2505 (only one called out) of the elongate members 2504 continuously bend or curl away from the interior tissue surface 2562a as the elongate members 2504 are advanced into left atrium 2562. A reduction of contact and other physical interaction with the interior tissue surface 2562a can reduce occurrences of, or the severity of, damage inflicted to various tissue structures within left atrium 2562 during this positioning. In this illustrated embodiment, the arcuate stacked array 2532 is preferably sized to be positionable within left atrium 2562 with at most, minor amounts of contact with the interior tissue surface 2562a of left atrium 2562. This illustrated embodiment may additionally reduce potential damage to various tissue structures within left atrium 2562 over embodiments employing benders (e.g., benders 1430, and 1730) that bend the elongate members as they are advanced into a bodily cavity. Many benders can impart potential energy into the elongate members during the bending of various portions of the elongate members within a bodily cavity. A failure of either the bender or the elongate member itself can release at least a portion of the potential energy and possibly damage various tissue structures in the bodily cavity. Unlike those embodiments, the elongate members 2504 in the arcuate stacked array 2532 have little potential energy since they are substantially already in their low energy state.

Figure 6E:
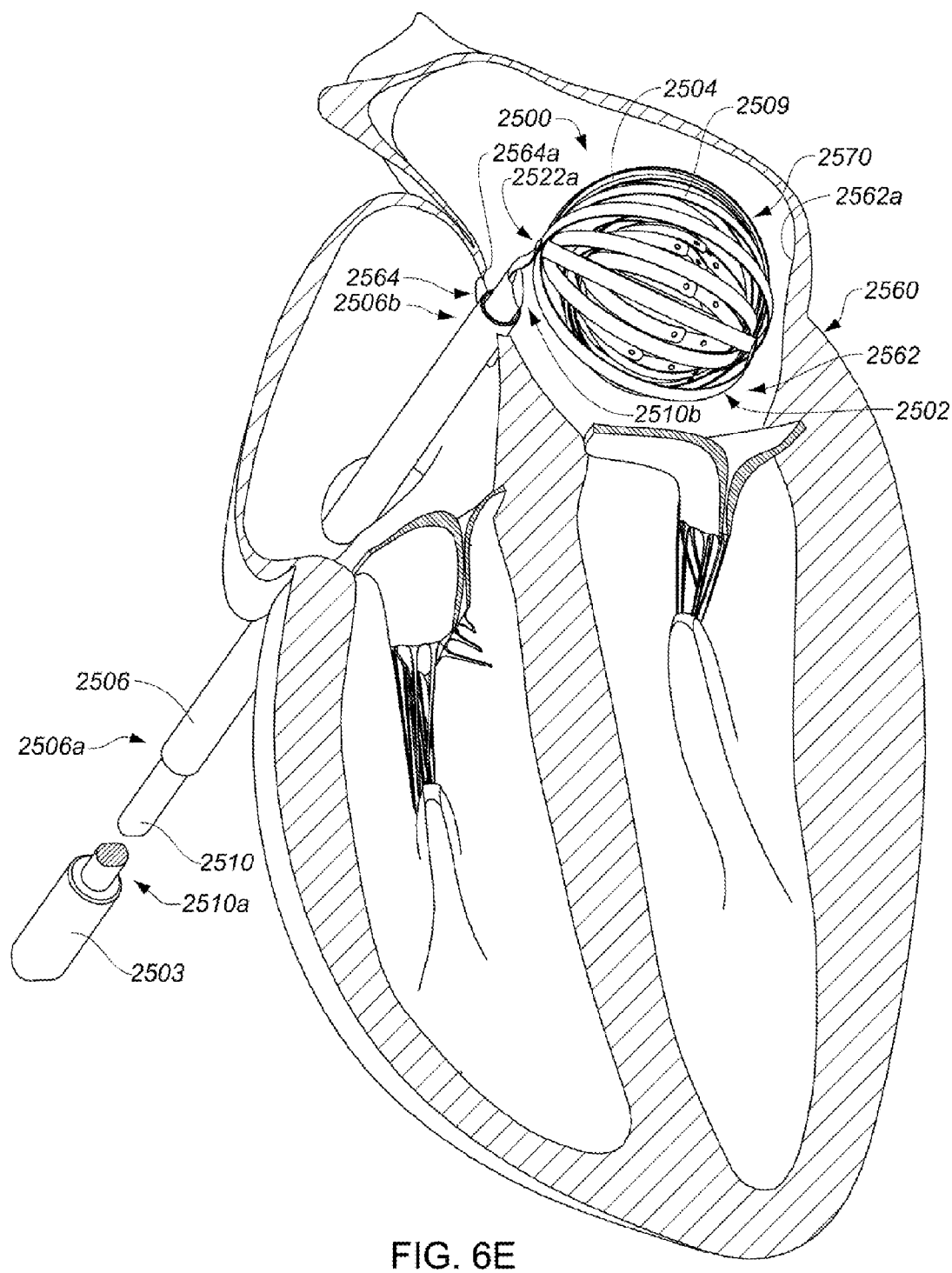

FIG. 6E shows the portion of the device 2500 in a deployed configuration also referred to as a third or expanded or fanned configuration in left atrium 2562. In this illustrated embodiment, the elongate members 2504 (only one called out) were moved from the second/bent configuration shown in FIG. 6D to the third/expanded or fanned configuration shown in FIG. 6E. In this illustrated embodiment, at least some of the elongate members 2504 in the arcuate stacked array 2515 shown in FIG. 6E are repositioned in left atrium 2562. In this example embodiment, various ones of the elongate members 2504 are moved to angularly space various portions of at least some of the elongate members 2504 with respect to one another within left atrium 2562. In this illustrated embodiment, various ones of the elongate members 2504 are fanned with respect to one another about one or more fanning axes (not shown in FIG. 6E) into a first fanned array 2570.

Figure 6F:
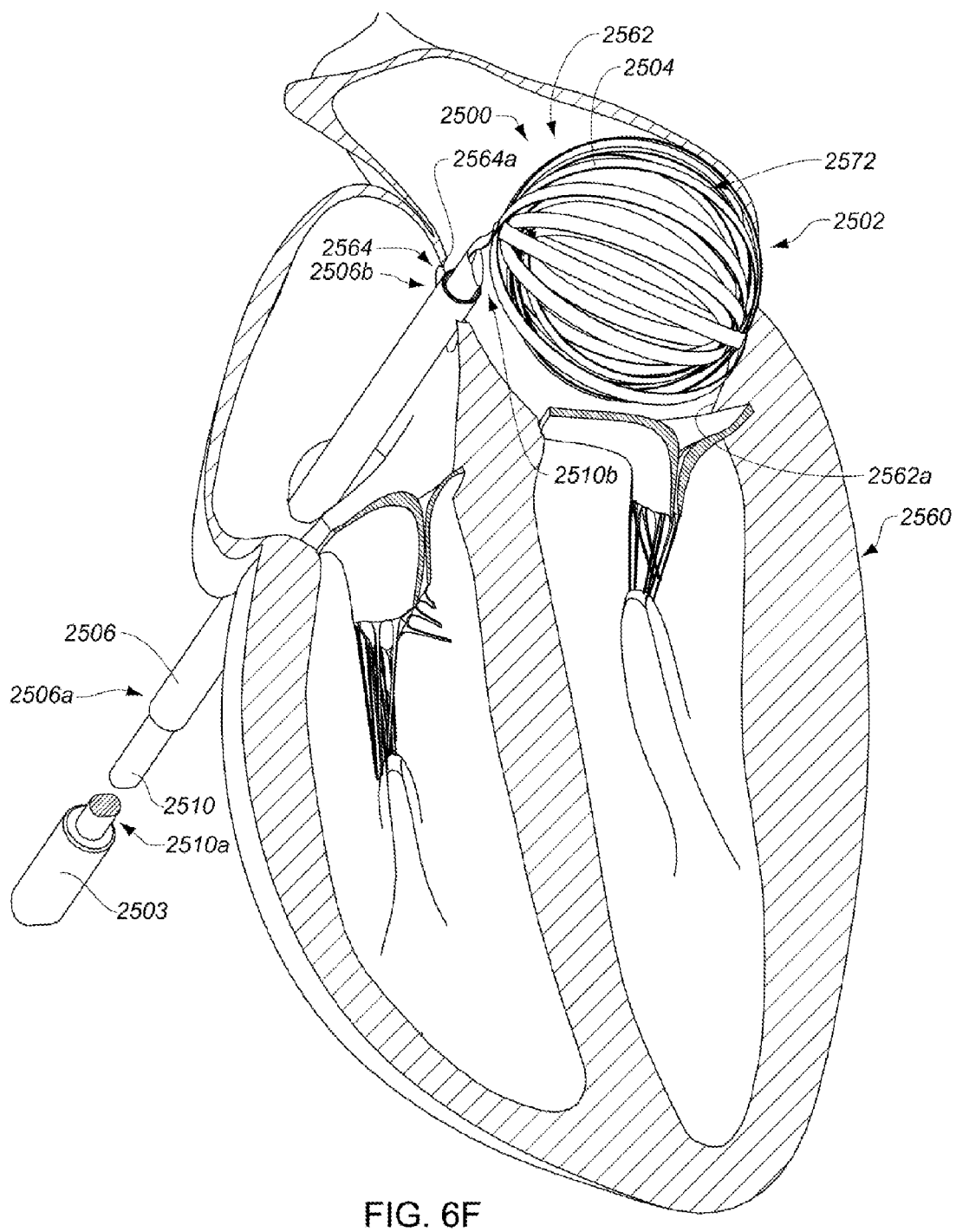
Figure 6G:
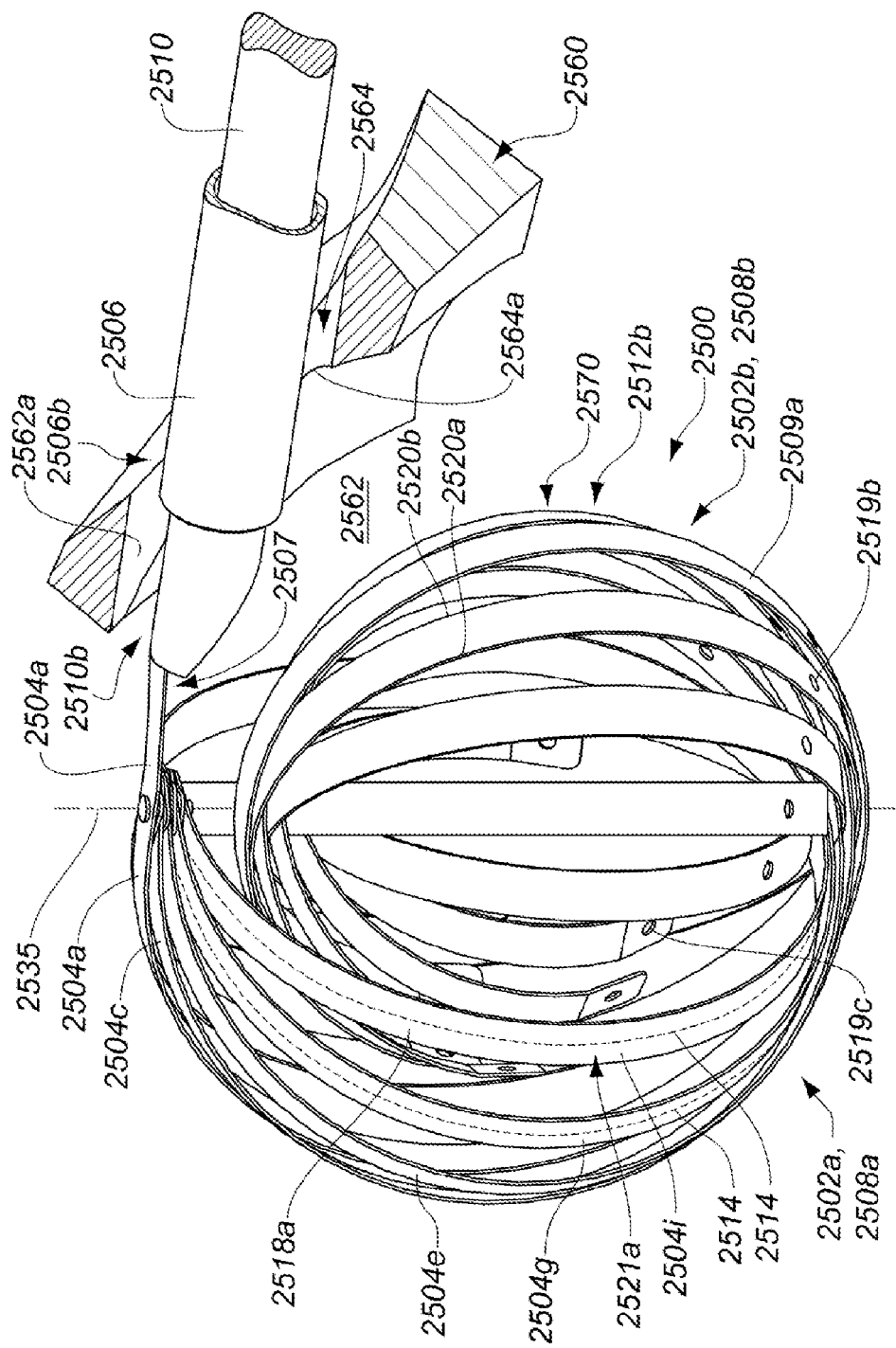
FIGS. 6G and 6H are various perspective views of the elongate members of the device of FIG. 6A extending from the catheter sheath, the elongate members arranged in a first expanded or fanned array.
Figure 6H:
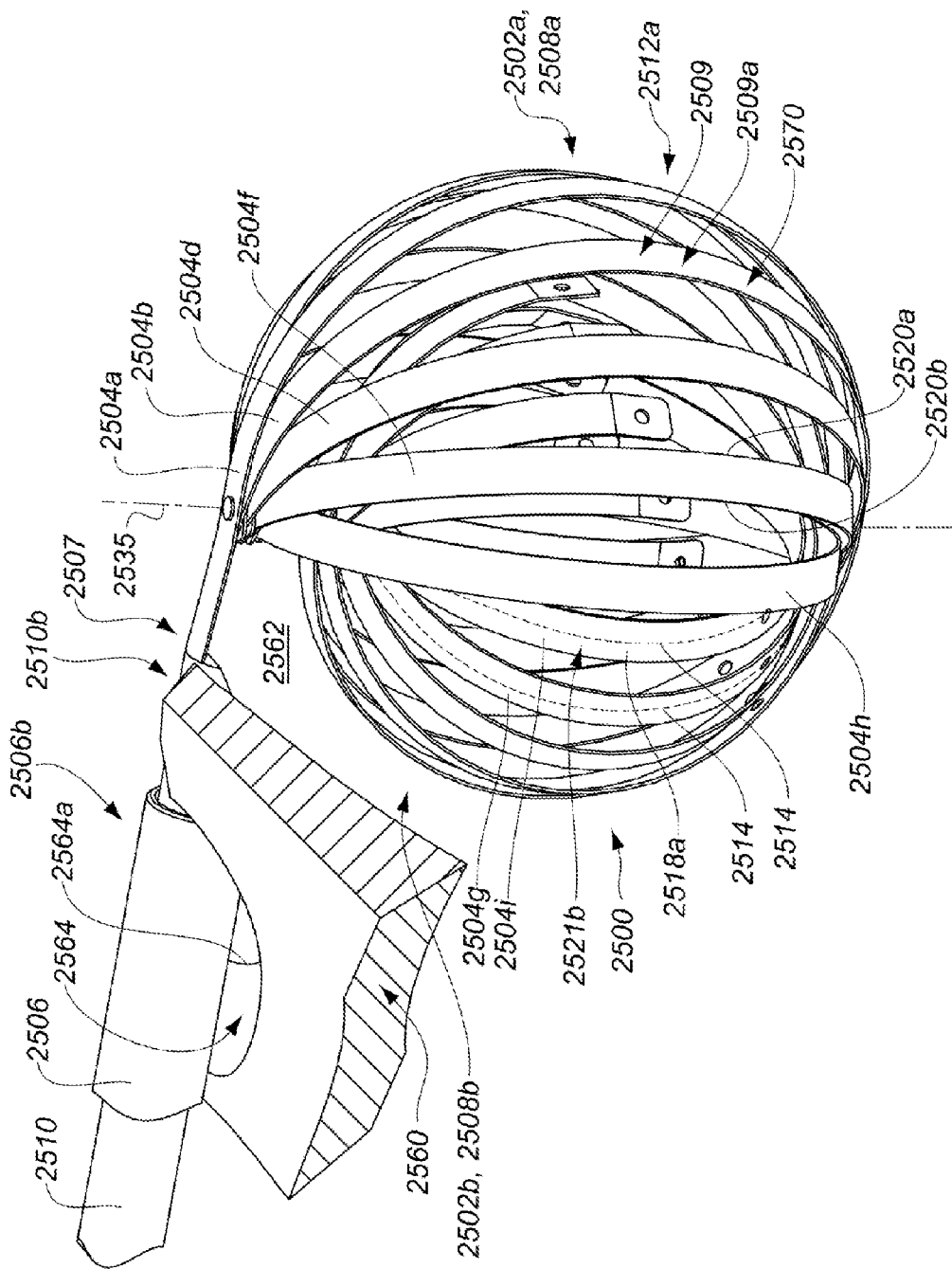
Figure 6I:
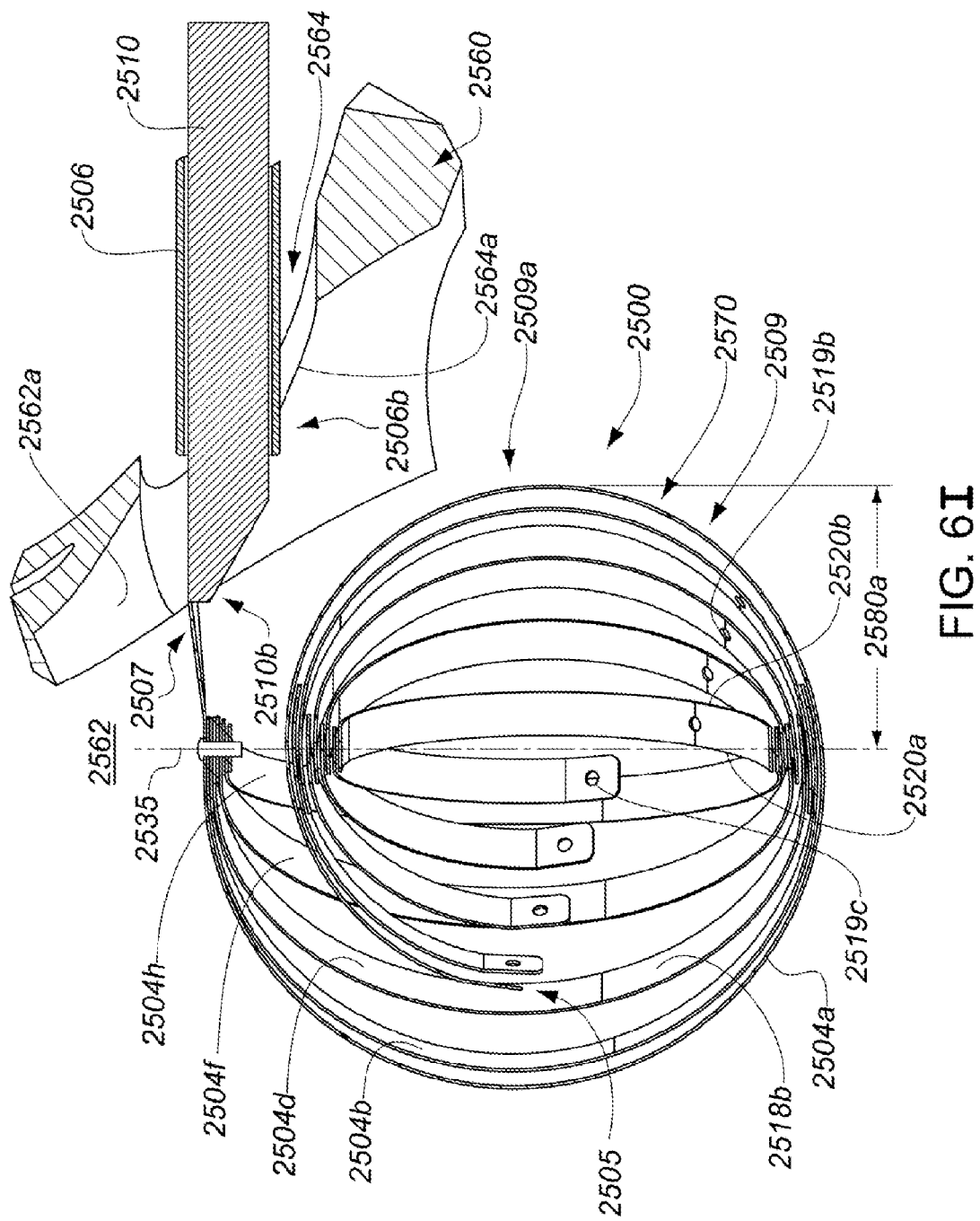
FIG. 6I is a sectioned side elevation view of the elongate members of the device of FIG. 6A extending from the catheter sheath, the elongate members arranged in a first expanded or fanned array.

As shown in FIGS. 6G, 6H, 6I and 6J, at least one of the elongate members 2504 crosses another of the elongate members 2504 in an X configuration at a location proximate a first axis 2535. As shown in FIGS. 6G, 6H, 6I and 6J, various ones of the elongate members 2504 are fanned about first axis 2535. In this example embodiment, first axis 2535 passes though a plurality of spaced apart locations along the respective length 2511 of each of at least some of the elongate members 2504 when the portion of the device is in the third/expanded or fanned configuration. In this example embodiment, the respective intermediate portions 2509 of each of at least some of the elongate members 2504 are angularly spaced with respect to one another about first axis 2535. In this illustrated embodiment, each of the at least some of the plurality of elongate members 2504 includes a curved portion 2509*a* (i.e., shown in FIGS. 6G, 6H, and 6I) arranged to extend along at least a portion of a respective curved path that intersects the first axis 2535 at each of a respective at least two spaced apart locations along first axis 2535 in the third/expanded configuration. In various embodiments, a curved portion 2509*a* of an elongate member 2504 can extend entirely along, or at least partway along a respective curved path that intersects the first axis 2535 at each of a respective at least two spaced apart locations along first axis 2535 in the third/expanded configuration. In various embodiments, the curved path is an arcuate path. In various embodiments, at least the portion of the curved path extended along by curved portion 2509*a* is arcuate. In this embodiment, at least a first elongate member 2504 crosses a second elongate member 2504 in an X configuration at each of at least one of the respective at least two spaced apart locations along the first axis 2535 intersected by at least the portion of the respective curved path extended along by the curved portion 2509*a* of the second elongate member 2504 in the third/expanded configuration. In this example embodiment, the first axis 2535 is shown as a single axis. It is understood that first axis 2535 can include one or more axes in various embodiments. As shown in FIG. 6I, in this example embodiment a portion of frame 2502 is radially spaced from first axis 2535 by a first dimension 2580*a* in the third/expanded configuration. In various example embodiments, the portion of frame 2502 that is radially spaced from first axis 2535 by first dimension 2580*a* may include the respective curved portion 2509*a* of at least one of the elongate members 2504.

In this illustrated embodiment, the second end portion 2510*b* of shaft member 2510 is not physically coupled or connected to frame 2502 at various locations on frame 2502 that are symmetrically positioned about first axis 2535 as viewed along first axis 2535 in the third/expanded configuration. Rather, in this example embodiment, the second end portion 2510*b* of shaft member 2510 is physically coupled or connected to frame 2502 at one or more locations on frame 2502, each of the one or more locations on the structure to which the second end portion 2510*b* is coupled positioned to one side of at least one spatial plane (not shown) that is coincident with first axis 2535. In this example embodiment, the second end portion 2510*b* of shaft member 2510 is physically coupled or connected at least proximate to the proximal ends 2507 of various ones of the elongate members 2504 in frame 2502. In this illustrated embodiment, the positioning between frame 2502 and the second end portion 2510*b* of shaft member 2510 results at least in part from the coiling of various ones of the elongate members 2504 within left atrium 2562. In this example embodiment, shaft member 2510 is positioned to avoid intersection by first axis 2535 in the third/expanded configuration. In this example embodiment, shaft member 2510 is positioned to avoid intersection of the second end portion 2510*b* by first axis 2535 in the third/expanded configuration. In some example embodiments, each of at least some of the plurality of elongate members 2504 may extend generally tangentially from the second end portion 2510*b* of shaft member 2510 in the third/expanded or fanned configuration. In this example embodiment, shaft member 2510 and frame 2502 have a projected outline in the shape of the Greek letter rho (ρ) in the third/expanded configuration. As noted above, the Greek letter rho may be represented as open at a point where a loop of the letter would intersect a tail of the letter if closed or not open, and either without or with an opening defined by a loop portion of the letter represented.

Various ones of the elongate members 2504 can be moved in various ways as the portion of the device 2500 is moved into the third/expanded or fanned configuration. In this example embodiment, elongate members 2504 are fanned in a manner similar to that illustrated in FIGS. 4G and 4H when the portion of device 2500 is moved from the second/bent configuration shown in FIG. 6D to the third/expanded configuration shown in FIG. 6E. In this example embodiment, a first set of "even" elongate members 2504 (i.e., elongate members 2504*b*, 2504*d*, 2504*f* and 2504*h*) in the sequential arrangement of elongate members 2504 in the arcuate stacked arrangement 2532 are fanned along an opposite direction than a second set of the "odd" elongate members 2504 (i.e., elongate members 2504*c*, 2504*e*, 2504*g* and 2504*i*) in the sequential arrangement of elongate members 2504 in the arcuate stacked arrangement 2532 are fanned along. In this context, the words "even" and "odd" relate to a position of a respective one of the elongate members 2504 in the arcuate stacked array 2532. In this example embodiment, the elongate members 2504 in the "even" set are interleaved with the elongate member 2504 in the "odd" set in the arcuate stacked array 2532. In this example embodiment, various fanning mechanisms (not shown) can be employed to move various ones of the elongate members 2504 into the third/expanded configuration. In some example embodiments, various separators similar to previously described separators 1452 and 1752 may be employed to partially or fully fan at least some of the elongate members 2504.

In this example embodiment, when the portion of the device 2500 is moved into the third/expanded configuration, a portion of the front face 2518*a* (not called out in FIG. 6E) of each of at least some of the elongate members 2504 in the arcuate stacked array 2532 that faces the back surface 2518*b* (not called out in FIG. 6E) of another elongate member 2504 in the arcuate stacked array 2532 is repositioned in left atrium 2562 such that the portion of the front face 2518*a* of each of the at least some of the elongate members 2504 in the first fanned array 2570 directly faces a portion of the interior tissue surface 2562*a* within left atrium 2562. FIGS. 6G and 6H are respective detailed isometric views of the elongate members 2504 arranged in the first fanned array 2570 during the third/expanded or fanned configuration, each of the views showing one of two opposing sides of the first fanned array 2570. Elongate member 2504*a* and the set of "odd" elongate members 2504*c*, 2504*e*, 2504*g* and 2504*i* are called out in FIG. 6G while elongate member 2504*a* and the set of "even" elongate members 2504*b*, 2504*d*, 2504*f* and 2504*h* are called out in FIG. 6H. In this example embodiment, each of a first portion 2521*a* (one called out) of the front surface 2518*a* of each elongate member 2504 is positioned diametrically opposite to a second portion 2521*b* (only one called out) of the front surface 2518*a* (i.e., as compared between FIGS. 6G and 6H) when the portion of device 2500 is in the third/expanded configuration.

In this embodiment, frame 2502 is a structure that includes a proximal portion 2502*a* and a distal portion 2502*b*, each of the proximal and distal portions 2502*a*, 2502*b* made up of a respective portion of each elongate member 2504 of the plurality of elongate members 2504. As best seen in FIG. 6C, frame 2502 is arranged to be advanced distal portion 2502b first into left atrium 2562 when the portion of the device 2500 is in the first/unexpanded configuration. As best seen in each of the FIGS. 6G and 6H, the proximal portion 2502a of frame 2502 defines a first domed shape 2508a and the distal portion 2502b of frame 2502 defines a second domed shape 2508b when the portion of the device is in the third/expanded or fanned configuration. In this example embodiment, first domed shape 2508a has a respective apex 2512a (i.e., shown in FIG. 6H) and second domed shape 2508b has a respective apex 2512b (i.e., shown in FIG. 6G). In some example embodiments, apex 2512b associated with the distal portion 2502b of frame 2502 is positioned relatively closer to the port 2564a of opening 2564 than apex 2512a associated with the proximal portion 2502a of frame 2502 when the portion of the device is in the third/expanded or fanned configuration. In some example embodiments, apex 2512b associated with the distal portion 2502b of frame 2502 is positioned between port 2564a and apex 2512a associated with the proximal portion 2502a of frame 2502 when the portion of device 2500 is in the third/expanded or fanned configuration. In some example embodiments, apex 2512b associated with the distal portion 2502b of frame 2502 is positioned between second end 2506b of catheter sheath 2506 and apex 2512a associated with the proximal portion 2502a of frame 2502 when the portion of device 2500 is in the third/expanded or fanned configuration. In some example embodiments, apex 2512b associated with the distal portion 2502b of frame 2502 is positioned between a portion of shaft member 2510 and apex 2512a associated with the proximal portion 2502a of frame 2502 when the portion of device 2500 is in the third/expanded or fanned configuration.

In various example embodiments, either of the first and the second domed shapes 2508a, 2508b need not be substantially hemispherical. For example, at least one of the first domed shape 2508a and the second domed shape 2508b may have a first radius of curvature in a first spatial plane and a second radius of curvature in a second spatial plane that intersects the first spatial plane, a magnitude of the second radius of curvature different than a magnitude of the first radius of curvature. In this example embodiment, each elongate member 2504 of at least some of the plurality of elongate members 2504 crosses at least one other elongate member 2504 of the plurality of elongate members 2504 at a location between the proximal and the distal portions 2502a, 2502b of frame 2502 when the portion of the device 2500 is in the third/expanded configuration. In this example embodiment, the proximal and the distal portions 2502a, 2502b of frame 2502 are arranged in a clam shell configuration in the third/expanded configuration.

FIG. 6I is a sectioned side elevation view of the detailed isometric view of the first fanned array 2570 shown in FIG. 6G. Each of FIGS. 6G, 6H, 6I and 6J additionally shows a respective portion of shaft member 2510 and catheter sheath 2506 as well as a portion of the port 2564a interrupting the interior tissue surface 2562a (not called out in FIG. 6H) of left atrium 2562. In this illustrated embodiment, each of the elongate members 2504 includes a scrolled or a volute shape profile in the third/expanded configuration as best exemplified by elongate member 2504a in FIG. 6I. In this illustrated embodiment, various portions of the elongate members 2504 are fanned such that the second opening 2519b (only one called out in each of FIGS. 6G, 6H, 6I and 6J) and third opening 2519c (only one called out in each of FIGS. 6G, 6H, 6I and 6J) of each of various ones of elongate members 2504 is not aligned with a respective one of the second opening 2519b and third opening 2519c of another of the elongate members 2504. For clarity, each of flexible line 2540b and the first portion 2541a of flexible line 2540c that form part of a respective one of intermediate coupler 2522b and distal coupler 2522c and which are arranged to pass through a respective one of the second opening 2519b and the third opening 2519c in each of the elongate members 2504 are not shown in each of FIGS. 6G, 6H and 6I.

Figure 6J:
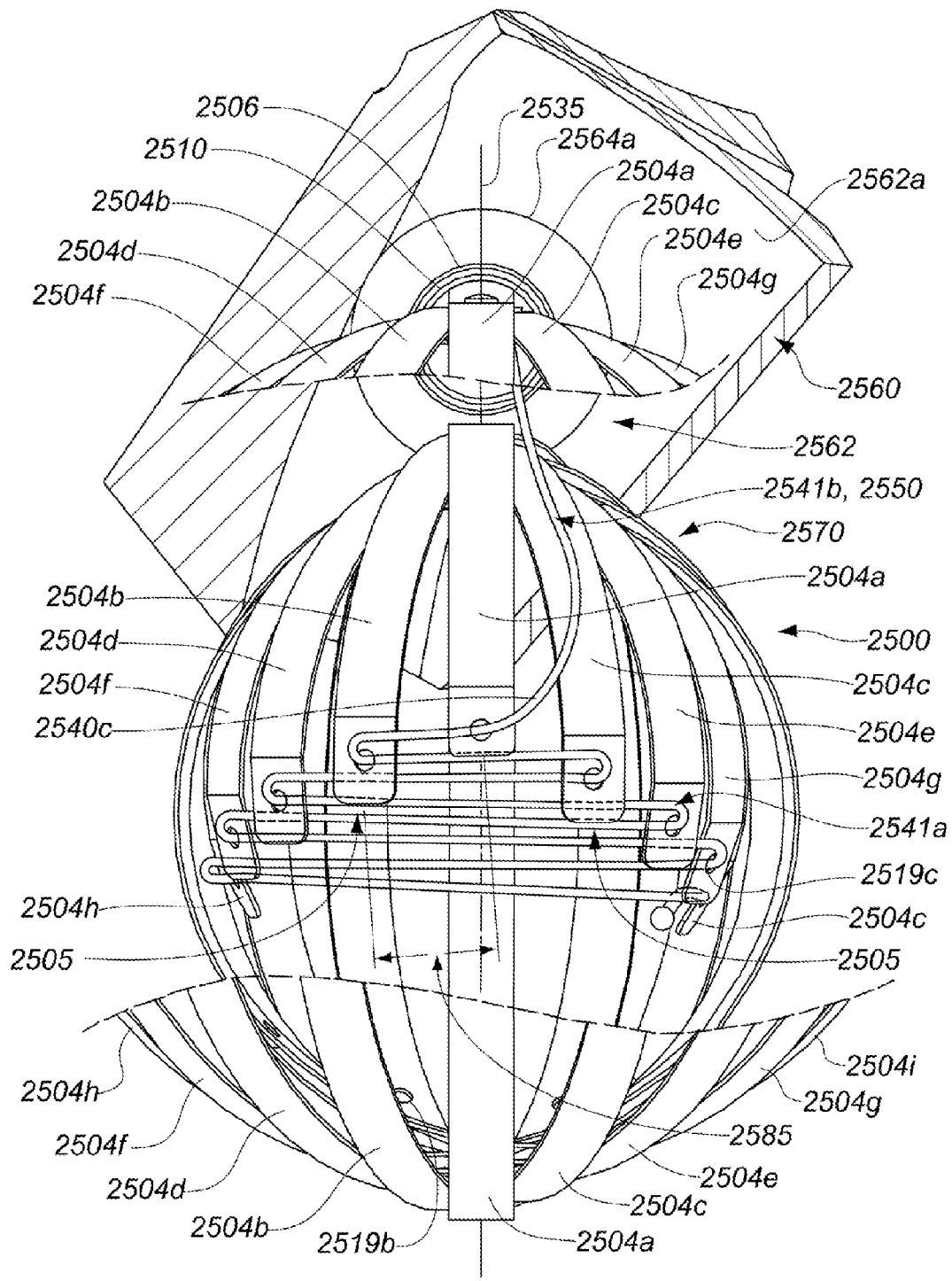
FIG. 6J is a partially sectioned end elevation view of the elongate members of the device of FIG. 6A extending from the catheter sheath, the elongate members arranged in a first expanded or fanned array.

FIG. 6J is a partially sectioned end elevation view of the first fanned array 2570 showing the respective distal ends 2505 (two called out) of the elongate members 2504. Various ones of the elongate members 2504 are partially sectioned in FIG. 6J to better show the respective distal ends 2505 of the elongate members 2504. FIG. 6J shows the first portion 2541a of flexible line 2540c follows a winding, zig-zag or serpentine path through the third openings 2519c (i.e., only one called out) of alternating ones of the "even" elongate members 2504b, 2504d, 2504f and 2504h and the "odd" elongate members 2504c, 2504e, 2504g and 2504i. Flexible line 2540b (not shown) may follow a similar path through the second openings 2519b (i.e., only one called out). The second portion 2541b of flexible line 2540c is also shown in FIG. 6J.

As best shown in FIGS. 6G and 6H, the respective geodesic 2514 of elongate member 2504g crosses the respective geodesic 2514 of at least one other elongate member 2504 (i.e., elongate member 2504i in this exemplary case) at various locations along the respective length 2511 (not called out) of the at least one other elongate member 2504 as viewed normally to a respective portion of the front surface 2518a of the at least one other elongate member 2504 over which each respective location is positioned in the third/expanded configuration. For clarity of illustration, the respective geodesics 2514 of various ones of the elongate members 2504 are not shown in FIGS. 6G and 6H.

Figure 6L:
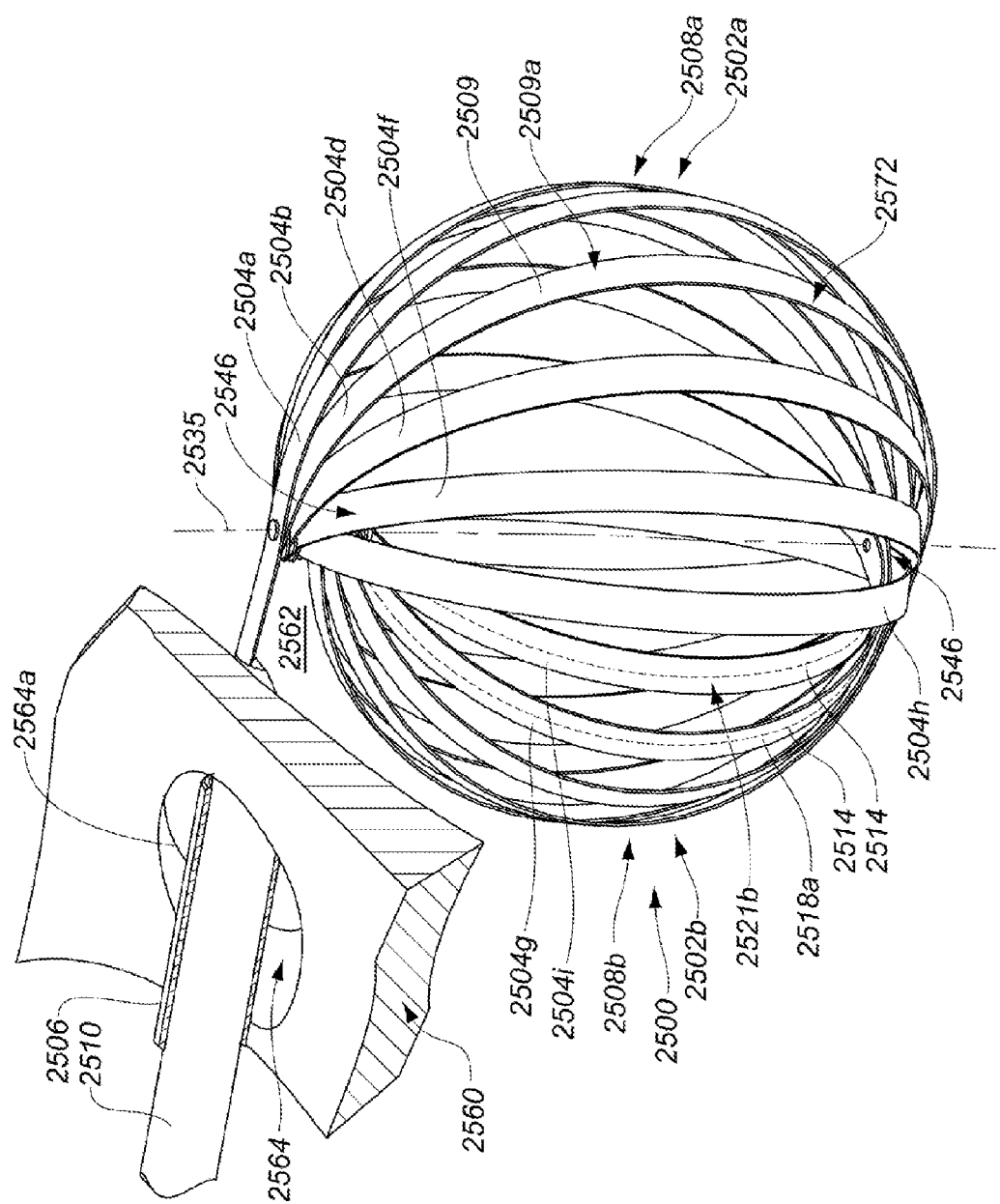
Figure 6N:
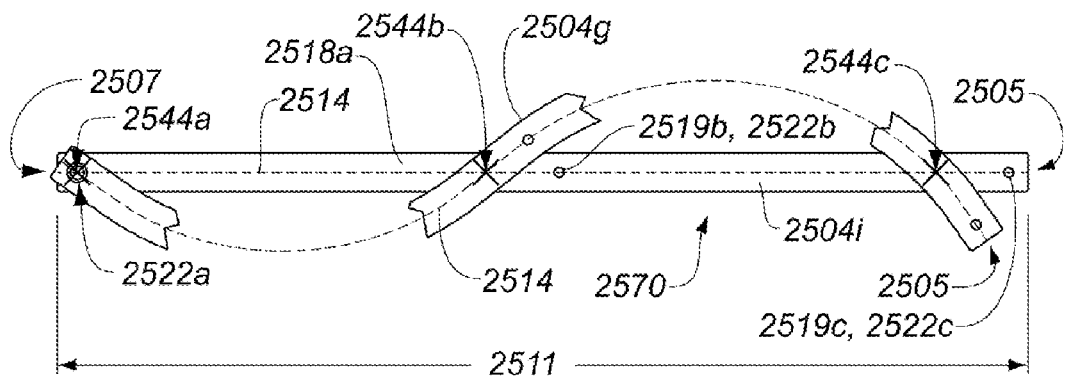
FIG. 6N is a schematic representation of an elongate member of the device of FIG. 6A crossed by various portions of another elongate member in a first expanded or fanned array.

FIG. 6N schematically shows a portion of the first fanned array 2570 that includes second elongate member (i.e., elongate member 2504i) with various portions of a first elongate member (i.e., elongate member 2504g) crossing the second elongate member 2504i in an X configuration at various locations in the third/expanded or fanned configuration. For clarity, each of elongate members 2504i and 2504g are shown in a "flattened" state and it is understood that these elongate members include respective arcuate profiles as exemplified in FIGS. 6G and 6H. The respective geodesic 2514 of the first elongate member 2504g crosses the respective geodesic 2514 of the second elongate member 2504i at a plurality of spaced apart locations (i.e., each represented by an "X" in FIG. 6N) including a first location 2544c positioned relatively closer to the respective distal end 2505 of the second elongate member 2504i than two other locations 2544a and 2544b along the respective geodesic 2514 of second elongate member 2504i in the third/expanded or fanned configuration. It is understood that each of the crossing locations 2544a, 2544b and 2544c is located on the front surface 2518a of the second elongate member 2504i and is overlapped by first elongate member 2504g in FIG. 6N. In this illustrated embodiment, the first location 2544c is positioned between the location of the proximal coupler 2522a and the respective distal end 2505 of the second elongate member 2504i. In this illustrated embodiment, the first location 2544c is positioned along the respective length 2511 of the second elongate member 2504i between the respective locations of distal coupler 2522c (i.e., the first portion 2541a of flexible line 2540c which is not shown but whose location in FIG. 6N is represented by third opening 2519c) and the intermediate coupler 2522b (i.e., flexible line 2540b whose location in FIG. 6N is represented by second opening 2519b). In this example embodiment, the first location 2544c is positioned along the respective length 2511 of second elongate member 2504i relatively closer to the respective distal end 2505 of second elongate member 2504i than a respective location of each of the intermediate coupler 2522b and the proximal coupler 2522a. In this example embodiment, the first location 2544c is spaced apart from the respective distal end 2505 of second elongate member 2504i. In this example embodiment, the first elongate member 2504g crosses the second elongate member 2504i in an X configuration at each of locations 2544b and 2544c.

In this example embodiment, additional manipulation of a portion of device 2500 including elongate members 2504 within a bodily cavity such as left atrium 2562 is initiated when the portion of the device 2500 is moved into the third/expanded or fanned configuration. Typically, when the elongate members 2504 arranged in arcuate stacked array 2532 are repositioned into a fanned array (i.e., first fanned array 2570 in this example embodiment), the elongate members 2504 are preferably arranged generally away from various tissue surfaces within the left atrium 2562 to avoid obstructions that could hinder repositioning or to avoid inflicting damage to the tissue surfaces. Referring to FIG. 6E, various portions of each of some of the elongate members 2504 are positioned away from the interior tissue surface 2562a within left atrium 2562 when the portion of the device 2500 is in the third/expanded configuration. As compared between FIGS. 6G and 6H, the first portions 2521a (only one called out) and the second portions 2521b (only one called out) of the front surface 2518a of each of least some of the elongate members 2504 in the first fanned array 2570 are angularly spaced about first axis 2535 when the portion of the device 2500 is in the third/expanded configuration. In this illustrated embodiment, at least some of the elongate members 2504 are further manipulated in the third/expanded configuration to vary a radial spacing between the first axis 2535 and at least one of the first portion 2521a and the second portion 2521b of the front surface 2518a of various ones of the elongate members 2504.

As shown in FIG. 6F, at least some of the elongate members 2504 (only one called out) are further manipulated in the third/expanded configuration to form a second fanned array 2572. In this example embodiment, at least some of the elongate members 2504 are further manipulated to increase a radial distance between the first axis 2535 and at least one of the first portion 2521a (not called out in FIG. 6F) and the second portion 2521b (not called out in FIG. 6F) of the front surface 2518a of various ones of the elongate members 2504. In this example embodiment, at least some of the elongate members 2504 are further manipulated to increase first dimension 2580a (not called out in FIG. 6F).

Further manipulation of the at least some of the elongate members 2504 may be motivated for various reasons. For example, the at least some of the elongate members 2504 may be further manipulated to adjust a positioning between various transducer elements carried by the elongate members 2504 and a tissue surface within a bodily cavity. The at least some of the elongate members 2504 may be further manipulated to create conformance with a tissue surface with a bodily cavity such as left atrium 2562 when the portion of the device 2500 is moved into the third/expanded or fanned configuration. In some example embodiments, a tissue surface within a bodily cavity such as left atrium 2562 is further manipulated to conform to a shape of a number of the elongate members 2504 when the portion of the device 2500 is moved into the third/expanded or fanned configuration. In some example embodiments, a portion of the elongate members 2504 and a tissue surface within a bodily cavity such as left atrium 2562 are each further manipulated to create conformance between a number of the elongate members 2504 and a portion of the tissue surface when the portion of the device 2500 is moved into the third/expanded or fanned configuration. In this example embodiment, shaft member 2510 and frame 2502 have a projected outline in the shape of the Greek letter rho ($\rho$), as noted above, when the elongate members 2504 are further manipulated into the second fanned array 2572.

FIGS. 6K and 6L are respective detailed isometric views of the elongate members 2504 arranged in the second fanned array 2572 shown in FIG. 6F, each of the views showing one of two opposing sides of the second fanned array 2572. In some example embodiments, the proximal and the distal portions 2502a, 2502b of frame 2502 are additionally manipulated when the portion of the device is moved into the third/expanded or fanned configuration. In some example embodiments, the respective dome shaped structures (i.e., first and second domed shapes 2508a, 2508b) of the proximal and the distal portions 2502a, 2502b of frame 2502 are physically coupled together to pivot with respect to one another when the structure is in the third/expanded configuration. In this example embodiment, the respective dome shaped structures (i.e., first and second domed shapes 2508a, 2508b) of the proximal and the distal portions 2502a, 2502b of frame 2502 may be pivoted with respect to one another about a region of reduced bending stiffness in frame 2502. In some example embodiments, portions of various ones of the elongate members 2504 provide a flexure portion of the frame 2502 between the proximal and the distal portions 2502a, 2502b that pivotably couples the proximal and the distal portions 2502a, 2502b together. In some example embodiments, the proximal and the distal portions 2502a, 2502b are pivoted with respect to one another to change a distance therebetween. For example, the proximal and the distal portions 2502a, 2502b may be pivoted apart to create conformance between frame 2502 and a portion of a tissue surface within a bodily cavity. In some example embodiments, the proximal and the distal portions 2502a, 2502b are pivoted with respect to one another to change a distance between apex 2512a and apex 2512b.

In this example embodiment, at least one of the proximal and the distal portions 2502a, 2502b of frame 2502 is additionally manipulated to distort a respective one of the first domed shape 2508a and the second domed shape 2508b to move between the first fanned array 2570 and the second fanned array 2572. Each of the first domed shape 2508a and the second domed shape 2508b has a respective volume therein. In some example embodiments, at least one of the proximal and the distal portions 2502a, 2502b of frame 2502 is acted upon to reduce a difference between the respective volumes of the first and the second domed shapes 2508a, 2508b. In some example embodiments, frame 2502 is acted upon to vary the respective volume of at least one of the first and the second domed shapes 2508a, 2508b. In this example embodiment, a respective volume associated with at least the second domed shape 2508b is increased to move between the first fanned array 2570 and the second fanned array 2572. In some example embodiments, each of the proximal and the distal portions 2502a, 2502b of frame 2502 are pivotable with respect to one another at a pivot location (e.g., near a crossing location of the elongate members) and each of the first and the second domed shapes 2508a, 2508b may be characterized at least in part by a respective height (not shown) extending normally from a respective spatial plane (not shown) to the respective apex (i.e., apex 2512a or apex 2512b) of the domed shape. Frame 2502 may be acted upon to vary at least one of a magnitude of the respective height of the first domed shape 2508a and a magnitude of the respective height of the second domed shape 2508b to move between the first fanned array 2570 and the second fanned array 2572.

FIG. 6M shows a sectioned elevation view of the detailed isometric view of FIG. 6K. Each of FIGS. 6K, 6L and 6M additionally includes a respective portion of shaft member 2510 and catheter sheath 2506 as well as the port 2564a interrupting the interior tissue surface 2562a (not called out in FIG. 6L) within left atrium 2562. As shown in FIGS. 6K and 6L, the respective intermediate portions 2509 (only one called out) are still fanned or angularly spaced about first axis 2535 in this example embodiment, albeit the first axis 2535 passes through at least some locations through various ones of the elongate members 2504 that are different than the respective locations passed through by the first axis 2535 in the first fanned array 2570 shown in FIGS. 6G and 6H. In this respect, the angular arrangement is similar to an arrangement of lines of longitude about a body of rotation, which may or may not be a spherical body of rotation. In this illustrated embodiment, each of at least some of the plurality of elongate members 2504 continues to include a curved portion 2509a arranged to extend along at least a portion of a respective curved path that intersects the first axis 2535 at each of a respective at least two spaced apart locations along first axis 2535 after the additional manipulation. As shown in FIGS. 6K and 6L, the first portions 2521a (only one called out) and the second portions 2521b (only one called out) of the front surfaces 2518a of the elongate members 2504 are circumferentially arranged about the first axis 2535, similar to lines of longitude about an axis of rotation of a body of revolution, which body of revolution may, or may not, be spherical. Use of the word circumference in the application, and derivatives thereof, such as circumferential, circumscribe, circumlocute and other derivatives, refers to a boundary line of a shape, volume or object which may, or may not, be circular or spherical. In this example embodiment, the first portion 2521a of the front surface 2518a of each elongate member 2504 is positioned to face a first portion of the interior tissue surface 2562a (not shown) within left atrium 2562 and the second portion 2521b of the front surface 2518a of the elongate member 2504 is positioned to face a second portion of the interior tissue surface 2562a (not shown) within left atrium 2562, the second portion of the interior tissue surface 2562a positioned diametrically opposite from the first portion of the interior tissue surface 2562a in the third/expanded or fanned configuration.

As shown in the sectioned view of FIG. 6M, the distal coupler 2522c is located with left atrium 2562 at a respective location positioned relatively closer to port 2564a than a respective location of intermediate coupler 2522b within the left atrium 2562 when the portion of the device 2500 is in the third/expanded or fanned configuration. In this example embodiment, the distal coupler 2522c is located within left atrium 2562 at a respective location positioned relatively closer to the proximal coupler 2522a than a respective location of intermediate coupler 2522b in the third/expanded or fanned configuration. In this example embodiment, the distal coupler 2522c is located within left atrium 2562 at a respective location positioned relatively closer to the proximal coupler 2522a in the third/expanded or fanned configuration than when each of the proximal coupler 2522a and the distal coupler 2522c are located within lumen 2506c of catheter 2506 in the first/unexpanded configuration (e.g., as shown in FIG. 6C).

As shown in FIG. 6M, proximal coupler 2522a is located within the left atrium 2562 at a respective location positioned relatively closer to port 2564a than the respective location of intermediate coupler 2522b in this illustrated embodiment. In some example embodiments, the respective location of the proximal coupler 2522a is located relatively closer to port 2564a than the respective location of distal coupler 2522c within the left atrium 2562 when the portion of the device 2500 is in the third/expanded or fanned configuration shown in FIG. 6F. In some example embodiments, the respective location of the distal coupler 2522c is located relatively closer to port 2564a than the respective location of the proximal coupler 2522a within the left atrium 2562 when the portion of the device 2500 is in the third/expanded or fanned configuration shown in FIG. 6F. In this illustrated embodiment, the proximal coupler 2522a is positioned within the left atrium 2562 when the portion of the device 2500 is in the third/expanded or fanned configuration shown in FIG. 6F. In some example embodiments, the proximal coupler 2522a is positioned in the bodily opening 2564 when the portion of the device 2500 is in the third/expanded or fanned configuration shown in FIG. 6F. In some example embodiments, the proximal coupler 2522a is positioned within the body at a respective location outside of the left atrium 2562 when the portion of the device 2500 is in the third/expanded or fanned configuration shown in FIG. 6F.

In this illustrated embodiment, various ones of the elongate members 2504 cross others of the elongate members 2504 at various crossing locations within left atrium 2562 when the portion of the device is in the third/expanded or fanned configuration shown in each of the FIGS. 6F, 6K, 6L and 6M. For example as best shown in FIGS. 6K and 6L, at least the first elongate member (i.e., elongate member 2504g) is positioned to cross the second elongate member (i.e., elongate member 2504i) at each of a number of crossing locations 2546 within the left atrium 2562. In this example embodiment, at least the first elongate member 2504g is positioned to cross the second elongate member 2504i in an X configuration at some of the crossing locations 2546. In this embodiment, each of the crossing locations 2546 is located on the front surface 2518a of second elongate member 2504i at a respective one of a number of locations along the respective geodesic 2514 of second elongate member 2504i that is crossed by the respective geodesic 2514 of first elongate member 2504g as viewed normally to a respective one of a number of portions of the front surface 2518a of the second elongate member 2504i over which each of the respective ones of the number of locations along the respective geodesic 2514 of second elongate member 2504i is located.

Figure 6O:
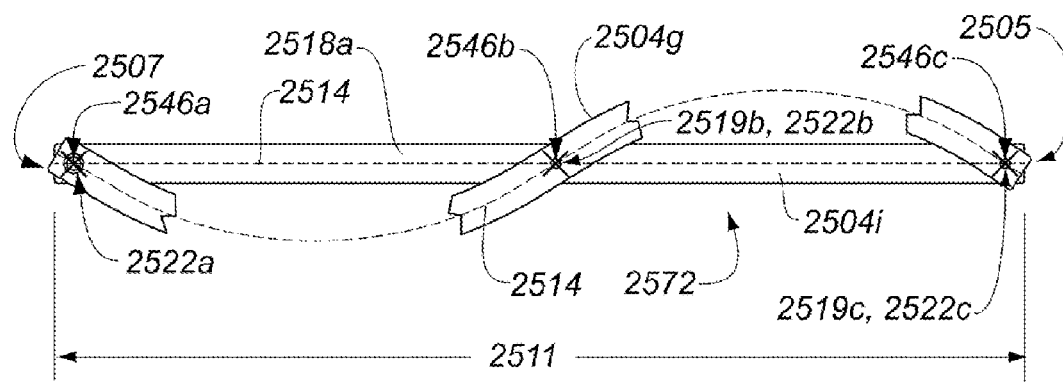
FIG. 6O is a schematic representation of an elongate member of the device of FIG. 6A crossed by various portions of another elongate member in a second expanded or fanned array.

The crossing locations 2546 are best shown in FIG. 6O which is a schematic representation of a portion of the second fanned array 2572 that includes second elongate member 2504i with various portions of first elongate member 2504g crossing second elongate member 2504i in the third/expanded or fanned configuration. For clarity, each of elongate members 2504g and 2504i are shown in a "flattened" state and it is understood that these elongate members include respective arcuate profiles as exemplified in FIGS. 6K and 6L. Each crossing location 2546 is represented by an "X" in FIG. 6O. In this illustrated embodiment, the plurality of crossing locations 2546 include a proximal crossing location 2546a, an intermediate crossing location 2546b and a distal crossing location 2546c. It is understood that each of the crossing locations 2546a, 2546b and 2546c is located on the front surface 2518a of the second elongate member 2504i and is overlapped by the first elongate member 2504g in FIG. 6O.

In this illustrated embodiment, the proximal crossing location 2546a is located on the front surface 2518a of the second elongate member 2504i at least proximate to proximal coupler 2522a, the intermediate crossing location 2546b is located on the front surface 2518a of the second elongate member 2504i at least proximate to intermediate coupler 2522b (i.e., whose location is represented by second opening 2519b in FIG. 6O) and the distal crossing location 2546c is located on the front surface 2518a of the second elongate member 2504i at least proximate to the distal coupler 2522c (i.e., whose location is represented by third opening 2519c in FIG. 6O). In this example embodiment, a location of the intermediate crossing location 2546b along the respective geodesic 2514 of the second elongate member 2504i is positioned along the respective length 2511 of the second elongate member 2504i between the respective locations of the proximal coupler 2522a and the distal coupler 2522c when the portion of the device 2500 is in the third/expanded or fanned configuration shown in each of the FIGS. 6F, 6K, 6L, and 6M. In this embodiment, a location of the distal crossing location 2546c along the respective geodesic 2514 of the second elongate member 2504i is positioned along the respective length 2511 of the second elongate member 2504i relatively closer to the respective distal end 2505 of the second elongate member 2504i than a respective location of each of proximal coupler 2522a and intermediate coupler 2522b when the portion of the device 2500 is in the third/expanded or fanned configuration shown in each of FIGS. 6F, 6K, 6L and 6M.

In this example embodiment, the back surface 2518b of the respective intermediate portion 2509 of the first elongate member 2504g is separated from the front surface 2518a of the respective intermediate portion 2509 of second elongate member 2504i at each of the crossing locations 2546 along the respective geodesic 2514 of the second elongate member 2504i when the portion of the device 2500 is in the third/expanded or fanned configuration shown in each of the FIGS. 6F, 6K, 6L and 6M. In some example embodiments, the back surface 2518b of the respective intermediate portion 2509 of a first elongate member 2504 contacts the front surface 2518a of the respective intermediate portion 2509 of a second elongate member 2504 at each of at least one of the crossing locations 2546 along the respective geodesic 2514 of the second elongate member 2504 when the portion of the device 2500 is in the third/expanded or fanned configuration shown in each of the FIGS. 6F, 6K, 6L and 6M. As best seen in FIG. 6M, the respective distal end 2505 (only one called out) of each elongate member 2504 is positioned within the left atrium 2562 at a respective location positioned relatively closer to port 2564a than at least one of the crossing locations 2546 (e.g., intermediate crossing locations 2546b in this example embodiment) when the portion of the device 2500 is in the third/expanded or fanned configuration shown in each of the FIGS. 6F, 6K, 6L and 6M. In this example embodiment, at least one or more of the other crossing locations 2546 (i.e., each of proximal crossing location 2546a and distal crossing location 2546c in this embodiment) are positioned within left atrium 2562 relatively closer to port 2564a than the intermediate crossing location 2546b when the portion of the device 2500 is in the third/expanded or fanned configuration shown in each of the FIGS. 6F, 6K, 6L and 6M. In this example embodiment, the respective proximal end 2507 (only one called out) of various ones of the elongate members 2504 is positioned within left atrium 2562 at a respective location located relatively closer to port 2564a than at least the intermediate crossing location 2546b when the portion of the device 2500 is in the third/expanded or fanned configuration shown in each of the FIGS. 6F, 6K, 6L and 6M.

In this embodiment, an actuator (not shown) associated with elongate member manipulator 2550 is employed in the third/expanded configuration to further manipulate various elongate members 2504 to reconfigure the first fanned array 2570 shown in FIG. 6E into the second fanned array 2572 shown in FIG. 6F. In this example embodiment, a suitable tension is applied to the second portion 2541b of flexible line 2540c in the third/expanded or fanned configuration to further manipulate first fanned array 2570 shown in FIG. 6E into the second fanned array 2572 shown in FIG. 6F. As shown in FIG. 6M the tension applied to the second portion 2541b of flexible line 2540c is sufficient to change the volute shaped profile of each of at least some of the elongate members 2504 in the first fanned array 2570 into a generally more uniform annular or ring-like profile as shown in the second fanned array 2572 of FIG. 6M. As compared between FIGS. 6I and 6M, the tension applied to the second portion 2541b of flexible line 2540c is sufficient to reduce a curvature of the curved portion 2509a of each of at least some of the elongate members 2504 along their respective lengths 2511 to manipulate the first fanned array 2570 into the second fanned array 2572. In this example embodiment, the curvature of at least one portion of an elongate member 2504 that is located between a respective distal end 2505 and a respective location passed through by the first axis 2535 is reduced when a suitable tension is applied to the second portion 2541b of flexible line 2540c. In this example embodiment, the reduction in curvature of the curved portion 2509a of each of at least some of the elongate members 2504 advantageously increases the first dimension 2580a associated with the first fanned array 2570 shown in FIG. 6I to have a larger magnitude as represented by the first dimension 2580b associated with the second fanned array 2572 shown in FIG. 6M. As used herein, the word "curvature" should be understood to mean a measure or amount of curving. In some example embodiments, the word "curvature" is associated with a rate of change of the angle through which the tangent to a curve turns in moving along the curve.

In some example embodiments, the first fanned array 2570 includes a second dimension along first axis 2535 (not shown) in the third/expanded or fanned configuration and elongate member manipulator 2550 is employed to reduce the curvature of the curved portion 2509a of each of at least some of the elongate members 2504 to increase the second dimension in the third/expanded or fanned configuration. For example, the second dimension may be an overall dimension 2581 of frame 2502 along the first axis 2535 that is increased as the curvature of various ones of the curved portions 2509a is reduced. In some example embodiments, the second dimension is a dimension between a first location where the first axis 2535 passes through at least one of the elongate members 2504 and a second location where the first axis 2535 passes through the at least one of the elongate members 2504. In some example embodiments, the curvature of each of at least some of the curved portions 2509a is reduced to concurrently increase the first dimension 2580a and the second dimension.

As compared between FIGS. 6I and 6M, a reduction in curvature of each of at least some of the curved portions 2609a results in the first axis 2535 passing through an elongate member 2504 at a location spaced relatively closer to the respective distal end 2505 of the elongate member 2504 when the first fanned array 2570 is additionally manipulated into the second fanned array 2572.

As compared between FIGS. 6N and 6O, tension applied to the second portion 2541b of flexible line 2540c causes at least one of the locations 2544 along the respective geodesic of the second elongate member 2504i that is crossed by the respective geodesic 2514 of the first elongate member 2504g in the first fanned array 2570 to be repositioned along the respective geodesic 2514 of the second elongate member 2504i to assume a position in the second fanned array 2572 as shown by the corresponding crossing locations 2546. In various embodiments, at least one of the first elongate member 2504g and the second elongate member 2504i is repositioned by the elongate member manipulator 2550 (not shown in FIGS. 6N and 6O) to cause a least one of the locations 2544 along the respective geodesic of the second elongate member 2504i that is crossed by the respective geodesic 2514 of the first elongate member 2504g in the first fanned array 2570 to be repositioned along the respective geodesic 2514 of the second elongate member 2504i into the second fanned array 2572. In this illustrated embodiment, the elongate member manipulator 2550 causes the first location 2544c along the respective geodesic 2514 of the second elongate member 2504i as shown in FIG. 6N to be repositioned relatively closer to the respective distal end 2505 of the second elongate member 2504i as shown by distal crossing location 2546c in FIG. 6O. In this illustrated embodiment, the respective distal ends 2505 of various ones of elongate members 2504 are spaced apart with respect to one another in the first fanned array 2570 as best shown in FIG. 6J by a first end-to-end distance 2585 (only one called out). In this embodiment, elongate member manipulator 2550 is employed to vary a distance between at least some of the distal ends 2505 and at least one of the crossing locations to manipulate the first fanned array 2570 into the second fanned array 2572. In this embodiment, elongate member manipulator 2550 is employed to reduce an end-to-end distance 2585 between the respective distal ends 2505 of at least some of the elongate members 2504 to manipulate the first fanned array 2570 into the second fanned array 2572. In this example embodiment, elongate member manipulator 2550 is employed to reduce an end-to-end distance 2585 between the respective distal ends 2505 of at least some of the elongate members 2504 while varying a respective distance between at least one of the crossing locations and each of the distal ends 2505 of the at least some of the elongate members 2504. It is noted that in some embodiments, the respective distance between the at least one of the crossing locations and each of the distal ends 2505 of the at least some of the elongate members 2504 may be varied by a different amount for each of the at least some of the elongate members while the respective end-to-end distance 2585 is reduced. For example, the respective distance between the at least one crossing location and a first one of the distal ends 2505 may be varied by a first amount and the respective distance between the at least one crossing location and a second one of the distal ends 2505 may be varied by a second amount different than the first amount. In some embodiments, the first and second amounts vary to expand frame 2502 by different amounts in different directions.

It is noted that relative movement between the ends need not be limited to the distal ends 2505. In various example embodiments, relative movement may be provided between at least some of the ends in a first set of the proximal ends 2507 of the elongate members 2504 to reduce an end-to-end distance between the at least some of the ends in the first set while expanding frame 2502 to have a size too large for delivery through the lumen 2506c of catheter sheath 2506. In various example embodiments, relative movement may be provided between at least some of the ends in a second set of the distal ends 2505 of the elongate members 2504 to reduce an end-to-end distance 2585 between the at least some of the ends in the second set while expanding frame 2502 to have a size too large for delivery through the lumen 2506c of catheter sheath 2506. In some of these various embodiments, the relative movement between the at least some of the ends in the first set or between the at least some of the ends in the second set is provided while restraining relative movement between at least some of the ends in the other of the first set and the second set along at least one direction during the expanding of frame 2502. In some of these various embodiments, the relative movement between the at least some of the ends in the first set or between the at least some of the ends in the second set is provided while restraining relative movement between the respective intermediate portions 2509 of at least some of elongate members 2504 during the expanding of frame 2502. In some of these various embodiments, the relative movement between the at least some of the ends in the first set or between the at least some of the ends in the second set is provided while decreasing a distance between the respective distal end 2505 and the respective proximal end 2507 of each of at least some of the plurality of elongate members 2504 during the expanding of frame 2502. For example, as compared between FIGS. 6I and 6M, a distance between the respective distal end 2505 and the respective proximal end 2507 of each of various ones of the elongate members 2504 is reduced as the end-to-end distance 2585 between the distal ends 2505 is reduced.

As shown in FIG. 6M, the second portion 2541b of the flexible line 2540c is manipulated to more substantially align the respective third openings 2519c of the elongate members 2504 in the second fanned array 2572. In this example embodiment, the second portion 2541b of the flexible line 2540c is manipulated to more substantially align the respective second openings 2519b of the elongate members 2504 in the second fanned array 2572. It is understood that alignment between the respective third openings 2519c and the alignment between the respective second openings 2519b in the second fanned array 2572 need not be a collinear one as shown in FIG. 6M. In embodiments in which the first fanned array 2570 is manipulated to cause the front surfaces 2518a of the various elongate members 2504 in the second fanned array 2572 to contact the interior tissue surface 2562a, variances in a local or global size of the left atrium 2562 may cause varying degrees of alignment between the respective groupings of openings 2519b, 2519c. Flexible line couplings (e.g., flexible lines 2540b and 2540c) may be employed to advantageously physically couple the elongate members 2504 together while having a reduced sensitivity to misalignments between the respective third openings 2519c and the respective second openings 2519b. Other embodiments may employ other types of couplings.

As shown in FIG. 6M, the respective intermediate portion 2509 of each of the various elongate members 2504 has a generally annular or ring-like profile interrupted by a separation in the third/expanded configuration. The separation may not be present in other embodiments. Device 2500 may further include at least one bridging portion arranged to bridge the separation in some embodiments. A bridging portion can include by way of non-limiting example, a portion of an elongate member 2504, a portion of a coupler (e.g., first coupler 2522a), a portion of shaft member 2510 or a portion of catheter sheath 2506.

In various example embodiments, once frame 2502 is deployed within atrium 2562, a sensing, investigation or treatment procedure may be undertaken. In this embodiment, each front surface 2518a includes, carries or supports a transducer element (i.e., not shown, e.g., transducer element 2490) that is positionable adjacent to a tissue surface in the bodily cavity when the first fanned array 2570 is manipulated into the second fanned array 2572. In this example embodiment, once the second fanned array 2572 has been appropriately positioned at a given location within left atrium 2562, determination of the locations of various components of device 2500 (e.g., transducer elements including sensors or electrodes, or related support structures such as elongate members 2504), or the locations of various anatomical features within left atrium 2562 may be determined by various methods. In this example embodiment, after the portion of the device 2500 has been appropriately positioned at a given location within left atrium 2562, ablation of various regions of a tissue surface within left atrium 2562 may commence. The portion of the device 2500 may be removed from the left atrium 2652 by reconfiguring the portion of the device 2500 back into the second/bent configuration and then further back into the first/unexpanded configuration.

Figure 7A:
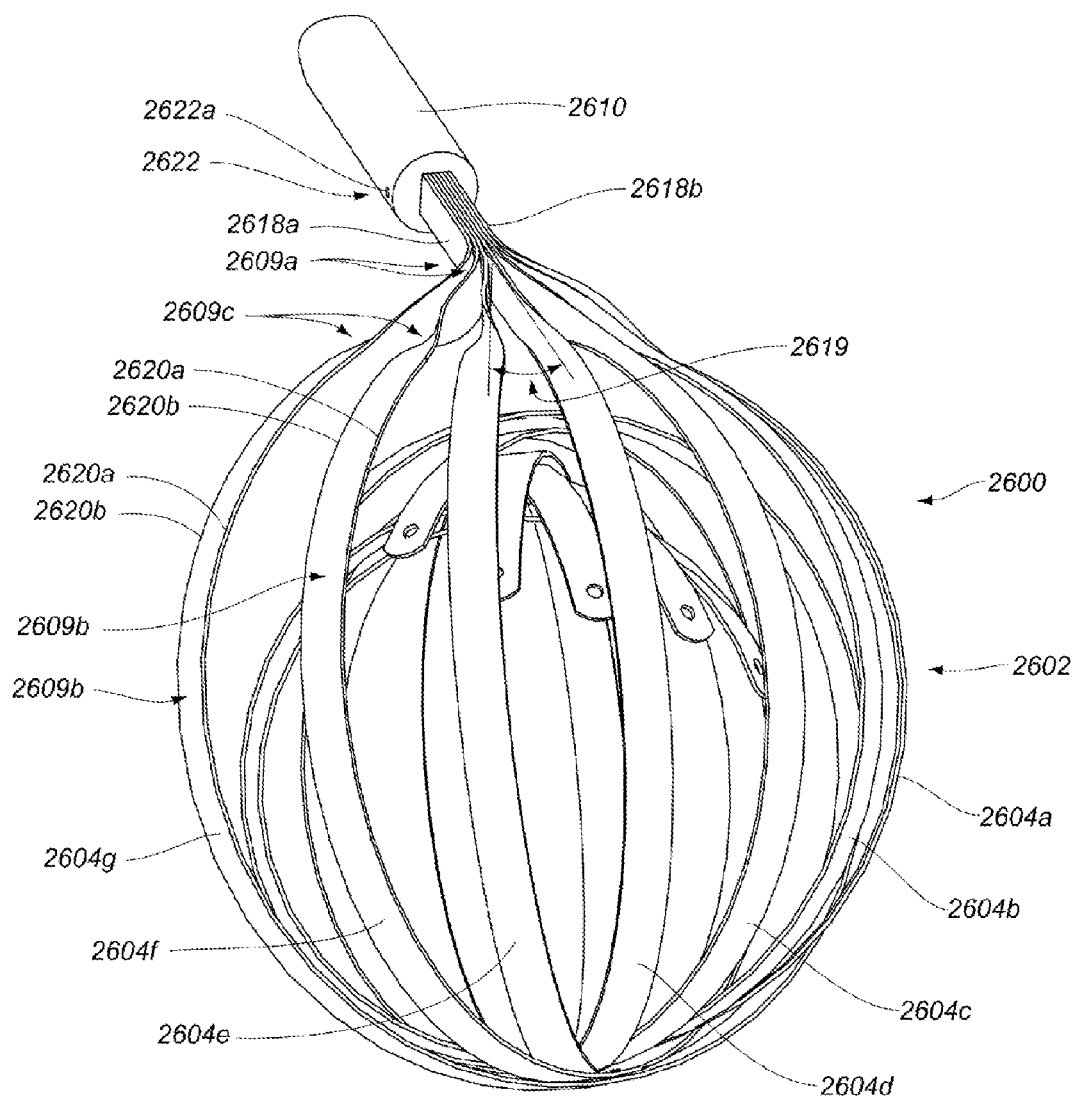
FIG. 7A is an isometric view of a portion of a device that includes a number of elongate members extending from a catheter sheath in an initial configuration according to another example embodiment.

FIG. 7A is an isometric view of a portion of a device 2600 in an initial configuration according to one example embodiment. Device 2600 includes a structure or frame 2602 that includes an arrangement of elongate members 2604a, 2604b, 2604c, 2604d, 2604e, 2604f, and 2604g, (collectively 2604). Various ones of the elongate members 2604 are physically coupled to shaft member 2610 which is employed to transport the elongate members 2604 through a catheter sheath 2606 (shown in FIGS. 7C, 7D, 7E and 7F) arranged for delivery through a bodily opening (not shown) leading to a bodily cavity (also not shown). The bodily cavity can include an intra-cardiac cavity by way of non-limiting example.

Figure 7B:
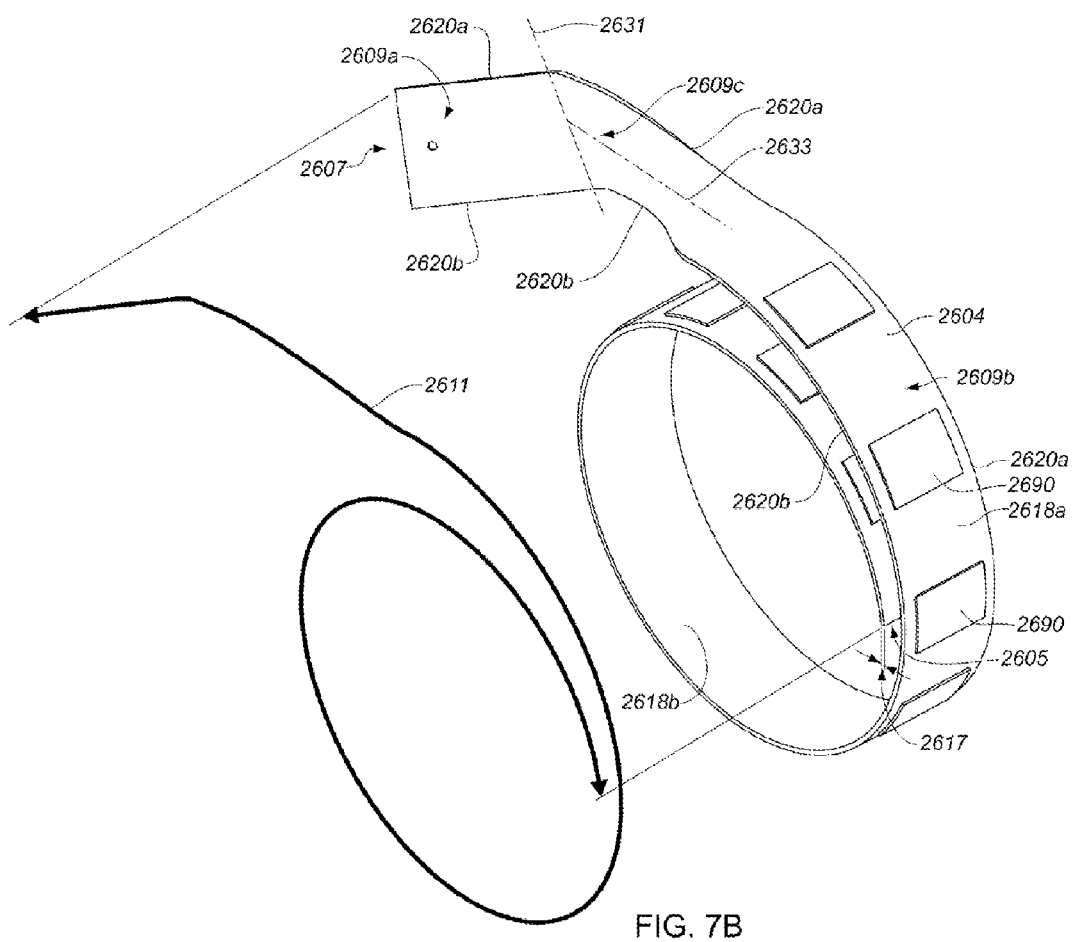
FIG. 7B is an isometric view of a representative one of the elongate members of the device of FIG. 7A.

FIG. 7B is an isometric view of a representative one of the elongate members 2604 in the initial configuration. Each of the elongate members 2604 includes a respective first or distal end 2605 and a respective second or proximal end 2607. Each elongate member 2604 includes a respective length 2611 (i.e., called out only in FIGS. 7B and 7G) between the respective proximal and distal ends 2607, 2605 of the elongate member 2604. In various embodiments, two or more of the elongate members 2604 may have substantially equal lengths 2611 or substantially unequal lengths 2611. In this example embodiment, a respective portion of each of the elongate members 2604 has a length that is at least approximately equal to or greater than a circumference of a portion of an interior tissue surface of a bodily cavity (not shown) into which the elongate member 2604 is to be positioned at least proximate to when the portion of the device 2600 is in a deployed configuration. The circumference of the portion of the interior tissue surface may have a measured or anticipated value. In a manner similar to other described embodiments, transducer elements 2690 (two called out) are distributed along a surface of each of various ones of the elongate members 2604. Transducer elements 2690 arranged on a given one of elongate members 2604 may be circumferentially distributed along a region of the interior tissue surface of a bodily cavity (again not shown) over which the given one of the elongate members 2604 is positioned at least proximate to in a deployed configuration.

In this example embodiment, each elongate member 2604 includes at least a portion of a flexible circuit structure 2680 (not shown or called out in FIGS. 7A, 7B, 7C, 7D, 7E and 7F for clarity) that at least provides an electrically communicative path to various ones of the transducer elements 2690.

Each of the elongate members 2604 includes a set of two opposing major faces or surfaces 2618 denominated as a front surface 2618a and a back surface 2618b. In this example embodiment, the two opposing surfaces 2618 are separated from one another by a thickness 2617 of the elongate member 2604. In this illustrated example, each elongate member 2604 includes a plurality of various portions 2609 arranged between the respective proximal and distal ends 2607, 2605 of the elongate member 2604. In this example embodiment, the portions 2609 include a first portion 2609a, a second portion 2609b and a third portion 2609c positioned between the first and the second portions 2609a, 2609b. In this example embodiment, first portion 2609a is positioned relatively closer to proximal end 2607 than to distal end 2605 and second portion 2609b is positioned relatively closer to distal end 2605 than to proximal end 2607. In this example embodiment, the various portions 2609 are combined in a unitary structure. In this example embodiment, each of the portions 2609 includes a pair of side edges including first side edge 2620a and second side edge 2620b (collectively 2620), the side edges of each pair of side edges 2620 are opposed to one another across at least a portion of the length 2611 of the respective elongate member 2604. In this example embodiment, each pair of side edges 2620 defines a portion or at least some of a periphery of the front surface 2618a of the elongate member 2604.

In this example embodiment, a number of the respective portions 2609 of various ones of the elongate members 2604 include various distortions or deformations. In this example embodiment, the words "distortion" or deformation are used interchangeably herein to mean modification in shape away from an elongated strip-like form that prior to any distortion or deformation predominately a body with a relatively small thickness as compared to a length or width, although major faces of the body may not necessarily have smooth planar surfaces. For example, the respective second portion 2609b of the representative elongate member 2604 shown in FIG. 7B has a coiled profile (e.g., a profile that curves back on itself). In this particular embodiment, the respective second portion 2609b includes a volute shaped profile in the initial configuration. Also for example, the respective third portion 2609c of the representative elongate member 2604 shown in FIG. 7B includes a twisted profile about a respective twist axis 2633 extending across at least a part of the third portion 2609c of the elongate member 2604, the twist in the third portion 2609c arranged to rotationally offset (e.g., angularly rotated or twisted out of plane about an axis that may extend generally along a length of the elongate member prior to any distortion of deformation thereof) the respective second portion 2609b of the elongate member 2604 from the respective first portion 2609a of the elongate member 2604 along a portion of the length 2611 of the elongate member 2604. In this example embodiment, the respective first portion 2609a of the representative elongate member 2604 includes a bent profile about a respective bending axis 2631.

In FIG. 7A, each of the elongate members 2604 is arranged in an arrangement having an initial configuration in which each elongate member 2604 is provided essentially in its distorted form. In this example embodiment, the initial configuration is representative of an initial or low energy state. In this example embodiment, each elongate member 2604 is a resilient member and further distortion of various portions 2609 of the elongate member 2604 can increase spring or potential energy of the elongate member 2604 and thereby bring it into a higher energy state.

As shown in FIG. 7A, at least the respective second portions 2609b of various ones of the elongate members 2604 each has a coiled profile (e.g., a profile that curves back on itself) in the initial or low energy state. In this example embodiment, at least the respective second portions 2609b (two called out) of various ones of the elongate members 2604 are fanned into a fanned array in the initial or low energy state. As shown in FIG. 7A, each of the respective first portions 2609a of the elongate members 2604 are arranged front surface 2618a-toward-back surface 2618b with respect to one another in the initial configuration. In this example embodiment, the bent profiles of the respective first portions 2609a (one called out) of various ones of the elongate members 2604 are arranged to fan or partially fan at least the respective second portions 2609b of various ones of elongate members 2604 into the fanned array in the initial configuration. In this embodiment, various ones of the second portions 2609b are fanned along a direction to increase a relative distance between the respective side edges 2620 (two respective sets of edges 2620a and 2620b called out) of adjacent ones of the second portions 2609b in the initial configuration. In this example embodiment, parts of the first portions 2609a are also fanned in the initial configuration. In this embodiment, various ones of the first portions 2609a are fanned along a direction to increase a relative front surface 2618a-to-back surface 2618b distance between adjacent ones of the first portions 2609a in the initial configuration.

In some example embodiments, the respective twist axis 2633 (FIG. 7B) about which one of the third portions 2609c (one called out) is twisted is arranged to rotationally offset a respective second portion 2609b from a respective first portion 2609a as well as to fan the respective second portion 2609b into the fanned array in the initial configuration as exemplified in FIG. 7A. It is noted however that relatively limited fanning angles 2619 (only one called out in FIG. 7A) are typically achieved between a respective pair of the first and the second portions 2609a, 2609b by positional adjustments of the twist axis 2633. Fanning angles 2619 generally greater than 45 degrees associated with at least some of the elongate members 2604 (e.g., elongate members 2604a and 2604g) in FIG. 7A may be difficult to achieve solely by a positional adjustment of various ones of the twist axes 2633. Greater fanning angles 2619 are typically associated with relatively large numbers of elongate members 2604 as shown in FIG. 7A. It is also noted that when various ones of the third portions 2609c are twisted to additionally fan respective second portions 2609b into a fanned array as shown in FIG. 7A, the twisted third portions 2609c typically do not nest well together when the various portions 2609 are arranged in an arrayed arrangement suitable for intravascular or percutaneous delivery (e.g., as shown in FIG. 7C). Nesting difficulties may arise because each of the respective third portions 2609c of various ones of the elongate members 2604 has a different twisted form in accordance with the particular fanning angle that the each of the various ones of the elongate members 2604 must be fanned by. Difficulties with the nesting of the respective third portions 2609c typically increase with increased fanning angles 2619. Nesting difficulties can require larger catheter sheaths to be employed to accommodate a bulkier arrangement of at least the third portions 2609c when delivered percutaneously. In some example embodiments, each of the respective second portions 2609b of various ones of the elongate members 2604 are fanned in the initial configuration based at least in part by a configuration of the twisted profile of a respective third portion 2609c and based at least in part by a configuration of the bent profile of a respective first portion 2609a.

In various example embodiments, various ones of the elongate members 2604 are physically coupled together with at least one other elongate member 2604 by at least one coupler. In this illustrated embodiment, device 2600 includes at least one coupler 2622 arranged to couple at least the respective first portions 2609a of the elongate members 2604 together in the initial array. In this example embodiment, coupler 2622 includes a pin member 2622a arranged to secure the first portions 2609a together. Other forms of couplers may be employed in other example embodiments. For example, in embodiments where various ones of the elongate members 2604 includes a flexible printed structure having a relatively large number of electrically conductive traces, a coupling that couples at least the side edges 2620 of the first portions 2609a may be better suited than a pin-type coupling that is arranged to pass through the flexible circuit structures in a manner that possibly imposes undesired space constraints on the placement of the electrically conductive traces. In various example embodiments, additional couplers (e.g., couplers 2522b, 2522c) may also be employed to couple various other portions 2609 of various ones of the elongate members 2604 together.

FIGS. 7C, 7D, 7E, and 7F are various side elevation views of a portion of the device 2600 positioned at four successive intervals of time as the portion of the device 2600 is selectively reconfigured according to an example embodiment. For clarity, transducer elements 2690 are not shown in FIGS. 7C, 7D, 7E, and 7F. As shown in FIG. 7C, the respective first portions 2609a (only one called out) of the elongate members 2604 (only one called out) are arranged with respect to one another front surface 2618a-toward-back surface 2618b along a first direction represented by arrow 2616a in a first stacked array 2615a sized to be delivered through lumen 2506c of catheter sheath 2606 that is positionable within a bodily opening (again, not shown) leading to a bodily cavity (also not shown) when a portion of the device 2600 is in a delivery configuration also known as a first or unexpanded configuration. As shown in FIG. 7C, the respective second portions 2609b (only one called out) of the elongate members 2604 are arranged with respect to one another front surface 2618a-toward-back surface 2618b along a second direction as represented by arrow 2616b in a second stacked array 2615b sized to be delivered through the lumen of catheter sheath 2606 when the portion of the device 2600 is in the delivery configuration. In this example embodiment, the first direction (i.e., arrow 2616a) and the second direction (i.e., arrow 2616b) are non-parallel directions. In this example embodiment, the elongate members 2604 are arranged within catheter sheath 2606 such that each elongate member 2604 is to be advanced distal end 2605 first into a bodily cavity. In this example embodiment, the elongate members 2604 are arranged within catheter sheath 2606 such that each elongate member 2604 is to be advanced out distal end 2605 first from an end of catheter sheath 2606 arranged to be positioned at least proximate to the bodily cavity.

Notably, as used herein and in the claims, the term stacked does not necessarily require the elongate members 2604 rest directly or even indirectly upon one another, but rather refers to an ordered arrangement which may include spaces or gaps between immediately adjacent or most immediate neighboring pairs of elongate members 2604. It is also noted that while illustrated in FIG. 7C as a plurality of substantially parallel stacked plates or strips, the elongate members 2604 are not perfectly rigid so there may be some flex, sag or curvature even when the catheter sheath 2606 is essentially straight. It is further noted that in use, the catheter sheath 2606 will often curve or even twist to follow a bodily lumen. The elongate members 2604 may adopt or conform to such curvatures or twists as the elongate members 2604 are advanced. In either of these situations, the elongate members 2604 maintain the relative positions to one another as a stacked arrangement.

In this example embodiment, the respective first, second and third portions 2609a, 2609b and 2609c (only one of each called out) of various ones of the elongate members 2604 in the initial configuration have been stressed into a higher energy state from their initial or low energy state shown in FIG. 7A. In this example embodiment, the respective second portions 2609b of various ones of the elongate members 2604 in the initial configuration (i.e., as shown in FIG. 7A) have been stressed into a higher energy state suitable for unbending or uncoiling them sufficiently enough to allow the elongate members 2604 to be delivered through catheter sheath 2606 in the delivery configuration as shown in FIG. 7C. In this example embodiment, the at least one of the respective first portions 2609a and the third portions 2609c of each of various ones of the elongate members 2604 (i.e., as shown in FIG. 7A) have been stressed into a higher energy state suitable for un-fanning at least the second portions 2609b of the elongate members 2604 sufficiently enough to allow the elongate members 2604 to be introduced into, and delivered though catheter sheath 2606. In this example embodiment, potential energy is imparted to the various elongate members 2604 in the delivery configuration by the higher energy state, the potential energy sufficient to return the arrangement of elongate members 2604 generally back to their initial energy state when released from the confines of catheter sheath 2606. In some example embodiments, the arrangement of elongate members 2604 is stressed into a higher energy state by retracting the arrangement of elongate members 2604 into catheter sheath 2606 prior to inserting catheter sheath 2606 into a body. In some example embodiments, the arrangement of elongate members 2604 is stressed into a higher energy state by uncoiling the elongate members 2604 and inserting the arrangement of elongate members 2604 into catheter sheath 2606. In some example embodiments, the arrangement of elongate members 2604 is reconfigured from the initial configuration shown in FIG. 7A to the delivery configuration shown in FIG. 7C at a point-of-use. In some example embodiments, the arrangement of elongate members 2604 is reconfigured from the initial configuration shown in FIG. 7A to the delivery configuration shown in FIG. 7C at a place of manufacture, assembly or distribution. In various embodiments, various devices including various guides or manipulators may be employed to reconfigure the arrangement of elongate members 2604 from the initial configuration shown in FIG. 7A to the delivery configuration shown in FIG. 7C. In some of these various embodiments, the devices form part of device 2600. In some of these various embodiments, the devices are extraneous to device 2600. Preferably, the higher energy states are controlled to not cause damage to device 2600 or catheter sheath 2606 during delivery therethrough.

Figure 7D:
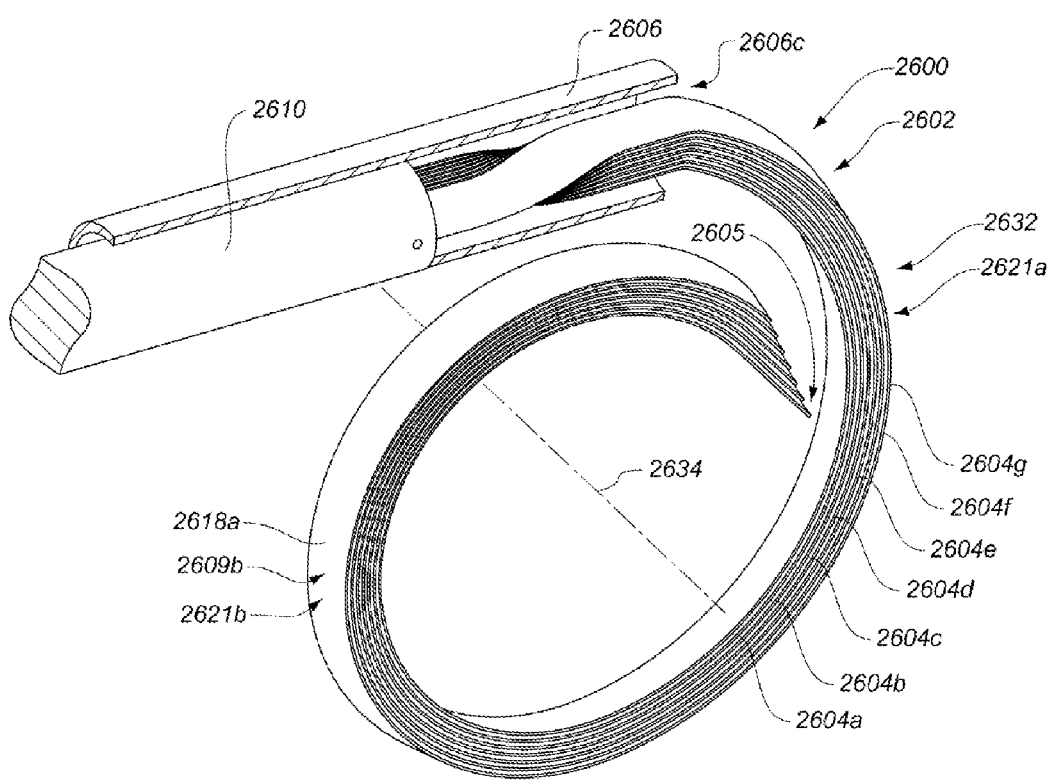

FIG. 7D shows a portion of the device 2600 including the plurality of elongate members 2604 positioned in a deployed configuration also referred to as a second or bent configuration. In this example embodiment, the respective second portions 2609b (only one called out) of various ones of the elongate members 2604 have cleared the confines of catheter sheath 2606 while other portions 2609 of the elongate members 2604 remain within the confines of catheter sheath 2606. In this example embodiment, at least the respective second portions 2609b of each elongate member 2604 are bent about a respective bending axis 2634 (only one shown) into an arcuate stacked array 2632. Each bending axis 2634 extends along a direction having a directional component transversely oriented to the respective length 2611 (not called out in FIG. 7D) of the elongate member 2604. In this example embodiment, each of the respective second portions 2609b of various ones of the elongate members 2604 in the arcuate stacked array 2632 is coiled about a respective bending axis 2634 into a coiled stacked array. In this example embodiment, each respective second portion 2609b is bent to have a scrolled or volute shaped profile. In this example embodiment, each second portion 2609b is bent to have a curvature that varies at least once along the respective length 2611 of the elongate member 2604. When positioned in the second/bent configuration, a first portion 2621a of the front surface 2618a (only one called out) of the respective second portion 2609b of each elongate member 2604 is positioned diametrically opposite to a second portion 2621b of the front surface 2618a in the volute shaped frame 2602. When positioned in the second/bent configuration, the coiled arrangement of elongate members 2604 is sized or dimensioned too large for delivery through a lumen of catheter sheath 2606.

In this illustrated embodiment, the respective second portions 2609b of various ones of the elongate members 2604 have been preformed to autonomously bend when the second portions 2609b are advanced out of catheter sheath 2606. As the respective second portions 2609b are advanced from the confines of catheter sheath 2606, they are urged or biased to seek their low energy state (i.e., their initial coiled configuration). In this example embodiment, the respective distal ends 2605 of various ones of the elongate members 2604 moves along a coiled path (e.g., a path that curves back on itself) when the portion of the device 2600 is moved between the first/unexpanded configuration and the second/bent configuration. In this example embodiment, the coiled path makes at least one full turn. In some embodiments, at least part of the coiled path may extend along a volute path.

In this embodiment, the respective second portions 2609b of various ones of the elongate members 2604 are preformed to autonomously coil as they are advanced into a bodily cavity (not shown) in a manner that may advantageously reduce physical interactions between elongate members 2604 and an interior tissue surface within the bodily cavity. In a manner similar to the elongate members 2504 shown in FIG. 6D, the respective distal ends 2605 (only one called out) of the elongate members 2604 are arranged to continuously bend or curl away from an interior tissue surface within a bodily cavity (not shown) into which they are introduced. A reduction of contact and other physical interaction with an interior tissue surface within a bodily cavity can reduce occurrences of, or the severity of, damage inflicted to various tissue structures during the positioning. In various embodiments, the arcuate stacked array 2632 is arranged to have a predetermined size that will allow the arcuate stacked array 2632 to be positioned within a bodily cavity with at most relatively minor amounts of contact with an interior tissue surface within the bodily cavity.

Figure 7E:
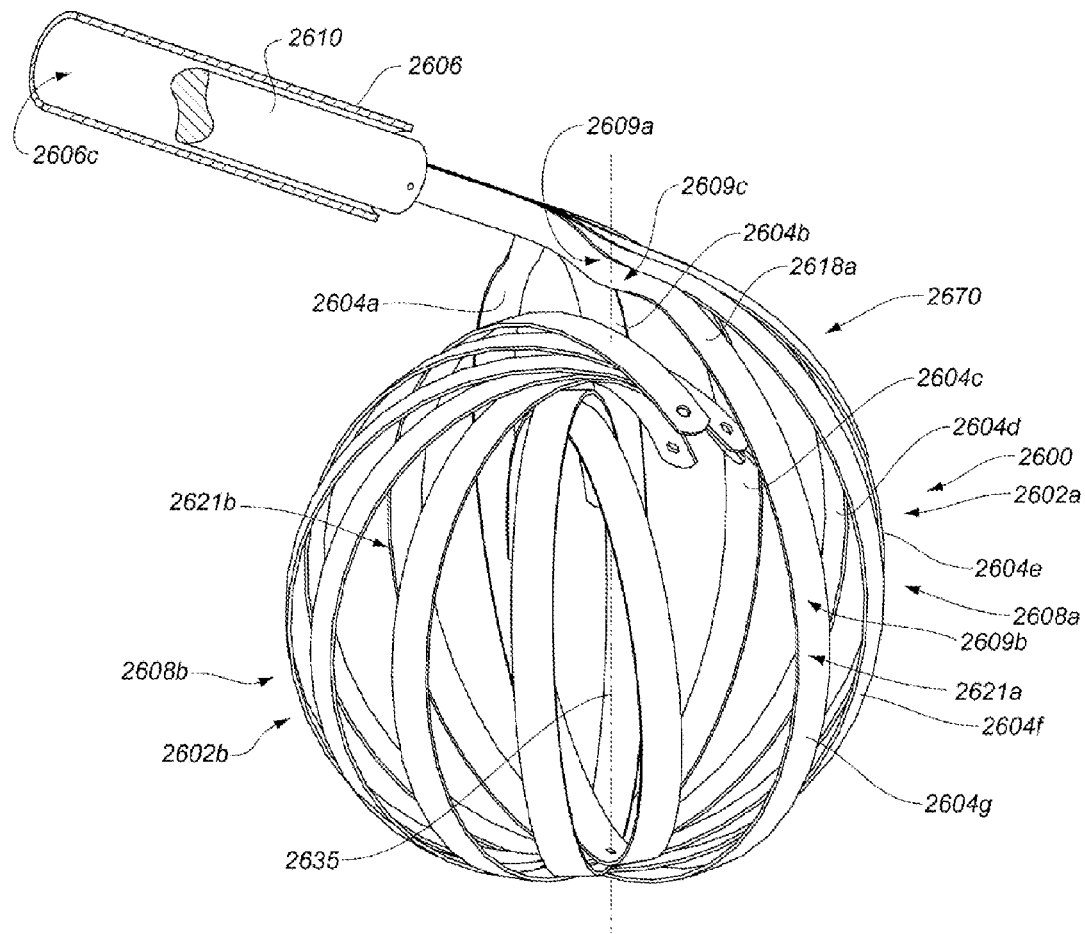

FIG. 7E shows the portion of the device 2600 in deployed configuration also referred to as a third or expanded configuration. In this illustrated embodiment, the elongate members 2604 were moved from the second/bent configuration shown in FIG. 7D to the third/expanded configuration shown in FIG. 7E. In this example embodiment, the portion of the device 2600 is further advanced through catheter sheath 2606 so that at least the respective third portions 2609c (only one called out) of various ones of the elongate members 2604 are clear of the confines of catheter sheath 2606. In this example embodiment, the portion of the device 2600 is further advanced through catheter sheath 2606 so that at least the respective first portions 2609a (only one called out) of various ones of the elongate members 2604 are clear of the confines of catheter sheath 2606. As shown in FIG. 7E, the respective second portions 2609b (only one called out) of various ones of the elongate members 2604 are spaced apart from one another in the third/expanded configuration. In this illustrated embodiment, at least the respective second portions 2609b of various ones of the elongate members 2604 are angularly spaced with respect to one another about an axis when the portion of the device 2600 is in the third/expanded configuration. In this illustrated embodiment, at least the respective second portions 2609b of at least some of the elongate members 2604 are fanned with respect to one another about one or more fanning axes 2635 into a first fanned array 2670 when the portion of the device 2600 is in the third/expanded configuration. As shown in FIG. 7E, in this example embodiment the one or more fanning axes 2635 are arranged to pass through a plurality of spaced apart locations along the respective length 2611 (not called out) of each of the at least some of the elongate members 2604 when the portion of the device 2600 is in the third/expanded or fanned configuration. In this example embodiment, the one or more fanning axes 2635 are shown as a single axis (i.e., also referred to as fanning axis 2635) for clarity. It is understood that one or more axes 2635 can include two or more axes in various embodiments. In this illustrated embodiment, each of the at least some of the plurality of elongate members 2604 includes a curved portion arranged to extend along at least a portion of a respective curved path that intersects fanning axis 2635 at each of a respective at least two spaced apart locations along fanning axis 2635 in the third/expanded or fanned configuration.

In this example embodiment, the respective first portions 2609a of various ones of the elongate members 2604 have been preformed to autonomously bend when the first portions 2609a are advanced out of catheter sheath 2606. As the respective first portions 2609a are advanced from the confines of catheter sheath 2606, stored potential energy is released and the first portions 2609a are urged or biased to assume a lower energy state (i.e., similar to their initial configuration shown in FIG. 7A) and cause at least the respective second portions 2609b of various ones of the elongate members 2604 to autonomously fan at least in part, with respect to one another into the third/expanded or fanned configuration. In some example embodiments, as the respective third portions 2609c are advanced from the confines of catheter sheath 2606, stored potential energy is released and the respective third portions 2609c are urged or biased into a lower energy state to cause at least the respective second portions 2609b of various ones of the elongate members 2604 to autonomously fan, at least in part, with respect to one another into the third/expanded or fanned configuration. In some example embodiments, as both the respective third portions 2609c and the respective first portions 2609a of various ones of the elongate members 2604 are advanced from the confines of catheter sheath 2606, stored potential energy is released and the respective first and third portions 2609a, 2609c are urged or biased into respective lower energy states to cause at least the respective second portions 2609b of various ones of the elongate members 2604 to autonomously fan at least in part, with respect to one another into the third/expanded or fanned configuration.

In some example embodiments, additional fanning mechanisms (not shown) may be employed to assist in the fanning of, or to promote an additional fanning of, various ones of the elongate members 2604 as the elongate members 2604 are moved into the third/expanded or fanned configuration. In some example embodiments, various separators similar to previously described separators 1452 and 1752 may be employed to further fan, or to assist in the fanning of, at least some of the elongate members 2604. In this example embodiment, the elongate members 2604 are fanned in a different manner than previously described elongate members 2504. In this example embodiment a first set made up elongate members 2604a, 2604b, and 2604c are fanned along an opposite direction from a second set made up of elongate members 2604e, 2604f and 2604g. Unlike the described embodiment employing elongate members 2504, the elongate members 2604 in the first set of elongate members 2604 are not interleaved with the elongate members 2604 in the second set of elongate members 2604 in this example embodiment.

FIG. 7E shows that various parts of the respective second portions 2609b of various ones of the elongate members 2604 cross one another at various crossing locations in the third/expanded configuration in a manner similar to that previously described for the elongate members 2504 shown in their respective third/expanded or fanned configurations in FIGS. 6E, 6G, 6H and 6I. In this example embodiment at least a first one of the plurality of elongate members 2604 crosses a second one of the plurality of elongate members 2604 in an X configuration at each of a plurality of locations spaced from one another along the respective length 2611 of the second one of the plurality of elongate members 2604 when a portion of device 2600 is moved into the third/expanded or fanned configuration. In this example embodiment, additional manipulation of a portion of device 2600 including elongate members 2604 may be initiated when the portion of the device 2600 is moved into the third/expanded configuration. Typically, when the elongate members 2604 are arranged within a bodily cavity in the third/expanded or fanned configuration, the arrangement of the elongate members 2604 is preferably sized sufficiently small enough to reduce occurrences where damage may be inflicted to the tissue surfaces within the bodily cavity by the arrangement of elongate members 2604. As shown in FIG. 7E, first portions 2621a (only one called out) and the second portions 2621b (only one called out) of the respective front surface 2618a (only one called out) of each of at least some of the elongate members 2604 in the first fanned array 2670 are angularly arranged about fanning axis 2635 when the portion of the device 2600 is in the third/expanded configuration. In this illustrated embodiment, at least some of the elongate members 2604 are further manipulated in the third/expanded or fanned configuration to vary a radial spacing between fanning axis 2635 and at least one of the first portion 2621a and the second portion 2621b of the respective front surface 2618a of each of various ones of the elongate members 2604. In this embodiment, frame 2602 includes a proximal portion 2602a having a first domed shape 2608a and a distal portion 2602b having a second domed shape 2508b, the proximal and distal portions 2602a, 2602b arranged in a clam shell configuration.

Figure 7F:
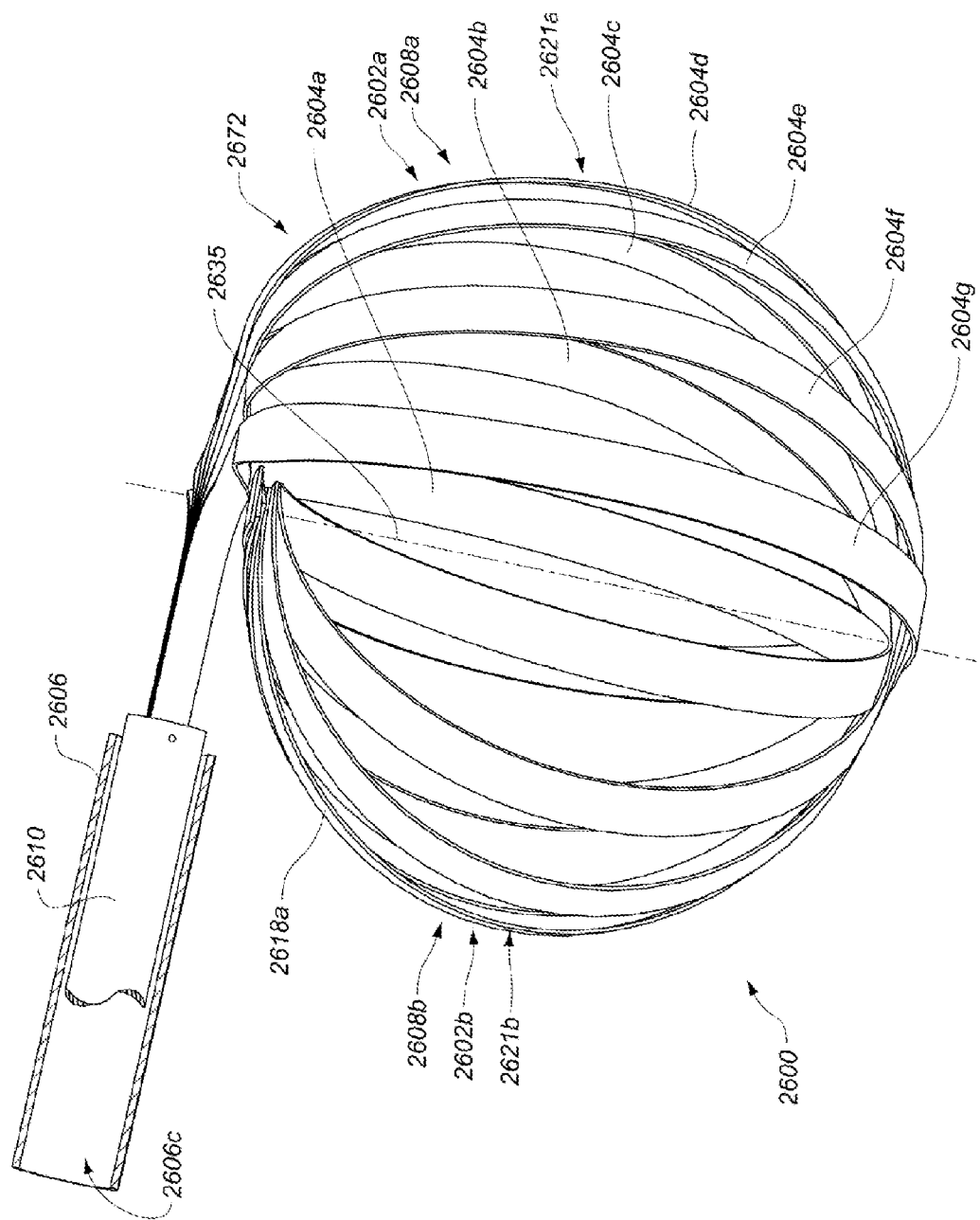

In FIG. 7F, at least some of the elongate members 2604 are further manipulated in the third/expanded configuration to form a second fanned array 2672. In this example embodiment, at least some of the elongate members 2604 are further manipulated to increase a radial spacing between fanning axis 2635 and at least one of the first portion 2621a (only one called out) and the second portion 2621b (only one called out) of the respective front surface 2618a (only one called out) of each of various ones of the elongate members 2604. In some example embodiments, at least some of the elongate members 2604 are further manipulated to distort at least one of the first and the second domed shapes 2608a, 2608b of a respective one of the proximal and the distal portion 2602a, 2602b of frame 2602. Further manipulation of the at least some of the elongate members 2604 may be motivated for various reasons. For example, the at least some of the elongate members 2604 may be further manipulated to create a conformance with a tissue surface with a bodily cavity (not shown in FIGS. 7C, 7D, 7E and 7F) when the portion of the device 2600 is moved into the third/expanded or fanned configuration. In some example embodiments, the at least some of the elongate members 2604 may be further manipulated to position various transducer elements 2690 (again not shown in FIGS. 7C, 7D, 7E and 7F) relatively closer to an interior tissue surface within a bodily cavity.

In this example embodiment, an end portion of shaft member 2610 is physically coupled or connected to frame 2602 at one or more locations on frame 2602, each of the one or more locations on the structure to which the end portion is coupled positioned to one side of at least one spatial plane (not shown) that is coincident with fanning axis 2635. In this example embodiment, shaft member 2610 and frame 2602 have a projected outline in the shape of the Greek letter rho (ρ) in the third/expanded or fanned configuration, as indicated above.

In this example embodiment, various ones of the elongate members 2604 cross at least one other of the elongate members 2604 at various crossing locations when the portion of the device 2600 is in the third/expanded or fanned configuration shown FIG. 7E. In this example embodiment, a number of the elongate members 2604 are additionally manipulated to vary at least one of the crossing locations to arrange the elongate members 2604 in the second fanned array 2672 shown in FIG. 7F. In some example embodiments, an elongate member manipulator (e.g., elongate member manipulator 2550) is employed to further manipulate the various elongate members 2604 to reconfigure the first fanned array 2670 shown in FIG. 7E into the second fanned array 2672 shown in FIG. 7F in the third/expanded or fanned configuration. It is noted that if a flexible line similar to the flexible line 2540c of elongate member manipulator 2550 is employed to further manipulate the first fanned array 2670 shown in FIG. 7E into the second fanned array 2672 shown in FIG. 7F, the flexible line may be arranged to follow a path less tortuous than the zig-zag path that the flexible line 2540c follows in FIG. 6J. A less tortuous path may be achieved at least in part because the elongate members 2604 in the first set of elongate members 2604 are not interleaved with the elongate members 2604 in the second set of elongate members 2604 in this example embodiment.

Other techniques may be employed to additionally manipulate or expand a structure of elongate members (e.g., frame 2602) in the deployed configuration. For example, FIGS. 9A and 9B respectively show an isometric view and a partially sectioned plan view of a portion of a device 2800 according to one example embodiment in a deployed configuration also known as third or expanded configuration similar to that employed by device 2600 in FIG. 7E. Device 2800 includes a structure or frame 2802 physically coupled to a shaft member 2810. Frame 2802 includes a plurality of elongate members 2804 that include elongate members 2804a, 2804b, 2804c, 2804d, 2804e, 2804f and 2804g. In this embodiment, each of the elongate members 2804 includes a distal end 2805, a twisted portion 2809c and a bent portion 2809a positioned proximate to shaft member 2810. Each of the elongate members 2804 includes a front surface 2818a that is positionable to face an interior tissue surface within a bodily cavity (not shown) and a back surface 2818b opposite the front surface 2818a. In some embodiments, each of the elongate members 2804 is arranged front surface 2818a-toward-back surface 2818b in a stacked array during a delivery configuration similar to that employed by other described embodiments. In this embodiment, each of the elongate members 2804 is arranged in a first fanned array 2870 that is similar to the first fanned array 2670 of elongate members 2604 shown in FIG. 7E. In this example embodiment, each elongate member 2804 includes a respective slot 2820. As best seen in the partially sectioned plan view of FIG. 9B, the slots 2820 of various ones of the elongate members 2804 cross one another at a crossing location 2825 in the first fanned array 2870. In some embodiments each of at least some of the slots 2820 are positioned to one side of a midline or centerline of a respective one of the elongate members 2804.

Figure 9A:
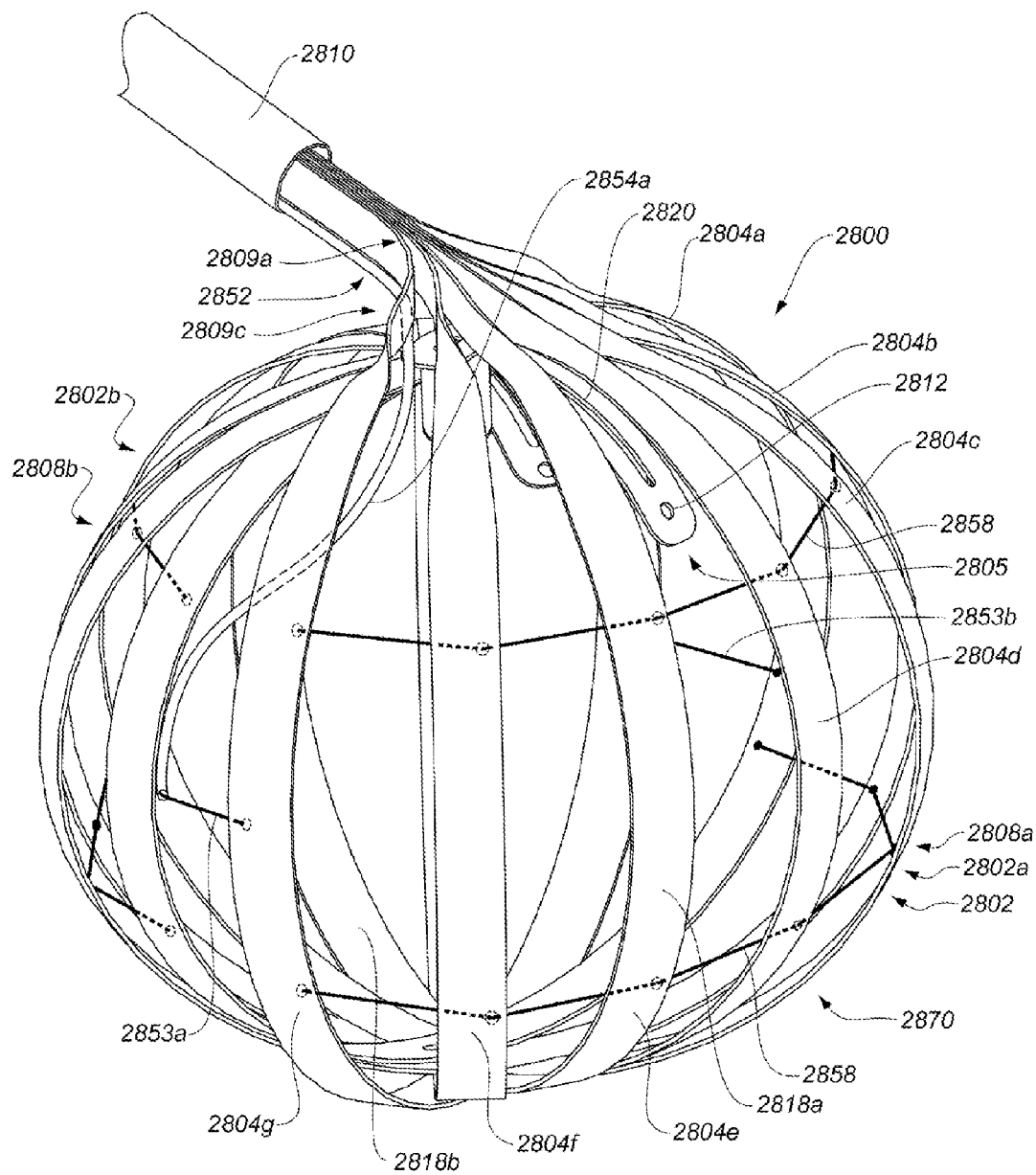
FIG. 9A is an isometric view of a portion of a device that includes a number of elongate members extending from a catheter sheath in a deployed configuration according to another example embodiment.
Figure 9B:
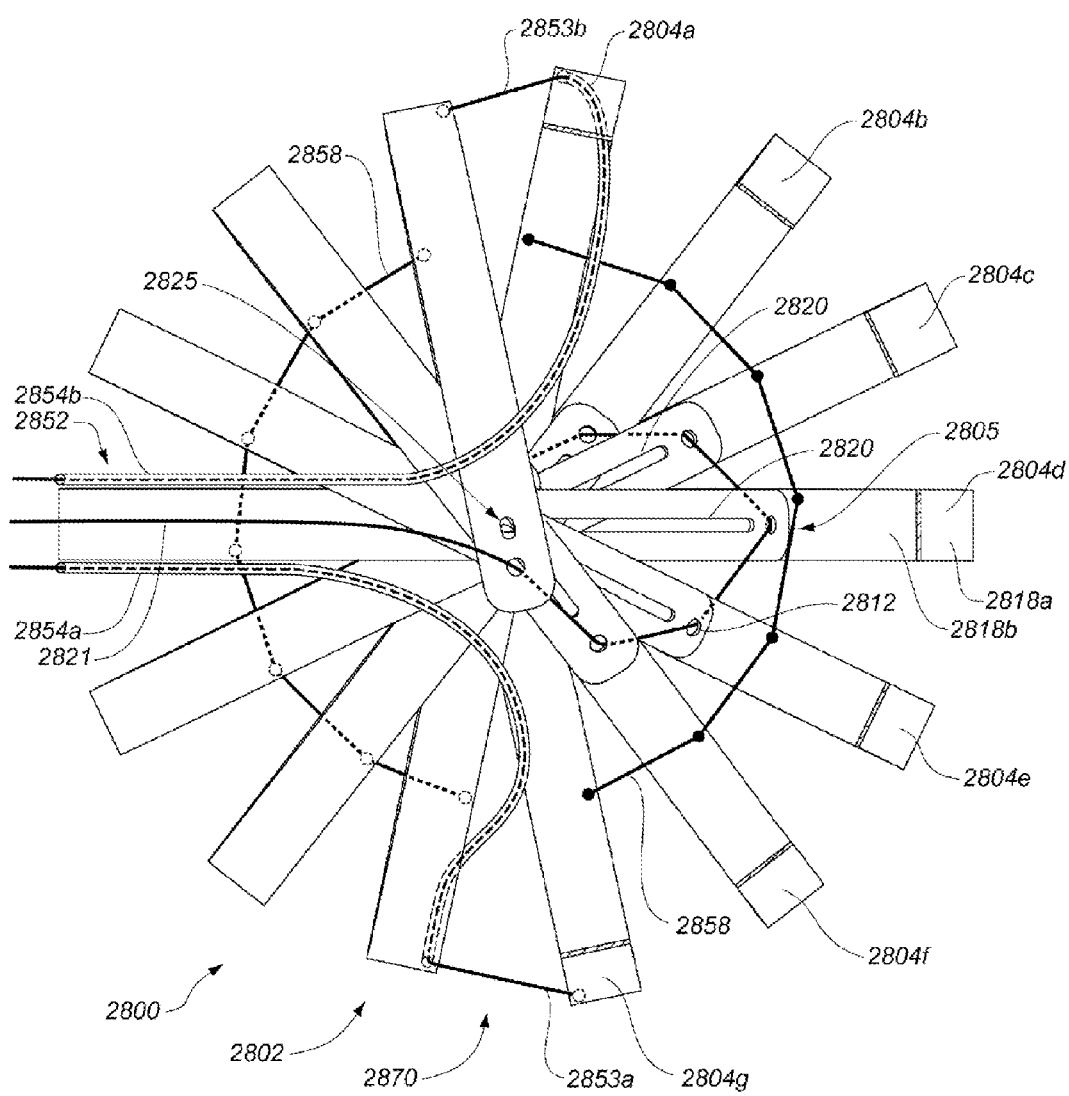
FIG. 9B is a partially sectioned plan view of the portion of the device of FIG. 9A.
Figure 9C:
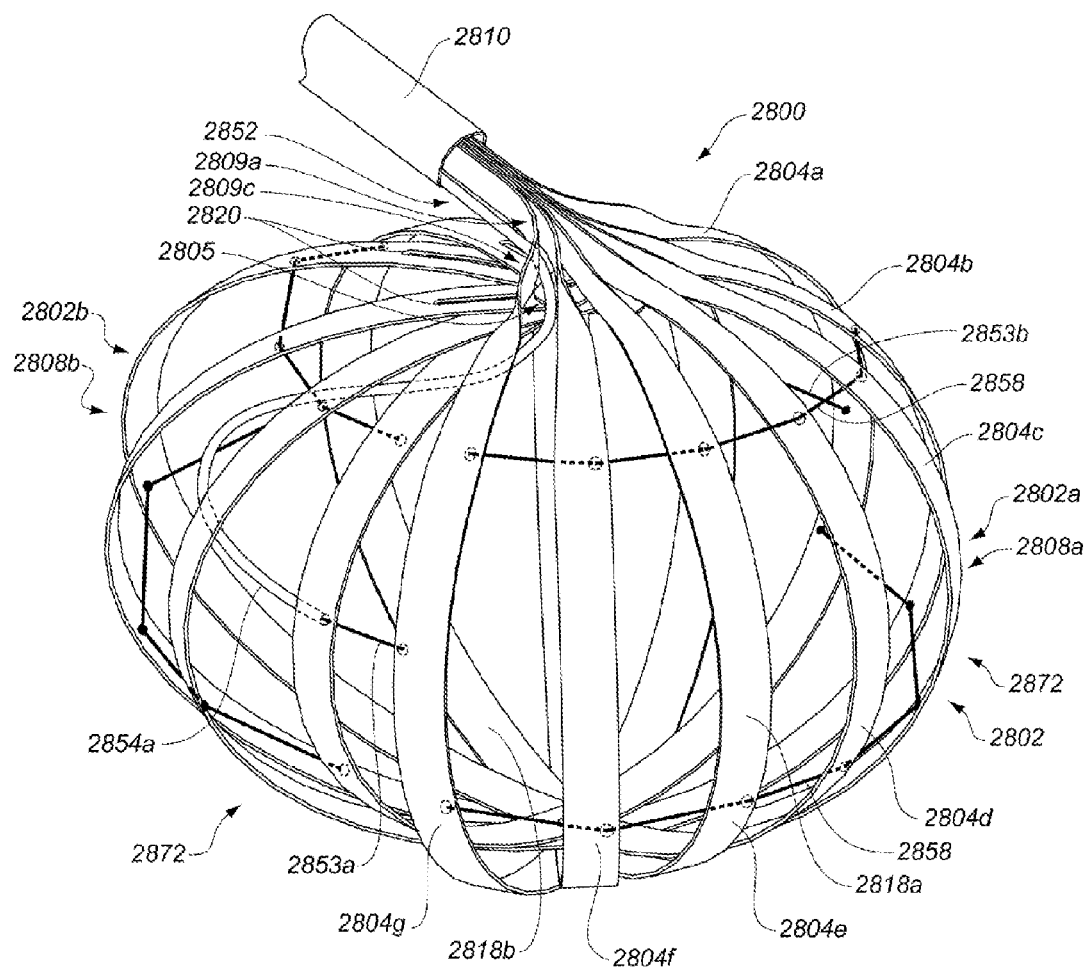
FIG. 9C is an isometric view of the portion of device of FIG. 9A extending from the catheter sheath after undergoing an additional manipulation in the deployed configuration.
Figure 9D:
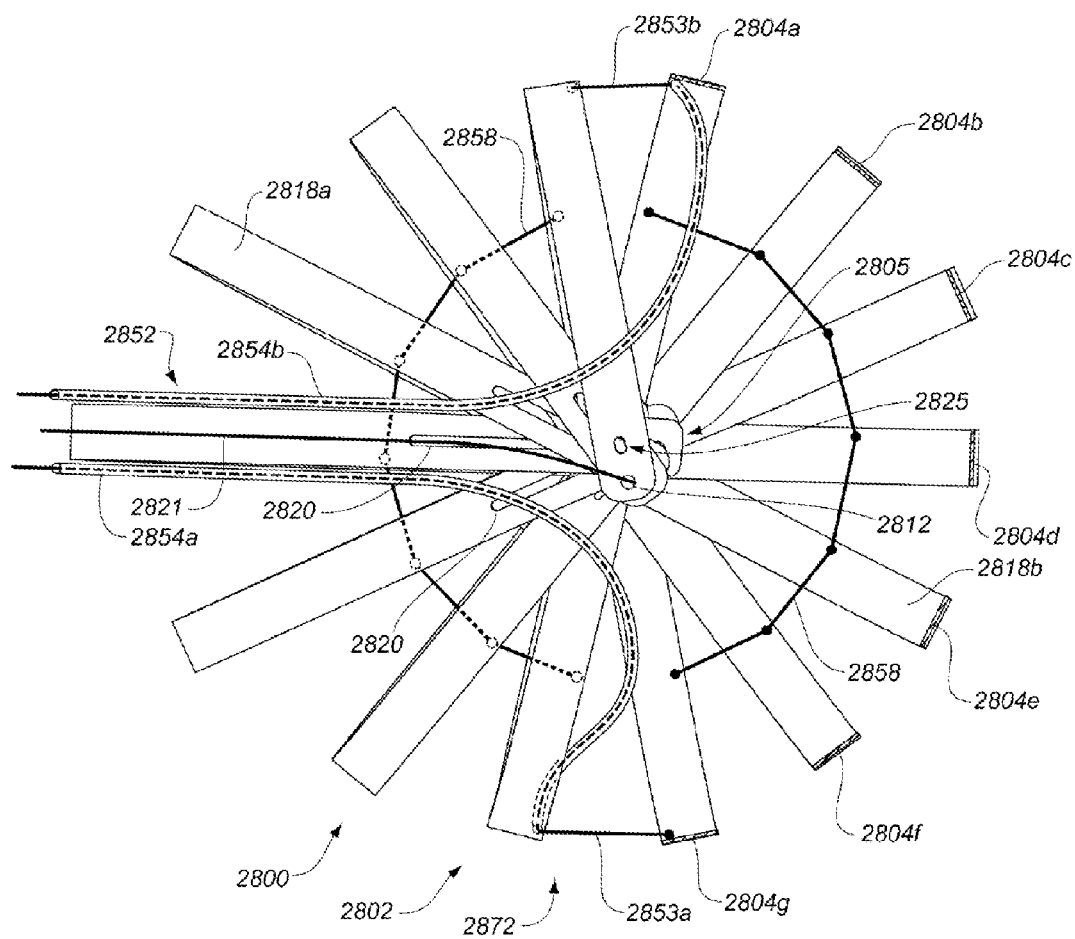
FIG. 9D is a partially sectioned plan view of the portion of the device of FIG. 9C.

FIGS. 9C and 9D respectively show an isometric view and a partially sectioned plan view of a portion of device 2800 which has been additionally manipulated from the first fanned array 2870 shown in FIGS. 9A, 9B to form a second fanned array 2872. As compared between FIGS. 9B and 9D, a change in the positioning where various ones of the slots 2820 cross one another accompanies a manipulation between the first fanned array 2870 and the second fanned array 2872. In this example embodiment, a movement of the respective distal ends 2805 of the elongate members 2804 generally along a direction toward crossing location 2825 accompanies a movement between the first fanned array 2870 and the second fanned array 2872. In this example embodiment, the respective distal ends 2805 of the elongate members 2804 are moved generally along a radial direction toward crossing location 2825. In this example embodiment, at least one flexible line 2821 (shown and called out only in FIGS. 9B and 9D for clarity) is employed to further manipulate between the first fanned array 2870 shown in FIGS. 9A, 9B and the second fanned array 2872 shown in FIGS. 9C, 9D. In this example embodiment, at least one flexible line 2821 is sized for passage through holes 2812 in various ones of the elongate members 2804. As compared with the embodiment shown in FIG. 6J, flexible line 2821 follows a less tortuous path than the flexible line 2540c of elongate member manipulator 2550. In various example embodiments, various ones of the elongate members 2804 may be physically coupled together by one or more coupling members (not shown for clarity) arranged to be slidably received in respective slots 2820 of the various ones of the elongate members 2804. In some embodiments, the one or more coupling members may include a relatively rigid member while in other embodiments, the one or more coupling members may include a relatively flexible member. In some example embodiments, the one or more coupling members may be employed to assist in establishing generally radial movement of various portions of the elongate members 2804 towards crossing location 2825. In some example embodiments, one or more flexible lines are sized and arranged to be received in the respective slots 2820 of various ones of the elongate members 2804.

As shown in FIGS. 9A and 9C, frame 2802 includes a proximal portion 2802a having a first domed shape 2808a and a distal portion 2802b having a second domed shape 2808b. In this example embodiment, the proximal and the distal portions 2802a, 2802b are arranged in a clam shell configuration in the third/expanded configuration. In this example embodiment, frame 2802 is additionally manipulated to distort a respective one of the first domed shape 2808a and the second domed shape 2808b to accompany a movement between the first fanned array 2870 and the second fanned array 2872. In this example embodiment, various ones of the slots 2820 have different longitudinal dimensions. In some example embodiments, various ones of the slots 2804 are sized differently to vary amounts of movement between various portions of respective elongate member 2804 during the manipulating. In some example embodiments, each of various ones of the slots 2804 is sized to vary amounts of distortion imparted to their respective elongate members 2804 during the manipulating. In this embodiment, the slots 2820 have been selectively sized to distort distal portion 2802b to have a more prolate second domed shape 2808b than the first domed shape 2808a of the proximal portion 2802a during the manipulating.

In this example embodiment, various ones of the elongate members 2804 are physically coupled together by coupling members 2858 (two called out in each of FIGS. 9A, 9B, 9C and 9D). In various example embodiments, each coupling member 2858 may allow movement of one of the elongate members 2804 coupled by the coupling member 2858 to also cause movement of another of the elongate members 2804 coupled by the coupling member 2858. In some example embodiments, the coupling members 2858 are arranged to restrict or limit an amount of movement that an elongate member 2804 undergoes as the portion of the device is moved into the third/expanded configuration. In this example embodiment, coupling members 2858 are positioned to extend across the back surfaces 2818b of the elongate members 2804 in the third/deployed configuration. In this embodiment, two quasi-circumferential arrangements of coupling members 2858 are provided. Different arrangements of coupling members 2858 may be employed in other embodiments.

In this embodiment, device 2800 includes separator 2852 arranged to manipulate various ones of the elongate members 2804. In this embodiment, separator 2852 includes a first flexible line 2853a and a second flexible line 2853b (collectively flexible lines 2853). In this example embodiment, each of the flexible lines 2853 is physically coupled to elongate member 2804g. Each of the flexible lines 2853 is sized to be slidably received in a lumen of a respective one of tubular members 2854a and 2854b (collectively tubular members 2854). Tubular member 2854b is not shown in each of FIGS. 9A and 9C. Tubular members 2854 are physically coupled to elongate member 2804a at respective spaced apart locations along a length of elongate member 2804a.

In this example embodiment, the flexible lines 2853 may be manipulated to move a portion of device 2800 into the third/expanded or fanned configuration. For example, flexible lines 2853 may be manipulated to move device 2800 from a second/bent configuration (e.g., similar to that shown by device 2600 in FIG. 7D) into the third/expanded or fanned configuration. In this example embodiment, the flexible lines 2853 may be manipulated to fan at least some of the elongate members 2804. In this example embodiment, the flexible lines 2853 may be manipulated to further fan at least some of the elongate members 2804 which have been initially fanned under an influence of a biasing action provided by one or more portions (e.g., the twisted portion 2809c or the bent portion 2809a, or both) of each of various ones of the at least some of the elongate members 2804. In some embodiments, the flexible lines 2853 are manipulated to vary a distance between the proximal and the distal portions 2802a, 2802b in the third/expanded configuration. In some embodiments, the flexible lines 2853 may be manipulated to vary a distance between adjacent elongate members (e.g., elongate members 2804a, 2804g) in the third/expanded configuration. In some embodiments, the flexible lines 2853 are manipulated to distort at least one of the first domed shape 2808a and the second domed shape 2808b. For example, when the portion of device 2800 is moved into the second fanned array 2872, flexible line 2853 may be manipulated to reduce a deviation in a shape of frame 2802 (e.g., a "radial step" between elongate members 2804a, 2804g as compared between FIGS. 9B and 9D). Reducing deviations in the shape of frame 2802 may be motivated by various reasons including providing a more uniform distribution in an arrangement of transducers (not shown) that may be carried by the device 2800. In various example embodiments, manipulation of the flexible lines 2853 may include relatively sliding the flexible lines 2853 within their respective tubular members 2854. In some example embodiments, manipulation of the flexible lines 2853 includes tensioning the flexible lines 2853. Other numbers of flexible lines 2853 may be employed in other embodiments.

Referring back to embodiments represented in FIG. 7, each front surface 2618a includes, carries or supports (i.e., directly or indirectly) at least one transducer element 2690 (i.e., not shown) that is positionable adjacent to an interior tissue surface in when the first fanned array 2670 is manipulated into the second fanned array 2672 within a bodily cavity having the interior tissue surface. In these example embodiments, once the second fanned array 2672 has been appropriately positioned at a given location within a bodily cavity, determination of the locations of various components of device 2600 (e.g., transducer elements including sensors or electrodes or related support structures such as elongate members 2604), or the locations of various anatomical features within the bodily cavity can be determined by various methods. In these example embodiments, after the portion of the device 2600 has been appropriately positioned at a given location within a bodily cavity, ablation of various regions of a tissue surface within bodily cavity can commence. The second fanned array 2672 may be removed from the bodily cavity by reconfiguring the portion of the device 2600 back into the second/bent configuration and then further back into the first/unexpanded configuration. In this example embodiment, the wedged or tapered form of the fanned first portions 2609a of the elongate members 2604 allows the elongate members 2604 to be readily drawn into a lumen of catheter sheath 2606 facilitating movement from the deployed configuration to the delivery configuration.

Figure 7G:
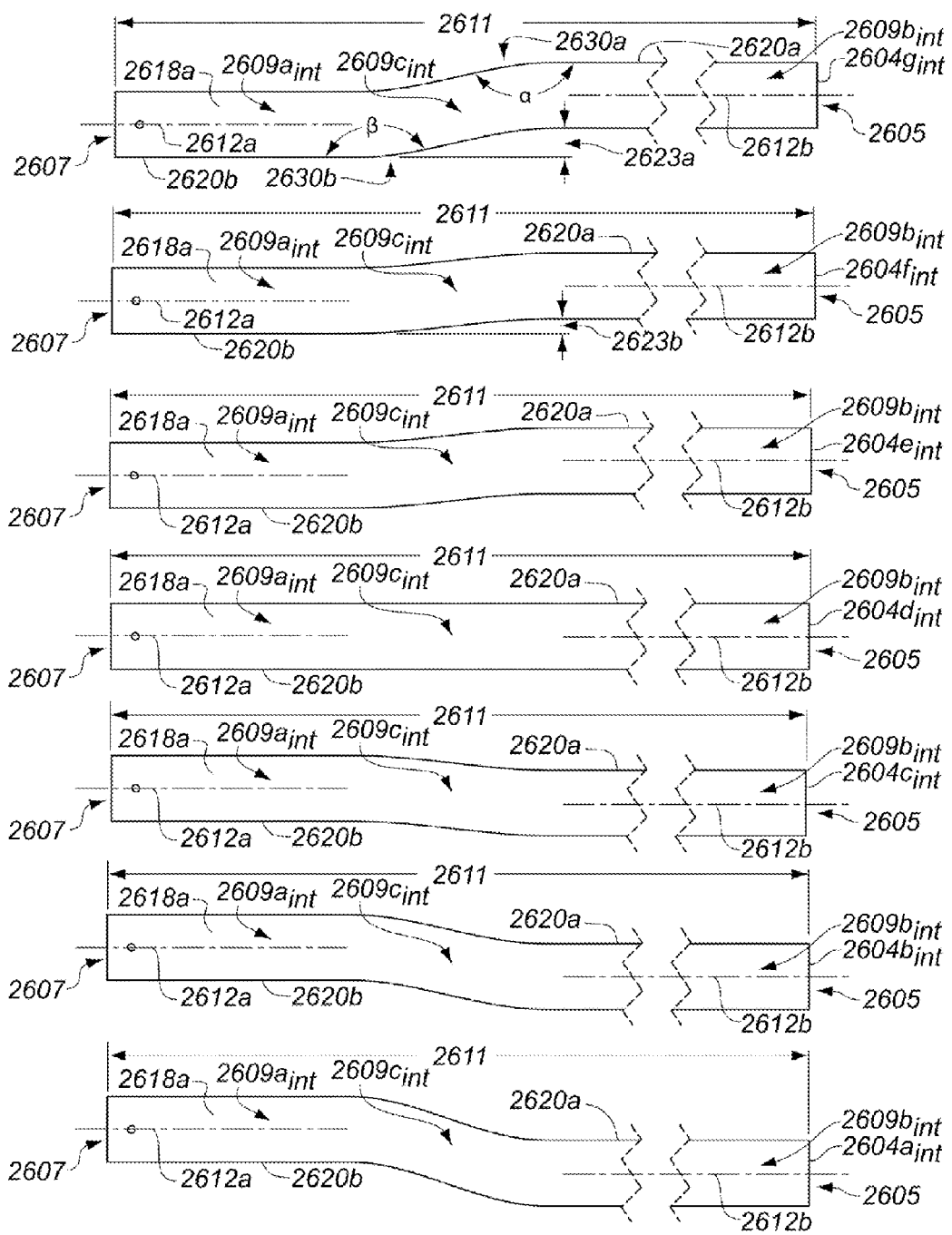
FIG. 7G is a plan view of various elongate members that are provided to form at least a portion of respective ones of the elongate members employed by the device of FIG. 7A.
Figure 7I:
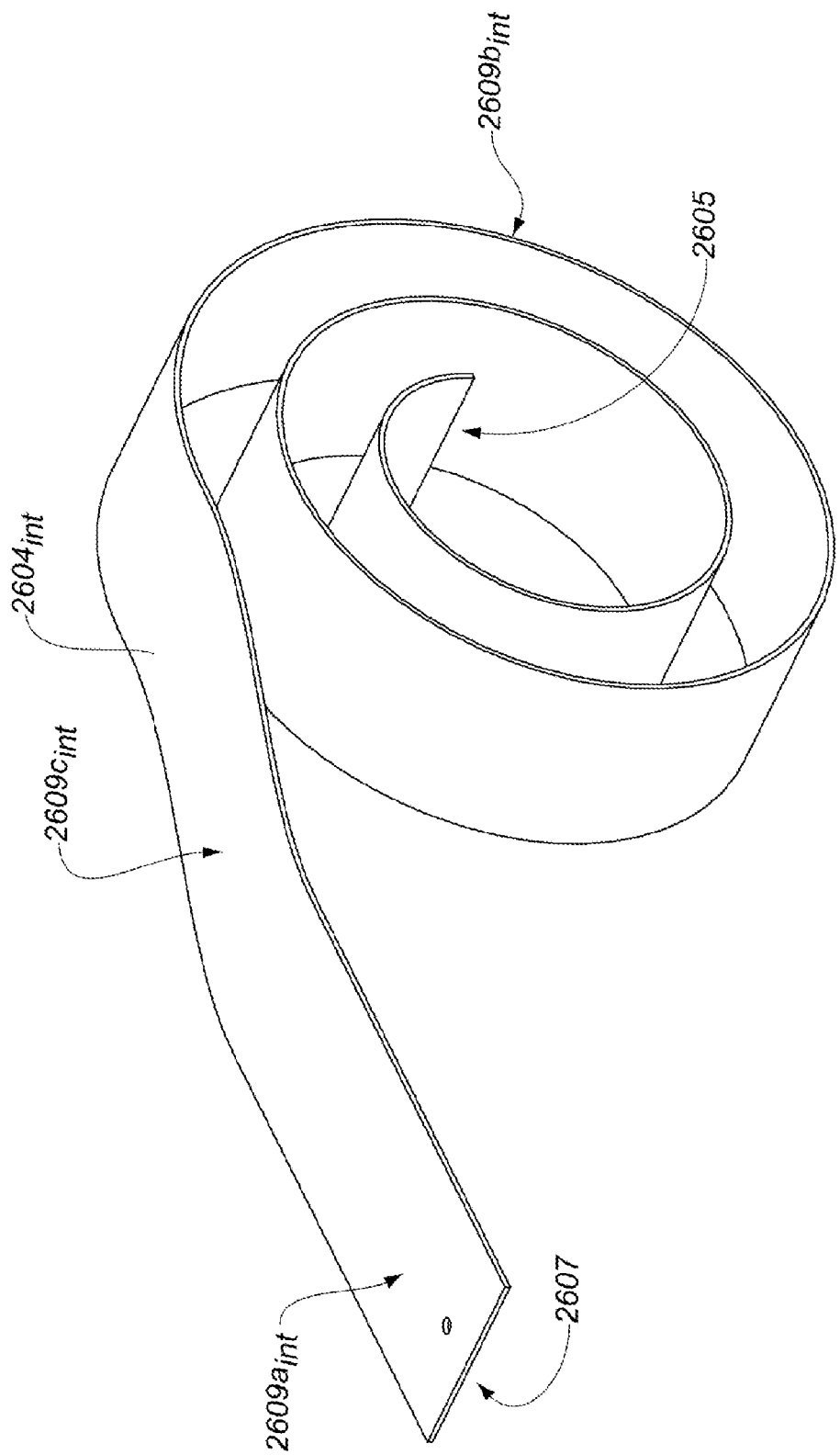
FIG. 7I is an isometric view of one of the provided elongate members of FIG. 7G distorted by a first distorting process according to an example embodiment.
Figure 7J:
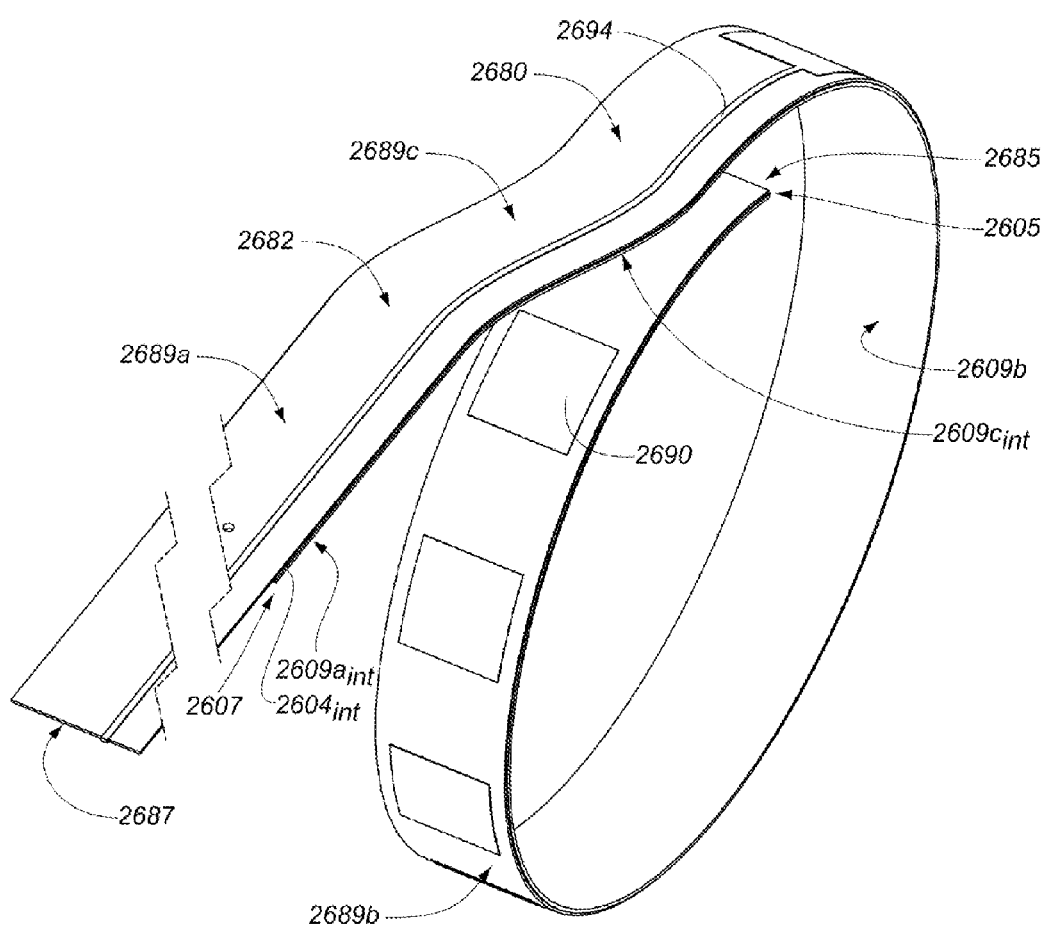
FIG. 7J is an isometric view of an assemblage of a portion of a flexible circuit structure and the provided elongate member of FIG. 7I.
Figure 7K:
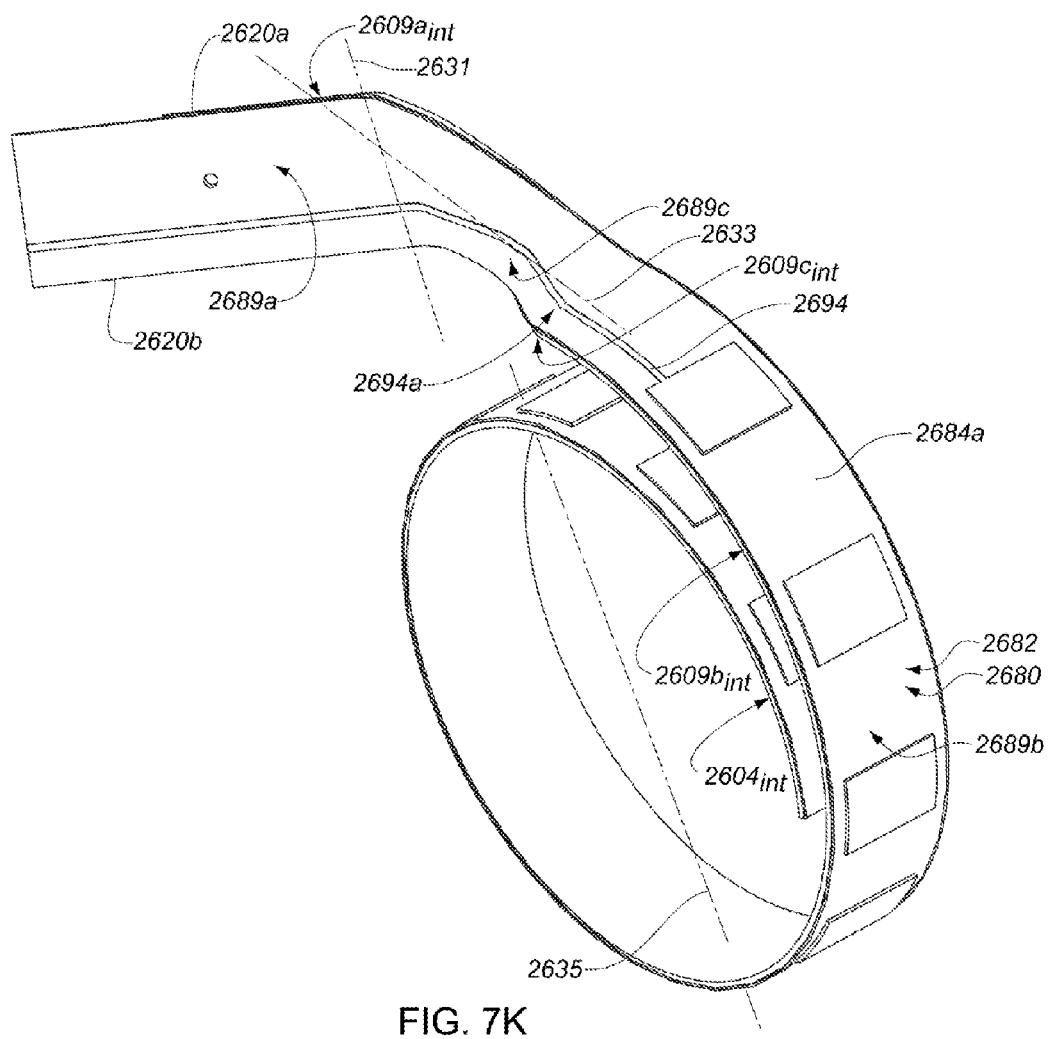
FIG. 7K is an isometric view of the assemblage of the flexible circuit structure and the provided elongate member of FIG. 7J distorted by a second distorting process according to an example embodiment.
Figure 7L:
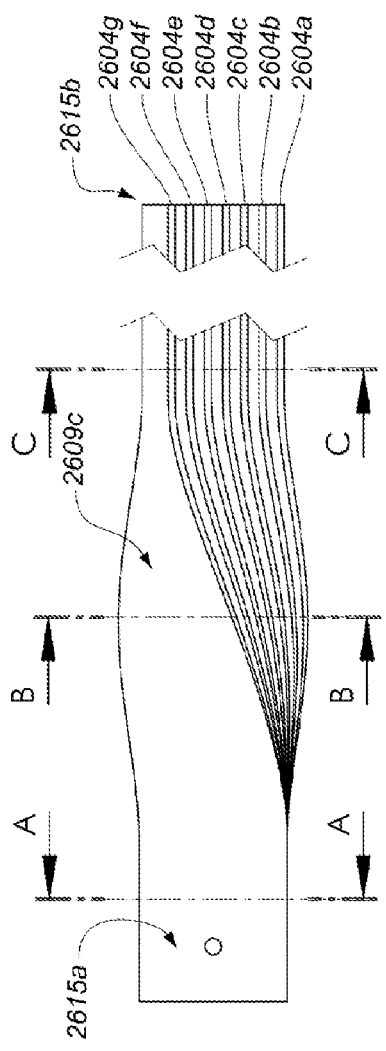
FIG. 7L is a side view of a portion of an arrangement of elongate members as per an example embodiment.
Figure 7L:
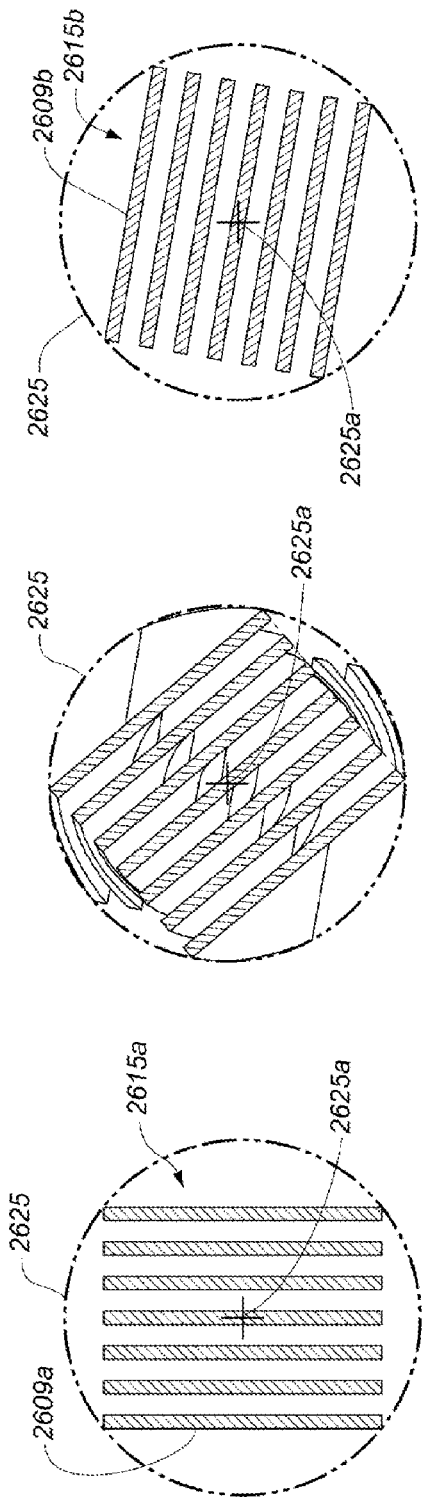
Figure 7M:
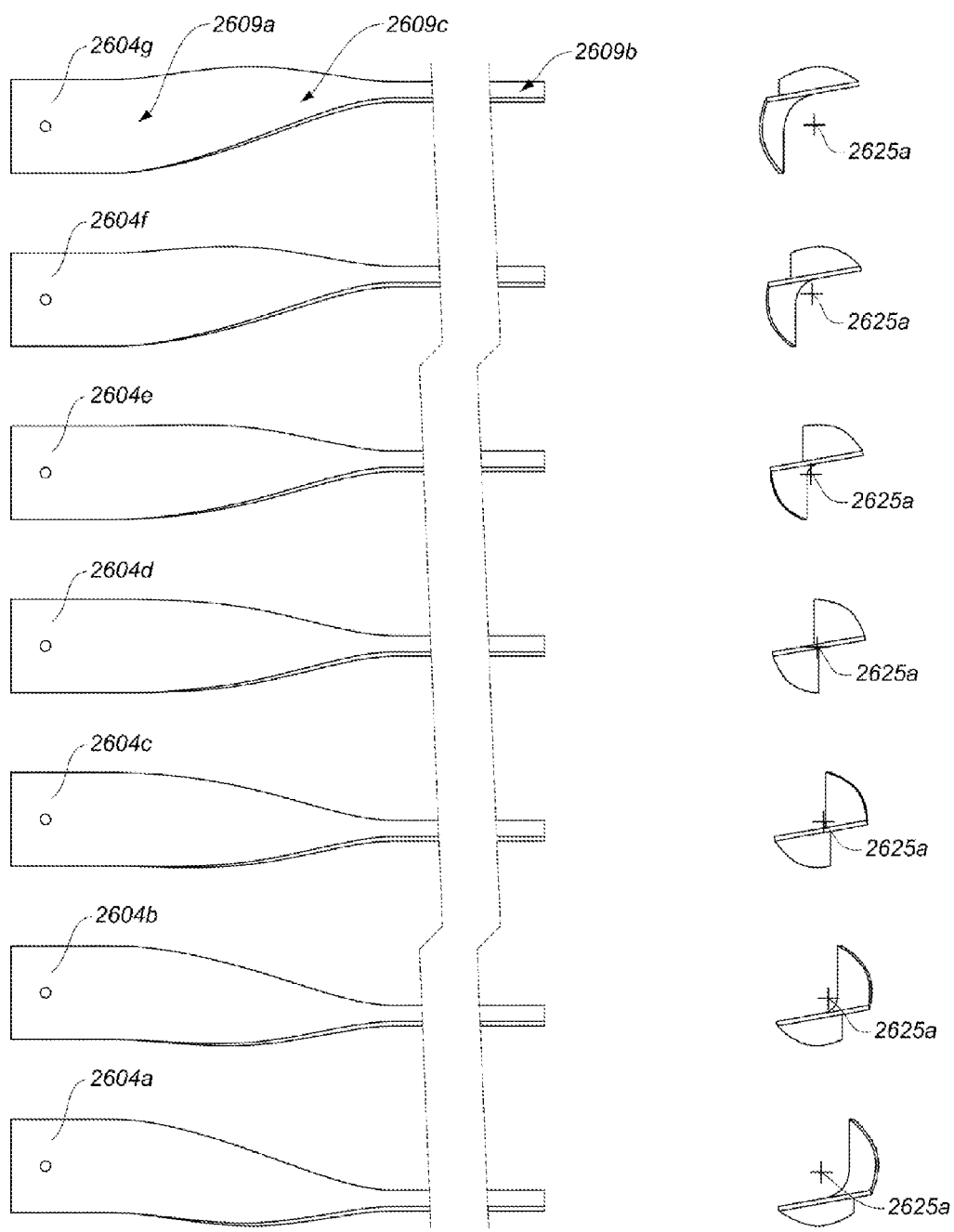
FIG. 7M are respective side and end elevation views of each elongate member of the arrangement of elongate members of FIG. 7L.
Figure 8:
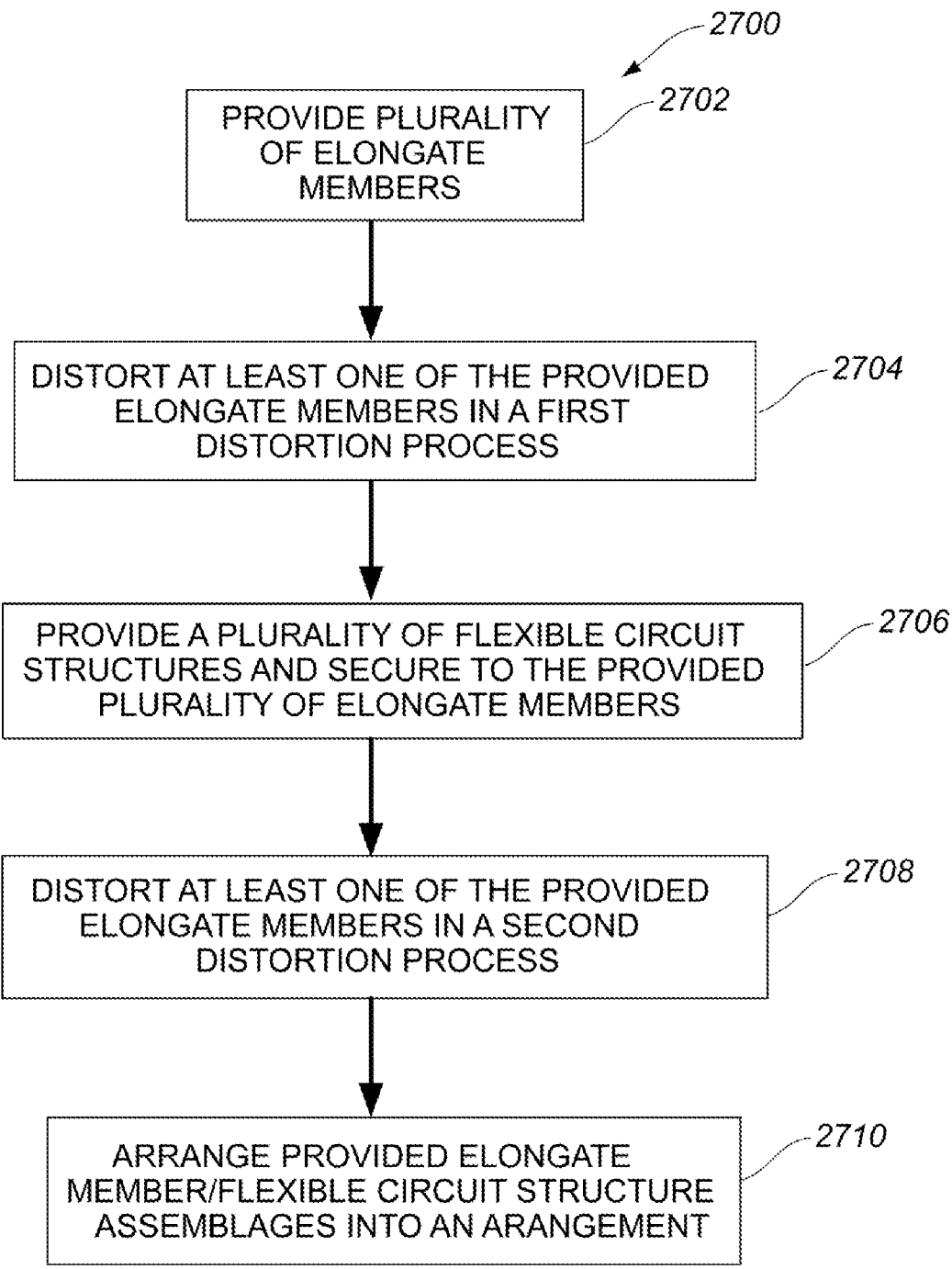
FIG. 8 is a flow diagram representing a method according to one example embodiment.

FIG. 8 is a flow diagram representing a method 2700 for forming, fabricating or manufacturing various elongate members employed in various embodiments. For convenience, the various procedures or acts described in method 2700 are made with reference to the elongate members 2604 shown in FIGS. 7A through 7M. It is understood that method 2700 may be applied to produce other elongate members employed in other embodiments.

Method 2700 begins with block 2702 in which a plurality of elongate members are provided. For example, FIG. 7G includes a respective plan view of each of various elongate members including elongate members $2604a_{int}$, $2604b_{int}$, $2604c_{int}$, $2604d_{int}$, $2604e_{int}$, $2604f_{int}$, and $2604g_{int}$ (collectively $2604_{int}$) that are provided to form at least a portion of respective ones of the elongate members 2604 employed by the example embodiment shown in FIG. 7A. In this example embodiment, provided elongate member $2604a_{int}$ corresponds to elongate member 2604a, provided elongate member $2604b_{int}$ corresponds to elongate member 2604b, provided elongate member $2604c_{int}$ corresponds to elongate member 2604c, provided elongate member $2604d_{int}$ corresponds to elongate member 2604d, provided elongate member $2604e_{int}$ corresponds to elongate member 2604e, provided elongate member $2604f_{int}$ corresponds to elongate member 2604f, and provided elongate member $2604g_{int}$ corresponds to elongate member 2604g. As shown in FIG. 7G, the respective proximal end 2607, the respective distal end 2605, the respective length 2611, and the respective front surface 2618a of each one of elongate members 2604a, 2604b, 2604c, 2604d, 2604e, 2604f, and 2604g is also represented in a respective one of provided elongate members $2604a_{int}$, $2604b_{int}$, $2604c_{int}$, $2604d_{int}$, $2604e_{int}$, $2604f_{int}$, and $2604g_{int}$. Accordingly, the same reference numbers have been employed.

In this example embodiment, each of the elongate members $2604_{int}$ is provided in a strip-like form. In some embodiments, each elongate member $2604_{int}$ is provided in a generally planar form or with material or geometric properties that allow the elongate member $2604_{int}$ to be deformed into assuming a generally planar or flat form under the influence of modest forces. Without limitation, various ones of the provided elongate members $2604_{int}$ may include various metallic compositions, non-metallic compositions or combinations thereof. In some embodiments, the provided elongate members $2604_{int}$ may include a shape memory material, for instance Nitinol. The incorporation of a specific material into various ones of the elongate members $2604_{int}$ may be motivated by various factors. In this example embodiment, various portions of each provided elongate member $2604_{int}$ include material properties and geometric dimensions suitable for undergoing a distortion or deformation process employed by method 2700. By way of non-limiting example, the distortion or deformation process can include a plastic deformation process. By way of non-limiting example, the distortion or deformation process can include a non-reversible distortion or deformation process in which a given one of the provided elongate members $2604_{int}$ that is distorted or deformed by the application of force does not generally return back to its original shape upon removal of the applied force. In this example embodiment, each provided elongate member $2604_{int}$ includes material properties and geometric dimensions that have been pre-selected to allow for a subsequent manipulation (e.g., during an actual use of device 2600) of the respective elongate member 2604 that is formed at least in part, from the provided elongate member $2604_{int}$. Manipulation of various portions 2609 of each resulting elongate member 2604 can include bending, flexing, twisting and combinations thereof by way of non-limiting example. Manipulation of various portions 2609 of each resulting elongate member 2604 can include relatively few manipulations or a relatively large number of manipulations. In some example embodiments, various ones of the provided elongate members $2604_{int}$ are made from a material whose material properties and geometric dimensions have been preselected so that the resulting elongate members 2604 can withstand cyclic manipulation. In some example embodiments, various ones of the provided elongate members $2604_{int}$ are made from a material having material properties and geometric dimensions that have been preselected such that the resulting elongate members 2604 can withstand anticipated conditions that can lead to possible fatigue failure. The present inventors have employed methods similar to method 2700 that employ provided elongate members $2604_{int}$ made from stainless steel (e.g., 17-7 SS) and having maximum cross-sectional dimensions of 0.127 millimeters by 4 millimeters by way of non-limiting example.

In this example embodiment, each provided elongate member $2604_{int}$ includes a plurality of different portions $2609_{int}$ including first portion $2609a_{int}$, second portion $2609b_{int}$, and a third portion $2609c_{int}$ positioned between the first and the second portions $2609a_{int}$ and $2609b_{int}$. Each of the various portions $2609_{int}$ corresponds to one of the various portions 2609 of elongate member 2604 that results from processing of the provided elongate member $2604_{int}$ under various processes undertaken in accordance with method 2700. Accordingly, the respective side edges of each of the portion $2609_{int}$ are identified by the same part numbers of the side edges 2620 of the corresponding portions 2609. In some embodiments, at least one of the first portion $2609a_{int}$, second portion $2609b_{int}$ and a third portion $2609c_{int}$ of a provided elongate member $2604_{int}$ may undergo one or more processes to transform the at least one of the first portion $2609a_{int}$, second portion $2609b_{int}$ and third portion $2609c_{int}$ into a corresponding one of one of the first portion 2609a, second portion 2609b and third portion 2609c of the elongate member 2604 produced by method 2700. It is noted that in some embodiments, not all of the various portions $2609_{int}$ including first portion $2609a_{int}$, second portion $2609b_{int}$ and third portion $2609c_{int}$ of a provided elongate member $2604_{int}$ may undergo a process as specified by method 2700 and may be provided substantially unaltered or undergo an alternate process to form the final elongate member 2604.

In this example embodiment, the respective second portion $2609b_{int}$ of each provided elongate member $2604_{int}$ of at least some of the plurality of provided elongate members $2604_{int}$ (e.g., provided elongate members $2604a_{int}$, $2604b_{int}$, $2604c_{int}$, $2604e_{int}$, $2604f_{int}$, and $2604g_{int}$) is laterally offset from the respective first portion $2609a_{int}$ of the provided elongate member $2604_{int}$ across at least a portion of the respective length 2611 of the provided elongate member $2604_{int}$. In this example embodiment, a center line or midline 2612b of the respective second portion $2609b_{int}$ of each provided elongate member $2604_{int}$ of at least some of the plurality of provided elongate members $2604_{int}$ (e.g., elongate members $2604a_{int}$, $2604b_{int}$, $2604c_{int}$, $2604e_{int}$, $2604f_{int}$, and $2604g_{int}$) is laterally offset from a center line or midline 2612a of the respective first portion $2609a_{int}$ of the provided elongate member $2604_{int}$ across at least a portion of the respective length 2611 of the provided elongate member $2604_{int}$. In some example embodiments, various ones of the midlines 2612a and 2612b form a line of symmetry of a respective one of the portions $2609_{int}$. In some example embodiments, various ones of the midlines 2612 extend across a centroid of a respective one of the portions $2609_{int}$. In this example embodiment, the respective pair of side edges 2620 of each of the first portion $2609a_{int}$ and second portion $2609b_{int}$ of each provided elongate member $2604_{int}$ includes a respective first side edge 2620a (only one called out for each provided elongate member $2604_{int}$) arranged on a first side of the provided elongate member $2604_{int}$ and a respective second side edge $2620b$ (only one called out for each provided elongate member $2604_{int}$) arranged on a second side of the provided elongate member $2604_{int}$. In various example embodiments, at least one of the first side edge $2620a$ and the second sided edge $2620b$ of the respective second portion $2609b_{int}$ of at least one of the provided elongate members $2604_{int}$ (i.e., both of the first and the second side edges $2620a$, $2620b$ in this illustrated embodiment) is laterally offset from the corresponding one of the first side edge $2620a$ and the second sided edge $2620b$ of the respective first portion $2609a_{int}$ of the at least one of the provided elongate members $2604_{int}$ across at least a portion of the respective length $2611$ of the at least one of the provided elongate members $2604_{int}$.

In this example embodiment, various ones of the provided elongate members $2604_{int}$ have different amounts of lateral offset between their respective second and first portions $2609b_{int}$, $2609a_{int}$. For example, the respective second portion $2609b_{int}$ of provided elongate member $2604a_{int}$ is laterally offset from the respective first portion $2609a_{int}$ of provided elongate member $2604a_{int}$ by a first distance $2623a$ over a portion of the respective length $2611$ of provided elongate member $2604a_{int}$. The respective second portion $2609b_{int}$ of provided elongate member $2604b_{int}$ is laterally offset from the respective first portion $2609a_{int}$ of provided elongate member $2604b_{int}$ by a second distance $2623b$ over a portion of the respective length $2611$ of provided elongate member $2604b_{int}$. In this example embodiment, the second distance $2623b$ is different than the first distance $2623a$. In this example embodiment, the second distance $2623b$ is less than the first distance $2623a$. In this example embodiment, the amount of lateral offset between their respective second and first portions $2609b_{int}$, $2609a_{int}$ of the various provided elongate members $2604_{int}$ arranged as shown in FIG. 7G reduces from top-to-middle and from middle-to-top in the illustrated arrangement. In this example embodiment, the respective second portion $2609b_{int}$ of each of provided elongate members $2604c_{int}$ and $2604e_{int}$ has relatively little lateral offset from the respective first portion $2609a_{int}$ of each of provided elongate members $2604c_{int}$ and $2604e_{int}$. In this example embodiment, the respective second portion $2609b_{int}$ of each of provided elongate members $2604a_{int}$ and $2604g_{int}$ has the greatest amount of lateral offset from the respective first portion $2609a_{int}$ of each of the provided elongate members $2604a_{int}$ and $2604g_{int}$. In this example embodiment, the respective second portion $2609b_{int}$ of provided elongate member $2604d_{int}$ is not laterally offset from the respective first portion $2609a_{int}$ of provided elongate member $2604d_{int}$. Rather, the respective first, second and third portions $2609a_{int}$, $2609b_{int}$, and $2609c_{int}$ of provided elongate member $2604d_{int}$ are all aligned along a substantially straight path.

As best seen in FIG. 7G, at least one of the provided elongate members $2604_{int}$ includes at least one corner $2630a$ (only one called out as shown in provided elongate member $2604a_{int}$) formed by a convergence of the respective first side edge $2620a$ of the third portion $2609c_{int}$ of the at least one of the provided elongate members $2604_{int}$ and the respective first side edge $2620a$ of the second portion $2609b_{int}$ of the at least one of the provided elongate members $2604_{int}$, the at least one corner $2630a$ enclosing a respective angle "α" extending across the front surface $2618a$ of the at least one of the provided elongate members $2604_{int}$. In this example embodiment, the enclosed angle α extends towards at least part of the respective second side edge $2620b$ of at least one of the portions $2609_{int}$ of the at least one of the provided elongate members $2604_{int}$. In this example embodiment, at least one of the provided elongate members $2604_{int}$ includes at least one corner $2630b$ (only one called out as shown in provided elongate member $2604a_{int}$) formed by a convergence of the respective second side edge $2620b$ of the third portion $2609c_{int}$ of the at least one of the provided elongate members $2604_{int}$ and the respective second side edge $2620b$ of the first portion $2609a_{int}$ of the at least one of the provided elongate members $2604_{int}$. In this example embodiment at least one corner $2630b$ encloses an angle "β" extending across the front surface $2620a$ of the provided at least one of the provided elongate members $2604_{int}$. In this example embodiment, each respective enclosed angle extends towards the respective first side edge $2620a$ of at least one of the portions $2609_{int}$ of the at least one of the provided elongate members $2604_{int}$. In this example embodiment each of corners $2630a$, $2630b$ encloses an obtuse angle. It is understood that other angles may be enclosed by various ones of corners $2630a$, $2630b$ in other example embodiments. In this example embodiment, each of corners $2630a$ and $2630b$ is a filleted corner. Other shapes or forms may be employed by various ones of the corners $2630a$ and $2630b$ in other example embodiments.

In some embodiments, various flexible circuit structures are employed to provide at least a signal path between a plurality of transducers employed by a medical device and a transducer controller. In some example embodiments, at least some of the transducer elements are used to sense a physical characteristic of a fluid (i.e., blood) or tissue, or both, that may be used to determine a position or orientation (i.e., pose), or both, of a portion of a device in a bodily cavity (e.g., a left atrium). For example, some transducer elements may be used to determine a location of pulmonary vein ostia or a mitral valve in a left atrium. In some example embodiments, at least some of the transducer elements may be used to selectively ablate portions of a tissue surface within a bodily cavity. For example, some of the transducer elements may be used to ablate a pattern around various bodily openings, ports or pulmonary vein ostia, for instance to reduce or eliminate the occurrence of atrial fibrillation. In various embodiments, transducer elements can include at least one of an electrode and a sensing element. In various embodiments, at least some of the transducer elements are provided on, or by various ones of the flexible circuit structures. The flexible circuit structures the may be mounted or otherwise carried on a frame, or may form an integral component of the frame itself. The frame may be flexible enough to slide within a catheter sheath in order to be deployed percutaneously. FIGS. 1, 2, 3, 4, 5, 6, 7 and 9 discussed previously show various example embodiments of such a frame.

In various example embodiments, the flexible circuit structures form part of a framed structure that is selectively movable between an unexpanded configuration in which respective portions of each of the flexible circuit structures are arranged successively along a first direction in a stacked arrangement sized to be percutaneously delivered through a bodily opening leading to a bodily cavity, and an expanded or fanned configuration in which the respective portions of the flexible circuit structures are angularly spaced with respect to one another about at least one axis. In some of these embodiments, each of the respective portions of at least some of the flexible printed circuit structures revolve, rotate, pivot or turn (used interchangeably herein) about at least one axis when the structure is moved between the unexpanded configuration and the expanded configuration.

In block $2706$, a plurality of flexible circuit structures $2680$ are provided and a portion of each of the flexible circuit structures 2680 is secured to a respective one of the plurality of provided elongate members 2604$_{int}$. In this example embodiment, each flexible circuit structure 2680 is a flexible printed circuit board (PCB) structure. FIG. 7H is an isometric view of a representative one of the flexible circuit structures 2680. Each flexible circuit structure 2680 includes at least one flexible material layer 2682. In this example embodiment, each at least one flexible material layer 2682 includes an electrical insulator layer (e.g., polyimide). In a manner similar to each of the provided elongate members 2604$_{int}$, the at least one material layer 2682 includes a first end 2687, a second end 2685, a respective length 2681 between the first and the second ends, 2687, 2685, a thickness 2683 and a front surface 2684a and a back surface 2684b opposite across the thickness 2683. The at least one flexible material layer 2682 further includes a plurality of portions 2689 including a first portion 2689a, a second portion 2689b and a third portion 2689c positioned between the first and the second portions 2689a, 2689b. In this example embodiment, the second portion 2689b is laterally offset from the first portion 2689a along at least a portion of the respective length 2681 of the at least one material layer 2682. In this example embodiment, each of the plurality of portions 2689 includes a respective pair of side edges 2686 including a first side edge 2686a (only one called out) arranged on a first side of the at least one material layer 2682 and a second side edge 2686b (only one called out) arranged on second opposite side of the at least one material layer 2682. Each of the pair of side edges 2686 forms a portion of a periphery of at least one of the front surface and the back surface 2684a and 2684b of the at least one material layer 2682. In this example embodiment, a portion of the periphery of at least one of the front surface and the back surface 2684a, 2684b of the at least one material layer 2682 is similar in shape to the periphery of at least one of the front surface and the back surface 2618a, 2618b of the provided elongate member 2604$_{int}$ to which the flexible circuit structure 2680 is to be secured. In this example embodiment, each of the second and the third portions 2689b, 2689c of the at least one material layer 2682 have a size and shape substantially similar to the second and the third portions 2609b, 2609c of the provided elongate member 2604$_{int}$ to which the flexible circuit structure 2680 is to be secured. In this example embodiment, the first portion 2689a of the at least one material layer 2682 is longer than the first portion 2609a of the provided elongate member 2604$_{int}$ to which the flexible circuit structure 2680 is to be secured. In other example embodiments, the at least one material layer 2682 may have different shapes and/or sizes than those illustrated. In this example embodiment, the lateral offset between the respective second and first portions 2689b, 2689a of each of the plurality of flexible circuit structures 2680 is generally similar to the lateral offset between the respective second and first portions 2609b$_{int}$, 2609a$_{int}$ of a respective one of the provided elongate members 2604$_{int}$ to which the flexible circuit structure 2680 is to be secured.

Transducer elements (e.g., electrodes or sensors, or both) may be built on the flexible circuit structure 2680 using conventional printed circuit board processes. In this example embodiment, each of the flexible circuit structures 2680 includes at least one electrically conductive layer 2692. In this example embodiment, the at least one electrically conductive layer 2692 is patterned to provide a portion of each of a set of transducer elements 2690 (two called out) and at least one electrically conductive trace 2694 on, at or carried by (i.e., directly or indirectly) a surface of the at least one material layer 2682. In this example embodiment, the at least one electrically conductive trace 2694 is electrically connected to various ones of the transducer elements 2690 (i.e., only one in this illustrated embodiment). It is understood that other electrical traces, each connected to one or more of the plurality of transducer elements 2690 can be present in various embodiments. In this example embodiment, the at least one electrically conductive trace 2694 extends on the front surface 2684a of the at least one material layer 2682 along a path across parts of each of the first portion 2689a, the third portion 2689c and the second portion 2689b of the at least one material layer 2682. In this example embodiment, the at least one electrically conductive trace 2694 includes various jogged portions 2694a (one called out) as viewed perpendicularly to a portion of the front surface 2684a of the at least one material layer 2682 located at least proximate to a location on the front surface 2684a where the path extends across the third portion 2689c of the at least one material layer 2682. In this example embodiment, the jogged portions 2694a are formed by a patterning process. In this example embodiment, the jogged portions 2694a are formed by employing flexible circuit patterning techniques. In other example embodiments, other techniques may be employed to form a jogged portion 2694a in the at least one electrically conductive trace 2694. By way of non-limiting example, other techniques can include manipulation of the at least one material layer 2682 before, during or after the formation of the at least one electrically conductive trace 2694.

Each of the flexible circuit structures 2680 can be secured to a respective one of the provided plurality of elongate members 2604$_{int}$ by various techniques. For example, in some embodiments, fasteners or fastening devices are employed. In some example embodiments, a flexible circuit structure 2680 is bonded to a respective one of the provided plurality of elongate members 2604$_{int}$ with an adhesive. The present inventors have created various assemblages by bonding polyimide and 17-7 stainless steel layers using LOCTITE® 4081 or LOCTITE® 435 medical device adhesives. Various factors such as, but not limited to, sterilization considerations, particulate generation, fastening reliability, etcetera can motivate the selection of a particular securement technique.

In block 2704, at least one of the provided elongate members 2604$_{int}$ undergoes a first distortion or deformation process. In this particular embodiment, at least one of the provided elongate members 2604$_{int}$ is distorted or deformed prior to the securing of a flexible circuit structure 2680 to the at least one of the provided elongate members 2604$_{int}$ in block 2706. The at least one of the provided elongate members 2604$_{int}$ may be distorted or deformed in various ways. In this example embodiment, the respective second portion 2609b of each of the provided elongate members 2604$_{int}$ is distorted or deformed to provide a coiled, scrolled or volute profile as shown in FIG. 7I. Each respective second portion 2609b$_{int}$ of the provided elongate members 2604$_{int}$ can be distorted or deformed using various bending or coiling mechanisms known in the art. For example, a particular second portion 2609b$_{int}$ may be run through a series of rolls arranged to impart a desired profile onto the particular second portion 2609b$_{int}$, especially when the desired profile is a coiled profile.

FIG. 7J shows a portion of a flexible circuit structure 2680 that has been secured to the provided elongate member 2604$_{int}$ of FIG. 7I that has been distorted or deformed in accordance with block 2704. In this example embodiment, a portion of the flexible circuit structure 2680 has been bonded to the provided elongate member $2604_{int}$. In this example embodiment, a portion of the assemblage of the provided elongate member $2604_{int}$ and flexible circuit structure 2680 provides the second portion 2609b generally with the desired coiled, scrolled or volute profile comprised by a respective one of the resulting elongate members 2604 shown in FIG. 7A. It is noted that when compared with the coiled profile of the provided elongate member $2604_{int}$ shown in FIG. 7I, the assemblage of the provided elongate member $2604_{int}$ and flexible circuit structure 2680 shown FIG. 7J has a larger coiled profile. The process of distorting or deforming the provided elongate member $2604_{int}$ can impart significant stress on the elongate member $2604_{int}$, sometimes deforming the elongate member $2604_{int}$ well beyond a yield point of the elongate member $2604_{int}$. Various factors may require that the coiled profile that is imparted to the provided elongate member $2604_{int}$ as per block 2704 be made relatively smaller than the coiled profile that the provided elongate member $2604_{int}$ has after the portion of the flexible circuit structure 2680 has been secured to the provided elongate member $2604_{int}$ as shown in FIG. 7J. For example, various material properties of the provided elongate member $2604_{int}$ may have a bearing. The particular material properties of the provided elongate member $2604_{int}$ can impart a certain amount of "spring-back" to the provided elongate member $2604_{int}$. Soft materials typically have limited spring-back whereas relatively harder materials (e.g., metals employed in medical devices such as stainless steel, Nitinol) can have a substantially more spring-back. If a provided elongate member $2604_{int}$ that included a material having a relatively high spring-back were to be distorted or deformed after the flexible circuit structure 2680 was bonded to the provided elongate member $2604_{int}$, the small coiled profile (i.e., similar to that shown in FIG. 7I) that would be required to be imparted on the provided elongate member $2604_{int}$/flexible circuit structure 2680 assemblage to account for the spring-back so as to form the coiled profile shown in FIG. 7J may impart substantially higher stress and strain rates on various features of the flexible circuit structure 2680 (e.g., the at least one electrically conductive trace 2694) than if the provided elongate member $2604_{int}$ was distorted or deformed prior to the bonding of the at least one flexible circuit structure 2680 to the provided elongate member $2604_{int}$ as per block 2706. These higher stress and strain rates may increase the risk of failures of various elements of the flexible circuit structure 2680 such as the at least one electrically conductive trace 2694 and thereby result in a less robust and reliable device. Further, these resulting higher stress and strain rates may increase the chances of bonding failures when an adhesive is employed to secure a portion of the flexible circuit structure 2680 to the provided elongate member $2604_{int}$ prior to distortion or deformation of the provided elongate member $2604_{int}$. Another possible reason for pre-distorting or pre-deforming the provided elongate member $2604_{int}$ prior to the securement of the flexible circuit structure 2680 is to provide a more uniform coiled profile. In some example embodiments, the stiffness of the flexible circuit structure 2680 may not be consistent along its respective length. For example, regions of the flexible circuit structure 2680 comprising transducer elements 2690 (only one called out in FIG. 7J) may be stiffer than other regions of the flexible circuit structure 2680 that do not include transducer elements 2690. Coiling the provided elongate element $2604_{int}$ after flexible circuit structure 2680 has been secured to the provided elongate element $2604_{int}$ may result in an undesired "step-bent" profile along the length of the assemblage.

In block 2708, at least one of the provided elongate members $2604_{int}$ undergoes at least a second distorting or deforming process after the securement of a flexible circuit structure 2680 to the at least one of the provided elongate members $2604_{int}$. FIG. 7K shows the provided elongate member $2604_{int}$/flexible circuit structure 2680 assemblage of FIG. 7J additionally processed as per block 2708. In this example embodiment, the respective third portion $2609c_{int}$ of each of various ones of the provided elongate members $2604_{int}$ is distorted or deformed to rotationally offset the respective second portion $2609b_{int}$ of the respective provided elongate member $2604_{int}$ from the respective first portion $2609a_{int}$ of the respective provided elongate member $2604_{int}$ along the respective length 2611 (not called out) of the provided elongate member $2604_{int}$. In this example embodiment, the respective third portion 2689c of the flexible printed circuit 2680 is also distorted or deformed to rotationally offset the second portion 2689b from the first portion 2689a of the flexible printed circuit 2680. In various example embodiments, a distortion or deformation of a particular portion of a provided elongate member $2604_{int}$ as per block 2708 can also result in a corresponding distortion or deformation to a portion of an associated one of the provided flexible circuit structures 2680.

In this example embodiment, distorting or deforming the respective third portion $2604c_{int}$ of the provided elongate member $2604_{int}$ to rotationally offset the respective second portion $2609b_{int}$ from the respective first portion $2609a_{int}$ along the respective length 2611 of the provided elongate member $2604_{int}$ causes the respective third portion $2609c_{int}$ of the provided elongate member $2604_{int}$ to have a twisted shape. The twisted shape can be imparted using various methods. In some example embodiments, a stamping or coining operation can be employed to impart the twisted shape onto the third portion $2609c_{int}$ of the provided elongate member $2604_{int}$. It is noted that care may need to be taken to not damage components such as the flexible printed circuit structure 2680 during the distorting or deforming. In this example embodiment, distorting or deforming the respective third portion $2604c_{int}$ of the provided elongate member $2604_{int}$ to rotationally offset the respective second portion $2609b_{int}$ from the respective first portion $2609a_{int}$ along the respective length 2611 of the provided elongate member $2604_{int}$ includes twisting the respective third portion $2609c_{int}$ of the provided elongate member $2604_{int}$ about a respective twist axis 2633 extending across at least part of the respective third portion $2609c_{int}$. In this example embodiment, the third portion 2689c of the at least one material layer 2682 of the flexible circuit structure 2680 also has a twisted shape. The twisted shape of the at least one third portion 2689c of the flexible circuit structure 2680 provides a relatively smooth and gradual transition for the at least one electrically conductive trace 2694 to follow along a path extending across the third portion 2689c between the first and the second portions 2689a, 2689b of the at least one material layer 2682. In some example embodiments, the jogged portion 2694a of the at least one electrically conductive trace 2694 is visible when viewed normally to a portion of the front surface 2684a of the at least one material layer 2682 located at least proximate to a location on the front surface 2684a of the at least one material layer 2682 where the path extends across the third portion 2689c.

In some example embodiments, the twist in the third portion $2609c_{int}$ of a provided elongate member $2604_{int}$ can be arranged to cause the second portion $2609b_{int}$ of the provided elongate member $2604_{int}$ to assume a skewed orientation with respect to the first portion $2609b_{int}$ of the provided elongate member $2604_{int}$ similar to that exemplified by the representative elongate member 2604 shown in FIG. 7B. In some example embodiments, additional or alternate distortions or deformations can also be made to various ones of the provided elongate members $2604_{int}$. For example, as shown in FIG. 7K, the respective first portion $2609a_{int}$ of the provided elongate member $2604_{int}$ (i.e., including the respective first portion 2689a of the secured flexible circuit structure 2680) is bent about a respective bending axis 2631 to cause the second portion $2609b_{int}$ of the provided elongate member $2604_{int}$ to assume at least in part, a required fanned orientation as exemplified by the representative elongate member 2604 shown in FIG. 7B.

In this example embodiment, each respective bending axis 2631 has a skewed orientation with respect to the respective side edges 2620 of the first portion $2609a_{int}$ of the provided elongate member $2604_{int}$. Each respective bending axis 2631 is skewed to cause at least the respective second portions 2609b of the resulting elongate members 2604 to fan about the one or more fanning axes 2635 which is/are in turn, oriented to intersect the second portions 2609b of the resulting elongate members 2604 at locations at least proximate to at least some of the number of crossing locations when various ones of the resulting elongate members 2604 are fanned in a manner similar to that shown in FIG. 7E. If the respective bending axes 2631 were not so oriented, additional forces could be required to distort or deform at least a portion of the stacked elongate members 2604 to accommodate possible fanning misalignment. In such a case, some of the elongate members 2604 may be required to undergo additional bending, twisting or combined bending and twisting to correct for misalignment and produce the desired fanned arrangement. The amount of skew of each bending axis 2631 is typically dependant on the various geometric factors including, but not limited to, the relative lengths of various ones of the portions 2609 of each of the elongate members. The present inventors have produced elongate members 2604 whose first portions 2609a are bent about a respective bending axis 2631 skewed by approximately 22 degrees in some example embodiments.

The assemblage of the provided elongate member $2604_{int}$/flexible circuit structure 2680 shown in FIG. 7K may be processed into an elongate member 2604 as represented in FIG. 7B. In block 2710, various ones of the provided elongate member $2604_{int}$/flexible circuit structure 2680 assemblages are arranged into an arrangement similar to that shown in FIG. 7A.

In this example embodiment, the twisted shape of the third portion 2609c of each elongate member 2604 arranged in the initial configuration shown in FIG. 7A advantageously allows various transducer elements 2690 (not shown in FIG. 7A) positioned on respective front faces 2618a of the elongate members 2604 to be appropriately oriented to face an interior tissue surface within a bodily cavity (not shown) when the portion of device 2600 is moved into the third/expanded configuration (i.e., FIGS. 7E and 7F). In this example embodiment, the twisted shape of the third portion 2609c of each elongate member 2604 arranged in the initial configuration shown in FIG. 7A advantageously orients the respective first portions 2609a of the elongate members 2604 to act as flexures which allow the respective second portions 2609b of the elongate members 2604 to fan and distribute the transducer elements 2690 across an interior tissue surface when the portion of device 2600 is moved into the third/expanded configuration (i.e., FIGS. 7E and 7F) within a bodily cavity having the interior tissue surface. The bent first portions 2609a further advantageously allow for some degree of autonomous fanning capability and may possibly reduce the need for additional fanning mechanisms or the complexity thereof. In this example embodiment, the twisted shape of the third portion 2609c of each elongate member 2604 arranged in the initial configuration shown in FIG. 7A advantageously allows at least one electrically conductive trace 2694 (not shown in FIG. 7A) to extend along a path having a relatively smooth and gradual transition between the first and the second portions 2609a, 2609b of the elongate member 2604 while reducing potentially harmful bending stresses acting on the at least one electrically conductive trace 2694 during the fanning of the elongate member 2604.

In some example embodiments, each of the third portions 2609c has a twisted form sufficient to rotationally offset the respective second portion 2609b from the respective first portion 2609a by a same angular amount for each of the plurality of the provided elongate members 2604. In other example embodiments, different ones of the elongate members 2604 employ different rotational offsets along their respective lengths 2611. The use of different rotational offsets may be motivated by various factors. For example, when skewed bending axes 2631 are employed to cause the fanning of the various portions 2609 as described above, bending about the skewed bending axes 2631 can also impart a twist during the fanning. The twisted form of the respective third portion 2609c can be adjusted to compensate for the additional twist that arises during fanning. In some example embodiments, the amount of additional twist typically varies based at least on the position of the elongate member 2604 in the arrayed arrangement of elongate members 2604. In this example embodiment, a first set of elongate members 2604a, 2604b, and 2604c is fanned along an opposite direction from a second set of elongate members 2604e, 2604f and 2604g. However, since the rotational offsets between the respective first and second portions 2609a, 2609b of each elongate member 2604 are along the same direction (i.e., each third portion 2609c is twisted in a same direction), the additional twist created by the bending about the respective skewed bending axes 2631 will decrease the rotational offset of the elongate members 2604 in one of the first set and the second set while increasing the rotational offset of the elongate members 2604 in the other of the first and second set during the fanning. The present inventors have created arrangements of elongate members 2604 with rotational offsets between the respective first and the second portions 2609a, 2609b varying from approximately 90 degrees to 70 degrees to compensate for an additional increase or decrease in the rotational offset of each elongate member 2604 that results from bending about the respective skewed bending axes 2631 during fanning.

In this example embodiment, the respective first and second portions 2609a, 2609b of the elongate members 2604 are arranged in the delivery configuration illustrated in FIG. 7C by arranging respective first portions 2609a of the elongate members 2604 front face 2618a-toward-back face 2618b along a first direction (i.e., arrow 2616a) in a first stacked array 2615a and arranging the respective second portions 2604b of the elongate members 2604 front surface 2618a-toward-back surface 2618b along a second direction (i.e., arrow 2616b) in a second array 2615b. The spatially efficient stacked arrays 2615a, 2615b advantageously allow for catheter sheaths 2606 of reduced size to be employed while the non-parallel first and second directions (i.e., arrows 2616a, 2616b) of the stacked array allow for various benefits including those described above. Ideally, the twisted third portions 2609c of the elongate members should also be efficiently arrayed, stacked or nested so as to not negate the spatial efficiency advantages provided by each of the first and the second stacked arrays 2615a, 2615b.

FIG. 7L is a side elevation view of an arrangement of stacked elongate members 2604 (i.e., in a configuration similar to the delivery configuration shown in FIG. 7C) in which the third portions 2609c (only one called out) of each elongate member 2604 is twisted to allow the third portions 2609c to be nested in a stacked arrangement with substantially similar overall cross-sectional stack dimensions as those of the first stacked array 2615a and the second stacked array 2615b. A cross-sectional view A-A of the stacked elongate members 2604 of FIG. 7L through first stacked array 2615a is provided by FIG. 7L (A-A). A cross-sectional view B-B of the stacked elongate members 2604 of FIG. 7L through the twisted third portions 2609c is provided by FIG. 7L (B-B). A cross-sectional view C-C of the stacked elongate members 2604 of FIG. 7L through second stacked array 2615b is provided by FIG. 7L (C-C). In this example embodiment, second portions 2609b (only one called out in FIG. 7L (C-C) are rotationally offset by less than 90 degrees from their respective first portions 2609a (only one called out in FIG. 7L (A-A). A comparison of each of FIGS. 7L (A-A), 7L (B-B), and 7L (C-C) shows that a reference circle 2625 representing a catheter sheath 2606 dimension sized to just enclose each of the first and second stacked arrays 2615a, 2615b also advantageously encloses the twisted portions 2609c. Each of the elongate members 2604 are shown spaced from one another in each of FIGS. 7L (A-A), 7L (B-B), and 7L (C-C) for clarity. Ideally, reduced spacings are desired to accommodate the smallest sized catheter sheath possible.

FIG. 7M provides respective side and end elevation views of each of the elongate members 2604 shown in FIG. 7L but separated from one another for clarity. Each of the first portions 2609a (only one called out) and the second portions 2609b (only one called out) is additionally shown unbent for clarity. Center 2625a is provided in the end view of each elongate member 2604 to reference a position of each of the elongate members 2604 when stacked as per FIG. 7L. The respective end views in FIG. 7M show that the respective first and second portions 2609a, 2609b of each elongate member 2604 require a different positioning with respect to center 2625a based on the required position of the elongate member 2604 in the arrayed arrangement shown in FIG. 7L. Accordingly, the twisted form of the third portion 2609c (only one called out) of each elongate member 2604 will also vary based on the required position of the elongate member 2604 in the arrayed arrangement shown in FIG. 7L. In this example embodiment, each elongate member 2604 of at least some of the elongate members 2604 (i.e., elongate members 2604a, 2604b, 2604c, 2604e, 2604f and 2604g) has a form that in the absence of the twist in the respective third portion 2609c of the elongate member 2604, the plurality of portions 2609 of the elongate member 2604 are arranged such that the second portion 2609b of the elongate member 2604 is laterally offset from the first portion 2609a of the elongate member 2604 across at least a portion of the respective length 2611 of the elongate member 2604. This is best visualized in FIG. 7G, in which the respective second portions $2609b_{int}$ of various ones of the provided elongate members $2604_{int}$ (i.e., from which the elongate members 2604 are produced from in this example embodiment) are laterally offset from the respective first portions $2609a_{int}$ of the provided elongate members $2604_{int}$. In this example embodiment, the amount of lateral offset varies for each provided elongate member $2604_{int}$ based at least on the intended position of the provided elongate member $2604_{int}$ in the arrayed arrangement shown in FIG. 7L.

Example embodiments in which an inherent lateral offset exists between the respective second and first portions $2609b$, $2609a$ of various ones of the elongate members 2604 in the absence of the required twist in the respective third portion 2609c allow the respective third portions 2609c when actually twisted to be stacked into a stacked array suitably sized to fit within catheters sheaths 2606 of reduced size (e.g., with respect to conventional catheter sheaths used for similar procedures) while still properly arranging the respective first and second portions 2609a, 2609b of the elongate members 2604 into the corresponding first and second stacked arrays 2615a, 2615b which are also suitably sized to fit in the catheter sheaths 2606 of reduced size. It is additionally noted that significant departures from these twist forms may cause the third portions 2609c of the elongate members to not nest well and thereby adversely impact the ability to pass the stacked third portions 2609c through catheter sheaths 2606 of reduced size.

In some example embodiments, the twisted third portions 2609c of the elongate members 2604 may be efficiently nested in a stacked arrangement with substantially similar overall cross-sectional stack dimensions as those of the first stacked array 2615a and the second stacked array 2615b while each twisted third portion 2609c maintains a cross-sectional shape having dimensions on the same order as those of the cross-sectional shape of respective ones of the first and the second portions 2609a, 2609b. This may be motivated for different reasons including employing twisted third portions 2609c which maintain a required width dimension sufficient to route the electrically conductive traces 2694 or that provided sufficient strength to address strength considerations while still allowing the stacked arrangement of the third portions 2609c to fit within catheter sheaths 2606 of reduced size. In some example embodiments, the cross-sectional shape of each twisted third portion 2609c remains fairly uniform, but with a different rotational alignment as the length of the twisted third portion 2609c is traversed between the rotationally offset first and second portions 2609a, 2609b. In some embodiments, each of the twisted third portions 2609c of the elongate members 2604 includes a substantially similar twist rate (i.e., turns/unit length). In some embodiments, each of the twisted third portions 2609c of the elongate members 2604 is twisted about a respective twist axis 2633, with each respective twist axis 2633 being substantially parallel to the each of the other respective twist axes 2633.

In this example embodiment, the provided elongate members $2604_{int}$ are strip-like members that are twisted to form the respective ones of the elongate members 2604. As shown in FIG. 7G, in the absence of the twist, the respective third portion $2609c_{int}$ of each of the provided elongate members $2604_{int}$ has a serpentine or "S" shape whose form varies depending on the geometry of the final stacked arrangement shown in FIG. 7L and the intended position of the provided elongate member $2604_{int}$ in the arrayed arrangement shown in FIG. 7L. This serpentine or "S" shape allows for reduced strain during the distortion or deformation that accompanies the twisting of the provided elongate member $2604_{int}$. If the respective third portion $2609c_{int}$ of a provided elongate member $2604_{int}$ included a significantly different shape (e.g., a linear strip with no lateral offset between the respective second and first portions $2609b_{int}$, $2609a_{int}$) and was distorted or deformed to create the required twist shape (i.e., as described above), much higher strains would be imparted onto the provided elongate member $2604_{int}$ as various additional bending components perpendicular to various ones of the surfaces 2618a, 2618b of third portion $2609c_{int}$ would be required to produce the required twisted shape. In some cases, the resulting increased strains may be greater than the provided elongate member $2604_{int}$ can tolerate. These distortion or deformation criteria are especially relevant for the provided elongate members $2604_{int}$ (i.e., elongate members $2604a_{int}$, $2604b_{int}$, $2604f_{int}$ and $2604g_{int}$) that are provided to form the outermost elongate members 2604 in the arrayed arrangement shown in FIG. 7L since each of these provided elongate members $2604_{int}$ would require the greater amounts of distortion or deformation to form the required twisted shape. In some cases however, the provided elongate members $2604_{int}$ that are provided to form some of the innermost elongate members 2604 in the arrayed arrangement shown in FIG. 7L (e.g., provided elongate members $2604c_{int}$, $2604d_{int}$) may be tolerant to increased strains if the shape of the respective third portions $2609c_{int}$ of these provided elongate members $2604_{int}$ deviated from the serpentine or "S" shape described above since little lateral offset is required between the respective first and second portions $2609a_{int}$, $2609b_{int}$ of these provided elongate members $2604_{int}$ as shown in FIG. 7G. In some embodiments, some of the innermost elongate members 2604 such as elongate members 2604c and 2604e may be formed from relatively straight strip-like members with no lateral offset between their respective second and first portions 2609b, 2609a as appears to be shown by Redmond et al. in U.S. Pat. No. 5,245,987 and U.S. Pat. No. 5,390,644. It is noted however that the distortion or deformation of provided elongate members $2604_{int}$ not having laterally offset second and first portions $2609b_{int}$, $2609a_{int}$ would not be suitable for the outermost elongate members 2604 in various arrangements such as those shown in FIG. 7L. It is noted however that the distortion or deformation of provided elongate members $2604_{int}$ not having laterally offset second and first portions $2609b_{int}$, $2609a_{int}$ would not be suitable for the outermost elongate members 2604 in stacked arrangements having relatively large number of elongate members (e.g., more than three) when it is desired to reduce the overall cross-sectional size of the arrangements.

In some example embodiments, method 2700 employs a subset of the blocks described. In some example embodiments, method 2700 may include additional/and or alternate processes. Method 2700 describes various processes that distort or deform a shape of the third portion $2609c_{int}$ of various ones of the provided elongate members $2604_{int}$ into a desired twisted shape. The twisted shape of the third portions 2609c of elongate members 2604 employed in other example embodiments can be formed by other manufacturing processes including, but are not limited to, materials removal processes (e.g., machining), material joining processes (e.g., welding, brazing, bonding), casting or molding processes, or combination thereof. Regardless of the process employed, the resulting elongate members 2604 are characterized in that in the absence of the twist in their respective third portions 2609c, their respective first, second and third portions 2609a, 2609b and 2609c may combine to form a unitary structure in which each respective second portion 2609b is not rotationally offset from the respective first portion 2609a along the respective length 2611 of the elongate member 2604 but is laterally offset from the first portion 2609a along at least a portion of the respective length 2611 of the elongate member 2604.

While some of the embodiments disclosed above are described with examples of cardiac mapping, the same or similar embodiments may be used for mapping other bodily organs, for example gastric mapping, bladder mapping, arterial mapping and mapping of any lumen or cavity into which the devices of the present invention may be introduced.

While some of the embodiments disclosed above are described with examples of cardiac ablation, the same or similar embodiments may be used for ablating other bodily organs or any lumen or cavity into which the devices of the present invention may be introduced.

Subsets or combinations of various embodiments described above can provide further embodiments. The various embodiments described above can be combined to provide further embodiments. All of the U.S. patents, U.S. patent application publications, U.S. patent applications, foreign patents, foreign patent applications and non-patent publications referred to in this specification or listed in the Application Data Sheet are incorporated herein by reference, in their entirety. Aspects of the invention can be modified, if necessary, to employ systems, circuits and concepts of the various patents, applications and publications to provide yet further embodiments of the invention.

These and other changes can be made to the invention in light of the above-detailed description. In general, in the following claims, the terms used should not be construed to limit the invention to the specific embodiments disclosed in the specification and the claims, but should be construed to include all medical treatment devices in accordance with the claims. Accordingly, the invention is not limited by the disclosure, but instead its scope is to be determined entirely by the following claims.

The invention claimed is:

1. A medical system comprising:
   a structure comprising a plurality of elongate members, each elongate member comprising a first end, a second end, and an intermediate portion positioned between the first and the second ends of the elongate member, each intermediate portion comprising a thickness, a front surface and a back surface opposite across the thickness from the front surface, the structure further comprising a proximal portion and a distal portion, each of the proximal and the distal portions of the structure comprising a respective part of each of the plurality of elongate members, the structure selectively moveable between:
      a delivery configuration in which the structure is sized for delivery through a bodily opening leading to a bodily cavity, at least the respective intermediate portions of at least three elongate members of the plurality of elongate members arrayed along a first direction front surface-toward-back surface in a stacked array when the structure is in the delivery configuration; and
      a deployed configuration in which the structure is sized too large for delivery through the bodily opening leading to the bodily cavity, the proximal portion of the structure forming a first domed shape and the distal portion of the structure forming a second domed shape when the structure is in the deployed configuration,
   wherein each of the first domed shape and the second domed shape comprises a respective apex, each of the at least three elongate members comprises a respective particular portion, and the particular portions of the at least three elongate members are arranged front surface-toward-back surface at a location spaced from the respective apex of each of the first domed shape and the second domed shape when the structure is in the deployed configuration.

2. The medical system of claim 1 wherein at least the first domed shape or the second domed shape has a first radius of curvature in a first spatial plane and a second radius of curvature in a second spatial plane that intersects the first spatial plane, a magnitude of the second radius of curvature different than a magnitude of the first radius of curvature.

3. The medical system of claim 1 wherein each elongate member of at least some of the plurality of elongate members crosses at least one other elongate member of the plurality of elongate members at least at one location between the proximal and the distal portions of the structure when the structure is in the deployed configuration.

4. The medical system of claim 1 wherein each elongate member of the plurality of elongate members comprises a respective length between the first end and the second end of the elongate member, each elongate member of at least some of the plurality of elongate members crossing at least one other elongate member of the plurality of elongate members at each of a respective plurality of spaced apart locations along the length of the one other elongate member when the structure is in the deployed configuration.

5. The medical system of claim 1 wherein at least some of the plurality of elongate members are fanned with respect to at least one of the plurality of elongate members about an axis passing through a location between the proximal and the distal portions of the structure when the structure is in the deployed configuration, the location located on one of the plurality of elongate members.

6. The medical system of claim 1 wherein at least two of the elongate members each comprises one or more transducers.

7. The medical system of claim 1 wherein the proximal portion of the structure does not form a domed shape when the structure is in the delivery configuration, and the distal portion of the structure does not form a domed shape when the structure is in the delivery configuration.

8. The medical system of claim 1 wherein each elongate member of the plurality of elongate members comprises a scrolled or volute shape profile when the structure is in the deployed configuration.

9. The medical system of claim 1, further comprising a plurality of transducers located at least on an outward-facing surface of at least the first domed shape formed by the proximal portion of the structure or the second domed shape formed by the distal portion of the structure.

10. The medical system of claim 1 wherein each elongate member of the plurality of elongate members comprises a respective length between the first and the second ends of the elongate member, and wherein the intermediate portions of the plurality of elongate members are circumferentially arranged about a first axis when the structure is in the deployed configuration, the first axis passing through each of at least a first elongate member of the plurality of elongate members when the structure is in the deployed configuration, the first axis passing through the first elongate member at two or more locations when the structure is in the deployed configuration, each location of the two or more locations spaced from another location of the two or more locations along the respective length of the first elongate member.

11. The medical system of claim 10 wherein the two or more locations comprise at least three locations spaced with respect to one another along the respective length of the first elongate member.

12. The medical system of claim 1 wherein each elongate member of the plurality of elongate members comprises a respective length between the first and the second ends of the elongate member, and at least a first elongate member of the plurality of elongate members crosses a second elongate member of the plurality of elongate members in an X configuration at each of one or more locations along the respective length of the second elongate member when the structure is in the deployed configuration, each of the one or more locations spaced from each of the respective first end and the respective second end of the second elongate member when the structure is in the deployed configuration.

13. The medical system of claim 12, further comprising a plurality of couplers, each of which physically couples at least the second elongate member together with at least one other elongate member of the plurality of elongate members, each coupler of the plurality of couplers spaced from another of the plurality of couplers along the respective length of the second elongate member,
wherein at least one location of the one or more locations is located along the respective length of the second elongate member between at least two of the plurality of couplers when the structure is in the deployed configuration.

14. The medical system of claim 13 wherein the front surface of the respective intermediate portion of the second elongate member outwardly faces the back surface of the respective intermediate portion of at least the first elongate member at the at least one location of the one or more locations when the structure is in the deployed configuration.

15. The medical system of claim 14 wherein the front surfaces of the intermediate portions of the plurality of elongate members face outwardly away from an interior region within the structure when the structure is in the deployed configuration, and the back surfaces of the intermediate portions of the plurality of elongate members face inwardly toward the interior region within the structure when the structure is in the deployed configuration.

16. The medical system of claim 12 wherein each elongate member of the plurality of elongate members is arranged to be advanced first end ahead of the second end through the bodily opening leading to the bodily cavity when the structure is in the delivery configuration, wherein the medical system further comprises a plurality of couplers, each of which physically couples at least the second elongate member together with at least one other elongate member of the plurality of elongate members, each coupler of the plurality of couplers spaced from another of the plurality of couplers along the respective length of the second elongate member, and wherein at least one location of the one or more locations is located along the respective length of the second elongate member relatively closer to the respective first end of the second elongate member than each of at least two of the plurality of couplers when the structure is in the deployed configuration.

17. The medical system of claim 16 wherein the front surface of the respective intermediate portion of the second elongate member outwardly faces the back surface of the respective intermediate portion of at least the first elongate member at the at least one location of the one or more locations when the structure is in the deployed configuration, and wherein the front surfaces of the intermediate portions of the plurality of elongate members face outwardly away from an interior region within the structure when the structure is in the deployed configuration, and the back surfaces of the intermediate portions of the plurality of elongate members face inwardly toward the interior region within the structure when the structure is in the deployed configuration.

18. The medical system of claim 1 wherein each of the at least three elongate members is arranged to be advanced first end ahead of the second end through the bodily opening leading to the bodily cavity when the structure is in the delivery configuration.

19. The medical system of claim 18 wherein the plurality of elongate members comprises a first set of the elongate members and a second set of the elongate members, the first set of the elongate members different than the second set of the elongate members, and wherein, when the structure is moved from the delivery configuration toward the deployed configuration or from the deployed configuration toward the delivery configuration, the first set of the elongate members is moved along an angular direction that is opposite to an angular direction that the second set of the elongate members is moved along.

20. The medical system of claim 1 wherein the intermediate portions of the plurality of elongate members are circumferentially arranged about an axis when the structure is in the deployed configuration, the respective intermediate portions of the at least three elongate members spaced from the axis when the structure is in the deployed configuration.

21. The medical system of claim 1 wherein the plurality of elongate members comprises a first set of the elongate members and a second set of the elongate members, the first set of the elongate members different than the second set of the elongate members, and wherein, when the structure is moved from the delivery configuration toward the deployed configuration or from the deployed configuration toward the delivery configuration, the first set of the elongate members is moved along an angular direction that is opposite to an angular direction that the second set of the elongate members is moved along.

22. The medical system of claim 1 wherein:
the structure is arranged to be advanced distal portion first through the bodily opening leading to the bodily cavity when the structure is in the delivery configuration,
each particular elongate member of the plurality of elongate members comprises a respective length between the respective first and the respective second ends of the particular elongate member, and
at least a first elongate member of the plurality of elongate members is crossed by each of at least two others of the plurality of elongate members at each of one or more locations along the respective length of the first elongate member when the structure is in the deployed configuration, each of the one or more locations spaced along the respective length of the first elongate member from the respective apex of each of the first domed shape and the second domed shape when the structure is in the deployed configuration.

23. The medical system of claim 1 wherein the respective particular portion of at least a first elongate member of the at least three elongate members is crossed by the respective particular portion of each elongate member of at least two others of the at least three elongate members at least between the proximal and the distal portions of the structure when the structure is in the deployed configuration.

24. The medical system of claim 1 wherein the particular portions of the elongate members of the at least three elongate members are fanned with respect to one another at least between the proximal and the distal portions of the structure when the structure is in the deployed configuration.

25. The medical system of claim 1 wherein the stacked array comprises a plurality of successive pairs of the elongate members when the structure is in the delivery configuration, and wherein the medical system further comprises a plurality of individually activatable transducer elements, a respective group of the plurality of individually activatable transducer elements arranged between the elongate members of each successive pair of the elongate members in the stacked array when the structure is in the delivery configuration.

26. The medical system of claim 1 wherein the front surfaces of the intermediate portions of the at least three elongate members face outwardly away from an interior region within the structure when the structure is in the deployed configuration and the back surfaces of the intermediate portions of the at least three elongate members face inwardly toward the interior region within the structure when the structure is in the deployed configuration.

27. A medical system comprising:
a structure comprising a proximal portion and a distal portion, the structure selectively moveable between:
a delivery configuration in which the structure is sized for delivery through a bodily opening leading to a bodily cavity, the structure arranged to be advanced distal portion ahead of the proximal portion into the bodily cavity, and
a deployed configuration in which the structure is sized too large for delivery through the bodily opening leading to the bodily cavity,
wherein the proximal portion of the structure forms a first domed shape and the distal portion of the structure forms a second domed shape when the structure is in the deployed configuration, the proximal and the distal portions of the structure pivotable at least apart in a clam shell configuration when the structure is in the deployed configuration.

28. The medical system of claim 27 wherein at least the first domed shape or the second domed shape has a first radius of curvature in a first spatial plane and a second radius of curvature in a second spatial plane that intersects the first spatial plane, a magnitude of the second radius of curvature different than a magnitude of the first radius of curvature.

29. The medical system of claim 27 wherein the proximal and the distal portions of the structure are physically coupled together to pivot with respect to one another when the structure is in the deployed configuration.

30. The medical system of claim 27 wherein the proximal and the distal portions of the structure are pivotably coupled together by a flexure portion of the structure when the structure is in the deployed configuration.

31. The medical system of claim 27, further comprising at least one actuator operably coupled to the structure to selectively pivot the proximal and the distal portions of the structure with respect to one another when the structure is in the deployed configuration.

32. The medical system of claim 27, further comprising at least one flexible line arranged to physically couple the proximal and the distal portions of the structure together, the at least one flexible line manipulable to vary a distance between the proximal and the distal portions of the structure when the structure is in the deployed configuration.

33. The medical system of claim 27, further comprising at least one actuator selectively operable to act on at least the proximal portion or the distal portion of the structure to distort a respective one of the first domed shape or the second domed shape when the structure is in the deployed configuration.

34. The medical system of claim 27 wherein each of the first domed shape and the second domed shape has a respective volume therein, and the medical system further comprises at least one actuator selectively operable to act on the structure to vary the respective volume of at least the first domed shape or the second domed shape when the structure is in the deployed configuration.

35. The medical system of claim 27 wherein each of the proximal and the distal portions of the structure are arranged to pivot with respect to one another about a pivot location when the structure is in the deployed configuration, each of the first domed shape and the second domed shape comprising a respective apex and a respective height extending normally from a respective spatial plane to the respective apex, each respective spatial plane positioned to intersect the pivot location, and wherein the medical system further comprises at least one actuator selectively operable to act on at least the proximal portion or the distal portion of the structure to vary at least a magnitude of the respective height of the first domed shape or a magnitude of the respective height of the second domed shape when the structure is in the deployed configuration.

36. The medical system of claim 27 wherein the structure comprises a plurality of elongate members, each of the proximal and the distal portions of the structure comprising a respective part of each elongate member of the plurality of elongate members.

37. The medical system of claim 36 wherein each elongate member of at least some of the plurality of elongate members crosses at least one other elongate member of the plurality of elongate members at least at one location between the proximal and the distal portions of the structure when the structure is in the deployed configuration.

38. The medical system of claim 36 wherein each elongate member of the plurality of elongate members comprises a first end, a second end, and a respective length between the first end and the second end of the elongate member, each elongate member of at least some of the plurality of elongate members crossing at least one other elongate member of the plurality of elongate members at each of a respective plurality of spaced apart locations along the length of the one other elongate member when the structure is in the deployed configuration.

39. The medical system of claim 38 wherein each respective plurality of spaced apart locations along the length of the one other elongate member comprises at least one location between the respective part of the one other elongate member comprised by the proximal portion of the structure and the respective part of the one other elongate member comprised by the distal portion of the structure.

40. The medical system of claim 36 wherein at least some of the plurality of elongate members are fanned with respect to one another about an axis that passes through a location between the proximal and the distal portions of the structure when the structure is in the deployed configuration, the location located on one of the plurality of elongate members.

41. The medical system of claim 36 wherein each elongate member of the plurality of elongate members comprises a first end, a second end, an intermediate portion positioned between the first end and the second end of the elongate member, and a thickness, the respective intermediate portion of each elongate member comprising a front surface and a back surface opposite across the thickness from the front surface, and wherein the intermediate portions of the plurality of elongate members are arranged front surface-toward-back surface in a stacked array when the structure is in the delivery configuration.

42. The medical system of claim 41 wherein the stacked array comprises a plurality of successive pairs of the elongate members when the structure is in the delivery configuration, and wherein the medical system further comprises a plurality of individually activatable transducer elements, a respective group of the plurality of individually activatable transducer elements arranged between the elongate members of each successive pair of the elongate members in the stacked array when the structure is in the delivery configuration.

43. The medical system of claim 36 wherein each elongate member of the plurality of elongate members comprises a first end, a second end, and an intermediate portion positioned between the first end and the second end of the elongate member, the respective intermediate portion of each elongate member of at least some of the plurality of elongate members comprising a slotted opening between the respective first and the respective second ends of the elongate member, at least two of the slotted openings arranged to cross one another when the structure is in the deployed configuration.

44. The medical system of claim 43, further comprising at least one actuator selectively operable to act on the structure to change a location where the at least two slotted openings cross one another when the structure is in the deployed configuration.

45. The medical system of claim 27, further comprising one or more transducers moveable with one or more parts of the structure.

46. The medical system of claim 27 wherein the proximal portion of the structure does not form a domed shape when the structure is in the delivery configuration, and the distal portion of the structure does not form a domed shape when the structure is in the delivery configuration.

47. The medical system of claim 27 wherein the structure comprises a plurality of elongate members, each of the plurality of elongate members comprising a scrolled or volute shape profile when the structure is in the deployed configuration.

48. The medical system of claim 27, further comprising a plurality of transducers located at least on an outward-facing surface of at least the first domed shape formed by the proximal portion of the structure or the second domed shape formed by the distal portion of the structure.

49. The medical system of claim 27 wherein the structure comprises a plurality of elongate members, each elongate member of the plurality of elongate members comprising a first end, a second end, a respective intermediate portion between the first and the second ends of the elongate member, and a respective length between the first and the second ends of the elongate member, and wherein the intermediate portions of the plurality of elongate members are circumferentially arranged about a first axis when the structure is in the deployed configuration, the first axis passing through each of at least a first elongate member of the plurality of elongate members when the structure is in the deployed configuration, the first axis passing through the first elongate member at two or more locations when the structure is in the deployed configuration, each location of the two or more locations spaced from another location of the two or more locations along the respective length of the first elongate member.

50. The medical system of claim 49 wherein the two or more locations comprise at least three locations spaced with respect to one another along the respective length of the first elongate member.

51. The medical system of claim 27 wherein the structure comprises a plurality of elongate members, each elongate member of the plurality of elongate members comprising a first end, a second end, a respective intermediate portion between the first and the second ends of the elongate member, and a respective length between the first and the second ends of the elongate member, and at least a first elongate member of the plurality of elongate members crosses a second elongate member of the plurality of elongate members in an X configuration at each of one or more locations along the respective length of the second elongate member when the structure is in the deployed configuration, each of the one or more locations spaced from each of the respective first end and the respective second end of the second elongate member when the structure is in the deployed configuration.

52. The medical system of claim 51 further comprising a plurality of couplers, each of which physically couples at least the second elongate member together with at least one other elongate member of the plurality of elongate members, each coupler of the plurality of couplers spaced from another of the plurality of couplers along the respective length of the second elongate member,
wherein at least one location of the one or more locations is located along the respective length of the second elongate member between at least two of the plurality of couplers when the structure is in the deployed configuration.

53. The medical system of claim 52 wherein, for each elongate member of the plurality of elongate members, the respective intermediate portion comprises a thickness, a front surface and a back surface opposite across the thickness from the front surface, and wherein the front surface of the respective intermediate portion of the second elongate member outwardly faces the back surface of the respective intermediate portion of at least the first elongate member at the at least one location of the one or more locations when the structure is in the deployed configuration.

54. The medical system of claim 53 wherein the front surfaces of the intermediate portions of the plurality of elongate members face outwardly away from an interior region within the structure when the structure is in the deployed configuration, and the back surfaces of the intermediate portions of the plurality of elongate members face inwardly toward the interior region within the structure when the structure is in the deployed configuration.

55. The medical system of claim 51 wherein each elongate member of the plurality of elongate members is arranged to be advanced first end ahead of the second end through the bodily opening leading to the bodily cavity when the structure is in the delivery configuration, wherein the medical system further comprises a plurality of couplers, each of which physically couples at least the second elongate member together with at least one other elongate member of the plurality of elongate members, each coupler of the plurality of couplers spaced from another of the plurality of couplers along the respective length of the second elongate member, and wherein at least one location of the one or more locations is located along the respective length of the second elongate member relatively closer to the respective first end of the second elongate member than each of at least two of the plurality of couplers when the structure is in the deployed configuration.

56. The medical system of claim 55 wherein, for each elongate member of the plurality of elongate members, the respective intermediate portion comprises a thickness, a front surface and a back surface opposite across the thickness from the front surface, wherein the front surface of the respective intermediate portion of the second elongate member outwardly faces the back surface of the respective intermediate portion of at least the first elongate member at the at least one location of the one or more locations when the structure is in the deployed configuration, and wherein the front surfaces of the intermediate portions of the plurality of elongate members face outwardly away from an interior region within the structure when the structure is in the deployed configuration, and the back surfaces of the intermediate portions of the plurality of elongate members face inwardly toward the interior region within the structure when the structure is in the deployed configuration.

57. A medical system comprising:
a structure comprising a plurality of elongate members, each elongate member comprising a first end, a second end, and an intermediate portion positioned between the first and the second ends of the elongate member, each intermediate portion comprising a thickness, a front surface and a back surface opposite across the thickness from the front surface, the structure further comprising a proximal portion and a distal portion, the structure selectively moveable between:
a delivery configuration in which the structure is sized for delivery through a bodily opening leading to a bodily cavity, the distal portion of the structure arranged to be advanced ahead of the proximal portion when the structure is in the delivery configuration, and at least the respective intermediate portions of at least three elongate members of the plurality of elongate members arrayed along a first direction front surface-toward-back surface in a stacked array when the structure is in the delivery configuration; and
a deployed configuration in which the structure is sized too large for delivery through the bodily opening leading to the bodily cavity, the proximal portion of the structure forming a first domed shape and the distal portion of the structure forming a second domed shape when the structure is in the deployed configuration,
wherein each of the first domed shape and the second domed shape comprises a respective apex, each of the at least three elongate members comprises a respective particular portion, and the particular portions of the at least three elongate members are arranged front surface-toward-back surface at a location spaced from the respective apex of each of the first domed shape and the second domed shape when the structure is in the deployed configuration.

58. The medical system of claim 57 wherein at least the first domed shape or the second domed shape has a first radius of curvature in a first spatial plane and a second radius of curvature in a second spatial plane that intersects the first spatial plane, a magnitude of the second radius of curvature different than a magnitude of the first radius of curvature.

59. The medical system of claim 57 wherein each elongate member of at least some of the plurality of elongate members crosses at least one other elongate member of the plurality of elongate members at least at one location between the proximal and the distal portions of the structure when the structure is in the deployed configuration.

60. The medical system of claim 57 wherein each elongate member of the plurality of elongate members comprises a respective length between the first end and the second end of the elongate member, each elongate member of at least some of the plurality of elongate members crossing at least one other elongate member of the plurality of elongate members at each of a respective plurality of spaced apart locations along the length of the one other elongate member of the plurality of elongate members when the structure is in the deployed configuration.

61. The medical system of claim 57 wherein at least some of the plurality of elongate members are fanned with respect to at least one of the plurality of elongate members about an axis passing through a location between the proximal and the distal portions of the structure when the structure is in the deployed configuration, the location located on one of the plurality of elongate members.

62. The medical system of claim 57 wherein at least two of the elongate members each comprises one or more transducers.

63. The medical system of claim 57 wherein the proximal portion of the structure does not form a domed shape when the structure is in the delivery configuration, and the distal portion of the structure does not form a domed shape when the structure is in the delivery configuration.

64. The medical system of claim 57 wherein each elongate member of the plurality of elongate members comprises a scrolled or volute shape profile when the structure is in the deployed configuration.

65. The medical system of claim 57, further comprising a plurality of transducers located at least on an outward-facing surface of at least the first domed shape formed by the proximal portion of the structure or the second domed shape formed by the distal portion of the structure.

66. The medical system of claim 57 wherein each elongate member of the plurality of elongate members comprises a respective length between the first and the second ends of the elongate member, and wherein the intermediate portions of the plurality of elongate members are circumferentially arranged about a first axis when the structure is in the deployed configuration, the first axis passing through each of at least a first elongate member of the plurality of elongate members when the structure is in the deployed configuration, the first axis passing through the first elongate member at two or more locations when the structure is in the deployed configuration, each location of the two or more locations spaced from another location of the two or more locations along the respective length of the first elongate member.

67. The medical system of claim 66 wherein the two or more locations comprise at least three locations spaced with respect to one another along the respective length of the first elongate member.

68. The medical system of claim 57 wherein each elongate member of the plurality of elongate members comprises a respective length between the first and the second ends of the elongate member, and at least a first elongate member of the plurality of elongate members crosses a second elongate member of the plurality of elongate members in an X configuration at each of one or more locations along the respective length of the second elongate member when the structure is in the deployed configuration, each of the one or more locations spaced from each of the respective first end and the respective second end of the second elongate member when the structure is in the deployed configuration.

69. The medical system of claim 68, further comprising a plurality of couplers, each of which physically couples at least the second elongate member together with at least one other elongate member of the plurality of elongate members, each coupler of the plurality of couplers spaced from another of the plurality of couplers along the respective length of the second elongate member, wherein at least one location of the one or more locations is located along the respective length of the second elongate member between at least two of the plurality of couplers when the structure is in the deployed configuration.

70. The medical system of claim 69 wherein the front surface of the respective intermediate portion of the second elongate member outwardly faces the back surface of the respective intermediate portion of at least the first elongate member at the at least one location of the one or more locations when the structure is in the deployed configuration.

71. The medical system of claim 70 wherein the front surfaces of the intermediate portions of the plurality of elongate members face outwardly away from an interior region within the structure when the structure is in the deployed configuration, and the back surfaces of the intermediate portions of the plurality of elongate members face inwardly toward the interior region within the structure when the structure is in the deployed configuration.

72. The medical system of claim 68 wherein each elongate member of the plurality of elongate members is arranged to be advanced first end ahead of the second end through the bodily opening leading to the bodily cavity when the structure is in the delivery configuration, wherein the medical system further comprises a plurality of couplers, each of which physically couples at least the second elongate member together with at least one other elongate member of the plurality of elongate members, each coupler of the plurality of couplers spaced from another of the plurality of couplers along the respective length of the second elongate member, and wherein at least one location of the one or more locations is located along the respective length of the second elongate member relatively closer to the respective first end of the second elongate member than each of at least two of the plurality of couplers when the structure is in the deployed configuration.

73. The medical system of claim 72 wherein the front surface of the respective intermediate portion of the second elongate member outwardly faces the back surface of the respective intermediate portion of at least the first elongate member at the at least one location of the one or more locations when the structure is in the deployed configuration.

74. The medical system of claim 73 wherein the front surfaces of the intermediate portions of the plurality of elongate members face outwardly away from an interior region within the structure when the structure is in the deployed configuration, and the back surfaces of the intermediate portions of the plurality of elongate members face inwardly toward the interior region within the structure when the structure is in the deployed configuration.

75. The medical system of claim 57 wherein each of the at least three elongate members is arranged to be advanced first end ahead of the second end through the bodily opening leading to the bodily cavity when the structure is in the delivery configuration.

76. The medical system of claim 75 wherein the plurality of elongate members comprises a first set of the elongate members and a second set of the elongate members, the first set of the elongate members different than the second set of the elongate members, and wherein, when the structure is moved from the delivery configuration toward the deployed configuration or from the deployed configuration toward the delivery configuration, the first set of the elongate members is moved along an angular direction that is opposite to an angular direction that the second set of the elongate members is moved along.

77. The medical system of claim 57 wherein the intermediate portions of the plurality of elongate members are circumferentially arranged about an axis when the structure is in the deployed configuration, the respective intermediate portions of the at least three elongate members spaced from the axis when the structure is in the deployed configuration.

78. The medical system of claim 57 wherein the plurality of elongate members comprise a first set of the elongate members and a second set of the elongate members, the first set of the elongate members different than the second set of the elongate members, and wherein, when the structure is moved from the delivery configuration toward the deployed configuration or from the deployed configuration toward the delivery configuration, the first set of the elongate members is moved along an angular direction that is opposite to an angular direction that the second set of the elongate members is moved along.

79. The medical system of claim 57 wherein:
each particular elongate member of the plurality of elongate members comprises a respective length between the respective first and the respective second ends of the particular elongate member, and
at least a first elongate member of the plurality of elongate members is crossed by each of at least two others of the plurality of elongate members at each of one or more locations along the respective length of the first elongate member when the structure is in the deployed configuration, each of the one or more locations spaced along the respective length of the first elongate member from the respective apex of each of the first domed shape and the second domed shape when the structure is in the deployed configuration.

80. The medical system of claim 57 wherein the respective particular portion of at least a first elongate member of the at least three elongate members is crossed by the respective particular portion of each elongate member of at least two others of the at least three elongate members at least between the proximal and the distal portions of the structure when the structure is in the deployed configuration.

81. The medical system of claim 57 wherein the respective particular portions of the at least three elongate members are fanned with respect to one another at least between the proximal and the distal portions of the structure when the structure is in the deployed configuration.

82. The medical system of claim 57 wherein the stacked array comprises a plurality of successive pairs of the elongate members when the structure is in the delivery configuration, and wherein the medical system further comprises a plurality of individually activatable transducer elements, a respective group of the plurality of individually activatable transducer elements arranged between the elongate members of each successive pair of the elongate members in the stacked array when the structure is in the delivery configuration.

83. The medical system of claim 57 wherein the front surfaces of the intermediate portions of the at least three elongate members face outwardly away from an interior region within the structure when the structure is in the deployed configuration and the back surfaces of the intermediate portions of the at least three elongate members face inwardly toward the interior region within the structure when the structure is in the deployed configuration.

84. A medical system comprising:
a structure comprising a plurality of elongate members and at least one coupler arranged to physically couple at least a first elongate member of the plurality of elongate members together with a second elongate member of the plurality of elongate members, each elongate member of the plurality of elongate members comprising a proximal end, a distal end, an intermediate portion positioned between the proximal end and the distal end of the elongate member, and a thickness, each intermediate portion comprising a front surface and a back surface opposite across the thickness of the elongate member from the front surface, a respective geodesic extending along a portion of each elongate member of the plurality of elongate members between a location at least proximate the proximal end of the elongate member and another location at least proximate the distal end of the elongate member, each geodesic located at least on the front surface of the respective intermediate portion of the elongate member, and wherein the structure is selectively moveable between:
an unexpanded configuration in which the structure is sized for delivery through a bodily opening leading to a bodily cavity and in which at least the respective intermediate portions of at least three elongate members of the plurality of elongate members are arranged with respect to one another along a first direction front surface-toward-back surface in a stacked array, each elongate member of the plurality of elongate members arranged to be advanced distal end ahead of the proximal end through the bodily opening leading to the bodily cavity when the structure is in the unexpanded configuration, and
an expanded configuration in which the structure is sized too large for delivery through the bodily opening leading to the bodily cavity, at least the first elongate member positioned such that the respective geodesic of the first elongate member crosses the respective geodesic of the second elongate member at a first location along the respective geodesic of the second elongate member as viewed normally to a respective portion of the front surface of the intermediate portion of the second elongate member over which the first location along the respective geodesic of the second elongate member is positioned, the first location spaced from the one coupler along the second elongate member, and the first location positioned along the second elongate member between the one coupler and the distal end of the second elongate member when the structure is in the expanded configuration,
wherein the structure comprises at least one other coupler arranged to physically couple at least the first elongate member together with the second elongate member, the one other coupler positioned relatively closer to the distal end of the second elongate member than the one coupler, and wherein the first location is positioned between the one coupler and the one other coupler along the second elongate member when the structure is in the expanded configuration, the first location spaced from the one other coupler along the second elongate member, and
wherein the back surface of the respective intermediate portion of at least the first elongate member contacts the front surface of the respective intermediate portion of the second elongate member at the first location when the structure is in the expanded configuration.

85. The medical system of claim 84 wherein at least some of the plurality of elongate members are fanned with respect to at least the second elongate member about one or more axes when the structure is in the expanded configuration, the second elongate member curved such that the one or more axes pass through the second elongate member at each of two or more locations, each location of the two or more locations spaced from each other along a length of the second elongate member between the proximal and distal ends of the second elongate member.

86. The medical system of claim 85 wherein the two or more locations comprise three or more locations, each location of the three or more locations spaced from each other along the length of the second elongate member between the proximal and distal ends of the second elongate member.

87. The medical system of claim 84 wherein, when the structure is moved from the unexpanded configuration toward the expanded configuration, a first set of elongate members of the plurality of elongate members is moved along a first angular direction while a second set of elongate members of the plurality of elongate members is moved along a second angular direction opposite the first angular direction.

88. The medical system of claim 84 wherein the stacked array comprises a plurality of successive pairs of the elongate members when the structure is in the unexpanded configuration, and wherein the medical system further comprises a plurality of individually activatable transducer elements, a respective group of the plurality of individually activatable transducer elements arranged between the elongate members of each successive pair of the elongate members in the stacked array when the structure is in the unexpanded configuration.

89. The medical system of claim 84 wherein the front surfaces of the intermediate portions of the at least three elongate members face outwardly away from an interior region within the structure when the structure is in the expanded configuration and the back surfaces of the intermediate portions of the at least three elongate members face inwardly toward the interior region within the structure when the structure is the expanded configuration.

90. A medical system comprising:
a structure comprising a plurality of elongate members, each elongate member of the plurality of elongate members comprising a first end and a second end, an intermediate portion between the first end and the second end of the elongate member, and a respective length between the first end and the second end of the elongate member, the structure further comprising a plurality of couplers comprising a proximal coupler, a distal coupler and at least one intermediate coupler, each coupler of the plurality of couplers spaced from another of the plurality of couplers along the respective length of each of at least a first elongate member of the plurality of elongate members with the at least one intermediate coupler positioned between the proximal coupler and the distal coupler, each coupler of the plurality of couplers arranged to couple at least the first elongate member together with least one other elongate member of the plurality of elongate members, and wherein the structure is selectively moveable between:
an unexpanded configuration in which the elongate members of the plurality of elongate members are sized and arranged to be deliverable through a bodily opening leading to a bodily cavity within a body, the bodily cavity having an interior tissue surface interrupted by a port of the bodily opening, and the plurality of couplers arranged to be advanced distal coupler first into the bodily cavity when the structure is in the unexpanded configuration, and
an expanded configuration in which at least part of the structure is locatable at a position in the bodily cavity with at least both the proximal coupler and the distal coupler positioned relatively closer to the port of the bodily opening than each of the at least one intermediate coupler.

91. The medical system of claim 90 wherein, when the structure is in the expanded configuration, the at least part of the structure is locatable at the position in the bodily cavity with the proximal coupler positioned relatively closer to the port of the bodily opening than the distal coupler.

92. The medical system of claim 90 wherein, when the structure is in the expanded configuration, the at least part of the structure is locatable at the position in the bodily cavity with the distal coupler positioned relatively closer to the port of the bodily opening than the proximal coupler.

93. The medical system of claim 90 wherein each elongate member of the plurality of elongate members comprises a thickness, each intermediate portion comprising a front surface and a back surface opposite across the thickness of the elongate member from the front surface, wherein at least the respective intermediate portions of at least three elongate members of the plurality of elongate members arrayed along a first direction front surface-toward-back surface in a stacked array when the structure is in the unexpanded configuration, and wherein the front surfaces of the intermediate portions of the at least three elongate members face outwardly from the structure when the structure is in the expanded configuration.

94. The medical system of claim 90 wherein at least the intermediate portions of the elongate members of the plurality of elongate members are arranged successively with respect to one another along a first direction in a stacked array when the structure is in the unexpanded configuration, wherein the stacked array comprises a plurality of successive pairs of the elongate members when the structure is in the unexpanded configuration, and wherein the medical system further comprises a plurality of individually activatable transducer elements, a respective group of the plurality of individually activatable transducer elements arranged between the elongate members of each successive pair of the elongate members in the stacked array when the structure is in the unexpanded configuration.

95. The medical system of claim 90 wherein, in the expanded configuration, the structure has a size too large to be deliverable through the bodily opening leading to the bodily cavity.

96. A medical system comprising:
a catheter sheath comprising a first end, a second end and a lumen therebetween; and
a structure comprising a plurality of elongate members, each elongate member of the plurality of elongate members comprising a proximal end, a distal end, and an intermediate portion positioned between the proximal and the distal ends of the elongate member, the structure selectively moveable between:
an unexpanded configuration in which the elongate members of the plurality of elongate members are arranged successively with respect to one another along a first direction in a stacked arrangement, the stacked arrangement sized to be deliverable through the lumen of the catheter sheath from the first end of the catheter sheath toward the second end of the catheter sheath, a particular portion of one elongate member of the plurality of elongate members in the stacked arrangement positioned to be advanced from the second end of the catheter sheath prior to each of at least some of the other elongate members of the plurality of elongate members in the stacked arrangement when the stacked arrangement is delivered through the lumen of the catheter sheath from the first end of the catheter sheath toward the second end of the catheter sheath, and an expanded configuration in which the structure is expanded to have a size too large to be delivered through the lumen of the catheter sheath.

97. The medical system of claim 96 wherein each elongate member of the plurality of elongate members comprises a respective length between the proximal and the distal ends of the elongate member, and the respective length of the one elongate member is longer than each of the respective lengths of the at least some of the other elongate members of the plurality of elongate members.

98. The medical system of claim 96 wherein the particular portion of the one elongate member is cantilevered from the stacked arrangement when the structure is in the unexpanded configuration.

99. The medical system of claim 96 wherein the one elongate member is an outermost elongate member in the stacked arrangement when the structure is in the unexpanded configuration.

100. The medical system of claim 96
wherein each intermediate portion of each elongate member of the plurality of elongate members comprises a thickness, a front surface and a back surface opposite across the thickness from the front surface,
wherein, in the unexpanded configuration, the front surface of the intermediate portion of the one elongate member faces the back surface of the intermediate portion of a first elongate member of the plurality of elongate members in the stacked arrangement, and
wherein, in the unexpanded configuration, the back surface of the intermediate portion of the one elongate member faces the front surface of the intermediate portion of a second elongate member of the plurality of elongate members in the stacked arrangement.

101. The medical system of claim 96
wherein respective particular portions of at least two of the plurality of elongate members in the stacked arrangement are positioned to be advanced from the second end of the catheter sheath prior to each of the at least some of the other elongate members of the plurality of elongate members in the stacked arrangement, and
wherein the at least two of the plurality of elongate members include the one elongate member.

102. The medical system of claim 96 wherein each elongate member of the plurality of elongate members comprises a respective length between the proximal and the distal ends of the elongate member, and at least a first elongate member of the plurality of elongate members crosses a second elongate member of the plurality of elongate members in an X configuration at each of one or more locations along the respective length of the second elongate member when the structure is in the expanded configuration, each of the one or more locations spaced from each of the proximal end and the distal end of the second elongate member when the structure is in the expanded configuration.

103. The medical system of claim 102, further comprising a plurality of couplers, each of which physically couples at least the second elongate member together with at least one other particular elongate member of the plurality of elongate members, each coupler of the plurality of couplers spaced from another of the plurality of couplers along the respective length of the second elongate member,
wherein at least one location of the one or more locations is located along the respective length of the second elongate member between at least two of the plurality of couplers when the structure is in the expanded configuration.

104. The medical system of claim 102 wherein each elongate member of the plurality of elongate members is arranged to be advanced distal end ahead of the proximal end through the lumen of the catheter sheath from the first end of the catheter sheath toward the second end of the catheter sheath when the structure is in the unexpanded configuration, wherein the medical system further comprises a plurality of couplers, each of which physically couples at least the second elongate member together with at least one other particular elongate member of the plurality of elongate members, each coupler of the plurality of couplers spaced from another of the plurality of couplers along the respective length of the second elongate member, and wherein at least one location of the one or more locations is located along the respective length of the second elongate member relatively closer to the distal end of the second elongate member than each of at least two of the plurality of couplers when the structure is in the expanded configuration.

105. The medical system of claim 96 wherein the respective intermediate portion of each elongate member of at least one particular elongate member of the plurality of elongate members is preformed to autonomously bend about a respective bending axis as the respective intermediate portion of the elongate member of the at least one particular elongate member is advanced from the second end of the catheter sheath.

106. The medical system of claim 96, further comprising a bending unit that acts on at least one particular elongate member of the plurality of elongate members to bend each elongate member of a set of the plurality of elongate members about a respective bending axis when the respective intermediate portion of the elongate member of the set of the plurality of elongate members is advanced from the second end of the catheter sheath.

107. The medical system of claim 96 wherein each elongate member of the plurality of elongate members is arranged to be advanced distal end first as the stacked arrangement is delivered through the lumen of the catheter sheath from the first end of the catheter sheath toward the second end of the catheter sheath.

108. The medical system of claim 96 wherein the stacked arrangement comprises a plurality of successive pairs of the elongate members when the structure is in the unexpanded configuration, and wherein the medical system further comprises a plurality of individually activatable transducer elements, a respective group of the plurality of individually activatable transducer elements arranged between the elongate members of each successive pair of the elongate members in the stacked arrangement when the structure is in the unexpanded configuration.

109. A medical system comprising:
a structure comprising a plurality of elongate members, each elongate member comprising a first end, a second end, and an intermediate portion positioned between the first and the second ends of the elongate member, each intermediate portion comprising a thickness, a front surface and a back surface opposite across the thickness from the front surface, the structure further comprising a proximal portion and a distal portion, each of the proximal and the distal portions of the structure comprising a respective part of each of the plurality of elongate members, the structure selectively moveable between:
   a delivery configuration in which the structure is sized for delivery through a bodily opening leading to a bodily cavity, at least the respective intermediate portions of at least three elongate members of the plurality of elongate members linearly arrayed along a first direction front surface-toward-back surface in a stacked array when the structure is in the delivery configuration; and
   a deployed configuration in which the structure is sized too large for delivery through the bodily opening leading to the bodily cavity, the proximal portion of the structure forming a first domed shape and the distal portion of the structure forming a second domed shape when the structure is in the deployed configuration,
wherein each of the plurality of elongate members comprises a scrolled or volute shape profile when the structure is in the deployed configuration.

110. The medical system of claim 109 wherein:
each elongate member of the plurality of elongate members comprises a respective length between the first end and the second end of the elongate member;
each elongate member of at least one of the plurality of elongate members crosses at least one other elongate member of the plurality of elongate members at each of a respective plurality of spaced apart locations along the respective length of the one other elongate member when the structure is in the deployed configuration; and
for each elongate member of the at least one of the plurality of elongate members, the front surface of the intermediate portion of the one other elongate member faces toward the respective back surface of the respective intermediate portion of the elongate member of the at least one of the plurality of elongate members at each of the respective plurality of spaced apart locations along the respective length of the one other elongate member when the structure is in the deployed configuration.

111. The medical system of claim 109 wherein each elongate member of the plurality of elongate members comprises a respective length between the first and the second ends of the elongate member, and wherein the elongate members of the plurality of elongate members are circumferentially arranged about a first axis when the structure is in the deployed configuration, the first axis passing through each of at least a first elongate member of the plurality of elongate members when the structure is in the deployed configuration, the first axis passing through the first elongate member at two or more locations when the structure is in the deployed configuration, each location of the two or more locations spaced from another location of the two or more locations along the respective length of the first elongate member.

112. The medical system of claim 111 wherein the two or more locations comprise at least three locations spaced with respect to one another along the respective length of the first elongate member.

113. The medical system of claim 109 wherein:
each of the first domed shape and the second domed shape comprises a respective apex;
the structure is arranged to be advanced distal portion first through the bodily opening leading to the bodily cavity when the structure is in the delivery configuration;
each particular elongate member of the plurality of elongate members comprises a respective length between the first end and the second end of the particular elongate member; and
at least a first elongate member of the plurality of elongate members is crossed by each of at least two others of the plurality of elongate members at each of one or more locations along the respective length of the first elongate member when the structure is in the deployed configuration, each of the one or more locations spaced along the respective length of the first elongate member from the respective apex of each of the first domed shape and the second domed shape when the structure is in the deployed configuration.

114. The medical system of claim 109 wherein, when the structure is moved from the delivery configuration toward the deployed configuration, a first set of elongate members of the plurality of elongate members is moved along a first angular direction while a second set of elongate members of the plurality of elongate members is moved along a second angular direction opposite the first angular direction.

115. The medical system of claim 109 wherein the stacked array comprises a plurality of successive pairs of the elongate members when the structure is in the delivery configuration, and wherein the medical system further comprises a plurality of individually activatable transducer elements, a respective group of the plurality of individually activatable transducer elements arranged between the elongate members of each successive pair of the elongate members in the stacked array when the structure is in the delivery configuration.

* * * * *